United States Patent
Hyde et al.

(10) Patent No.: US 8,908,941 B2
(45) Date of Patent: Dec. 9, 2014

(54) GUIDANCE INFORMATION INDICATING AN OPERATIONAL PROXIMITY OF A BODY-INSERTABLE DEVICE TO A REGION OF INTEREST

(75) Inventors: Roderick A. Hyde, Redmond, WA (US); Jordin T. Kare, Seattle, WA (US); Eric C. Leuthardt, St. Louis, MO (US); Erez Lieberman, Cambridge, MA (US); Dennis J. Rivet, Chesapeake, VA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 419 days.

(21) Appl. No.: 13/200,112

(22) Filed: Sep. 16, 2011

(65) Prior Publication Data

US 2013/0070981 A1 Mar. 21, 2013

Related U.S. Application Data

(63) Continuation-in-part of application No. 13/200,114, filed on Sep. 16, 2011, which is a continuation-in-part
(Continued)

(51) Int. Cl.
- *G06K 9/00* (2006.01)
- *H04N 7/18* (2006.01)
- *G06T 7/00* (2006.01)

(52) U.S. Cl.
CPC .. *G06K 9/00* (2013.01); *H04N 7/18* (2013.01); *G06T 7/003* (2013.01); *G06T 2207/30028* (2013.01); *G06T 2207/10068* (2013.01); *G06T 7/0012* (2013.01)
USPC ............ 382/128; 382/100; 382/130; 382/131

(58) Field of Classification Search
None
See application file for complete search history.

(56) References Cited

U.S. PATENT DOCUMENTS

| 4,963,960 A | 10/1990 | Takami |
| 5,638,819 A | 6/1997 | Manwaring et al. |

(Continued)

OTHER PUBLICATIONS

PCT International Search Report; International App. No. PCT/US2012/055397; Dec. 7, 2012; pp. 1-2.
(Continued)

*Primary Examiner* — Avinash J Yentrapati
(74) *Attorney, Agent, or Firm* — Dorsey & Whitney LLP

(57) ABSTRACT

Described embodiments include a system, method, and computer program product. A described system includes a receiver circuit that receives a first reference image that includes an objective landmark subsurface feature of a mammalian body part, and a second reference image that includes a present-location landmark subsurface feature of the mammalian body part. A feature matching circuit determines a substantial correspondence between the objective landmark subsurface feature and a first atlas subsurface feature, and a substantial correspondence between the present-location landmark subsurface feature and a second atlas subsurface feature. A location analysis circuit determines a fourth spatial relationship between the destination region of interest and a distal end portion of the body-insertable device deployed operationally proximate to the mammalian body part. An indicator circuit generates informational data indicative of the determined fourth spatial relationship. The system includes a computer-readable media configured to maintain the informational data.

30 Claims, 150 Drawing Sheets

Related U.S. Application Data of application No. 13/200,110, filed on Sep. 16, 2011, which is a continuation-in-part of application No. 13/200,107, filed on Sep. 16, 2011, which is a continuation-in-part of application No. 13/200,108, filed on Sep. 16, 2011, which is a continuation-in-part of application No. 13/200,104, filed on Sep. 16, 2011, which is a continuation-in-part of application No. 13/200,111, filed on Sep. 16, 2011, which is a continuation-in-part of application No. 13/200,103, filed on Sep. 16, 2011, which is a continuation-in-part of application No. 13/200,105, filed on Sep. 16, 2011, now Pat. No. 8,634,598, which is a continuation-in-part of application No. 13/200,109, filed on Sep. 16, 2011.

(56) References Cited

U.S. PATENT DOCUMENTS

| | | | |
|---|---|---|---|
| 5,749,362 A | 5/1998 | Funda et al. | |
| 6,017,513 A | 1/2000 | Betbeder et al. | |
| 6,159,445 A | 12/2000 | Klaveness et al. | |
| 6,173,068 B1 | 1/2001 | Prokoski | |
| 6,236,742 B1 | 5/2001 | Handel | |
| 6,350,431 B1 | 2/2002 | Snow et al. | |
| 6,379,302 B1* | 4/2002 | Kessman et al. | 600/437 |
| 6,384,915 B1 | 5/2002 | Everett et al. | |
| 6,468,203 B2 | 10/2002 | Belson | |
| 6,514,082 B2 | 2/2003 | Kaufman et al. | |
| 6,529,617 B1 | 3/2003 | Prokoski | |
| 6,537,211 B1 | 3/2003 | Wang et al. | |
| 6,540,981 B2 | 4/2003 | Klaveness et al. | |
| 6,690,963 B2 | 2/2004 | Ben-Haim et al. | |
| 6,754,374 B1 | 6/2004 | Miller et al. | |
| 6,855,810 B2 | 2/2005 | Mostov et al. | |
| 6,915,154 B1 | 7/2005 | Docherty et al. | |
| 6,928,314 B1 | 8/2005 | Johnson et al. | |
| 7,006,111 B1 | 2/2006 | Rothrock | |
| 7,235,045 B2 | 6/2007 | Wang et al. | |
| 7,415,139 B2 | 8/2008 | Takiguchi | |
| 7,479,106 B2 | 1/2009 | Banik et al. | |
| 7,544,163 B2 | 6/2009 | MacKinnon et al. | |
| 7,546,156 B2 | 6/2009 | Madden et al. | |
| 7,634,301 B2 | 12/2009 | Meijer | |
| 7,935,048 B2 | 5/2011 | Yaron et al. | |
| 7,945,310 B2 | 5/2011 | Gattani et al. | |
| 8,090,429 B2 | 1/2012 | Vija et al. | |
| 8,111,885 B2 | 2/2012 | Von Berg et al. | |
| 8,221,402 B2 | 7/2012 | Francischelli et al. | |
| 8,233,075 B2 | 7/2012 | Lavrentiev et al. | |
| 8,675,939 B2 | 3/2014 | Moctezuma De La Barrera | |
| 2001/0036302 A1 | 11/2001 | Miller | |
| 2002/0023652 A1 | 2/2002 | Riaziat et al. | |
| 2003/0129750 A1 | 7/2003 | Schwartz | |
| 2003/0167007 A1 | 9/2003 | Belson | |
| 2004/0204651 A1 | 10/2004 | Freeman et al. | |
| 2004/0218792 A1 | 11/2004 | Spoonhower et al. | |
| 2005/0020926 A1 | 1/2005 | Wiklof et al. | |
| 2005/0027187 A1 | 2/2005 | Barth et al. | |
| 2005/0033142 A1 | 2/2005 | Madden et al. | |
| 2005/0059873 A1 | 3/2005 | Glozman et al. | |
| 2005/0107679 A1 | 5/2005 | Geiger et al. | |
| 2005/0159648 A1 | 7/2005 | Freed | |
| 2005/0182434 A1 | 8/2005 | Docherty et al. | |
| 2005/0192615 A1 | 9/2005 | Torre et al. | |
| 2005/0228231 A1 | 10/2005 | MacKinnon et al. | |
| 2005/0234302 A1 | 10/2005 | MacKinnon et al. | |
| 2005/0272975 A1 | 12/2005 | McWeeney et al. | |
| 2006/0004275 A1 | 1/2006 | Vija et al. | |
| 2006/0184040 A1 | 8/2006 | Keller et al. | |
| 2006/0229594 A1 | 10/2006 | Francischelli et al. | |
| 2006/0241576 A1 | 10/2006 | Diederich et al. | |
| 2006/0247514 A1 | 11/2006 | Panasyuk et al. | |
| 2006/0262544 A1 | 11/2006 | Piepgras et al. | |
| 2006/0262545 A1 | 11/2006 | Piepgras et al. | |
| 2007/0036402 A1 | 2/2007 | Cahill et al. | |
| 2007/0055128 A1 | 3/2007 | Glossop | |
| 2007/0142707 A1 | 6/2007 | Wiklof et al. | |
| 2007/0160276 A1 | 7/2007 | Chen et al. | |
| 2007/0179368 A1 | 8/2007 | Backman et al. | |
| 2007/0185384 A1 | 8/2007 | Bayer et al. | |
| 2007/0217665 A1 | 9/2007 | Kiraly et al. | |
| 2007/0269837 A1 | 11/2007 | McGreevy et al. | |
| 2007/0282190 A1 | 12/2007 | Dekel et al. | |
| 2007/0289207 A1 | 12/2007 | May et al. | |
| 2007/0297657 A1 | 12/2007 | Mattes et al. | |
| 2008/0021301 A1 | 1/2008 | Gonzalez et al. | |
| 2008/0052593 A1 | 2/2008 | Lee et al. | |
| 2008/0058593 A1 | 3/2008 | Gu et al. | |
| 2008/0058785 A1 | 3/2008 | Boyden et al. | |
| 2008/0085042 A1 | 4/2008 | Trofimov et al. | |
| 2008/0097155 A1 | 4/2008 | Gattani et al. | |
| 2008/0118125 A1 | 5/2008 | Mahesh et al. | |
| 2008/0118135 A1 | 5/2008 | Averbuch et al. | |
| 2008/0130968 A1 | 6/2008 | Daw et al. | |
| 2008/0159653 A1 | 7/2008 | Dunki-Jacobs et al. | |
| 2008/0242978 A1 | 10/2008 | Simon et al. | |
| 2008/0292194 A1 | 11/2008 | Schmidt et al. | |
| 2009/0010540 A1 | 1/2009 | Mullick et al. | |
| 2009/0012361 A1 | 1/2009 | MacKinnon et al. | |
| 2009/0023991 A1 | 1/2009 | Gono et al. | |
| 2009/0023993 A1 | 1/2009 | Davidson et al. | |
| 2009/0046196 A1 | 2/2009 | Lavrentiev et al. | |
| 2009/0082629 A1 | 3/2009 | Dotan et al. | |
| 2009/0101153 A1 | 4/2009 | Boyden et al. | |
| 2009/0177071 A1 | 7/2009 | Harlev et al. | |
| 2009/0196473 A1* | 8/2009 | Fujii et al. | 382/128 |
| 2009/0324038 A1 | 12/2009 | Assmann | |
| 2010/0034436 A1 | 2/2010 | Kono | |
| 2010/0158330 A1 | 6/2010 | Guissin et al. | |
| 2010/0179820 A1 | 7/2010 | Harrison et al. | |
| 2010/0254911 A1 | 10/2010 | Sharma et al. | |
| 2010/0278405 A1 | 11/2010 | Kakadiaris et al. | |
| 2010/0316277 A1 | 12/2010 | Fan et al. | |
| 2010/0332475 A1 | 12/2010 | Birdwell et al. | |
| 2011/0004059 A1 | 1/2011 | Arneson et al. | |
| 2011/0022133 A1 | 1/2011 | Diederich et al. | |
| 2011/0038414 A1 | 2/2011 | Song et al. | |
| 2011/0087104 A1 | 4/2011 | Moore et al. | |
| 2012/0035457 A1 | 2/2012 | Subramaniam et al. | |
| 2012/0041446 A1 | 2/2012 | Wong et al. | |
| 2012/0155731 A1 | 6/2012 | Weersink et al. | |
| 2012/0254747 A1 | 10/2012 | Bocirnea | |

OTHER PUBLICATIONS

"2-D and 3-D Image Registration: A Tutorial"; Computer Vision and Pattern Recognition 2004 (CVPRO4); bearing dates of Feb. 27, 2004 and Jun. 27, 2004, printed on Aug. 4, 2009; pp. 1-4.

Dey et al.; "Mixed Reality Merging of Endoscopic Images and 3-D Surfaces"; printed on Jun. 10, 2011; pp. 1-8.

Foroughi et al.; "Localization of Pelvic Anatomical Coordinate System Using US/Atlas Registration for Total Hip Replacement"; bearing a date of 2008, printed on Aug. 4, 2009; pp. 1-2 (Only the Abstract is being provided); Springer Berlin / Heidelberg.

Gebhardt, Chris; "RCC Imagery Analysis Procedures Explored in STS-127 TPS Documentation"; NASASpaceFlight.com; bearing dates of Jul. 23, 2009 and 2005-2009, printed on Aug. 18, 2011; pp. 1-6; NASASpaceFlight.com; located at: http://www.nasaspaceflight.com/2009/07/rcc-procedures-explored-sts-127-tps/.

"Image Feature Extraction Engine"; printed on Dec. 28, 2010; pp. 1-2; Information Grand Voyage.

"Image registration"; Wikipedia; printed on Aug. 4, 2009; pp. 1-6; located at: http://en.wikipedia.org/wiki/Image_registration.

"Internal body part"; printed on Dec. 28, 2010; pp. 1-4.

Little et al.; "A practical model of low-volume high-intensity interval training induces mitochondrial biogenesis in human skeletal muscle: potential mechanisms"; The Journal of Physiology; bearing dates of Sep. 18, 2009 and 2010; pp. 1011-1022; vol. 588.6; The Physiological Society.

"Medcyclopaedia—Medcyclo.com"; bearing dates of 1997-2011, printed on Aug. 16, 2011; p. 1; General Electric Company; located at: http://www.medcyclopaedia.com/?tt_topic=.

(56) References Cited

OTHER PUBLICATIONS

"PhotoModeler Dec. 2010 Newsletter"; PhotoModeler Newsletter, Measuring & Modeling the Real World.; bearing dates of Dec. 2010 and 2010, printed on Aug. 17, 2011; pp. 1-3; Eos Systems Inc.; located at: http://photomodeler.com/newsletters/Dec2010/letter.html.

"RF—The Next Generation Capsule Endoscope Sayaka"; bearing a date of 2010, printed on Aug. 16, 2011; pp. 1-3; RF Co., Ltd.; located at: http://www.rfamerica.com/sayaka/index.html.

Hazlett, Ph.D. et al.; "Abnormal Glucose Metabolism in the Mediodorsal Nucleus of the Thalamus in Schizophrenia"; American Journal of Psychiatry; Feb. 2004; pp. 305-314; vol. 161, No. 2; American Journal of Psychiatry.

Saporta et al.; "Multimodality Neuroimaging to Study Tourette Syndrome: Correlating AMT-PET and DT-MRI"; bearing a date of 2009; pp. 498; Proceedings of the International Society for Magnetic Resonance in Medicine.

Wang et al.; "A Region Based Approach for SAR Image Co-registration"; bearing a date of 2008; pp. 1-4; IEEE.

Yu et al.; "Coregistered FDG PET/CT-Based Textural Characterization of Head and Neck Cancer for Radiation Treatment Planning"; IEEE Transactions on Medical Imaging; Mar. 2009; pp. 374-383; vol. 28, No. 3; IEEE.

\* cited by examiner

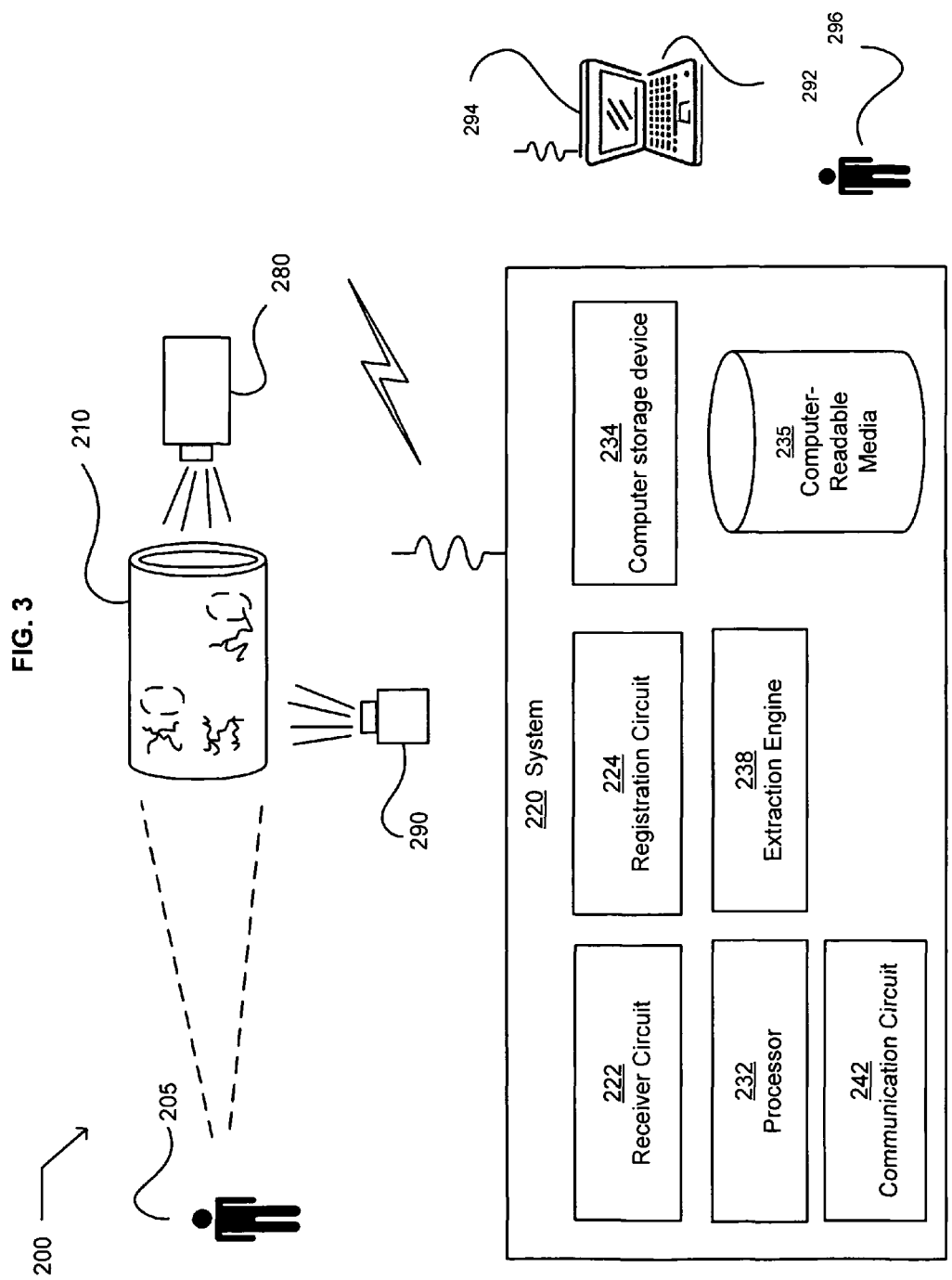

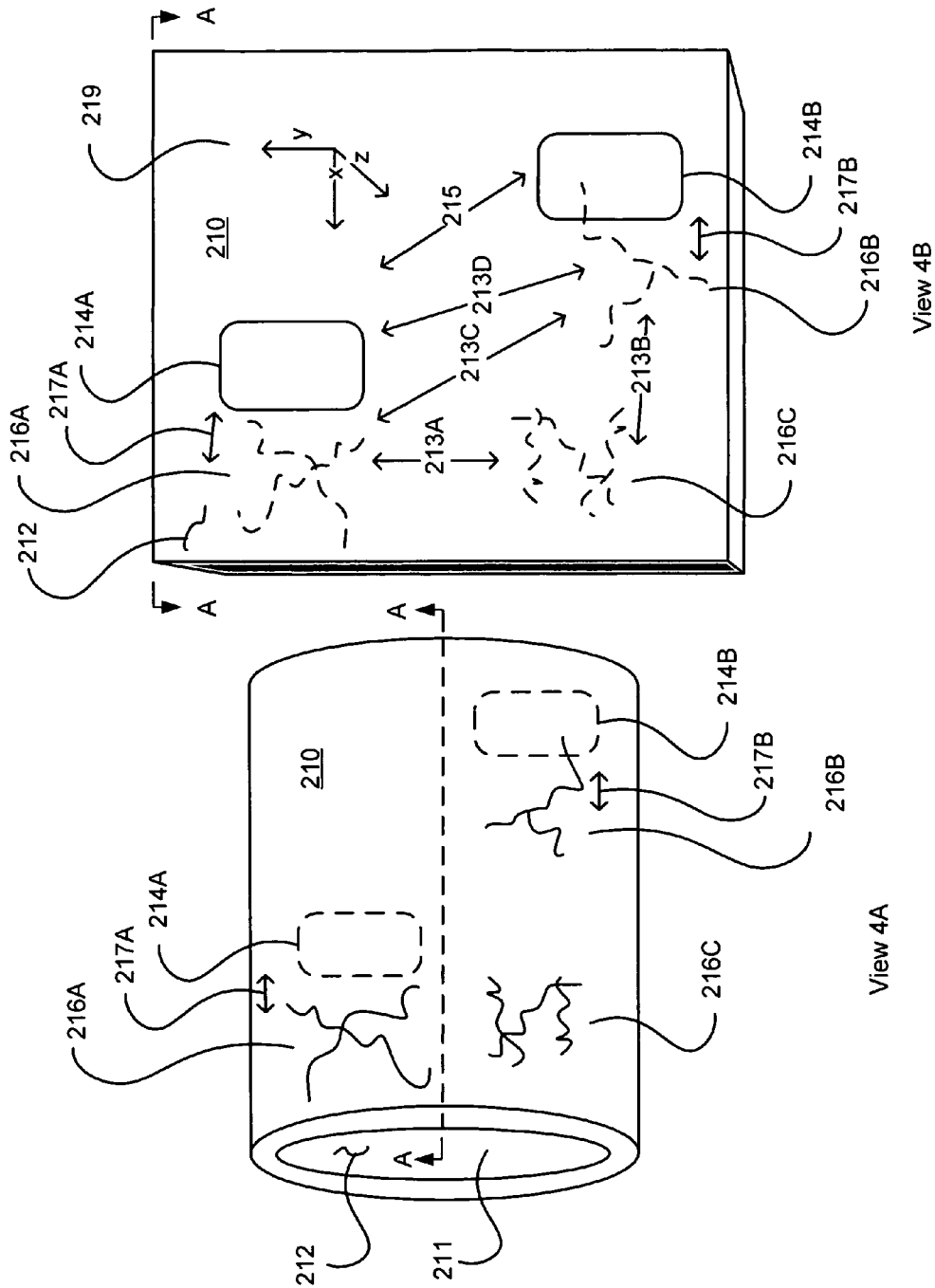

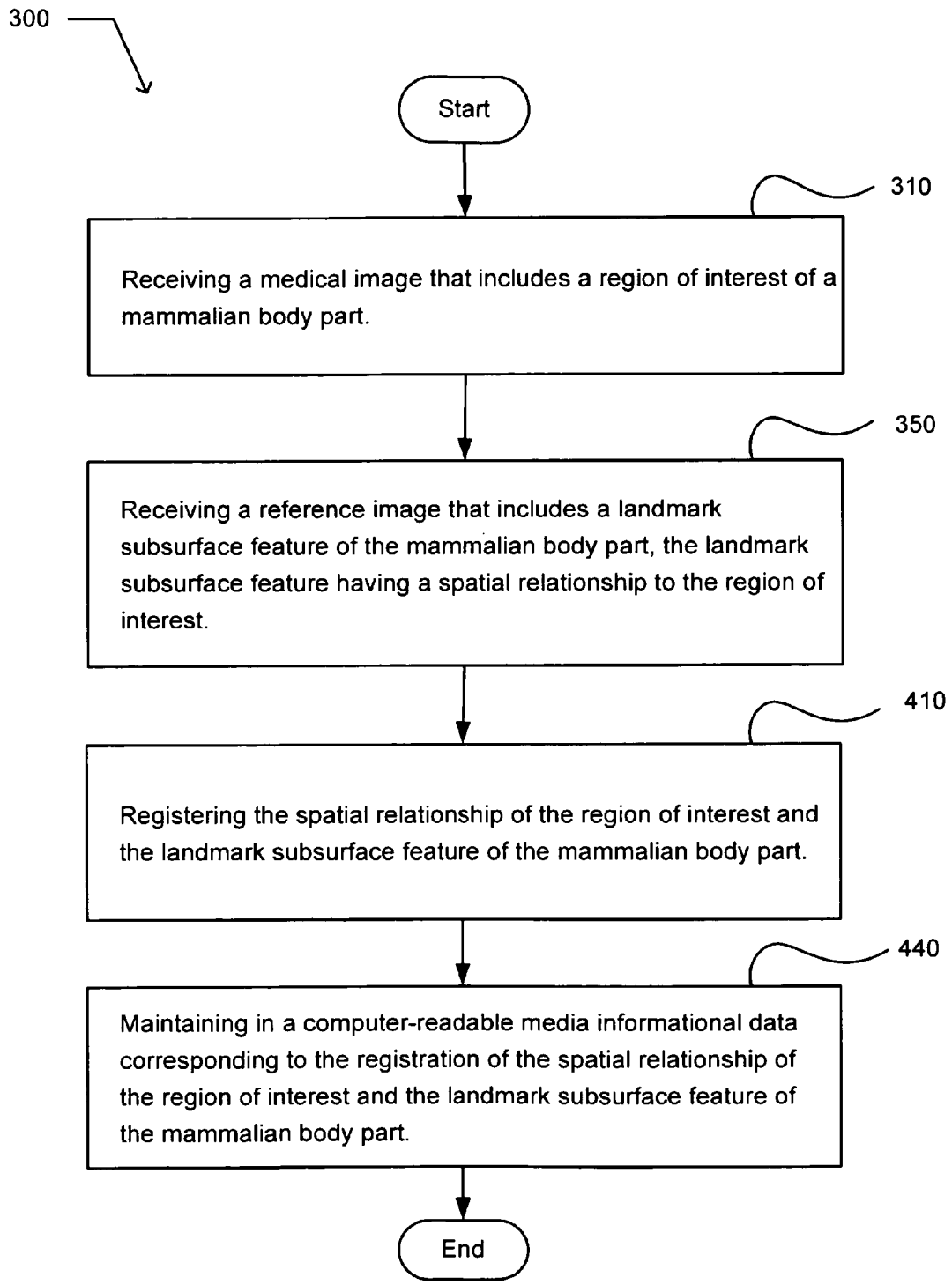

FIG. 6

310 — Receiving a medical image that includes a region of interest of a mammalian body part.

312 Receiving a medical image that includes a region of interest of a cavity or lumen of a mammalian body part.

314 Receiving a medical image that includes a region of interest of a surface of a cavity or lumen of a mammalian body part.

316 Receiving a medical image that includes a region of interest of a wall, membrane, or epithelial layer of a mammalian body part.

318 Receiving a medical image that includes a region of interest of an orifice, canal, cavity, or hollow region of a mammalian body part.

322 Receiving a medical image that includes information or data indicative of a region of interest of a mammalian body part.

324 Receiving a digital image indicative of a region of interest of a mammalian body part and acquired using at least one of a PET, x-ray, CAT, coherence tomography (CT) image, magnetic resonance imaging (MRI) image, fluoroscopy, fluorescence based imaging, or ultrasound based image technology.

326 Receiving a medical image that includes a region of interest of a mammalian body part and that was acquired using at least one of a visible light, near infrared light, infrared light, passive thermal, or active thermal imaging modality.

328 Facilitating an acquisition of a medical image of a region of interest of a mammalian body part.

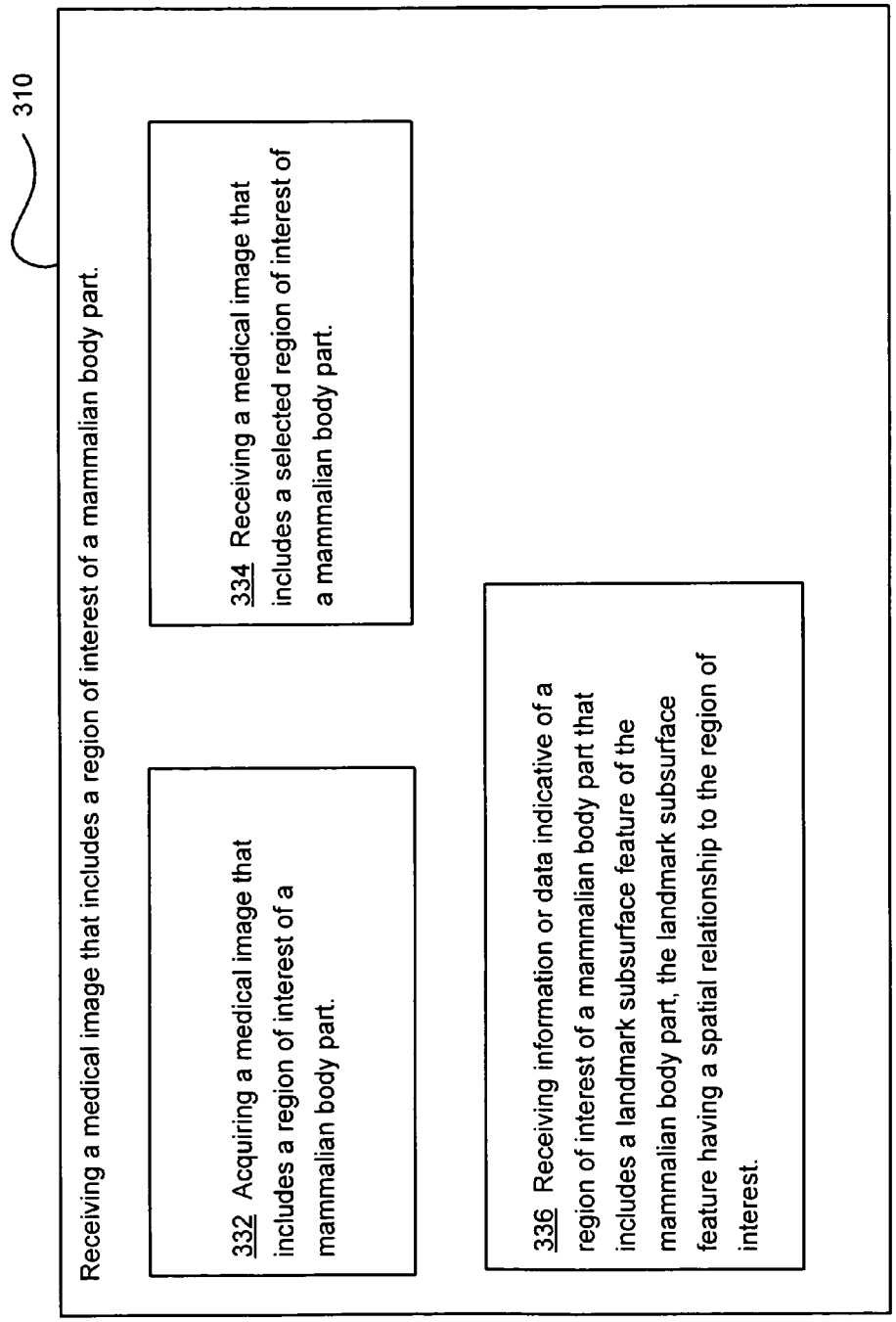

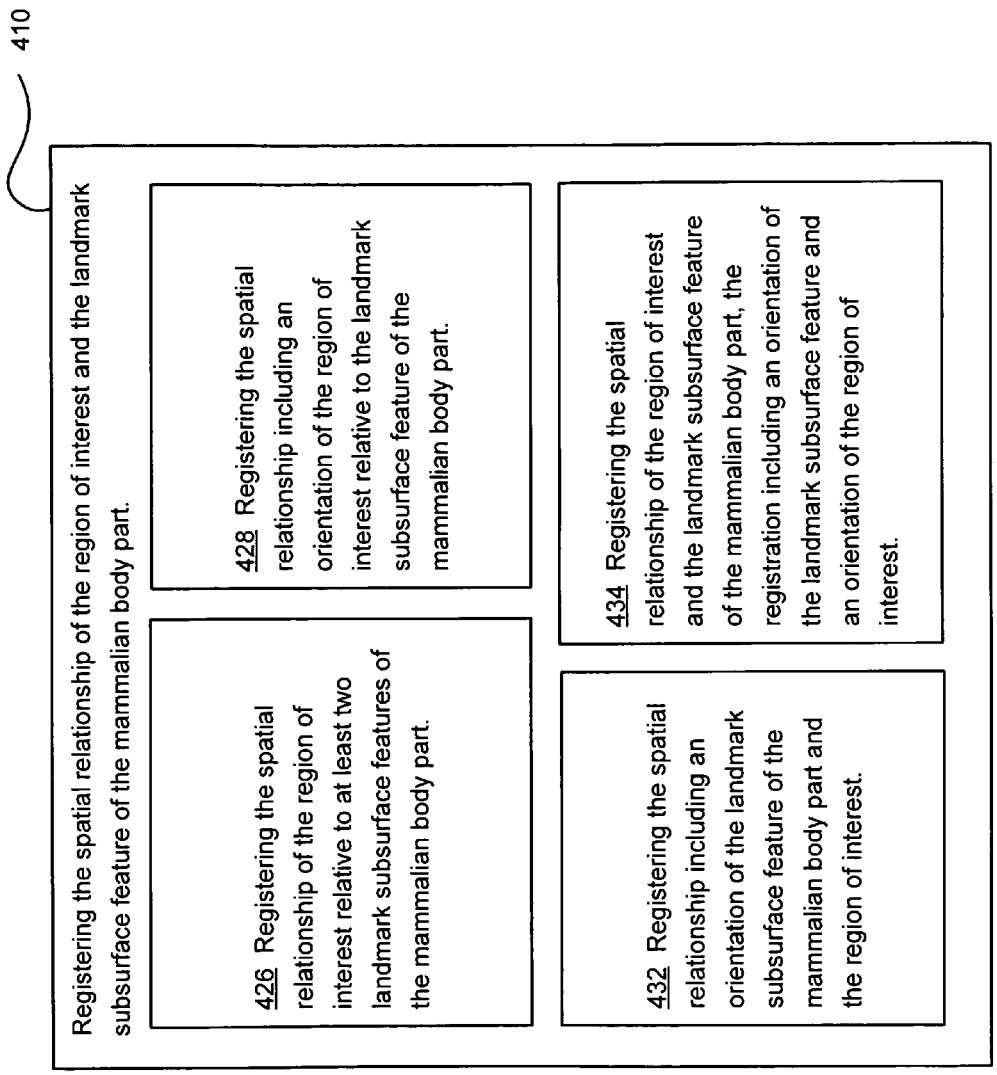

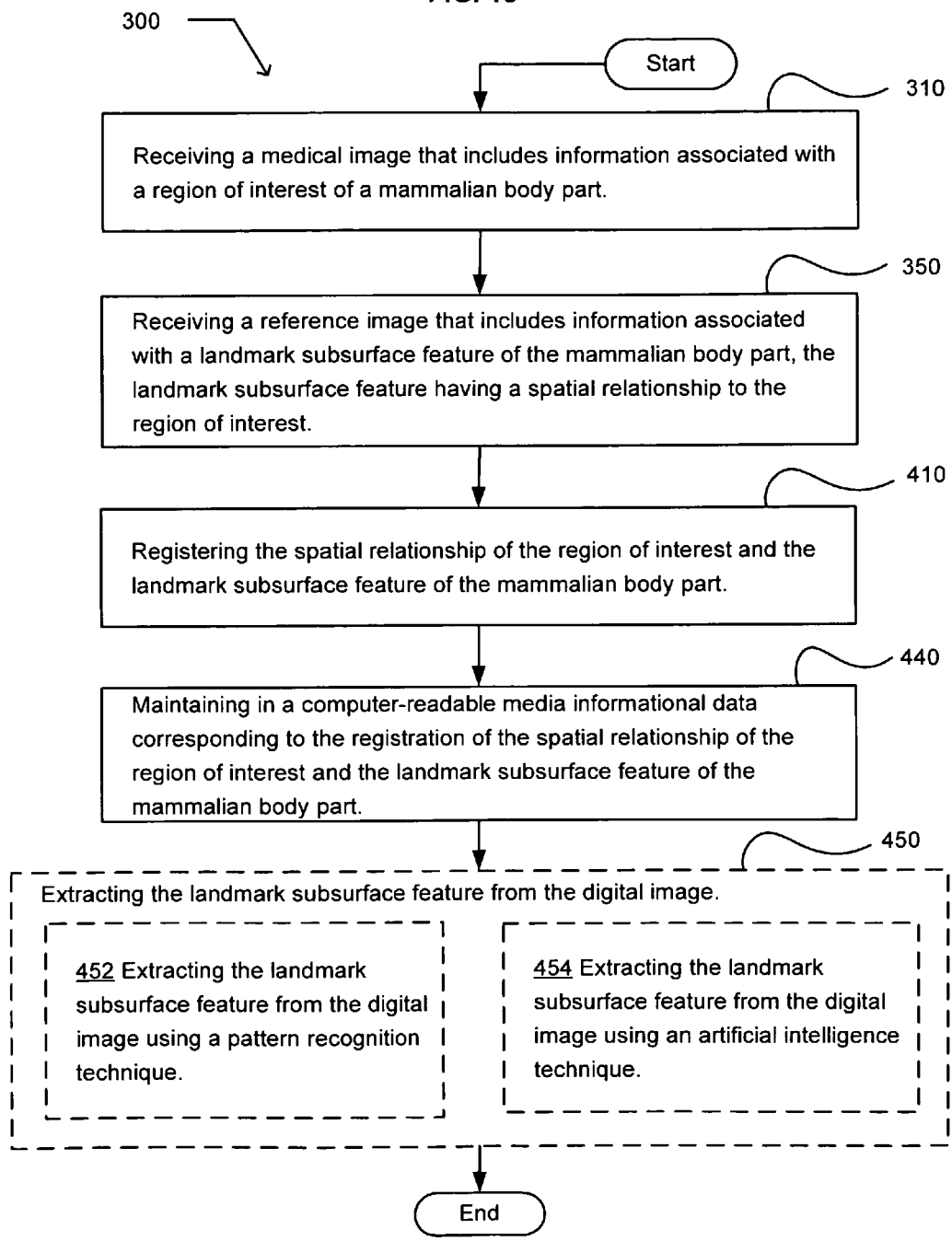

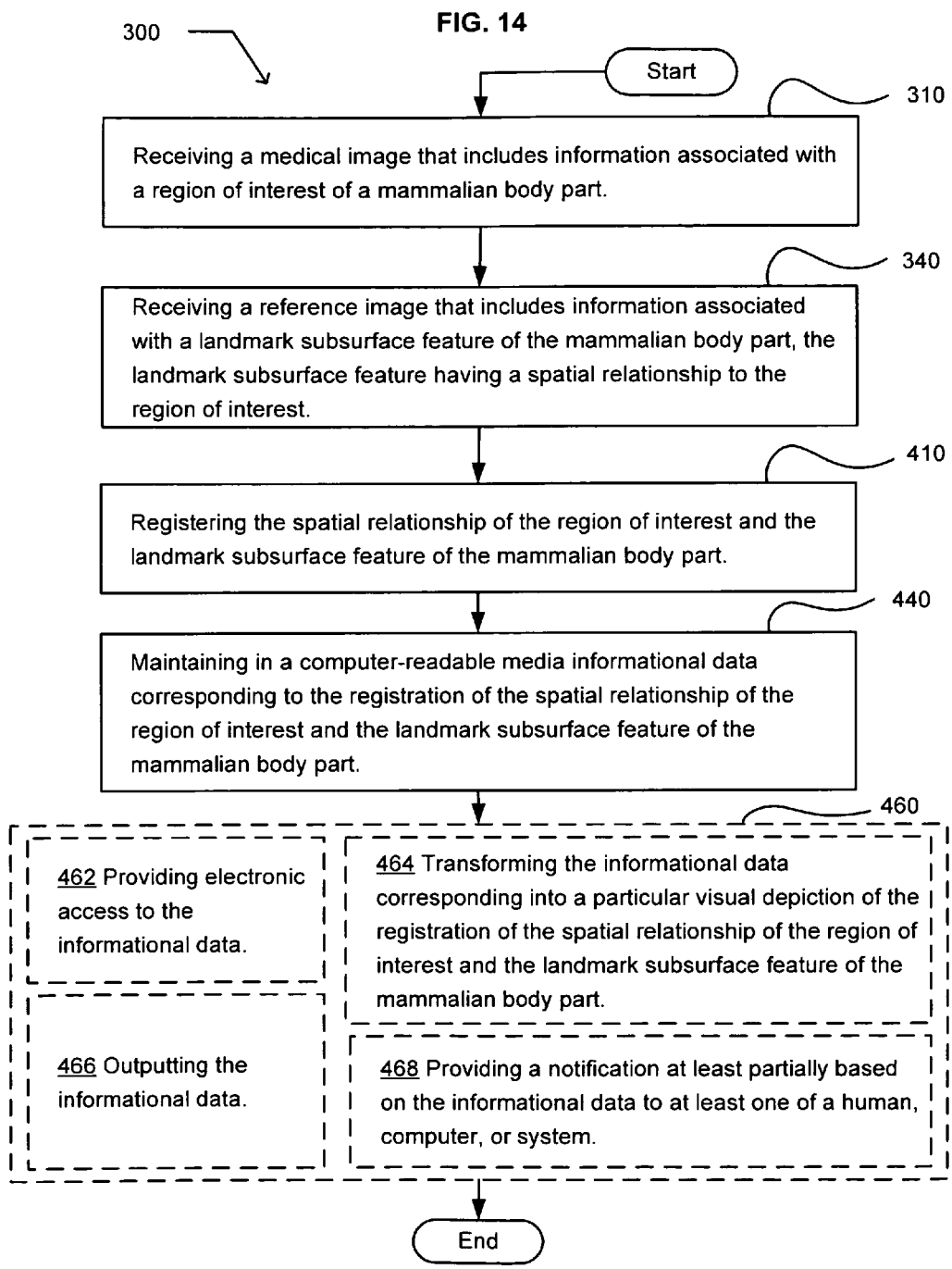

510 A computer-readable media.

520 Program instructions which, when executed by a processor of a digital computing device, cause the digital computing device to perform a process including:

(i) receiving data indicative of a region of interest portion of a mammalian body part;

(ii) receiving a digital image that includes a landmark subsurface feature of the mammalian body part, the landmark subsurface feature having a spatial relationship to the region of interest;

(iii) registering the region of interest and the landmark subsurface feature of the mammalian body part, the landmark subsurface feature having a spatial relationship to the region of interest; and (iv) storing in another computer-readable media operably coupled with the processor informational data corresponding to the registration of the region of interest and the landmark subsurface feature of the mammalian body part.

522 Transform the informational data into data useable in providing a particular visual depiction of the region of interest relative to the landmark subsurface feature of the mammalian body part.

524 Provide a notification at least partially based on the informational data to at least one of a human, computer, or system.

526 The computer-readable media includes a tangible computer-readable media.

528 The computer-readable media includes a communications media.

Receiving a first reference image that includes a first landmark subsurface feature of the mammalian body part, the first landmark subsurface feature having a first spatial relationship to the first region of interest.

1031 Receiving a first two-dimensional or three-dimensional reference image that includes a first landmark subsurface feature of the mammalian body part, the first landmark subsurface feature having a first spatial relationship to the first region of interest.

1032 Receiving a first reference image that includes a first landmark subsurface feature of the mammalian body part, the first landmark subsurface feature having an indicated, determinable, estimable, or inferable first spatial relationship to the first region of interest.

1033 Receiving a first reference image that includes a first landmark subsurface feature of the mammalian body part, and receiving data indicative of an environment of the mammalian body part when the first reference image was acquired, the first landmark subsurface feature having a first spatial relationship to the first region of interest.

1034 Receiving a first reference image that includes a first landmark subsurface feature of the mammalian body part, the first landmark subsurface feature having a first spatial relationship to the first region of interest, and the first reference image acquired by a body-insertable device while a portion of the body-insertable device was present in a cavity or lumen of the mammalian body part.

1035 Receiving a first reference image that includes a first landmark subsurface feature of the mammalian body part, the first landmark subsurface feature having a first spatial relationship to the first region of interest, and the first reference image acquired by an *ex vivo* device.

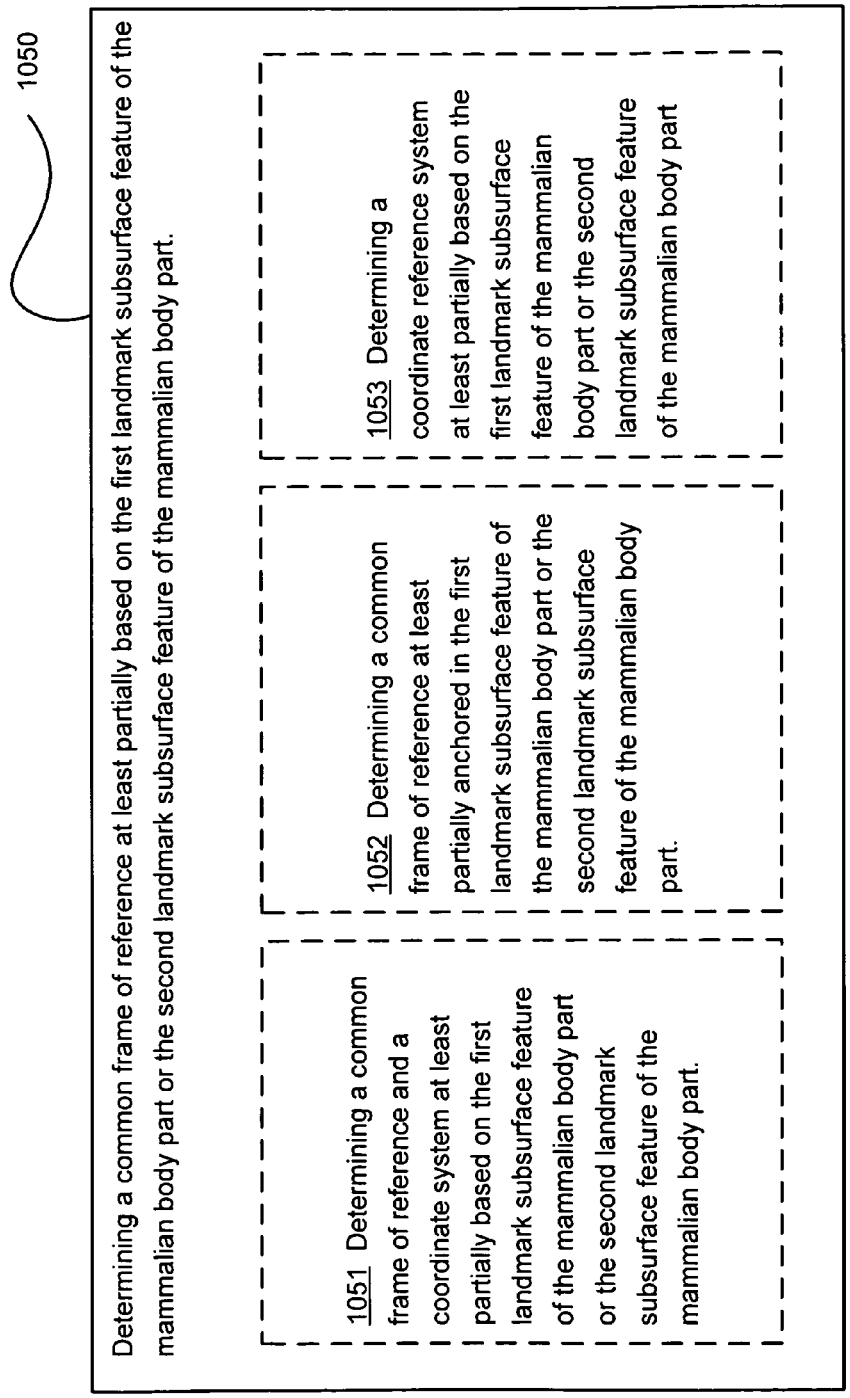

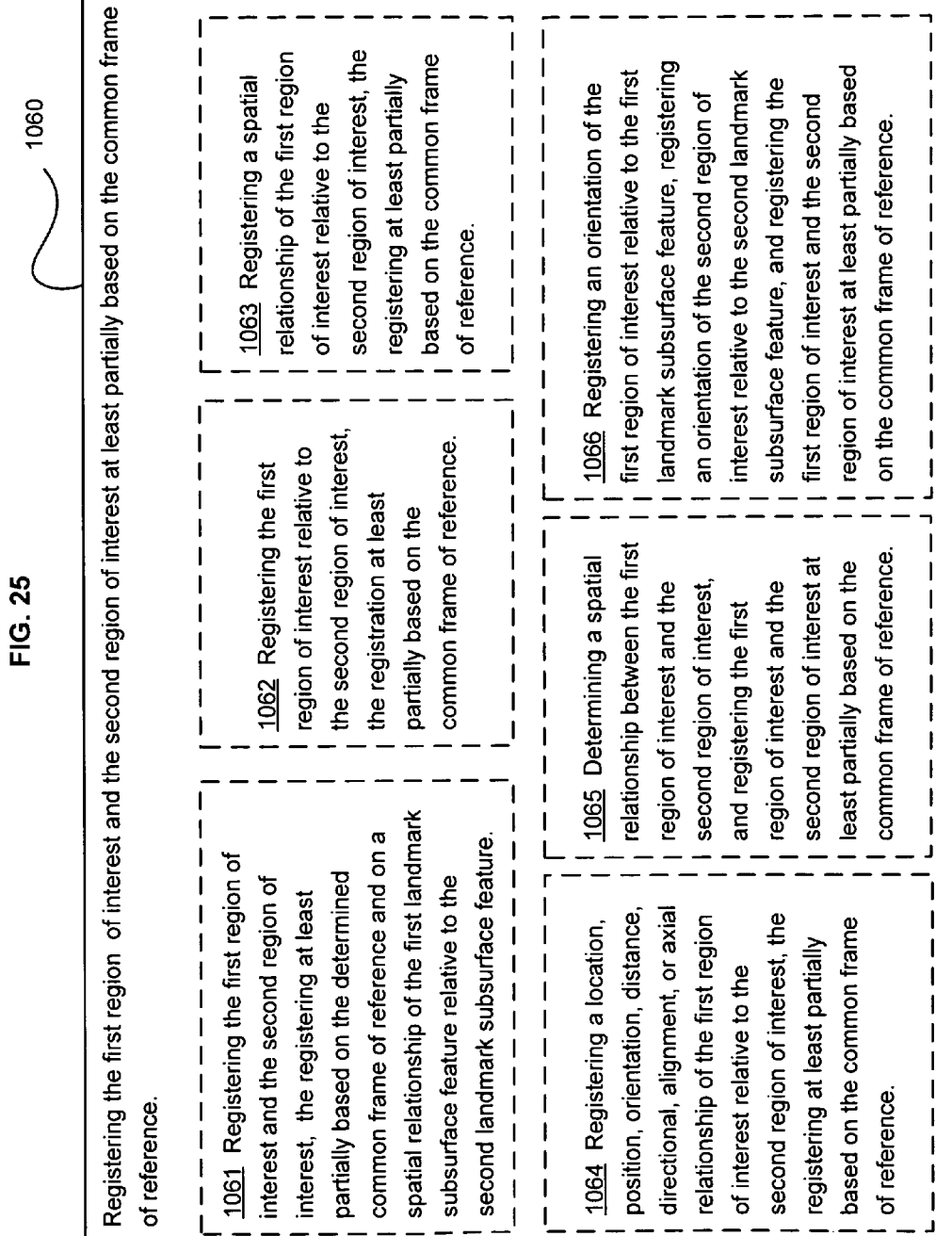

FIG. 26

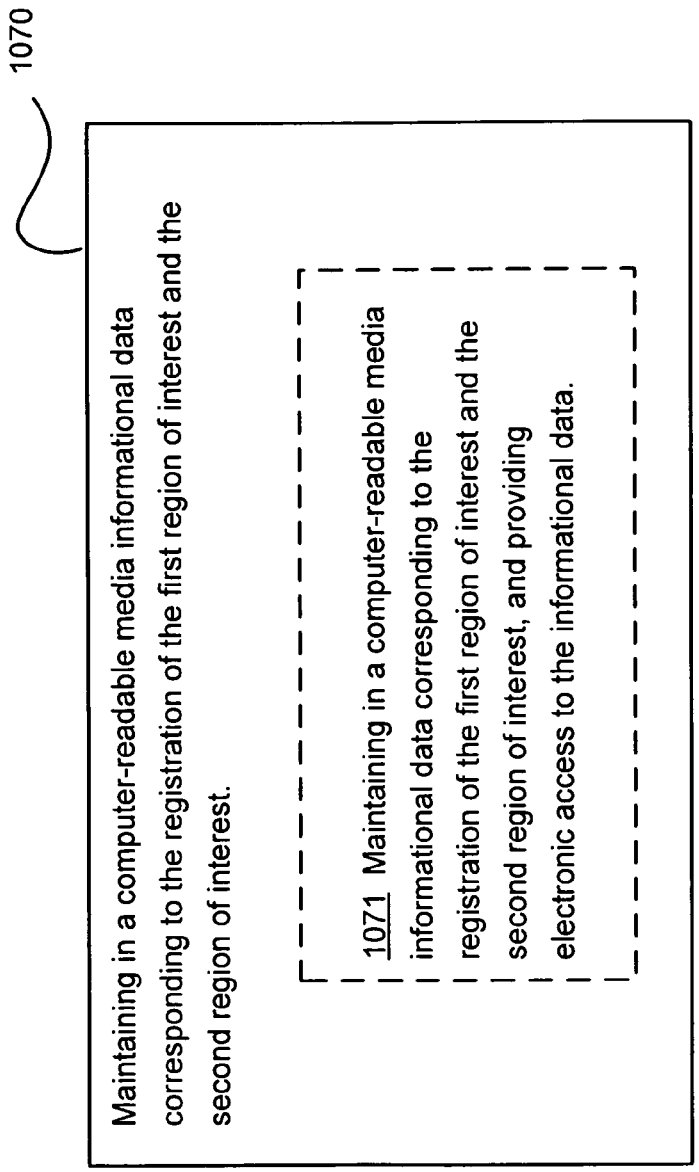

1070 Maintaining in a computer-readable media informational data corresponding to the registration of the first region of interest and the second region of interest.

1071 Maintaining in a computer-readable media informational data corresponding to the registration of the first region of interest and the second region of interest, and providing electronic access to the informational data.

1310 A computer-readable media.

1320 Program instructions which, when executed by a processor of a computing device, cause the computing device to perform a process including:

(i) determining a common frame of reference at least partially based on a first landmark subsurface feature of a mammalian body part or a second landmark subsurface feature of the mammalian body part, the first landmark subsurface feature having a spatial relationship to a first region of interest of the mammalian body part, and the second landmark subsurface feature having a spatial relationship to a second region of interest of the mammalian body part;

(ii) registering the first region of interest and the second region of interest at least partially based on the common frame of reference; and (iii) storing in another computer-readable media operably coupled with the processor informational data corresponding to the registration of the first region of interest and the second region of interest.

1322 Registering the first region of interest and the second region of interest, the registration at least partially based on the determined common frame of reference and on a spatial relationship of the first landmark subsurface feature and the second landmark subsurface feature.

1330 Transforming the informational data into another informational data usable in providing a particular visual depiction of the registration of the first region of interest and the second region of interest.

1312 The computer-readable media includes a tangible computer-readable media.

1314 The computer-readable media includes a communications media.

A system.

1410 Means for determining a common frame of reference at least partially based on a first landmark subsurface feature of a mammalian body part or a second landmark subsurface feature of the mammalian body part, the first landmark subsurface feature having a spatial relationship to a first region of interest of the mammalian body part, and the second landmark subsurface feature having a spatial relationship to a second region of interest of the mammalian body part 1420 Means for registering the first region of interest relative to the second region of interest at least partially based on the common frame of reference.

1430 Means for persistently maintaining computer-readable informational data corresponding to the registration of the first region of interest and the second region of interest.

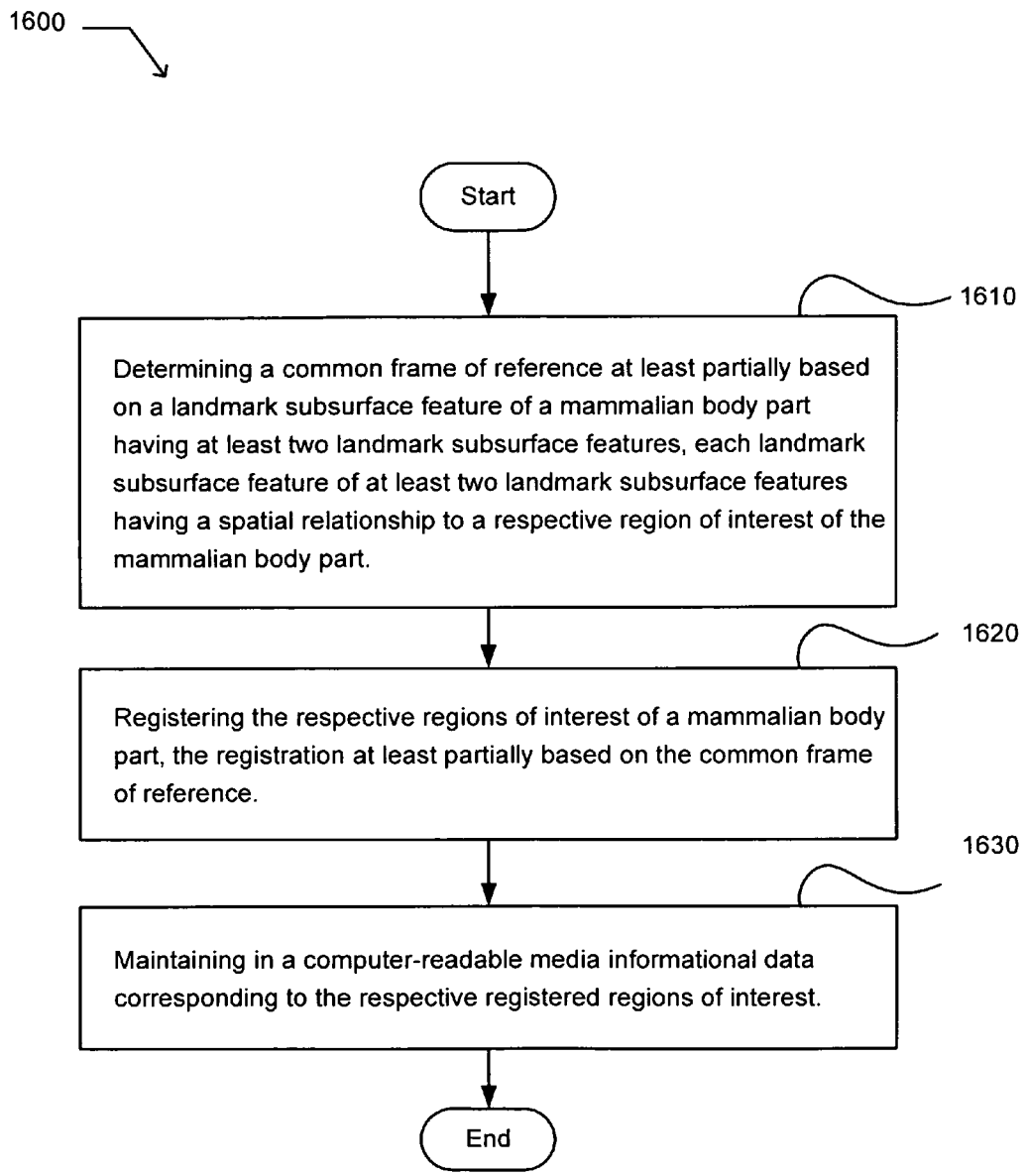

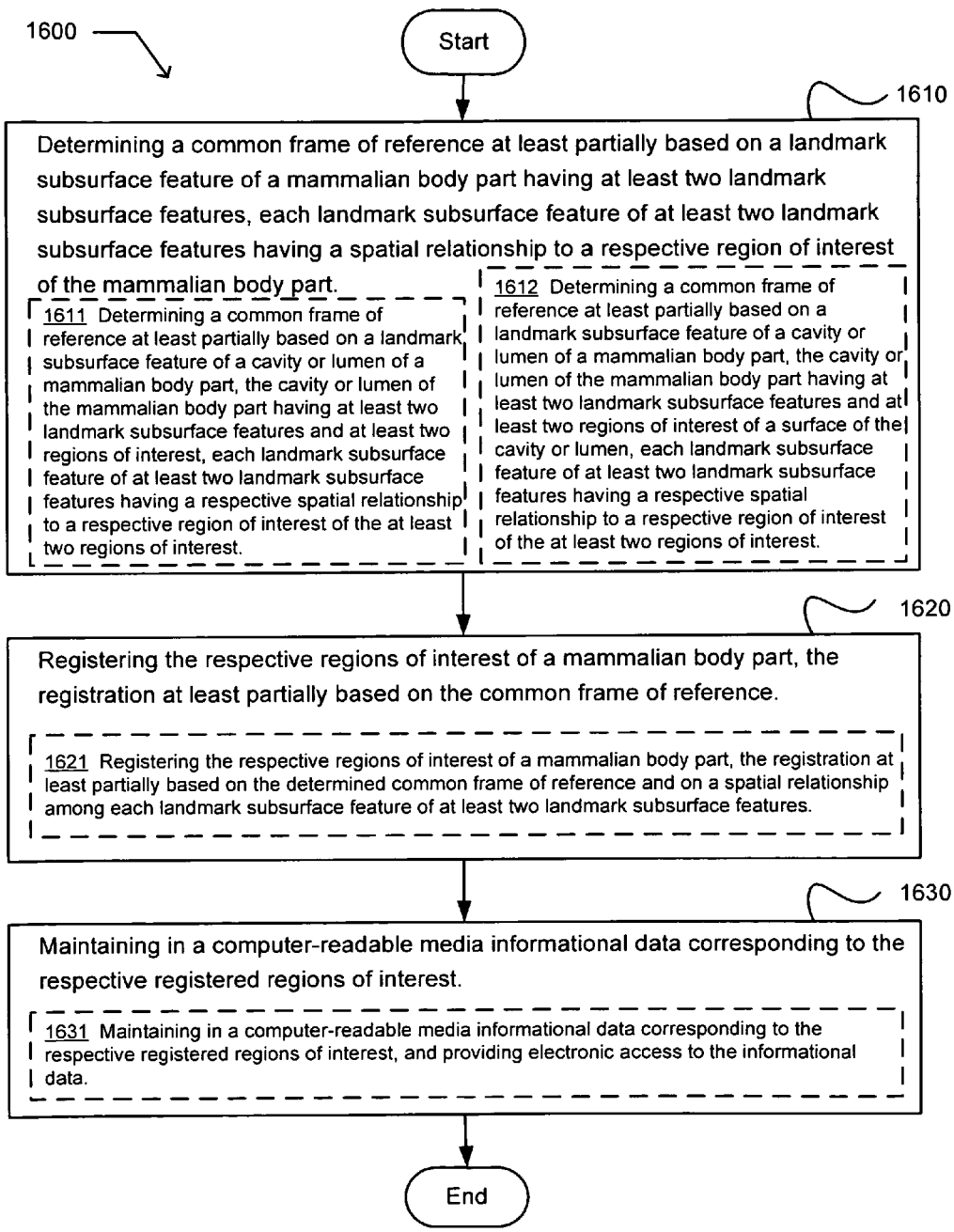

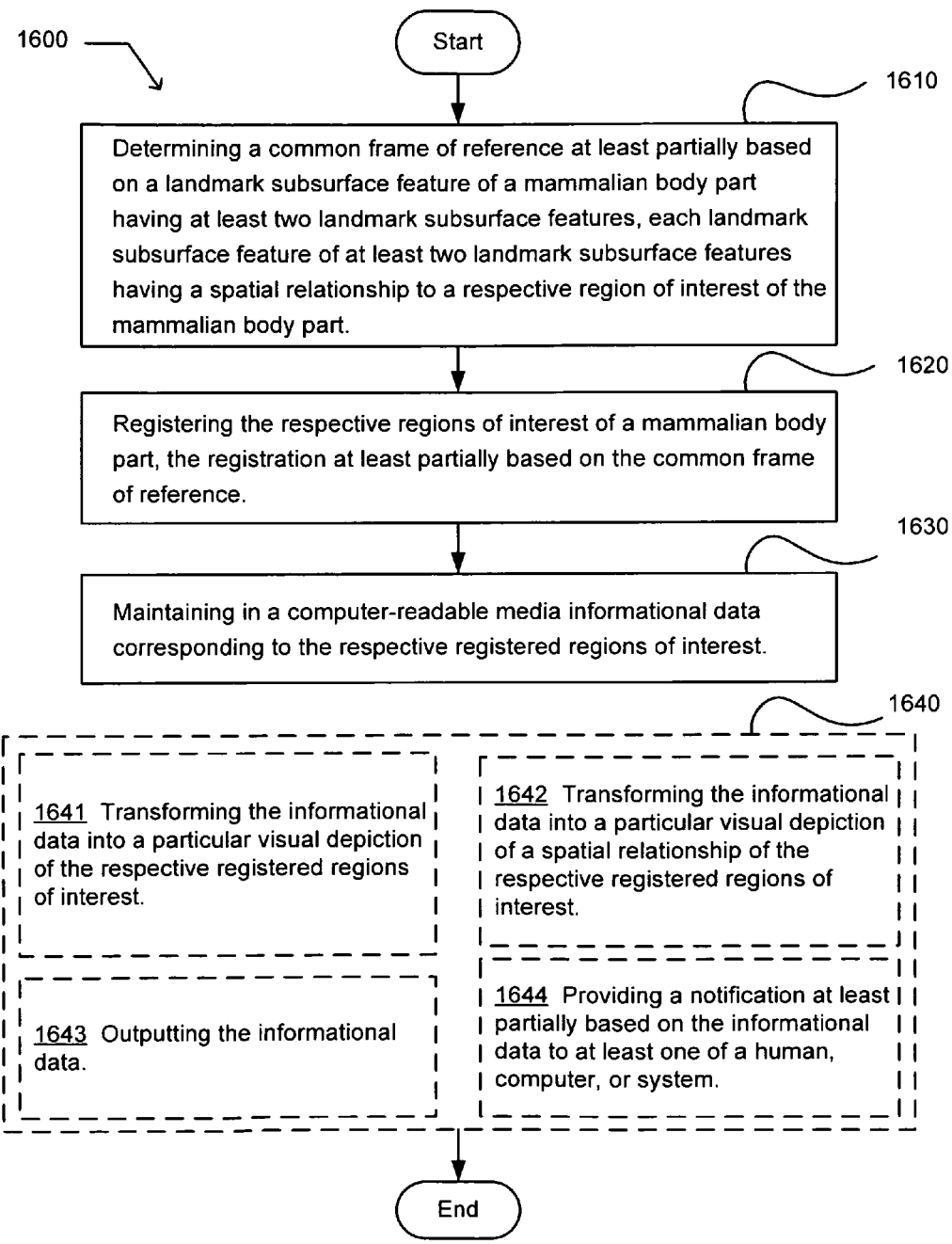

1710 A computer-readable media.

1720 Program instructions which, when executed by a processor of a computing device, cause the computing device to perform a process including:

(i) determining a common frame of reference at least partially based on a landmark subsurface feature of a mammalian body part having at least two landmark subsurface features and at least two regions of interest, each landmark subsurface feature of at least two landmark subsurface features having a respective spatial relationship to a respective region of interest of the at least two regions of interest;

(ii) registering the respective regions of interest of a mammalian body part, the registration at least partially based on the common frame of reference; and (iii) storing in another computer-readable media operably coupled with the processor informational data corresponding to the respective registered regions of interest.

1732 Transforming the informational data into another informational data useable in providing a particular visual depiction of the respective registered regions of interest.

1734 Providing a notification at least partially based on the informational data to at least one of a human, computer, or system.

1712 The computer-readable media includes a tangible computer-readable media.

1714 The computer-readable media includes a communications media.

2110 A computer-readable media.

2120 Program instructions which, when executed by a processor of a computing device, cause the digital computing device to perform a process including:

(i) receiving at least two medical images, each medical image of the at least two medical images includes a respective region of interest of a mammalian body part;

(ii) receiving at least two reference images, each reference image of the at least two reference images includes a respective landmark subsurface feature of the mammalian body part, each landmark subsurface feature having a respective spatial relationship to a respective region of interest included in a medical image of the at least two medical images;

(iii) determining a common frame of reference at least partially based on a landmark subsurface feature included in a reference image of the at least two reference images;

(iv) registering the respective regions of interest included in the at least two medical images, the registration at least partially based on the common frame of reference; and (v) storing in another computer-readable media operably coupled with the processor informational data corresponding to the registration of the respective regions of interest included in the at least two medical images.

2121 Determining a common frame of reference and determining a spatial relationship among each respective landmark subsurface feature of the at least two reference images, the determinings at least partially based on a landmark subsurface feature included in a reference image of the at least two reference images.

2122 Registering the respective regions of interest included in the at least two medical images, the registration at least partially based on the determined common frame of reference and on the spatial relationship among each respective landmark subsurface feature of the at least two reference images.

2112 The computer-readable media includes a tangible computer-readable media.

2114 The computer-readable media includes a communications media.

2510 A computer-readable media.

2520 Program instructions which, when executed by a processor of a digital computing device, cause the digital computing device to perform a process including:

(i) coregistering (x) a first depiction by a reference medical image of a region of interest of a mammalian body part during a first condition, the region of interest having a first spatial relationship to a landmark subsurface feature of the mammalian body part during the first condition, and (y) a second depiction by a target medical image of the region of interest of the mammalian body part during a second condition, the region of interest having a second spatial relationship to the landmark subsurface feature of the mammalian body part during the second condition, the coregistration of the first depiction and the second depiction at least partially based on the first spatial relationship and on the second spatial relationship;

(ii) storing in another computer-readable media operably coupled with the processor informational data corresponding to the coregistration of the first depiction of the region of interest and the second depiction of the region of interest.

2522 Storing in another computer-readable media operably coupled with the processor informational data corresponding to the coregistration of the first depiction of the region of interest and the second depiction of the region of interest, and provide electronic access to the informational data.

2512 The computer-readable media includes a tangible computer-readable media

2514 The computer-readable media includes a communications media.

FIG. 55

2520 Program instructions which, when executed by a processor of a digital computing device, cause the digital computing device to perform a process including:
 (i) coregistering
  (x) a first depiction by a reference medical image of a region of interest of a mammalian body part during a first condition, the region of interest having a first spatial relationship to a landmark subsurface feature of the mammalian body part during the first condition, and
  (y) a second depiction by a target medical image of the region of interest of the mammalian body part during a second condition, the region of interest having a second spatial relationship to the landmark subsurface feature of the mammalian body part during the second condition,
 the coregistration of the first depiction and the second depiction at least partially based on the first spatial relationship and on the second spatial relationship;
 (ii) storing in another computer-readable media operably coupled with the processor informational data corresponding to the coregistration of the first depiction of the region of interest and the second depiction of the region of interest.

2531 Outputting the informational data.

2532 Outputting a signal usable in displaying a human-perceivable indication of the informational data.

2533 Transforming the informational data into a particular visual depiction of the coregistration of the first depiction of the region of interest and the second depiction of the region of interest.

2534 Providing a notification at least partially based on the informational data to at least one of a human, computer, or system.

FIG. 56

2600 — A system.

2610 Means for coregistering
(x) a first depiction by a reference medical image of a region of interest of a mammalian body part during a first condition, the region of interest having a first spatial relationship to a landmark subsurface feature of the mammalian body part during the first condition, and
(y) a second depiction by a target medical image of the region of interest of the mammalian body part during a second condition, the region of interest having a second spatial relationship to the landmark subsurface feature of the mammalian body part during the second condition,
the coregistration of the first depiction of the region of interest and the second depiction of the region of interest at least partially based on the first spatial relationship and on the second spatial relationship.

2620 Means for persistently maintaining computer-readable informational data corresponding to the coregistration of the first depiction of the region of interest and the second depiction of the region of interest.

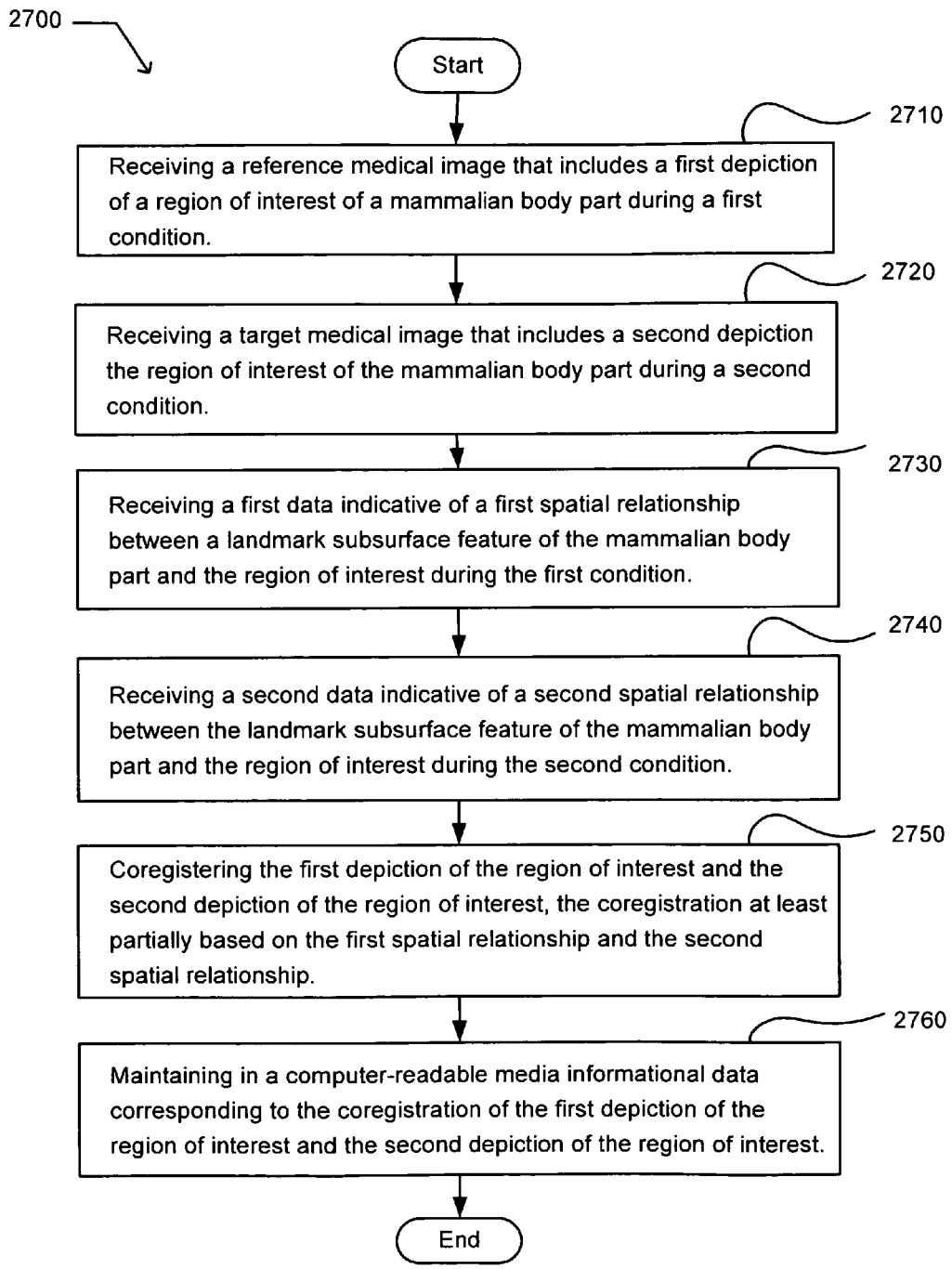

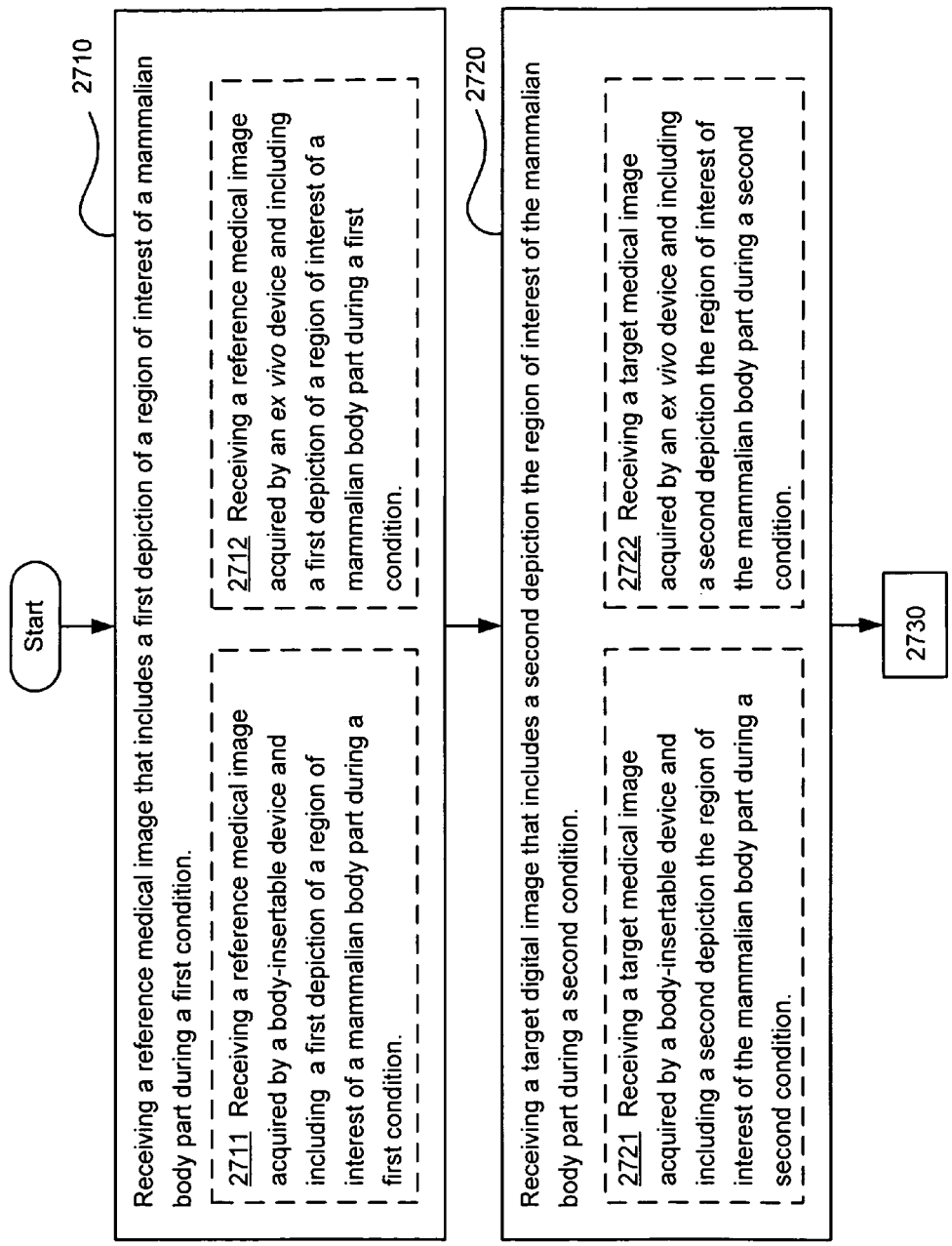

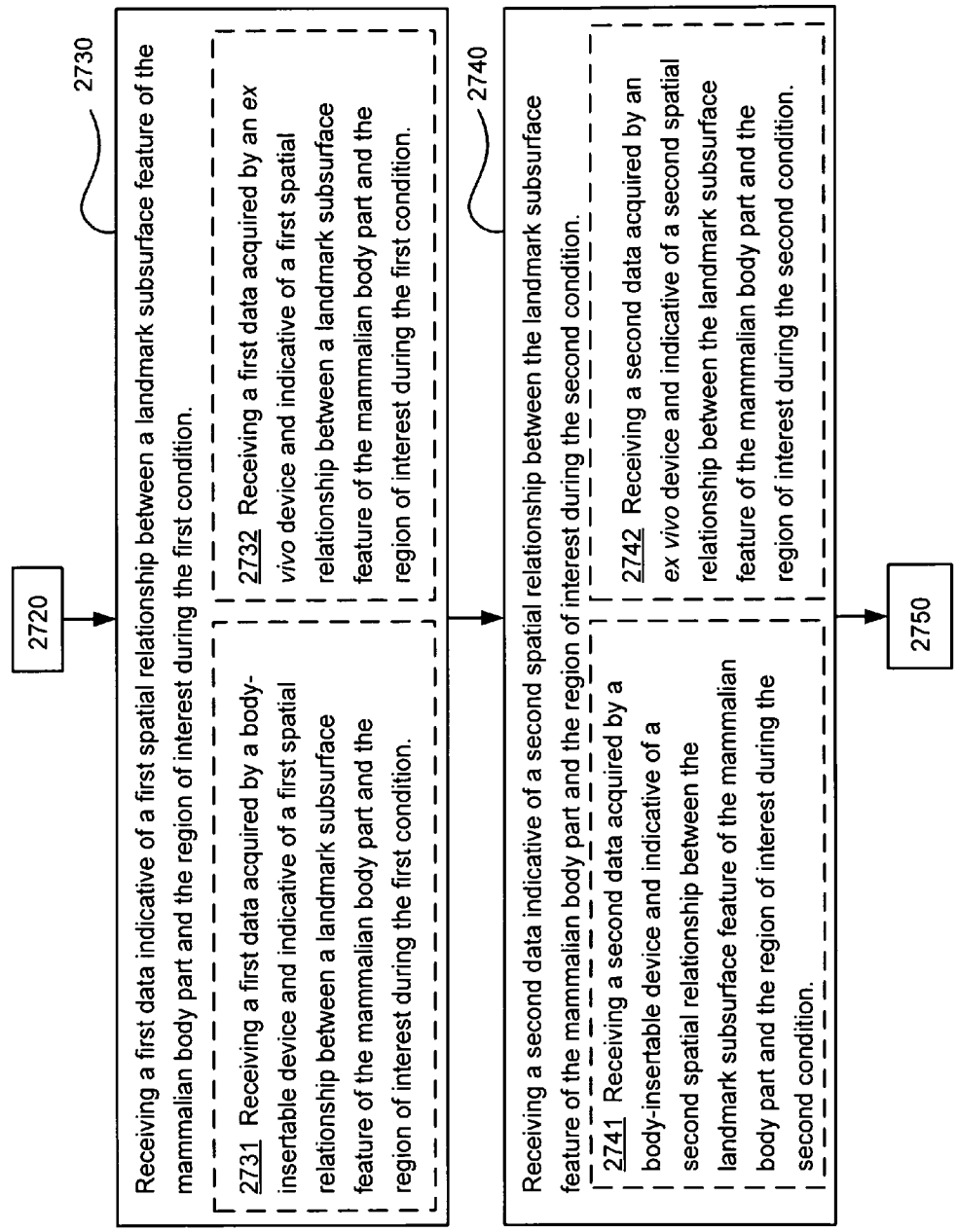

2810 A computer-readable media.

2820 Program instructions which, when executed by a processor of a digital computing device, cause the digital computing device to perform a process including:

(i) receiving a reference medical image that includes a first depiction of a region of interest of a mammalian body part during a first condition;

(ii) receiving a target medical image that includes a second depiction the region of interest of the mammalian body part during a second condition;

(iii) receiving a first data indicative of a first spatial relationship between a landmark subsurface feature of the mammalian body part and the region of interest during the first condition;

(iv) receiving a second data indicative of a second spatial relationship between the landmark subsurface feature of the mammalian body part and the region of interest during the second condition;

(v) coregistering the first depiction of the region of interest and the second depiction of the region of interest; and (vi) storing in another computer-readable media operably coupled with the processor informational data corresponding to the coregistration of the first depiction of the region of interest and the second depiction of the region of interest.

2812 The computer-readable media includes a tangible computer-readable media.

2814 The computer-readable media includes a communications media.

FIG. 65

2820 Program instructions which, when executed by a processor of a digital computing device, cause the digital computing device to perform a process including:

(i) receiving a reference medical image that includes a first depiction of a region of interest of a mammalian body part during a first condition;

(ii) receiving a target medical image that includes a second depiction the region of interest of the mammalian body part during a second condition;

(iii) receiving a first data indicative of a first spatial relationship between a landmark subsurface feature of the mammalian body part and the region of interest during the first condition;

(iv) receiving a second data indicative of a second spatial relationship between the landmark subsurface feature of the mammalian body part and the region of interest during the second condition;

(v) coregistering the first depiction of the region of interest and the second depiction of the region of interest; and (vi) storing in another computer-readable media operably coupled with the processor informational data corresponding to the coregistration of the first depiction of the region of interest and the second depiction of the region of interest.

2822 Outputting the informational data.

2826 Transforming the informational data into a particular visual depiction of the coregistration of the first depiction of the region of interest and the second depiction of the region of interest.

2824 Outputting a signal usable in displaying a human-perceivable indication of the coregistration of the first depiction of the region of interest and the second depiction of the region of interest.

2828 Providing a notification at least partially based on the informational data to at least one of a human, computer, or system.

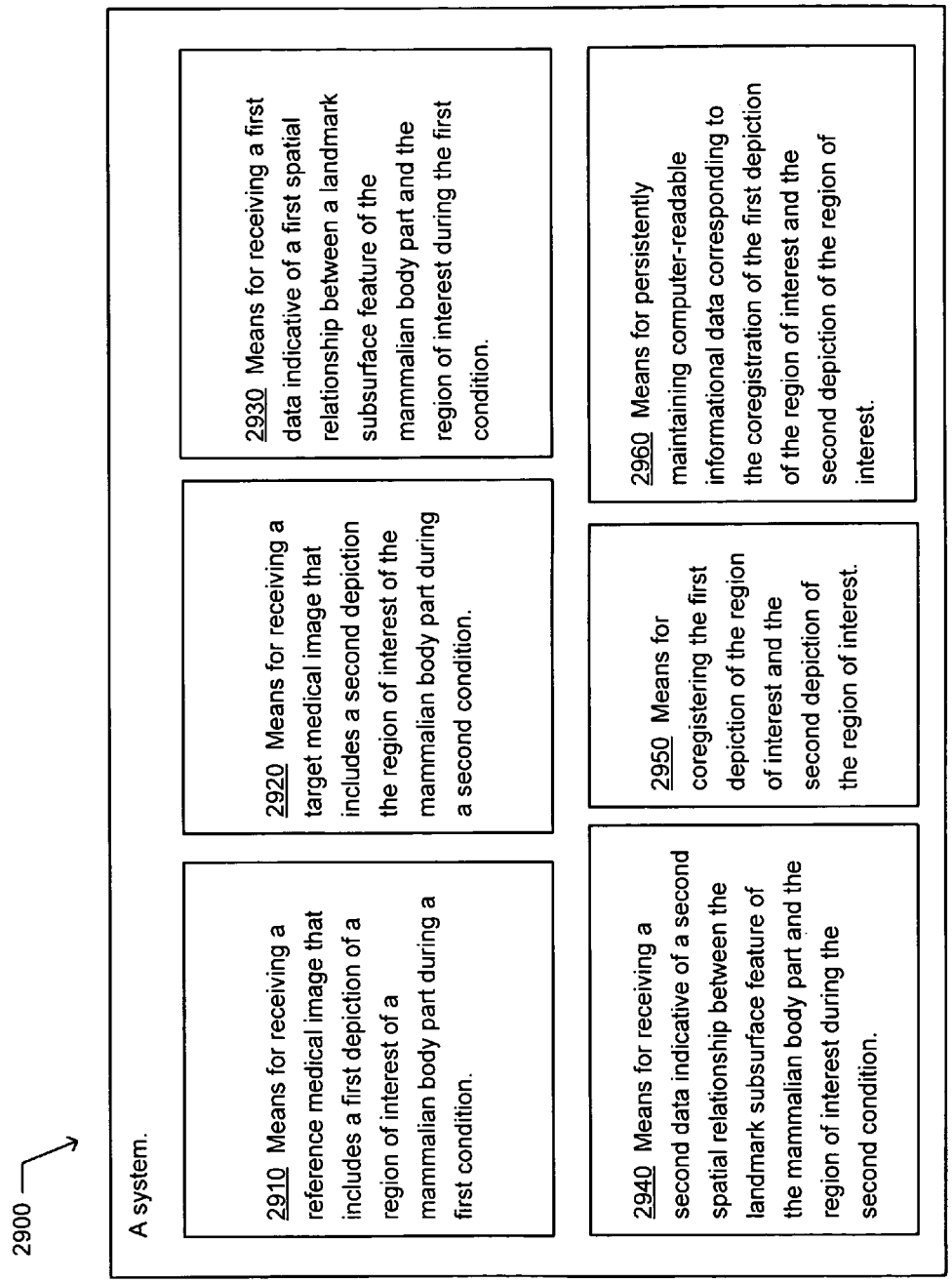

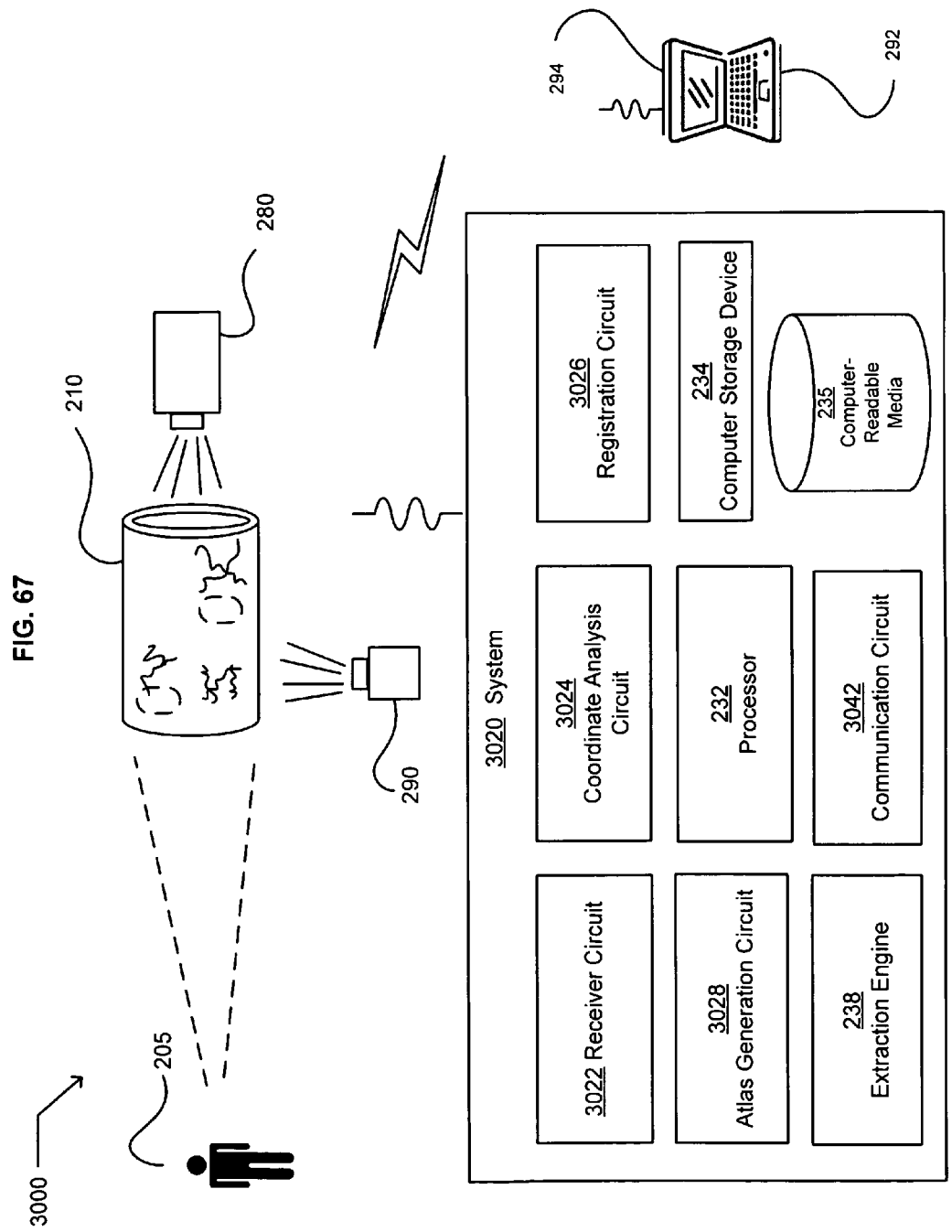

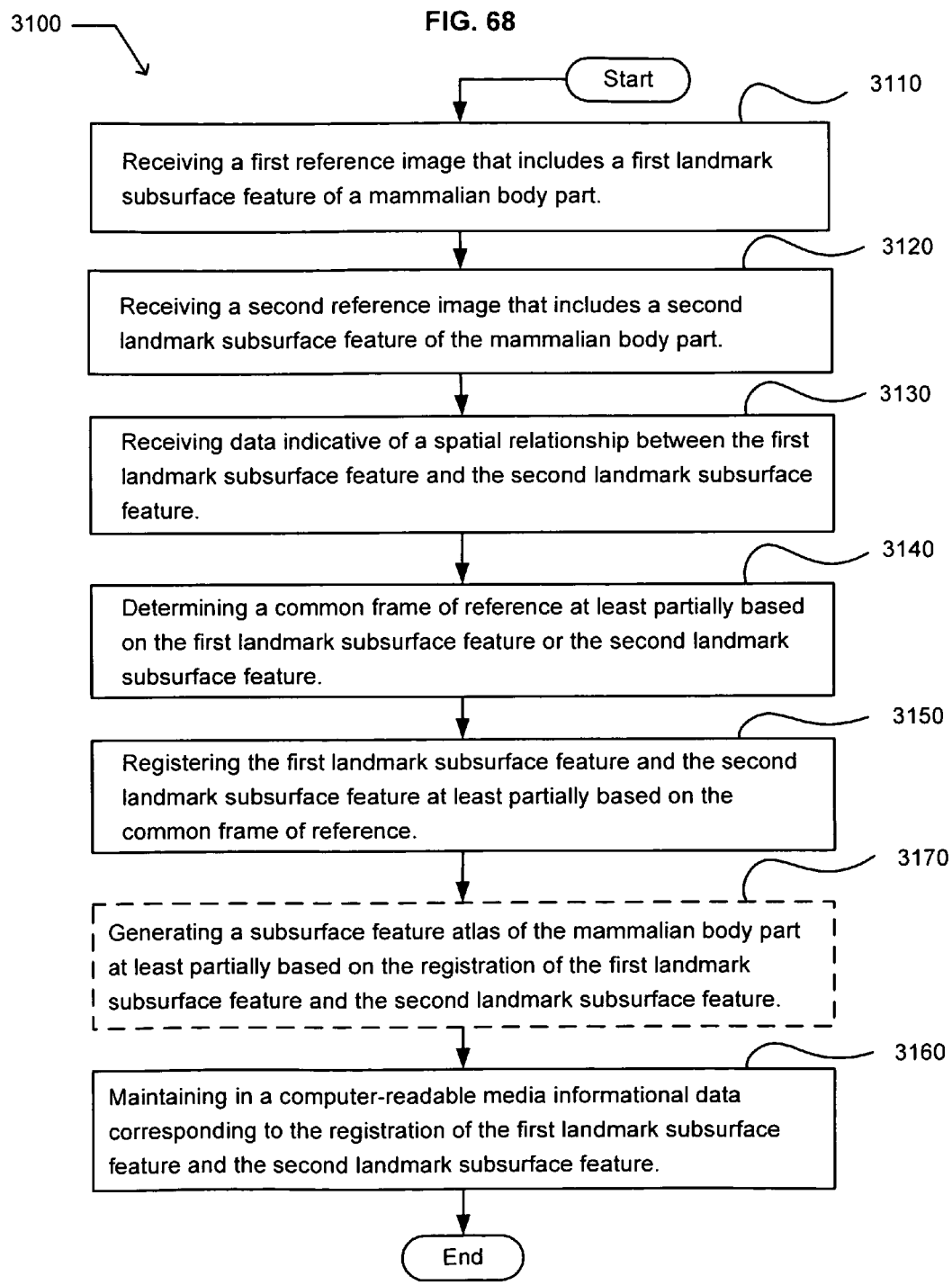

3210 A computer-readable media.

3220 Program instructions which, when executed by a processor of a computing device, cause the computing device to perform a process including:

(i) receiving a first reference image that includes a first landmark subsurface feature of a mammalian body part;

(ii) receiving a second reference image that includes a second landmark subsurface feature of the mammalian body part;

(iii) receiving data indicative of a spatial relationship between the first landmark subsurface feature and the second landmark subsurface feature;

(iv) determining a common frame of reference at least partially based on the first landmark subsurface feature or the second landmark subsurface feature;

(v) registering the first landmark subsurface feature and the second landmark subsurface feature at least partially based on the common frame of reference; and (vi) storing in another computer-readable media operably coupled with the processor informational data corresponding to the registration of the first landmark subsurface feature and the second landmark subsurface feature; and (vii) a computer-readable media bearing the program instructions.

3222 Registering the first landmark subsurface feature and the second landmark subsurface feature, the registration at least partially based on the determined common frame of reference and on a spatial relationship of the first landmark subsurface feature and the second landmark subsurface feature.

3224 Generating a subsurface feature atlas of the mammalian body part at least partially based on the registration of the first landmark subsurface feature and the second landmark subsurface feature.

3212 The computer-readable media includes a tangible computer-readable media.

3214 The computer-readable media includes a communications media.

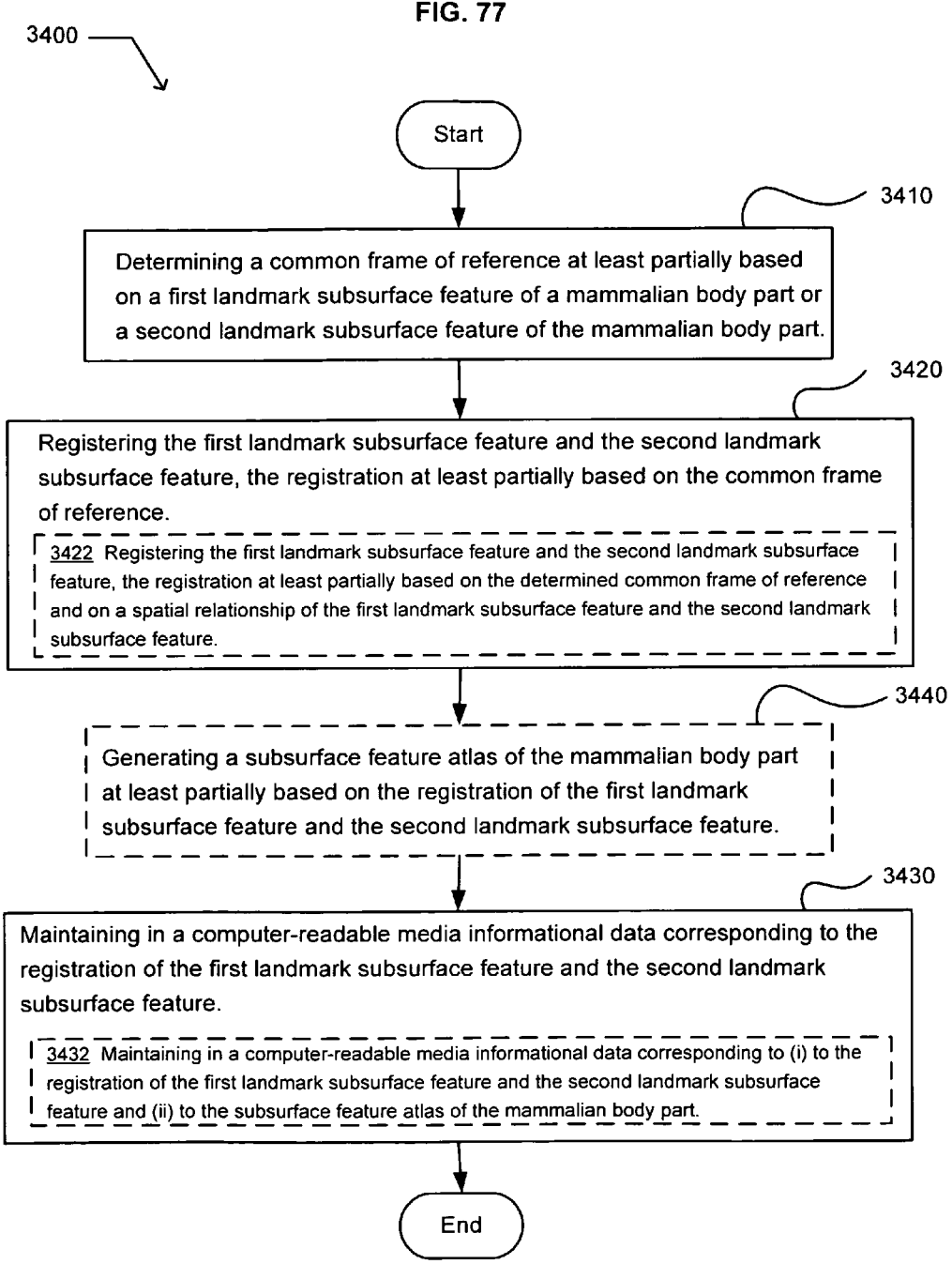

FIG. 78

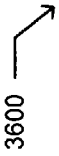

3600

3610 A computer-readable media.

3620 Program instructions which, when executed by a processor of a computing device, cause the computing device to perform a process including:
  (i) determining a common frame of reference at least partially based on a first landmark subsurface feature of a mammalian body part or the second landmark subsurface feature of the mammalian body part;
  (ii) registering the first landmark subsurface feature and the second landmark subsurface feature, the registration at least partially based on the common frame of reference; and
  (iii) storing in another computer-readable media operably coupled with the processor informational data corresponding to the registration of the first landmark subsurface feature and the second landmark subsurface feature.

3622 Registering the first landmark subsurface feature and the second landmark subsurface feature, the registration at least partially based on the determined common frame of reference and on a spatial relationship of the first landmark subsurface feature and the second landmark subsurface feature.

3624 Generating a subsurface feature atlas of the mammalian body part, the subsurface atlas at least partially based on the registration of the first landmark subsurface feature and the second landmark subsurface feature.

3612 The computer-readable media includes a tangible computer-readable media.

3614 The computer-readable media includes a communications media.

FIG. 79

3700 — A system.

3710 Means for determining a common frame of reference at least partially based on a first landmark subsurface feature of a mammalian body part or the second landmark subsurface feature of the mammalian body part.

3720 Means for registering the first landmark subsurface feature and the second landmark subsurface feature, the registration at least partially based on the common frame of reference.

3730 Means for persistently maintaining in a computer-readable media informational data corresponding to the registration of the first landmark subsurface feature and the second landmark subsurface feature.

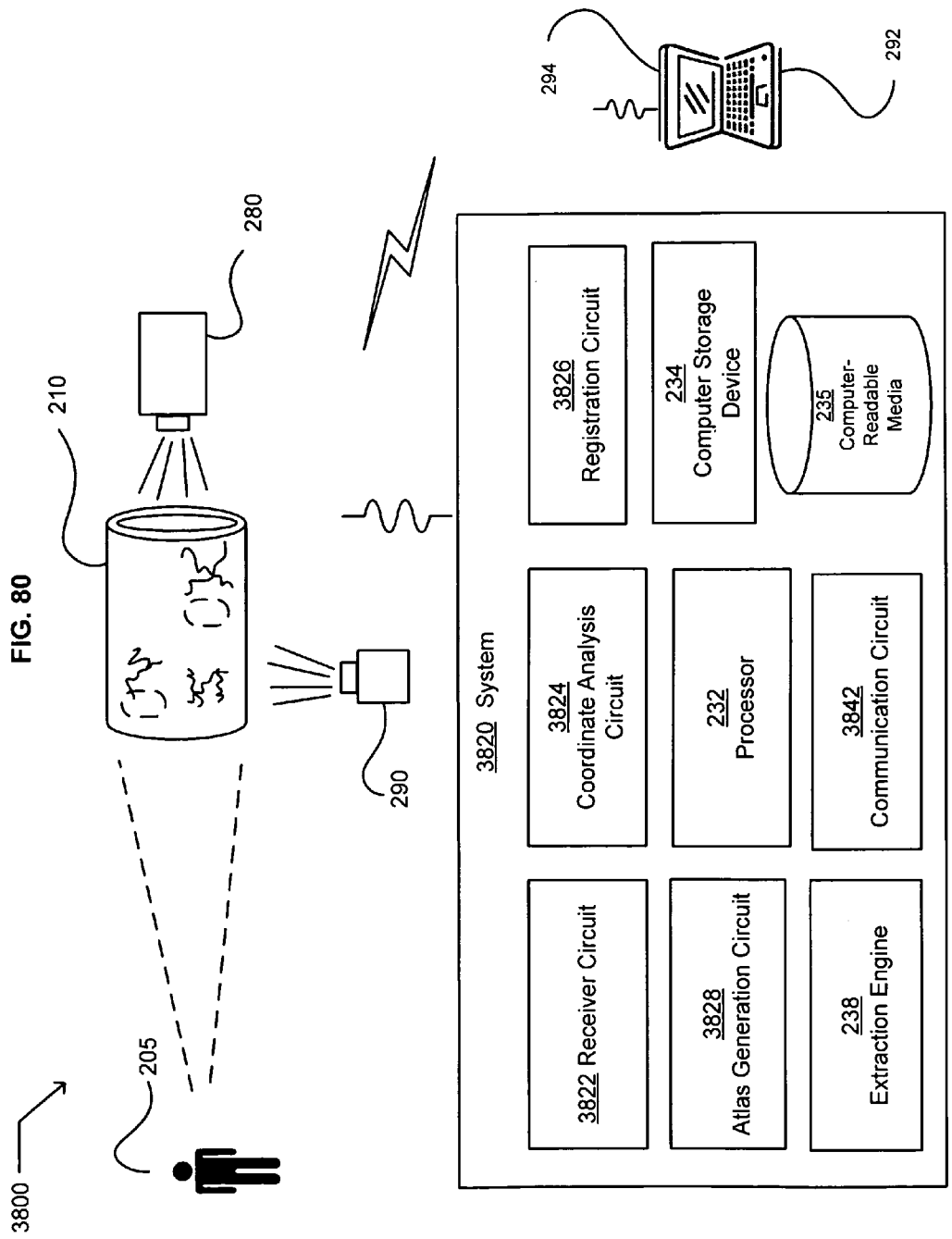

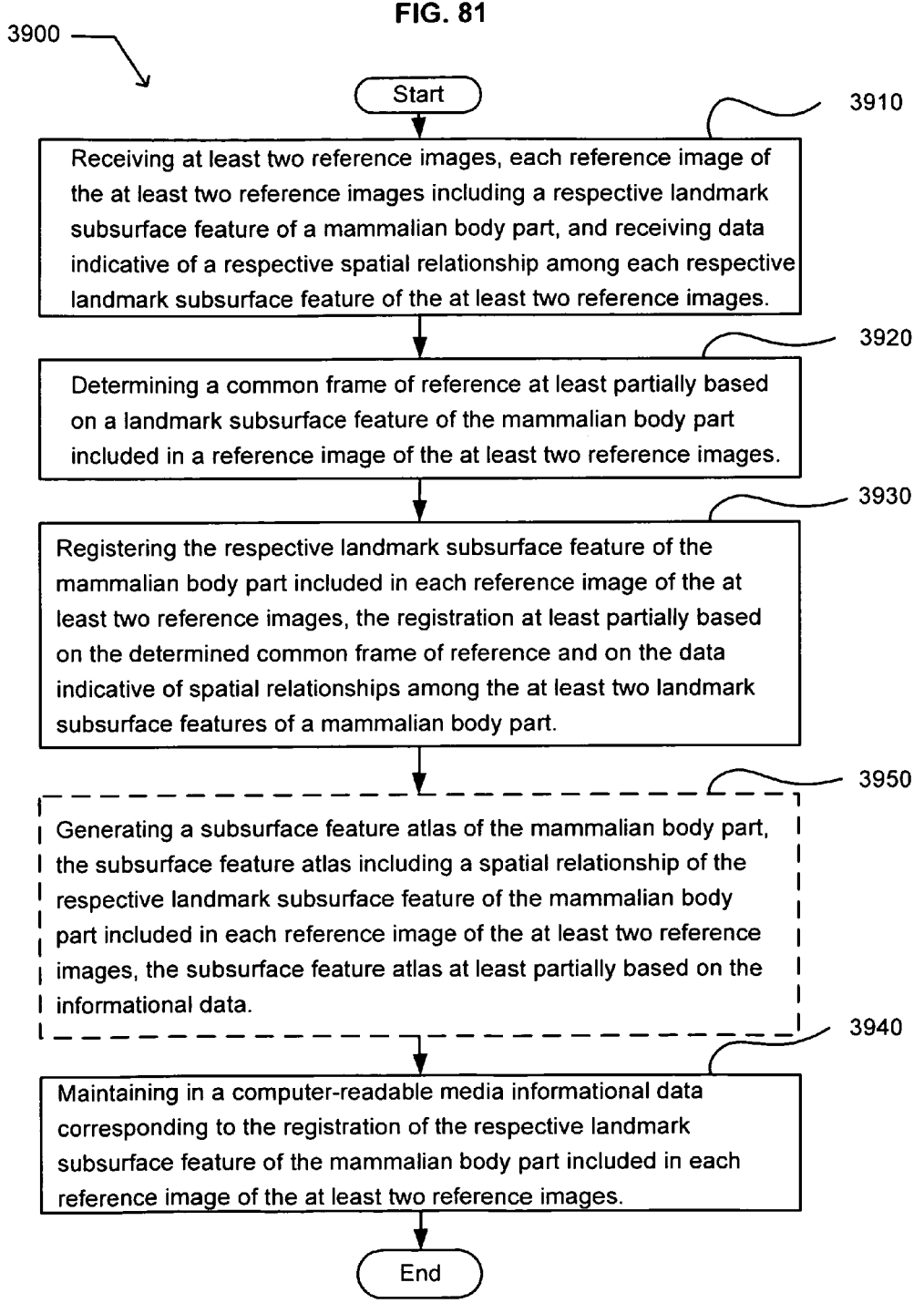

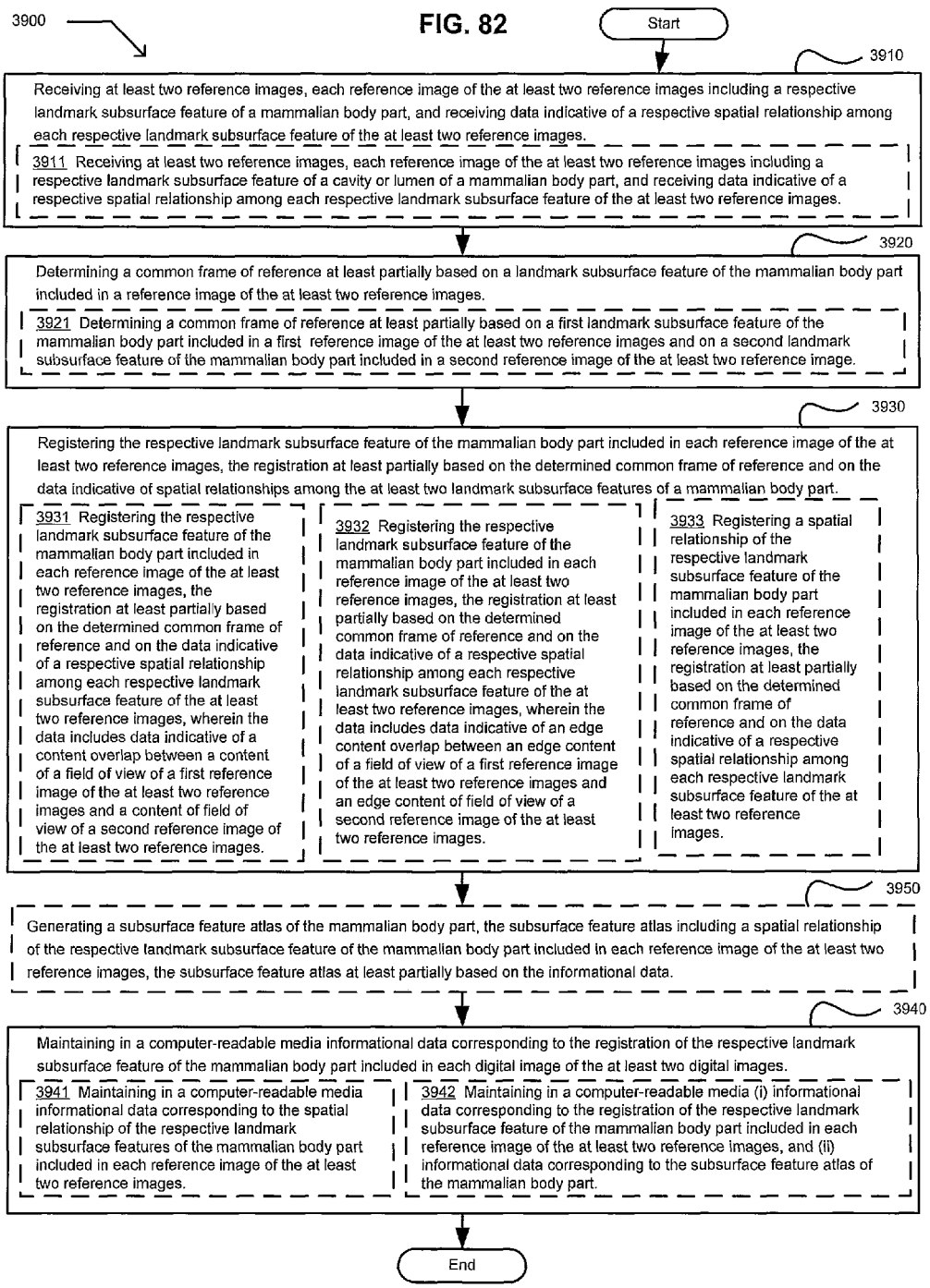

4010 A computer-readable media.

4020 Program instructions which, when executed by a processor of a computing device, cause the computing device to perform a process comprising:

(i) receiving at least two reference images, each reference image of the at least two reference images including a respective landmark subsurface feature of a mammalian body part;

(ii) receiving data indicative of a respective spatial relationship among each respective landmark subsurface feature of the at least two reference images;

(iii) determining a common frame of reference at least partially based on a landmark subsurface feature of the mammalian body part included in a reference image of the at least two reference images;

(iv) registering the respective landmark subsurface feature of the mammalian body part included in each reference image of the at least two reference images, the registration at least partially based on the determined common frame of reference and on the data indicative of a respective spatial relationship among each respective landmark subsurface feature of the at least two reference images; and (v) storing in another computer-readable media operably coupled with the processor informational data corresponding to the registration of the respective landmark subsurface feature of the mammalian body part included in each reference image of the at least two reference images.

4012 The computer-readable media includes a tangible computer-readable media.

4014 The computer-readable media includes a communications media.

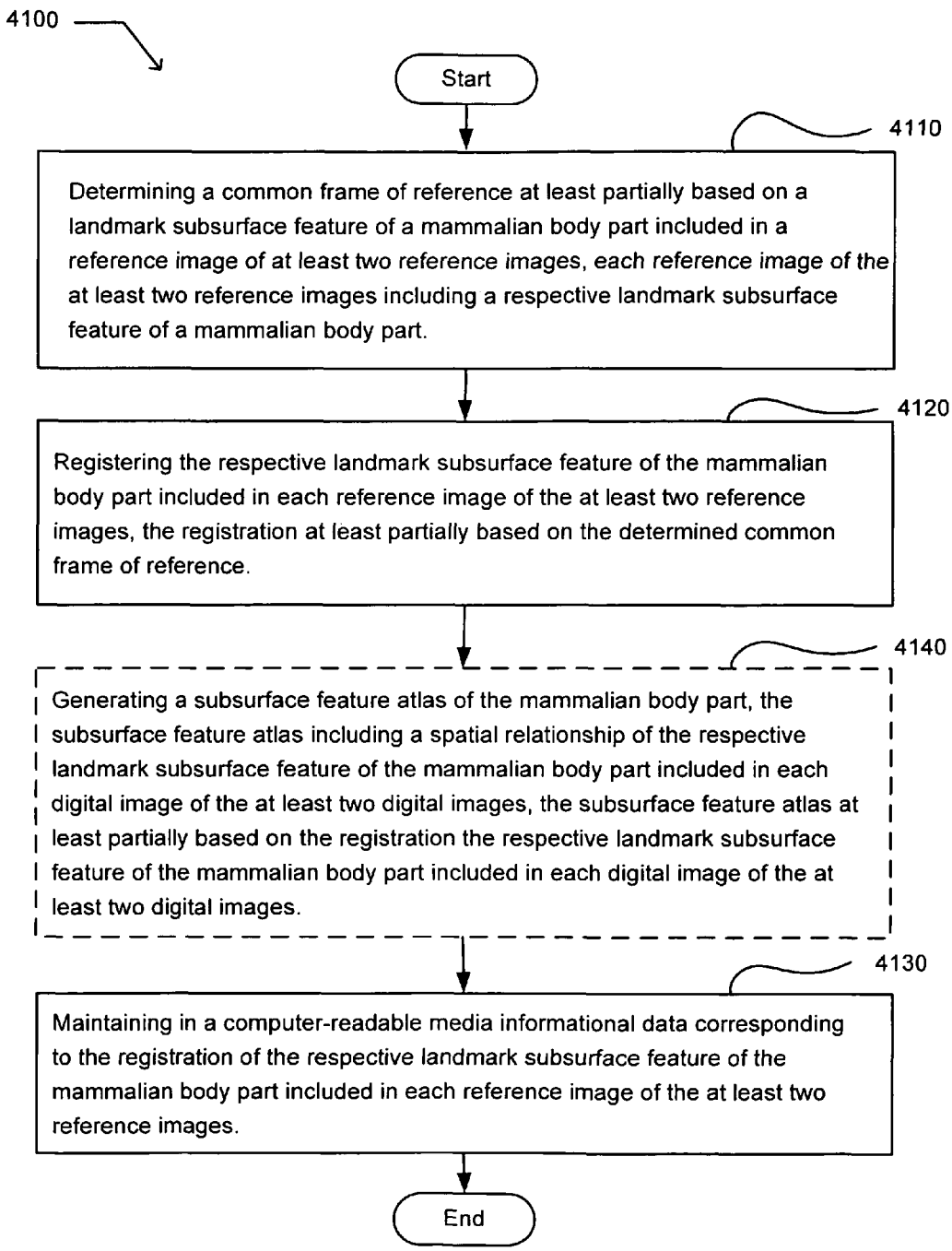

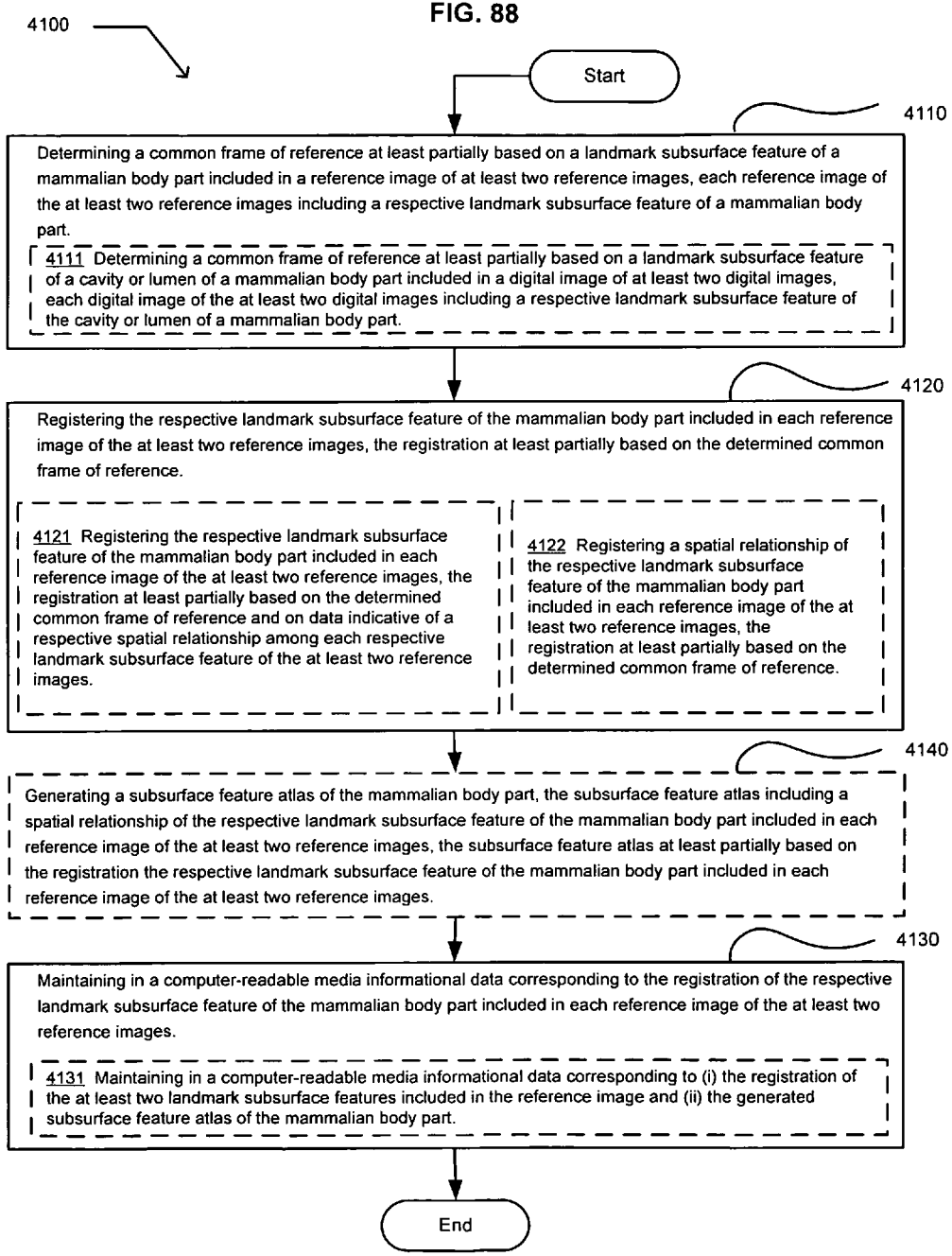

4210 A computer-readable media.

4220 Program instructions which, when executed by a processor of a computing device, cause the computing device to perform a process comprising:

(i) determining a common frame of reference at least partially based on a landmark subsurface feature of a mammalian body part included in a reference image of at least two reference images, each reference image of the at least two reference images including a respective landmark subsurface feature of a mammalian body part;

(ii) registering the respective landmark subsurface feature of the mammalian body part included in each reference image of the at least two reference images, the registration at least partially based on the determined common frame of reference; and (iii) storing in another computer-readable media operably coupled with the processor informational data corresponding to the registration of the respective landmark subsurface feature of the mammalian body part included in each reference image of the at least two reference images.

4222 Registering the respective landmark subsurface feature of the mammalian body part included in each reference image of the at least two reference images, the registration at least partially based on the determined common frame of reference and on data indicative of a spatial relationship among each respective landmark subsurface feature of the at least two reference images.

4224 Generating a subsurface feature atlas of the mammalian body part, the subsurface feature atlas including a spatial relationship of the respective landmark subsurface feature of the mammalian body part included in each reference image of the at least two reference images, the subsurface feature atlas at least partially based on the registration of the respective landmark subsurface feature of the mammalian body part included in each reference image of the at least two reference images.

4212 The computer-readable media includes a tangible computer-readable media.

4214 The computer-readable media includes a communications media.

FIG. 92
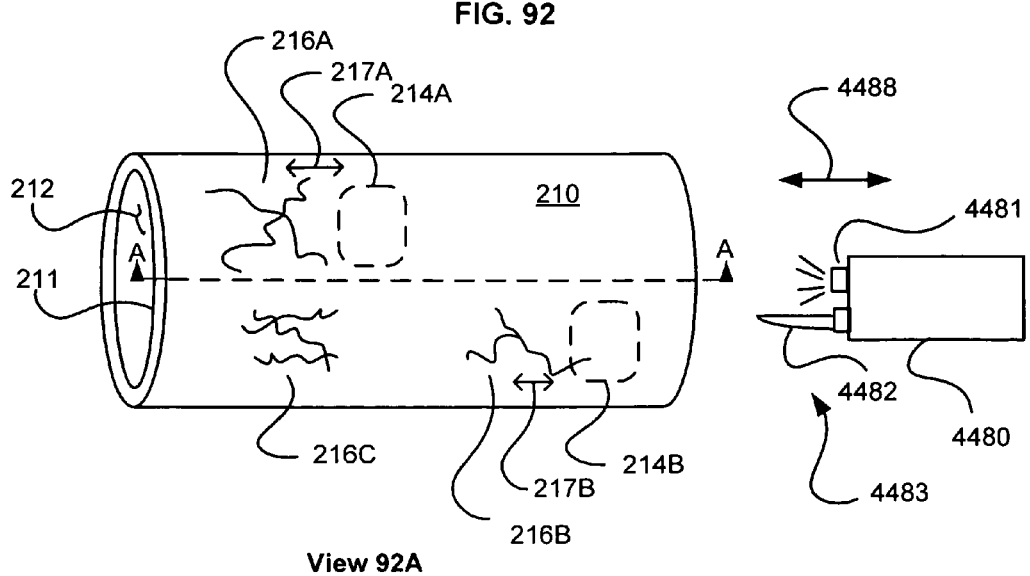
View 92A
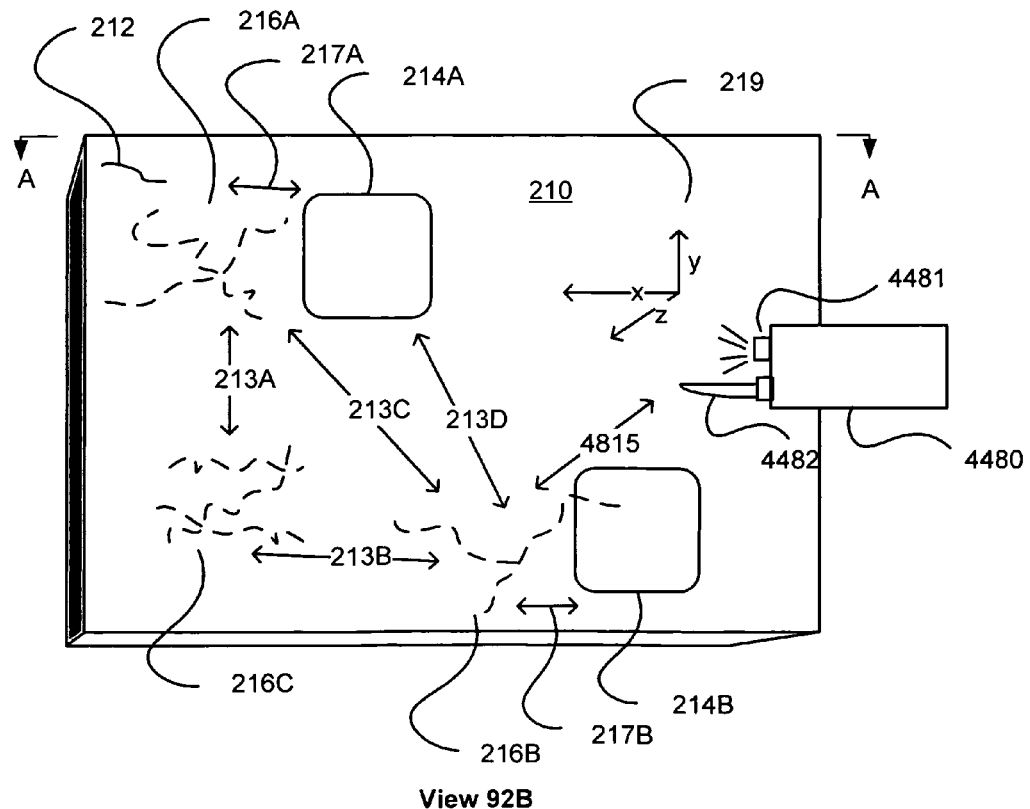
View 92B

Generating informational data indicative of an operational proximity of the distal end portion of the body-insertable device to the destination region of interest, the informational data indicative of operational proximity at least partially based on the determined substantial correspondence.

4531 Generating informational data indicative of an operational proximity of the distal end portion of the body-insertable device to the destination region of interest, the informational data at least partially based on a scale suitable for medical use of the body-insertable device with respect to the destination region of interest, the informational data further at least partially based on the determined substantial correspondence between the present-location landmark subsurface feature and the objective landmark subsurface feature.

4532 Generating informational data indicative of a proximity distance of less than four centimeters between the distal end portion of the body-insertable device and the destination region of interest, the informational data at least partially based on the determined substantial correspondence between the present-location landmark subsurface feature and the objective landmark subsurface feature.

4610 A computer-readable media.

4620 Program instructions which, when executed by a processor of a computing device, cause the computing device to perform a process comprising:
  (i) receiving a first reference image that includes an objective landmark subsurface feature of a mammalian body part, the objective landmark subsurface feature having a first spatial relationship to a destination region of interest of the mammalian body part; and
  (ii) receiving a second reference image that includes a present-location landmark subsurface feature of the mammalian body part, the present-location landmark subsurface feature having a second spatial relationship to a distal end portion of a body-insertable device deployed [operationally proximate to the mammalian body part];
  (iii) determining a substantial correspondence between the present-location landmark subsurface feature and the objective landmark subsurface feature;
  (iv) generating informational data indicative of an operational proximity of the distal end portion of the body-insertable device to the destination region of interest, the informational data indicative of operational proximity at least partially based on the determined substantial correspondence between the present-location landmark subsurface feature and the objective landmark subsurface feature; and
  (v) outputting the informational data.

4612 The computer-readable media includes a tangible computer-readable media.

4614 The computer-readable media includes a communications media.

5410 A computer-readable media.

5420 Program instructions which, when executed by a processor of a computing device, cause the computing device to perform a process including:

(i) receiving a first reference image that includes an objective landmark subsurface feature of a mammalian body part, the objective landmark subsurface feature having a first spatial relationship to a destination region of interest of the mammalian body part;

(ii) receiving a second reference image that includes a present-location landmark subsurface feature of the mammalian body part, the present-location landmark subsurface feature having a second spatial relationship to a distal end portion of a body-insertable device deployed operationally proximate to the mammalian body part;

(iii) determining a substantial correspondence between the objective landmark subsurface feature and a first atlas subsurface feature included in a subsurface feature atlas of the mammalian body part, the subsurface feature atlas includes at least two registered subsurface features of the mammalian body part, including the first atlas subsurface feature and a second atlas subsurface feature, the registration including an indication of a third spatial relationship between the first atlas subsurface feature and the second atlas subsurface feature;

(iv) determining a substantial correspondence between the present-location landmark subsurface feature and the second atlas subsurface feature included in the subsurface feature atlas of the mammalian body part;

(v) determining a fourth spatial relationship between the destination region of interest and the distal end portion of the body-insertable device deployed operationally proximate to the mammalian body part, the determined fourth spatial relationship at least partially based on the third spatial relationship; and (vi) outputting informational data indicative of the determined fourth spatial relationship between the destination region of interest and the distal end portion of the body-insertable device.

| 5412 The computer-readable media includes a tangible computer-readable media . | 5414 The computer-readable media includes a communications media. |

5410 A computer-readable media.

5420 Program instructions which, when executed by a processor of a computing device, cause the computing device to perform a process including:
(i) receiving a first reference image that includes an objective landmark subsurface feature of a mammalian body part, the objective landmark subsurface feature having a first spatial relationship to a destination region of interest of the mammalian body part;
(ii) receiving a second reference image that includes a present-location landmark subsurface feature of the mammalian body part, the present-location landmark subsurface feature having a second spatial relationship to a distal end portion of a body-insertable device deployed operationally proximate to the mammalian body part;
(iii) determining a substantial correspondence between the objective landmark subsurface feature and a first atlas subsurface feature included in a subsurface feature atlas of the mammalian body part, the subsurface feature atlas includes at least two registered subsurface features of the mammalian body part, including the first atlas subsurface feature and a second atlas subsurface feature, the registration including an indication of a third spatial relationship between the first atlas subsurface feature and the second atlas subsurface feature;
(iv) determining a substantial correspondence between the present-location landmark subsurface feature and the second atlas subsurface feature included in the subsurface feature atlas of the mammalian body part;
(v) determining a fourth spatial relationship between the destination region of interest and the distal end portion of the body-insertable device deployed operationally proximate to the mammalian body part, the determined fourth spatial relationship at least partially based on the third spatial relationship; and
(vi) outputting informational data indicative of the determined fourth spatial relationship between the destination region of interest and the distal end portion of the body-insertable device.

5422 Transforming the informational data into a signal usable in displaying a particular visual indication of the determined fourth spatial relationship between the destination region of interest and the distal end portion of the body-insertable device, and outputting the data.

5424 Providing a notification at least partially based on the informational data to at least one of a human, computer, or system.

5426 Storing the informational data in another computer-readable media operably coupled with the processor.

FIG. 113

A system. (5500)

5510 Means for receiving a first reference image that includes an objective landmark subsurface feature of a mammalian body part, the objective landmark subsurface feature having a first spatial relationship to a destination region of interest of the mammalian body part.

5520 Means for receiving a second reference image that includes a present-location landmark subsurface feature of the mammalian body part, the present-location landmark subsurface feature having a second spatial relationship to a distal end portion of a body-insertable device deployed operationally proximate to the mammalian body part.

5530 Means for determining a substantial correspondence between the objective landmark subsurface feature and a first atlas subsurface feature included in a subsurface feature atlas of the mammalian body part, the subsurface feature atlas includes at least two registered subsurface features of the mammalian body part, including the first atlas subsurface feature and a second atlas subsurface feature, the registration including an indication of a third spatial relationship between the first atlas subsurface feature and the second atlas subsurface feature.

5540 Means for determining a substantial correspondence between the present-location landmark subsurface feature and the second atlas subsurface feature included in the subsurface feature atlas of the mammalian body part.

5550 Means for determining a fourth spatial relationship between the destination region of interest and the distal end portion of the body-insertable device deployed operationally proximate to the mammalian body part, the determined fourth spatial relationship at least partially based on the third spatial relationship.

5560 Means for outputting informational data indicative of the determined fourth spatial relationship between the destination region of interest and the distal end portion of the body-insertable device.

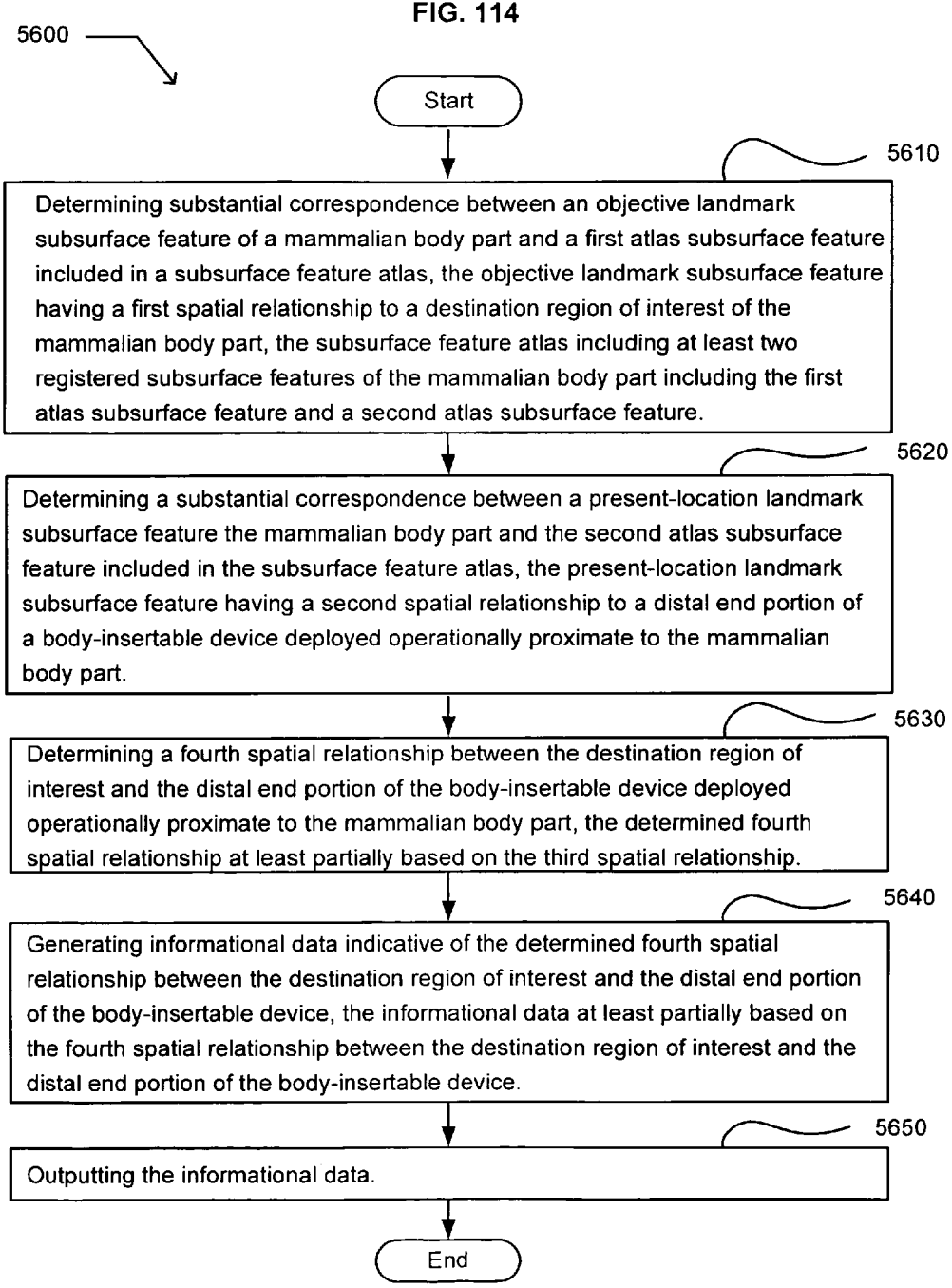

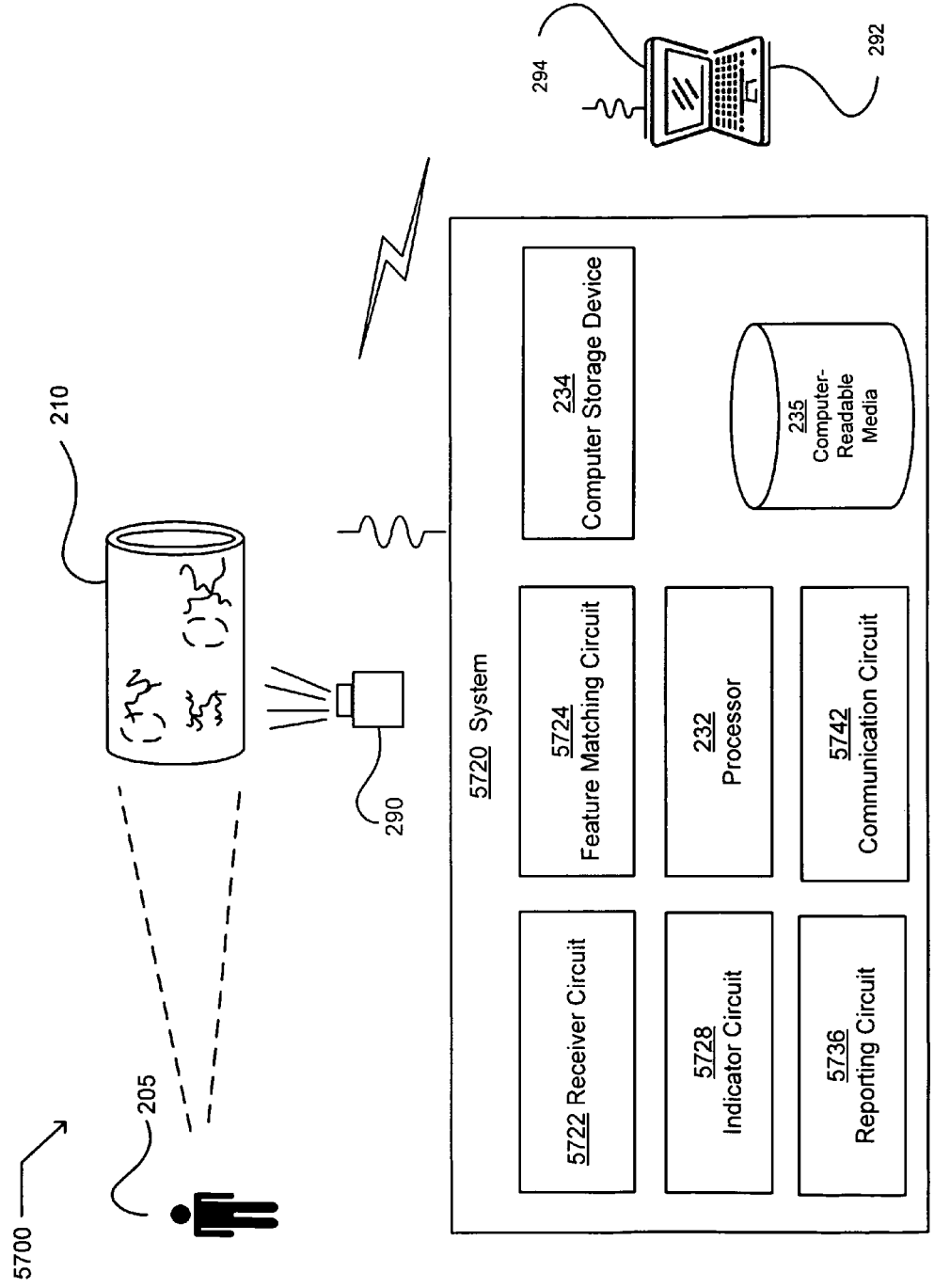

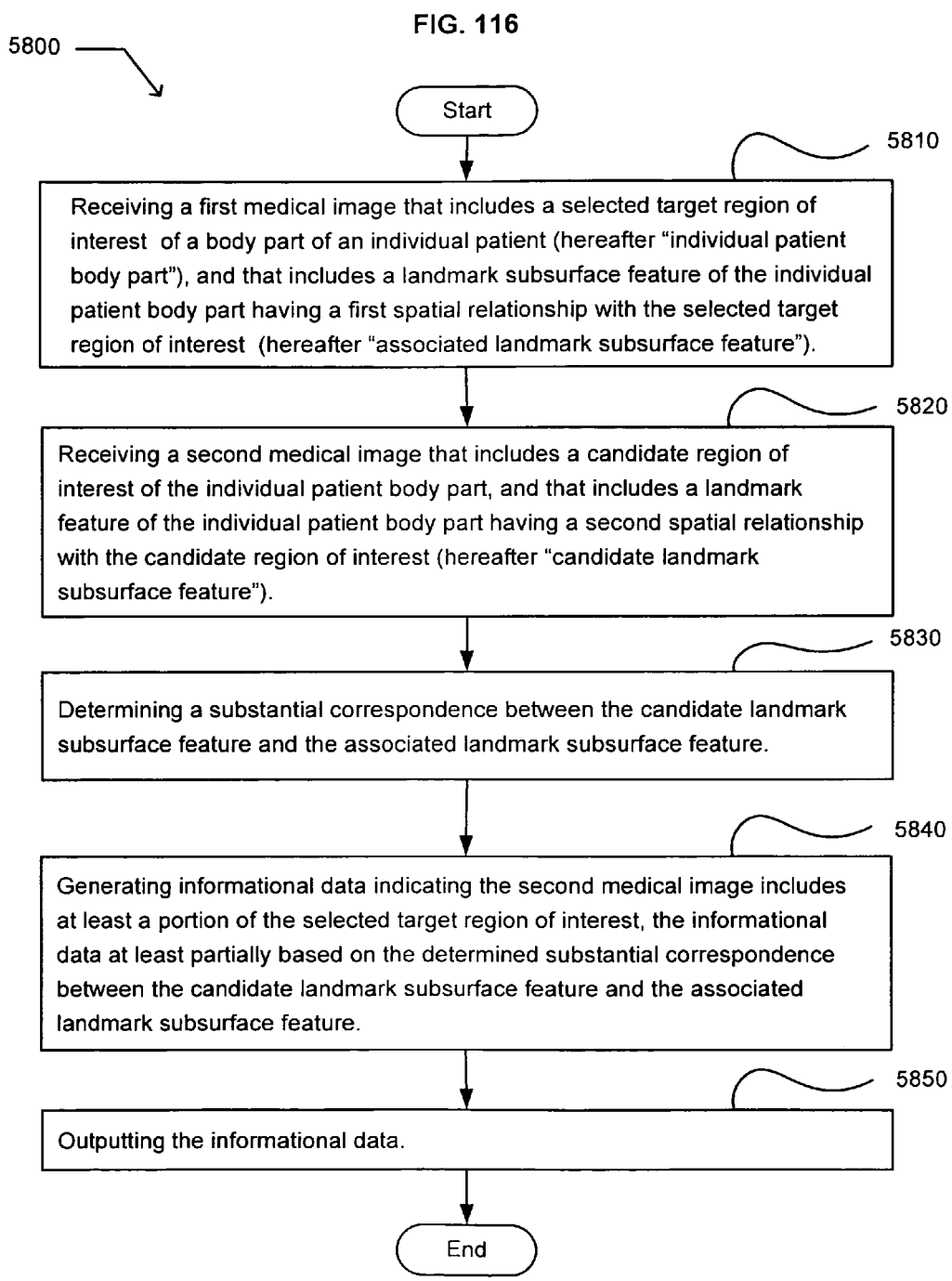

5810 Receiving a first medical image that includes a selected target region of interest of a body part of an individual patient, and that includes a landmark subsurface feature of the individual patient body part having a first spatial relationship with the selected target region of interest.

- 5811 Receiving a first medical image that includes a selected target region of interest of a cavity or lumen of an individual patient body part, and that includes an associated landmark subsurface feature.

- 5812 Receiving a first medical image that includes a target region of interest that includes a selected target region of interest of a surface of a cavity or lumen of an individual patient body part, and that includes an associated landmark subsurface feature.

- 5813 Receiving a first medical image that includes a selected surface region of interest of an individual patient body part, and that includes an associated landmark subsurface feature.

- 5814 Receiving a first medical image that includes a selected subsurface region of interest of an individual patient body part, and that includes an associated landmark subsurface feature.

- 5815 Receiving a first medical image that includes a selected target region of interest of an individual patient body part, and that includes an associated landmark subsurface feature machine-distinguishable from other landmark features of the individual patient body part.

↓

5820 Receiving a second medical image that includes a candidate region of interest of the individual patient body part, and that includes a landmark feature of the individual patient body part having a second spatial relationship with the candidate region of interest.

- 5821 Receiving a second medical image that includes a candidate region of interest of the cavity or lumen of the individual patient body part, and that includes a candidate landmark subsurface feature.

- 5822 Receiving a second medical image that includes a candidate region of interest of the surface of the cavity or lumen of the individual patient body part, and that includes a candidate landmark subsurface feature.

- 5823 Receiving a second medical image that includes a candidate surface region of interest of the individual patient body part, and that includes a candidate landmark feature of the individual patient body part.

- 5824 Receiving a second medical image that includes a candidate subsurface region of interest of the individual patient body part, and that includes a candidate landmark feature of the individual patient body part.

- 5825 Receiving a second medical image that includes a candidate region of interest of the individual patient body part and that includes a candidate landmark feature of the individual patient body part machine-distinguishable from other landmark features of the individual patient body part.

5910 A computer-readable media.

5920 Program instructions which, when executed by a processor of a computing device, cause the computing device to perform a process including:

(i) receiving a first medical image that includes a selected target region of interest of a body part of an individual patient (hereafter "individual patient body part"), and that includes a landmark subsurface feature of the individual patient body part having a first spatial relationship with the selected target region of interest (hereafter "associated landmark subsurface feature");

(ii) receiving a second medical image that includes a candidate region of interest of the individual patient body part, and that includes a landmark feature of the individual patient body part having a second spatial relationship with the candidate region of interest (hereafter "candidate landmark subsurface feature");

(iii) determining a substantial correspondence between the candidate landmark subsurface feature and the associated landmark subsurface feature ; and (iv) generating informational data indicating the second medical image includes at least a portion of the selected target region of interest, the informational data at least partially based on the determined substantial correspondence between the candidate landmark subsurface feature and the associated landmark subsurface feature; and (v) outputting the informational data.

5922 Storing in another computer-readable media operably coupled with the processor informational data indicating the second digital image includes at least a portion of the target region of interest.

5924 Transforming the informational data indicating the second digital image includes at least a portion of the target region of interest into informational data usable in providing a particular visual indication that the second digital image includes at least a portion of the target region of interest.

5926 Providing a notification to at least one of humans, computers, or systems, the notification that the second digital image includes at least a portion of the target region of interest.

5912 The computer-readable media includes a tangible computer-readable media.

5914 The computer-readable media includes a communications media.

A system.

6010 Means for receiving a first medical image that includes a selected target region of interest of a body part of an individual patient (hereafter "individual patient body part"), and that includes a landmark subsurface feature of the individual patient body part having a first spatial relationship with the selected target region of interest (hereafter "associated landmark subsurface feature").

6020 Means for receiving a second medical image that includes a candidate region of interest of the individual patient body part, and that includes a landmark feature of the individual patient body part having a second spatial relationship with the candidate region of interest (hereafter "candidate landmark subsurface feature").

6030 Means for determining a substantial correspondence between the candidate landmark subsurface feature and the associated landmark subsurface feature.

6040 Means for generating informational data indicating the second medical image includes at least a portion of the selected target region of interest, the informational data at least partially based on the determined substantial correspondence between the candidate landmark subsurface feature and the associated landmark subsurface feature.

6050 Means for outputting the informational data.

6060 Means for transforming the informational data into a signal usable in providing a particular visual indication that the second medical image includes at least a portion of the selected target region of interest.

6070 Means for providing a notification at least partially based on the informational data to at least one of a human, computer, or system.

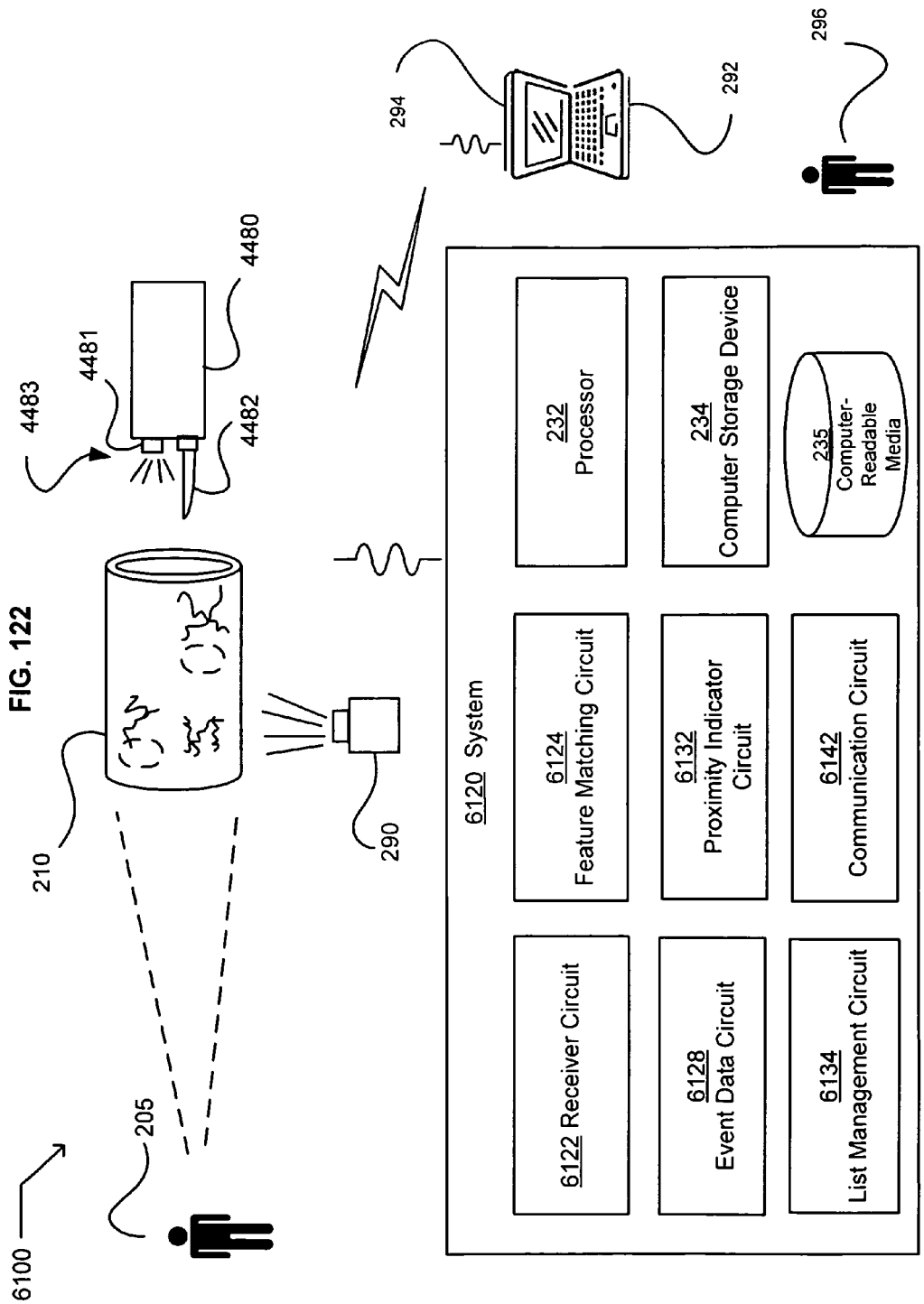

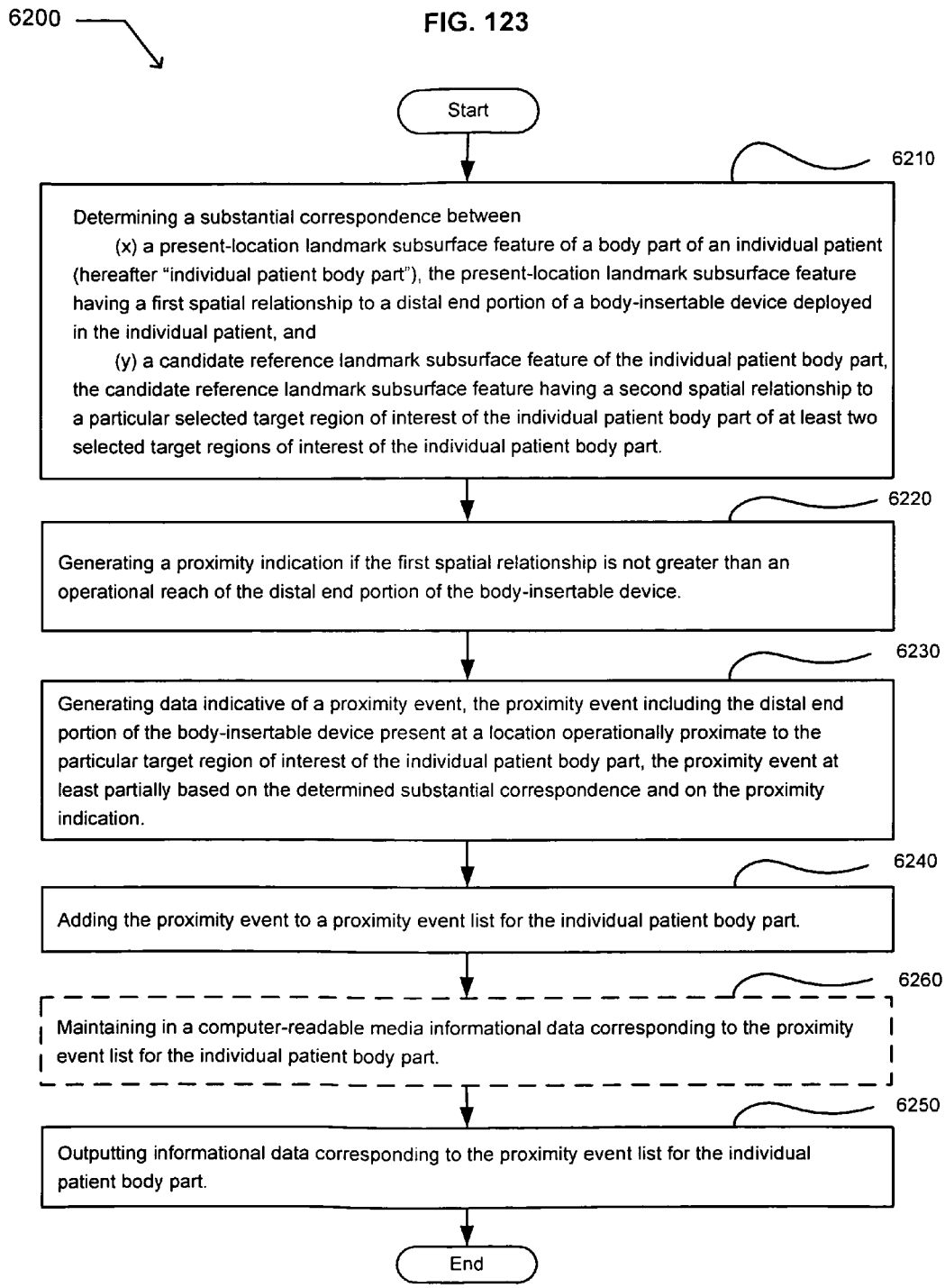

Determining a substantial correspondence between
  (x) a present-location landmark subsurface feature of a body part of an individual patient (hereafter "individual patient body part"), the present-location landmark subsurface feature having a first spatial relationship to a distal end portion of a body-insertable device deployed in the individual patient, and
  (y) a candidate reference landmark subsurface feature of the individual patient body part, the candidate reference landmark subsurface feature having a second spatial relationship to a particular selected target region of interest of the individual patient body part of at least two selected target regions of interest of the individual patient body part.

6211 Determining a substantial correspondence between
  (x) a present-location landmark subsurface feature of a cavity or lumen of an individual patient body part, the present-location landmark subsurface feature having a first spatial relationship to a distal end portion of a body-insertable device deployed in the cavity or lumen of the individual patient, and
  (y) a candidate reference landmark subsurface feature of the cavity or lumen of the individual patient body part, the candidate reference landmark subsurface feature having a second spatial relationship to a particular target region of interest of the cavity or lumen of the individual patient body part.

6212 Determining a substantial correspondence between
  (x) a present-location landmark subsurface feature of a cavity or lumen of an individual patient body part, the present-location landmark subsurface feature having a first spatial relationship to a distal end portion of a body-insertable device deployed in the cavity or lumen of the individual patient, and
  (y) a candidate reference landmark subsurface feature of the individual patient body part, the candidate reference landmark subsurface feature having a second spatial relationship to a particular target region of interest of a surface of the cavity or lumen of the individual patient body part.

6213 Determining a substantial correspondence between
  (x) a present-location landmark subsurface feature of a body part of an individual patient (hereafter "individual patient body part"), the present-location landmark subsurface feature having a first spatial relationship to a distal end portion of a body-insertable device deployed in the individual patient, and
  (y) a candidate reference landmark subsurface feature of the individual patient body part, the candidate reference landmark subsurface feature having a second spatial relationship to a particular selected target region of interest of the individual patient body part of at least two selected target regions of interest of the individual patient body part, the candidate reference landmark subsurface feature selected from a patient examination table that includes the at least two reference landmark subsurface features of the individual patient body part, each candidate reference landmark subsurface feature of the at least two candidate reference landmark subsurface features having a respective spatial relationship to a respective particular selected target region of interest.

6310 A computer-readable media.

6320 Program instructions which, when executed by a processor of a computing device, cause the computing device to perform a process including:

(i) determining a substantial correspondence between (x) a present-location landmark subsurface feature of a body part of an individual patient (hereafter "individual patient body part"), the present-location landmark subsurface feature having a first spatial relationship to a distal end portion of a body-insertable device deployed in the individual patient, and (y) a candidate reference landmark subsurface feature of the individual patient body part, the candidate reference landmark subsurface feature having a second spatial relationship to a particular selected target region of interest of the individual patient body part of at least two selected target regions of interest of the individual patient body part;

(ii) generating a proximity indication if the first spatial relationship is not greater than an operational reach of the distal end portion of the body-insertable device;

(iii) generating data indicative of a proximity event, the proximity event including the distal end portion of the body-insertable device present at a location operationally proximate to the particular target region of interest of the individual patient body part, the proximity event at least partially based on the determined substantial correspondence and on the proximity indication;

(iv) adding the proximity event to a proximity event list for the individual patient body part; and (v) storing in another computer-readable media operably coupled with the processor informational data corresponding to the proximity event list for the individual patient body part.

6322 Determining a substantial correspondence between (x) a present-location landmark subsurface feature of a body part of an individual patient (hereafter "individual patient body part"), the present-location landmark subsurface feature having a first spatial relationship to a distal end portion of a body-insertable device deployed in the individual patient, and (y) a candidate reference landmark subsurface feature of the individual patient body part, the candidate reference landmark subsurface feature having a second spatial relationship to a particular selected target region of interest of the individual patient body part of at least two selected target regions of interest of the individual patient body part, the candidate reference landmark subsurface feature selected from a patient examination table that includes the at least two reference landmark subsurface features of the individual patient body part, each candidate reference landmark subsurface feature of the at least two candidate reference landmark subsurface features having a respective spatial relationship to a respective particular selected target region of interest.

6312 The computer-readable media includes a tangible computer-readable media.

6314 The computer-readable media includes a communications media.

FIG. 129

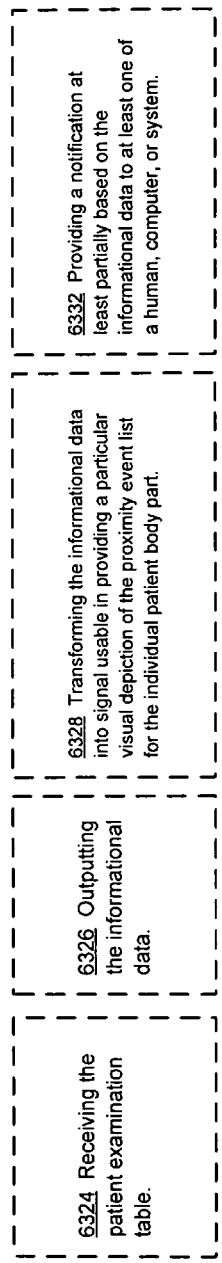

6300

6310 A computer-readable media.

6320 Program instructions which, when executed by a processor of a computing device, cause the computing device to perform a process including:
  (i) determining a substantial correspondence between
    (x) a present-location landmark subsurface feature of a body part of an individual patient (hereafter "individual patient body part"), the present-location landmark subsurface feature having a first spatial relationship to a distal end portion of a body-insertable device deployed in the individual patient, and
    (y) a candidate reference landmark subsurface feature of the individual patient body part, the candidate reference landmark subsurface feature having a second spatial relationship to a particular selected target region of interest of the individual patient body part of at least two selected target regions of interest of the individual patient body part;
  (ii) generating a proximity indication if the first spatial relationship is not greater than an operational reach of the distal end portion of the body-insertable device;
  (iii) generating data indicative of a proximity event, the proximity event including the distal end portion of the body-insertable device present at a location operationally proximate to the particular target region of interest of the individual patient body part, the proximity event at least partially based on the determined substantial correspondence and on the proximity indication;
  (iv) adding the proximity event to a proximity event list for the individual patient body part; and
  (v) storing in another computer-readable media operably coupled with the processor informational data corresponding to the proximity event list for the individual patient body part.

6324 Receiving the patient examination table.

6326 Outputting the informational data.

6328 Transforming the informational data into signal usable in providing a particular visual depiction of the proximity event list for the individual patient body part.

6332 Providing a notification at least partially based on the informational data to at least one of a human, computer, or system.

6610 A computer-readable media.

6620 Program instructions which, when executed by a processor of a computing device, cause the computing device to perform a process comprising:

(i) receiving a first reference image that includes a present-location landmark subsurface feature of a body part of an individual patient (hereafter "individual patient body part"), the present-location landmark subsurface feature having a first spatial relationship to a distal end portion of a body-insertable device deployed in the individual patient;

(ii) receiving a second reference image that includes a candidate reference landmark subsurface feature of the individual patient body part, the candidate reference landmark subsurface feature having a second spatial relationship to a particular selected target region of interest of the individual patient body part of at least two selected target regions of interest of the individual patient body part;

(iii) generating a proximity indication if the first spatial relationship is not greater than an operational reach of the distal end portion of the body-insertable device;

(iv) determining a substantial correspondence between
 (x) present-location landmark subsurface feature and
 (y) the candidate reference landmark subsurface feature;

(v) generating data indicative of an occurrence of a proximity event, the occurrence of the proximity event including the distal end portion of the body-insertable device present at a location operationally proximate to the particular target region of interest of the individual patient body part, the occurrence of proximity event at least partially based on the determined substantial correspondence and on the proximity indication;

(vi) adding the proximity event to a proximity event list for the individual patient body part; and (vii) outputting informational data corresponding to the proximity event list.

6612 The computer-readable media includes a tangible computer-readable media.

6614 The computer-readable media includes a communications media.

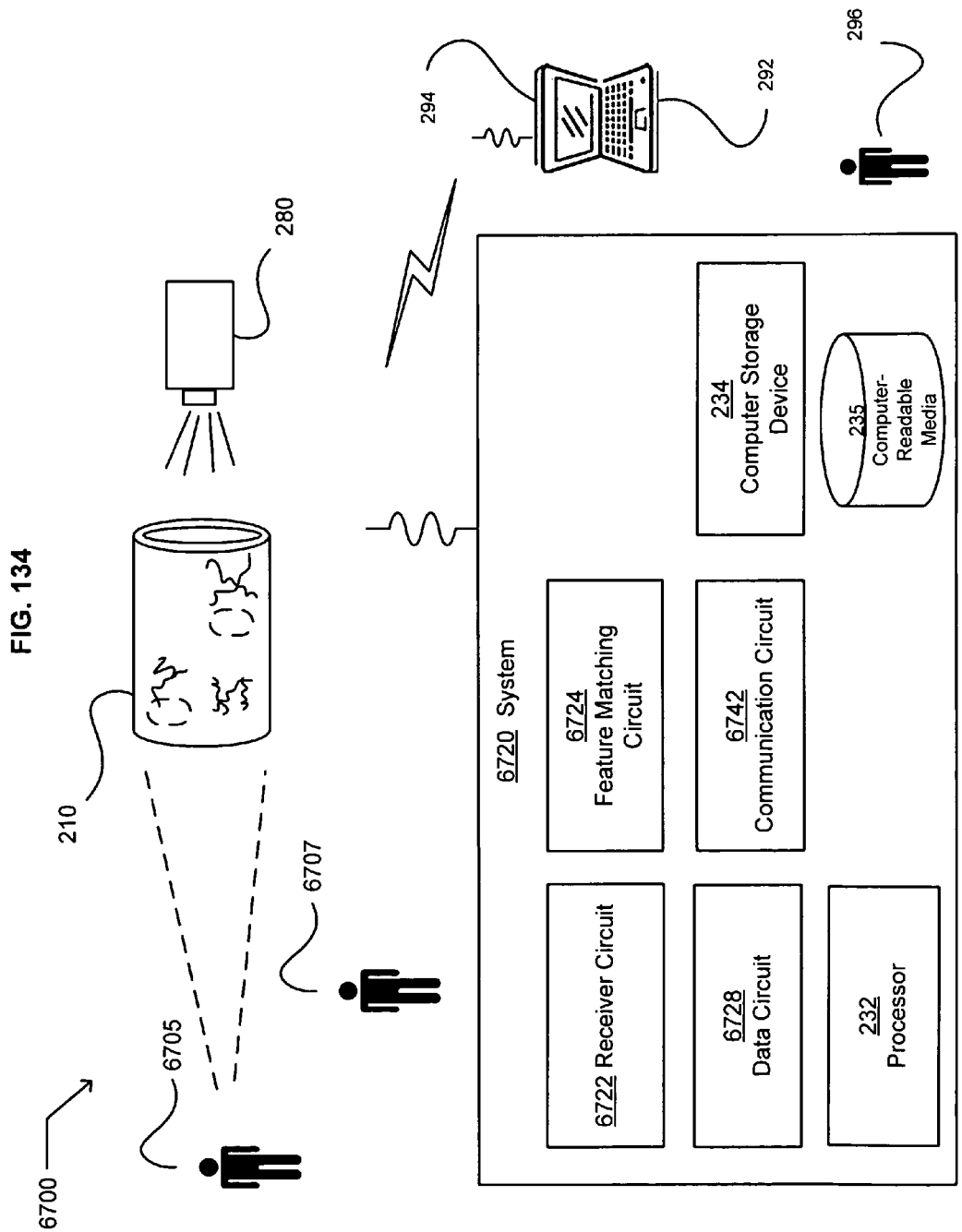

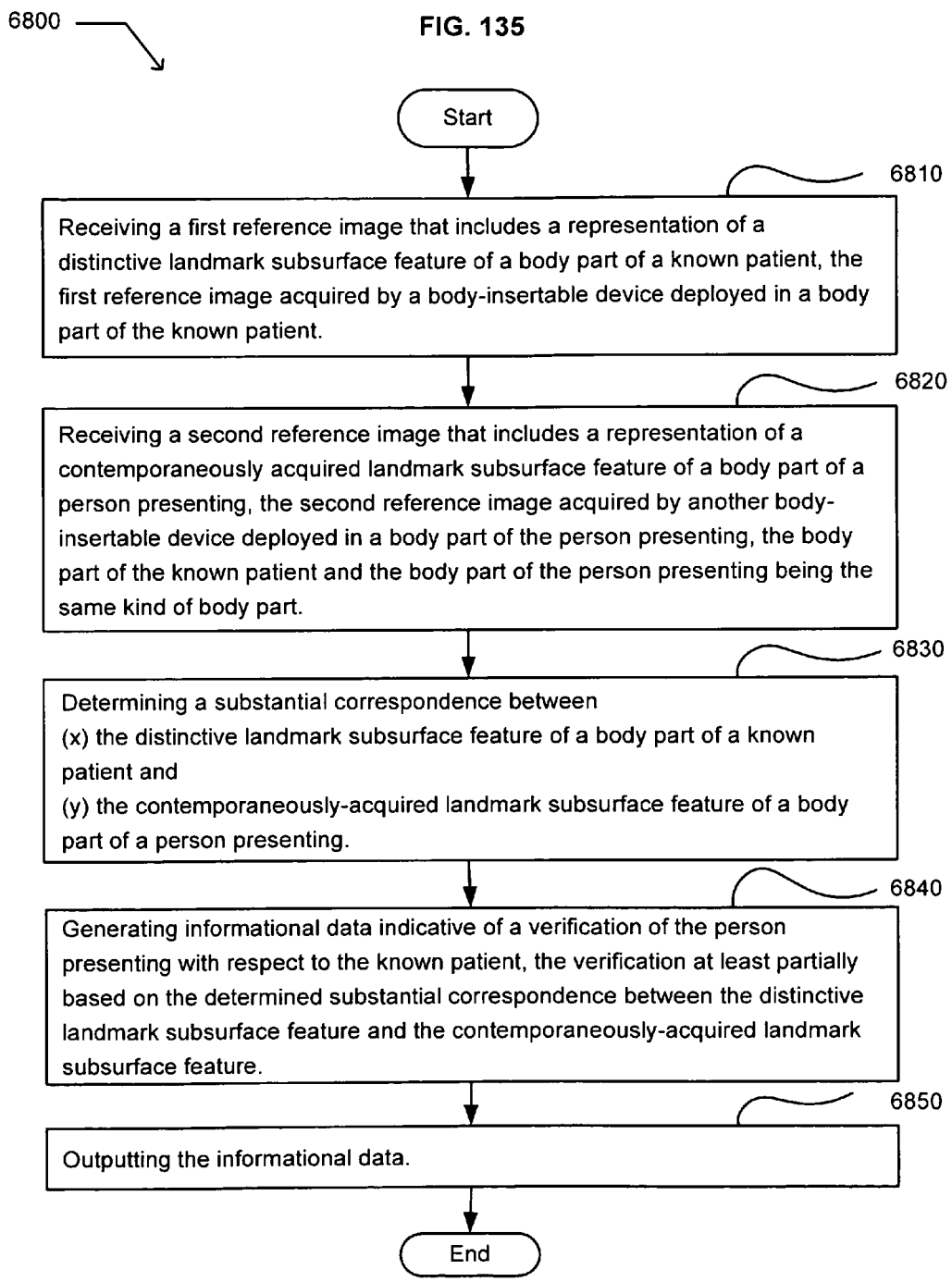

6910 A computer-readable media.

6920 Program instructions which, when executed by a processor of a computing device, cause the computing device to perform a process including:
(i) receiving a first reference image that includes a representation of a distinctive landmark subsurface feature of a body part of a known patient, the first reference image acquired by a body-insertable device deployed in a body part of the known patient;
(ii) receiving a second reference image that includes a representation of a contemporaneously acquired landmark subsurface feature of a body part of a person presenting, the second reference image acquired by another body-insertable device deployed in a body part of the person presenting, the body part of the known patient and the body part of the person presenting being the same kind of body part;
(iii) determining a substantial correspondence between
  (x) the distinctive landmark subsurface feature of a body part of a known patient and
  (y) the contemporaneously-acquired landmark subsurface feature of a body part of a person presenting;
(iv) generating informational data indicative of a verification of the person presenting with respect to the known patient, the verification at least partially based on the determined substantial correspondence between the distinctive landmark subsurface feature and the contemporaneously-acquired landmark subsurface feature; and
(v) outputting the informational data.

6922 Generating informational data indicative of a verification of the person presenting with respect to the known patient, the verification at least partially based on the determined substantial correspondence between the reference landmark subsurface feature and the contemporaneously acquired landmark subsurface feature, otherwise, generating informational data indicative of an absence of a verification of the person presenting with respect to the known patient, the absence of a verification at least partially based on an absence of a determined substantial correspondence between the reference landmark subsurface feature and the contemporaneously acquired landmark subsurface feature.

6924 Outputting the informational data indicative of a verification of the person presenting with respect to the known patient, or outputting the informational data indicative of an absence of a verification of the person presenting with respect to the known patient.

6932 Providing a notification at least partially based on the informational data to at least one of a human, computer, or system.

6934 Outputting a signal usable in displaying a human-perceivable depiction of the verification of the person presenting with respect to the known patient.

6936 Transforming the informational data into a signal usable in displaying a particular visual depiction of the verification of the person presenting with respect to the known patient.

6938 Storing in another computer-readable media operably coupled with the processor informational data corresponding to the verification of the person presenting with respect to the known patient.

6912 The computer-readable media includes a tangible computer-readable media.

6914 The computer-readable media includes a communications media.

FIG. 140

7000 A system.

7010 Means for receiving a first reference image that includes a representation of a distinctive landmark subsurface feature of a body part of a known patient, the first reference image acquired by a body-insertable device deployed in a body part of the known patient.

7020 Means for receiving a second reference image that includes a representation of a contemporaneously acquired landmark subsurface feature of a body part of a person presenting, the second reference image acquired by another body-insertable device deployed in a body part of the person presenting, the body part of the known patient and the body part of the person presenting being the same kind of body part.

7030 Means for determining a substantial correspondence between (x) the distinctive landmark subsurface feature of a known patient and (y) the contemporaneously acquired landmark subsurface feature of a body part of a person presenting.

7040 Means for generating informational data indicative of a verification of the person presenting with respect to the known patient, the verification at least partially based on the determined substantial correspondence between the distinctive landmark subsurface feature and the contemporaneously-acquired landmark subsurface feature.

7050 Means for outputting the informational data.

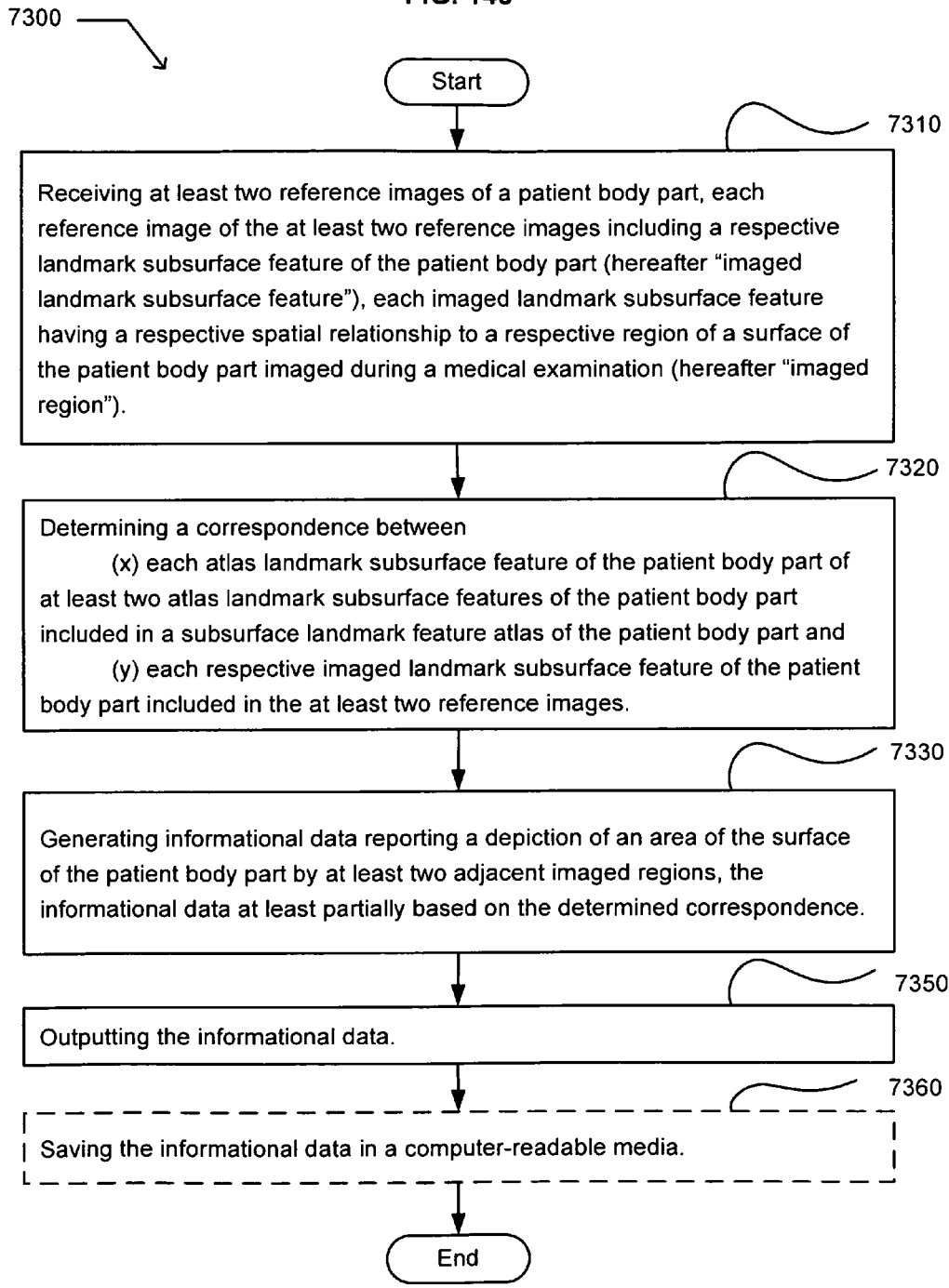

Receiving at least two reference images of a patient body part, each reference image of the at least two reference images including a respective landmark subsurface feature of the patient body part, each imaged landmark subsurface feature having a respective spatial relationship to a respective region of a surface of the patient body part imaged during a medical examination.

7311 Receiving at least two reference images of a patient body part having a cavity or lumen, each reference image of the at least two reference images including a respective landmark subsurface feature of the patient body part having a respective spatial relationship to a respective imaged region of a surface of the cavity or lumen of the patient body part.

7312 Receiving at least two reference images of a patient body part, each reference image of the at least two reference images acquired by a body-insertable device and including a respective landmark subsurface feature of the patient body part, each imaged landmark subsurface feature having a respective spatial relationship to a respective region of a surface of the patient body part imaged during a medical examination.

7313 Receiving at least two reference images of a patient body part, each reference image of the at least two reference images acquired by an *ex vivo* device and including a respective landmark subsurface feature of the patient body part, each imaged landmark subsurface feature having a respective spatial relationship to a respective region of a surface of the patient body part imaged during a medical examination.

Generating informational data reporting a depiction of an area of the surface of the patient body part by at least two adjacent imaged regions, the informational data at least partially based on the determined correspondence.

7335 Generating informational data reporting
(i) a determined positive correspondence between (x) a particular atlas landmark subsurface feature of the at least two atlas landmark subsurface features and (y) an imaged landmark subsurface feature of the patient body part; and
(ii) a determined negative correspondence between (x) another atlas landmark subsurface feature immediately spatially adjacent to the particular atlas landmark subsurface feature and (y) each other respective imaged landmark subsurface feature of the patient body part.

7336 Generating informational data reporting
(i) a determined positive correspondence between (x) a first atlas landmark subsurface feature of the at least two atlas landmark subsurface features and (y) an imaged landmark subsurface feature;
(ii) a first determined negative correspondence between (x) a second atlas landmark subsurface feature immediately spatially adjacent to the first atlas landmark subsurface feature and (y) each other respective imaged landmark subsurface feature of the patient body part; and
(iii) a second determined negative correspondence between (x) a third atlas landmark subsurface feature also immediately spatially adjacent to the first atlas landmark subsurface feature and (y) each other respective imaged landmark subsurface feature of the patient body part.

7337 Generating informational data reporting at least two spatially adjacent atlas landmark subsurface features respectively having a determined negative correspondence with each imaged landmark subsurface feature of the patient body part.

Outputting the informational data.

7351 Outputting informational data usable in displaying a human-perceivable indication of the determined correspondence for at least one atlas landmark subsurface feature of the at least two atlas landmark subsurface features included in the subsurface feature atlas.

7352 Transforming the informational data into a particular visual depiction of a location of an un-imaged region of the surface of the patient body part relative to a larger portion of the surface of the patient body part, and outputting the transformed informational data.

7353 Transforming the informational data into a particular visual depiction of a location of at least two un-imaged regions of the surface of the patient body part relative to a larger portion of the surface of the patient body part, and outputting the transformed informational data.

7354 Transforming the informational data into a particular visual depiction of relative spatial positions of the respective image regions of the surface of the patient body part and outputting the transformed informational data.

7410 A computer-readable media.

7420 Program instructions which, when executed by a processor of a computing device, cause the computing device to perform a process including:

(i) receiving at least two reference images of a patient body part, each reference image of the at least two reference images including a respective landmark subsurface feature of the patient body part (hereafter "imaged landmark subsurface feature"), each imaged landmark subsurface feature having a respective spatial relationship to a respective region of a surface of the patient body part imaged during a medical examination (hereafter "imaged region");

(ii) determining a correspondence between (x) each atlas landmark subsurface feature of the patient body part of at least two atlas landmark subsurface features of the patient body part included in a subsurface landmark feature atlas of the patient body part and (y) each respective imaged landmark subsurface feature of the patient body part included in the at least two reference images;

(iii) generating informational data reporting a depiction of an area of the surface of the patient body part by at least two adjacent imaged regions, the informational data at least partially based on the determined correspondence; and (iv) outputting the informational data.

7422 Storing the informational data in another computer-readable media operably coupled with the processor.

7412 The computer-readable media includes a tangible computer-readable media .

7414 The computer-readable media includes a communications media.

FIG. 150

A system. 7500

7510 Means for receiving at least two reference images of a patient body part, each reference image of the at least two reference images including a respective landmark subsurface feature of the patient body part (hereafter "imaged landmark subsurface feature"), each imaged landmark subsurface feature having a respective spatial relationship to a respective region of a surface of the patient body part imaged during a medical examination (hereafter "imaged region").

7520 Means for determining a correspondence between (x) each atlas landmark subsurface feature of the patient body part of at least two atlas landmark subsurface features of the patient body part included in a subsurface landmark feature atlas of the patient body part and (y) each respective imaged landmark subsurface feature of the patient body part included in the at least two reference images.

7530 Means for generating informational data reporting a depiction of an area of the surface of the patient body part by at least two adjacent imaged regions, the informational data at least partially based on the determined correspondence.

7540 Means for outputting the informational data.

GUIDANCE INFORMATION INDICATING AN OPERATIONAL PROXIMITY OF A BODY-INSERTABLE DEVICE TO A REGION OF INTEREST

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 13/200,114, entitled REGISTERING A REGION OF INTEREST OF A BODY PART TO A LANDMARK SUBSURFACE FEATURE OF THE BODY PART, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,110, entitled REGISTERING REGIONS OF INTEREST OF A BODY PART TO A COORDINATE SYSTEM, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,107, entitled COREGISTERING IMAGES OF A REGION OF INTEREST DURING SEVERAL CONDITIONS USING A LANDMARK SUBSURFACE FEATURE, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,108, entitled CREATING A SUBSURFACE FEATURE ATLAS OF AT LEAST TWO SUBSURFACE FEATURES, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,104, entitled INDICATING PROXIMITY OF A BODY-INSERTABLE DEVICE TO A DESTINATION REGION OF INTEREST, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,111, entitled CONFIRMING THAT AN IMAGE INCLUDES AT LEAST A PORTION OF A TARGET REGION OF INTEREST, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,103, entitled LISTING INSTANCES OF A BODY-INSERTABLE DEVICE BEING PROXIMATE TO TARGET REGIONS OF INTEREST, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/200,105, entitled PATIENT VERIFICATION BASED ON A LANDMARK SUBSURFACE FEATURE OF THE PATIENT'S BODY PART, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011 now U.S. Pat. No. 8,634,598.

For purposes of the USPTO extra-statutory requirements, the present application constitutes a continuation-in-part of U.S. patent application Ser. No. 13/200,109, entitled REPORTING IMAGED PORTIONS OF A PATIENT'S BODY PART, naming Roderick A. Hyde, Jordin T. Kare, Eric C. Leuthardt, Erez Lieberman, Dennis J. Rivet, Elizabeth A. Sweeney, Lowell L. Wood, Jr., as inventors, filed Sep. 16, 2011, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

For example and without limitation, an embodiment of the subject matter described herein includes a system. For example, a health care provider may be moving a body-insertable device through a body part of a patient. The health care provider may wish to position the distal end of the body-insertable device close to a destination region of interest. Alternatively the health care provider may want to be informed when the a distal end portion of the endoscope, such as an effector or camera, is close to or at the destination region of interest so they can slow their rate of movement or reorient the endoscope. For example, the destination region of interest may be selected for any reason, including a possible disease state, a former surgery site, or a region selected for future return, such as for example, to monitor progression of disease or a lack thereof. For example, the destination region of interest may be selected by a health care provider, such as during a previous colonoscopy or by a machine, such as during a virtual colonoscopy, or in response to a virtual colonoscopy. For example, the health care provider may want to be informed what direction to move a distal end portion of the endoscope, such as an effector or camera, toward the region of interest so they can perform a procedure.

In this embodiment, the system includes a receiver circuit configured to receive a first reference image that includes an objective landmark subsurface feature of a mammalian body part. The objective landmark subsurface feature has a first spatial relationship to a destination region of interest of the mammalian body part. For example, the objective landmark subsurface feature may in an embodiment be considered a goal or objective because of its first spatial relationship with the destination region of interest. The first reference image may have been acquired during a prior colonoscopy, or may have been acquired from a subsurface feature atlas of the body part. The receiver circuit is configured to receive a second reference image that includes a present-location landmark subsurface feature of the mammalian body part. The present-location landmark subsurface feature has a second spatial relationship to a distal end portion of a body-insertable device deployed operationally proximate to the mammalian body part. For example, the second reference image may have been acquired in real time as the endoscope is moved through the colon. For example, a fluoroscope may provide an image that includes both the present-location landmark subsurface feature and the distal end portion of the endoscope, such as an effector or camera of the endoscope. The system includes a feature matching circuit configured to determine a substantial correspondence between the objective landmark subsurface feature and a first atlas subsurface feature included in a subsurface feature atlas of the mammalian body part. The feature matching circuit is also configured to determine a substantial correspondence between the present-location landmark subsurface feature and a second atlas subsurface feature included in the subsurface feature atlas of the mammalian body part. For example, the subsurface feature atlas may be thought of as a map of landmarks, the map includes distances and directions between the landmark subsurface features of the mammalian body part. The subsurface feature atlas includes at least two registered subsurface features of the mammalian body part, including the first atlas subsurface feature and the second atlas subsurface feature. The registration in the subsurface feature atlas includes an indication of a third spatial relationship between the first atlas subsurface feature and the second atlas subsurface feature. In an embodiment, the subsurface feature atlas may have been created as described in this document.

In this embodiment, the system includes a location analysis circuit configured to determine a fourth spatial relationship between the destination region of interest and the distal end portion of the body-insertable device deployed operationally proximate to the mammalian body part. The determined fourth spatial relationship is at least partially based on the third spatial relationship. The system includes an indicator circuit configured to generate informational data indicative of the determined fourth spatial relationship between the destination region of interest and the distal end portion of the body-insertable device. The informational data is at least partially based on the fourth spatial relationship between the destination region of interest and the distal end portion of the body-insertable device. In an embodiment, the informational data based when communicated to a health care provider is expected to inform them whether the distal end of the body-insertable device is close enough to the destination region of interest to perform an action on the destination region of interest. The informational data may then be communicated to the health care provider so they may move the distal end portion appropriately toward the region of interest. The system includes a computer-readable media configured to maintain the informational data.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 3 illustrates an example environment in which embodiments may be implemented;

FIG. 4 illustrates additional details of the mammalian body part of FIG. 3;

FIG. 5 illustrates an example operational flow 300;

FIG. 6 illustrates alternative embodiments of the medical image receiving operation of FIG. 5;

FIG. 7 illustrates alternative embodiments of the medical image receiving operation of FIG. 5;

FIG. 12 illustrates alternative embodiments of the registration operation 410 of FIG. 5;

FIG. 13 illustrates alternative embodiments of the operational flow 300 of FIG. 5;

FIG. 14 illustrates alternative embodiments of the operational flow 300 of FIG. 5;

FIG. 15 illustrates a computer program product;

FIG. 22 illustrates an alternative embodiment of the third reception operation 1030 of FIG. 19;
FIG. 24 illustrates an alternative embodiment of the reference operation 1050 of FIG. 19;
FIG. 25 illustrates an alternative embodiment of the registration operation 1060 of FIG. 19;
FIG. 26 illustrates an alternative embodiment of the storage operation 1070 of FIG. 19;
FIG. 33 illustrates an example computer program product;
FIG. 34 illustrates an example system;
FIG. 36 illustrates an example operational flow;
FIG. 37 illustrates an alternative embodiment of the operational flow 1600 of FIG. 36;
FIG. 38 illustrates an alternative embodiment of the operational flow 1600 of FIG. 36;
FIG. 39 illustrates an example computer program product;
FIG. 46 illustrates a computer program product;
FIG. 54 illustrates a computer program product;
FIG. 55 illustrates an alternative embodiment of the program instructions of the computer program product of FIG. 54;
FIG. 56 illustrates an example system 2600;
FIG. 57 illustrates an example operational flow;
FIG. 58 illustrates an alternative embodiment of the operational flow 2700 of FIG. 57;
FIG. 59 illustrates an alternative embodiment of the operational flow 2700 of FIG. 57;
FIG. 64 illustrates an example computer program product;
FIG. 65 illustrates an alternative embodiment of computer program product of FIG. 64;
FIG. 66 illustrates an example system 2900;
FIG. 67 illustrates an example environment 3000;
FIG. 68 illustrates an example operational flow;
FIG. 73 illustrates an example computer program product;
FIG. 77 illustrates an alternative embodiment of the example operational flow 3400 of FIG. 76;
FIG. 78 illustrates an example computer program product;
FIG. 79 illustrates an example system;
FIG. 80 illustrates an example environment;
FIG. 81 illustrates an example operational flow;
FIG. 82 illustrates an alternative embodiment of the operational flow 3900 of FIG. 81;
FIG. 84 illustrates an example computer program product;
FIG. 87 illustrates an example operational flow;
FIG. 88 illustrates an alternative embodiment of the operational flow;
FIG. 89 illustrates a computer program product;
FIG. 92 illustrates an alternative embodiment of the environment 4400 of FIG. 91;
FIG. 95 illustrates an alternative embodiment of the operational flow 4500 of FIG. 93;
FIG. 97 illustrates a computer program product.

FIG. 111 illustrates an example computer program product;

FIG. 112 illustrates an alternative embodiment of the computer program product of FIG. 111;

FIG. 113 illustrates an example system;

FIG. 114 illustrates an example operational flow;

FIG. 115 illustrates an example environment;

FIG. 116 illustrates an example operational flow;

FIG. 117 illustrates an alternative embodiment of the operational flow of FIG. 116;

FIG. 120 illustrates a computer program product;

FIG. 121 illustrates an example system;

FIG. 122 illustrates an example environment;

FIG. 123 illustrates an example operational flow;

FIG. 124 illustrates an alternative embodiment of the operational flow 6200 of FIG. 123;

FIG. 128 illustrates an example computer program product;

FIG. 129 illustrates an alternative embodiment of the program instructions;

FIG. 133 illustrates an example computer program product;

FIG. 134 illustrates an example environment;

FIG. 135 illustrates an example operational flow;

FIG. 139 illustrates a computer program product;

FIG. 140 illustrates an example system;

FIG. 143 illustrates an operational flow;

FIG. 144 illustrates an alternative embodiment of the operational flow 7200 of FIG. 142;

FIG. 146 illustrates an alternative embodiment of the operational flow 7200 of FIG. 142;

FIG. 148 illustrates an alternative embodiment of the operational flow 7200 of FIG. 142;

FIG. 149 illustrates an example computer program product; and

FIG. 150 illustrates an example system.

DETAILED DESCRIPTION

Figure 1:
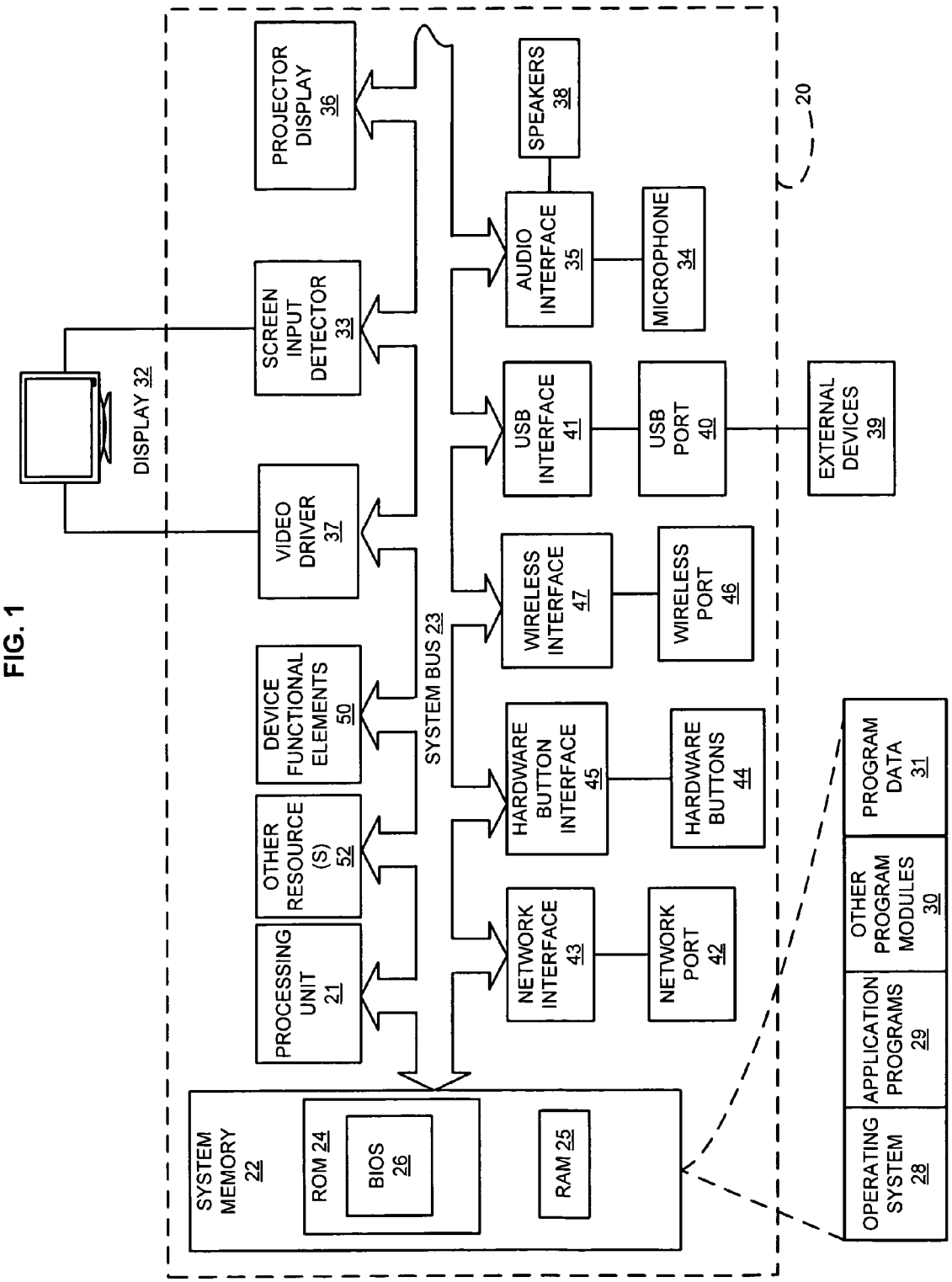
FIG. 1 illustrates an example embodiment of a thin computing device in which embodiments may be implemented.

In the following detailed description, reference is made to the accompanying drawings, which form a part hereof. In the drawings, similar symbols typically identify similar components, unless context dictates otherwise. The illustrated embodiments described in the detailed description, drawings, and claims are not meant to be limiting. Other embodiments may be utilized, and other changes may be made, without departing from the spirit or scope of the subject matter presented here.

FIG. 1 and the following discussion are intended to provide a brief, general description of an environment in which embodiments may be implemented. FIG. 1 illustrates an example system that includes a thin computing device 20, which may be included in an electronic device that also includes a device functional element 50. For example, a thin computing device may include a computing device having limited resources or limited processing capability. In an embodiment, the electronic device may include any item having electrical or electronic components playing a role in a functionality of the item, such as, for example, a limited resource computing device, a wireless communication device, a mobile wireless communication device, a smart phone, an electronic pen, a handheld electronic writing device, a digital camera, a scanner, an ultrasound device, an x-ray machine, a non-invasive imaging device, a cell phone, a PDA, a Blackberry® device, or a printer. For example, a thin computing device may be included in a refrigerator, a car, or an airplane, and may interface with or control a functional element of the refrigerator, car, or airplane. In another example, the thin computing device may be included in an implantable medical apparatus or device. In a further example, the thin computing device may be operable to communicate with an implantable or implanted medical apparatus.

The thin computing device 20 includes a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system (BIOS) 26, containing the basic routines that help to transfer information between sub-components within the thin computing device 20, such as during start-up, is stored in the ROM 24. A number of program modules may be stored in the ROM 24 or RAM 25, including an operating system 28, one or more application programs 29, other program modules 30 and program data 31.

A user may enter commands and information into the computing device 20 through one of more input interfaces. An input interface may include a touch-sensitive display, or one or more switches or buttons with suitable input detection circuitry. A touch-sensitive display is illustrated as a display 32 and screen input detector 33. One or more switches or buttons are illustrated as hardware buttons 44 connected to the system via a hardware button interface 45. The output circuitry of the touch-sensitive display 32 is connected to the system bus 23 via a video driver 37. Other input devices may include a microphone 34 connected through a suitable audio interface 35, or a physical hardware keyboard (not shown). Output devices may include at least one of the display 32, or a projector display 36.

In addition to the display 32, the computing device 20 may include other peripheral output devices, such as at least one speaker 38. Other external input or output devices 39, such as a joystick, game pad, satellite dish, scanner or the like may be connected to the processing unit 21 through a USB port 40 and USB port interface 41, to the system bus 23. Alternatively, the other external input and output devices 39 may be connected by other interfaces, such as a parallel port, game port or other port. The computing device 20 may further include or be capable of connecting to a flash card memory (not shown) through an appropriate connection port (not shown). The computing device 20 may further include or be capable of connecting with a network through a network port 42 and network interface 43, and through wireless port 46 and corresponding wireless interface 47 may be provided to facilitate communication with other peripheral devices, including other computers, printers, and so on (not shown). It will be appreciated that the various components and connections shown are examples and other components and means of establishing communication links may be used.

The computing device 20 may be primarily designed to include a user interface. The user interface may include a character, a key-based, or another user data input via the touch sensitive display 32. The user interface may include using a stylus (not shown). Moreover, the user interface is not limited to an actual touch-sensitive panel arranged for directly receiving input, but may alternatively or in addition respond to another input device such as the microphone 34. For example, spoken words may be received at the microphone 34 and recognized. Alternatively, the computing device 20 may be designed to include a user interface having a physical keyboard (not shown).

The device functional elements 50 are typically application specific and related to a function of the electronic device, and are coupled with the system bus 23 through an interface (not shown). The functional elements may typically perform a single well-defined task with little or no user configuration or setup, such as a refrigerator keeping food cold, a cell phone connecting with an appropriate tower and transceiving voice or data information, a camera capturing and saving an image, or communicating with an implantable medical apparatus.

In certain instances, one or more elements of the thin computing device 20 may be deemed not necessary and omitted. In other instances, one or more other elements may be deemed necessary and added to the thin computing device.

Figure 2:
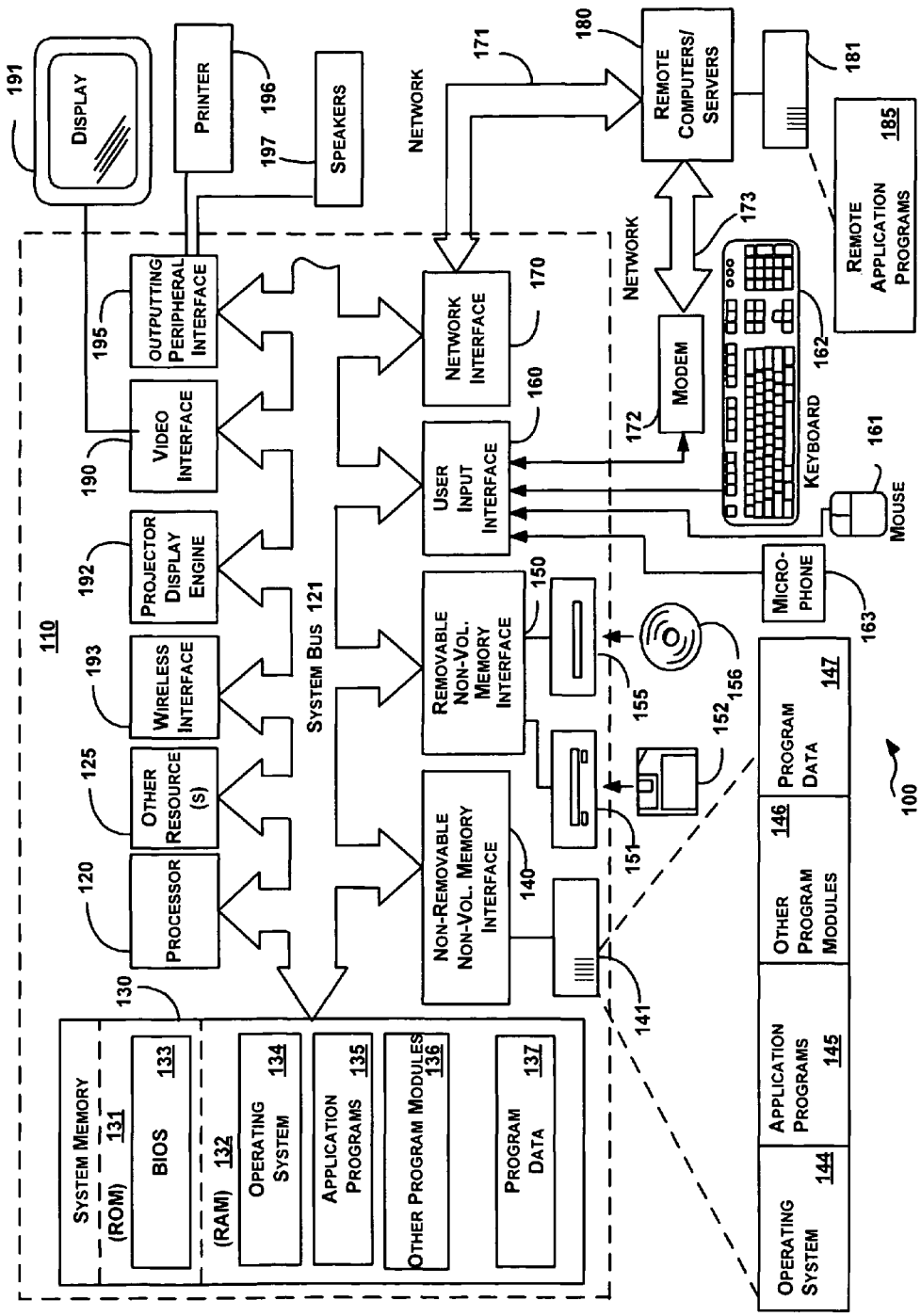
FIG. 2 illustrates an example embodiment of a general-purpose computing system in which embodiments may be implemented.

FIG. 2 and the following discussion are intended to provide a brief, general description of an environment in which embodiments may be implemented. FIG. 2 illustrates an example embodiment of a general-purpose computing system in which embodiments may be implemented, shown as a computing system environment 100. Components of the computing system environment 100 may include, but are not limited to, a computing device 110 having a processor 120, a system memory 130, and a system bus 121 that couples various system components including the system memory to the processor 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing system environment 100 typically includes a variety of computer-readable media products. Computer-readable media may include any media that can be accessed by the computing device 110 and include both volatile and nonvolatile media, removable and non-removable media. By way of example, and not of limitation, computer-readable media may include computer storage media. By way of further example, and not of limitation, computer-readable media may include a communication media.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 110. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communications media may include wired media, such as a wired network and a direct-wired connection, and wireless media such as acoustic, RF, optical, and infrared media.

The system memory 130 includes computer storage media in the form of volatile and nonvolatile memory such as ROM 131 and RAM 132. A RAM may include at least one of a DRAM, an EDO DRAM, a SDRAM, a RDRAM, a VRAM, or a DDR DRAM. A basic input/output system (BIOS) 133, containing the basic routines that help to transfer information between elements within the computing device 110, such as during start-up, is typically stored in ROM 131. RAM 132 typically contains data and program modules that are immediately accessible to or presently being operated on by the processor 120. By way of example, and not limitation, FIG. 2 illustrates an operating system 134, application programs 135, other program modules 136, and program data 137. Often, the operating system 134 offers services to applications programs 135 by way of one or more application programming interfaces (APIs) (not shown). Because the operating system 134 incorporates these services, developers of applications programs 135 need not redevelop code to use the services. Examples of APIs provided by operating systems such as Microsoft's "WINDOWS"® are well known in the art.

The computing device 110 may also include other removable/non-removable, volatile/nonvolatile computer storage media products. By way of example only, FIG. 2 illustrates a non-removable non-volatile memory interface (hard disk interface) 140 that reads from and writes for example to non-removable, non-volatile magnetic media. FIG. 2 also illustrates a removable non-volatile memory interface 150 that, for example, is coupled to a magnetic disk drive 151 that reads from and writes to a removable, non-volatile magnetic disk 152, or is coupled to an optical disk drive 155 that reads from and writes to a removable, non-volatile optical disk 156, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 141 is typically connected to the system bus 121 through a non-removable memory interface, such as the interface 140, and magnetic disk drive 151 and optical disk drive 155 are typically connected to the system bus 121 by a removable non-volatile memory interface, such as interface 150.

The drives and their associated computer storage media discussed above and illustrated in FIG. 2 provide storage of computer-readable instructions, data structures, program modules, and other data for the computing device 110. In FIG. 2, for example, hard disk drive 141 is illustrated as storing an operating system 144, application programs 145, other program modules 146, and program data 147. Note that these components can either be the same as or different from the operating system 134, application programs 135, other program modules 136, and program data 137. The operating system 144, application programs 145, other program modules 146, and program data 147 are given different numbers here to illustrate that, at a minimum, they are different copies.

A user may enter commands and information into the computing device 110 through input devices such as a microphone 163, keyboard 162, and pointing device 161, commonly referred to as a mouse, trackball, or touch pad. Other input devices (not shown) may include at least one of a touch sensitive display, joystick, game pad, satellite dish, and scanner. These and other input devices are often connected to the processing unit 120 through a user input interface 160 that is coupled to the system bus, but may be connected by other interface and bus structures, such as a parallel port, game port, or a universal serial bus (USB).

A display 191, such as a monitor or other type of display device or surface may be connected to the system bus 121 via an interface, such as a video interface 190. A projector display engine 192 that includes a projecting element may be coupled to the system bus. In addition to the display, the computing device 110 may also include other peripheral output devices such as speakers 197 and printer 196, which may be connected through an output peripheral interface 195.

The computing system environment 100 may operate in a networked environment using logical connections to one or more remote computers, such as a remote computer 180. The remote computer 180 may be a personal computer, a server, a router, a network PC, a peer device, or other common network node, and typically includes many or all of the elements described above relative to the computing device 110, although only a memory storage device 181 has been illustrated in FIG. 2. The network logical connections depicted in FIG. 2 include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system environment 100 is connected to the network 171 through a network interface, such as the network interface 170, the modem 172, or the wireless interface 193. The network may include a LAN network environment, or a WAN network environment, such as the Internet. In a networked environment, program modules depicted relative to the computing device 110, or portions thereof, may be stored in a remote memory storage device. By way of example, and not limitation, FIG. 2 illustrates remote application programs 185 as residing on memory storage device 181. It will be appreciated that the network connections shown are examples and other means of establishing communication link between the computers may be used.

In certain instances, one or more elements of the computing device 110 may be deemed not necessary and omitted. In other instances, one or more other elements may be deemed necessary and added to the computing device.

FIG. 3 illustrates an example environment 200 in which embodiments may be implemented. The environment includes a mammal 205, illustrated, for example, by a human profile, a mammalian body part 210, illustrated as tubular structure, and a system 220.

FIG. 4 illustrates additional details of the mammalian body part 210, including a region of interest 214, illustrated as regions of interest 214A-214B of the mammalian body part, and including a landmark subsurface feature, illustrated as landmark subsurface features 216A-216C. In an embodiment, the region of interest includes an area or region where a medical professional or patient has an interest, including a region for monitoring, for administration of a therapeutic agent, or for surgery or other procedure. View 4A of FIG. 4 illustrates the body part 210 as a tubular structure having a cavity or lumen 211 and an interior surface 212. View 4B of FIG. 4 illustrates a section view of the mammalian body part illustrated in View 4A after being cut along line "A"-"A" and unrolled.

A first region of interest 214A of the mammalian body part 210 has a spatial relationship 215 to a second region of interest 214B of the mammalian body part. In an embodiment, the first region of interest 214A or the second region of interest 214B may be located on the surface 212, or may be subsurface of the mammalian body part. A first landmark subsurface feature 216A has a first spatial relationship 217A to the first region of interest 214A. A second landmark subsurface feature 216B has a second spatial relationship 217B to the second region of interest 214B. The first landmark subsurface feature 216A has a spatial relationship 213C to the second landmark subsurface feature 216B. A third landmark subsurface feature 216C has a spatial relationship 213A to the first landmark subsurface feature, and has a spatial relationship 213B to the second landmark subsurface feature 216B. For example, a spatial relationship may be expressed in Cartesian coordinates 219x, y, and z. For example, a spatial relationship may be expressed in cylindrical coordinates, or spherical coordinates (not shown).

For example, a mammalian body part 210 may include a tissue, lumen or an internal organ of a mammal, such as by way of non-limiting example, heart, lung, bone, brain, muscle, esophagus, stomach, intestine, spleen, pancreas, kidney, liver, urinary bladder, vagina, fallopian tube, urethra, duodenum, colon, rectum, artery, vein, bronchus, or duct. In an embodiment, the mammalian body part may be machine differentiated from another body part of a mammal.

In an embodiment, the region of interest 214 of the mammalian body part may include any tissue of the mammalian body part 210. For example, the region of interest may include a portion of an interior surface 212 of the mammalian body part. For example, the region of interest may include a portion of an exterior surface of the mammalian body part. For example, the region of interest may include a subsurface region of interest of the mammalian body part. For example, the region of interest may include a mammalian internal organ. For example, the region of interest may include an internal anatomical mammalian body part. For example, an internal anatomical mammalian body may include more than one internal organ. For example, the region of interest may include an external mammalian body part. For example, an external mammalian body part may include an ear, a nose, or a portion of skin. For example, the region of interest may include a surface of a mammalian body part. For example, the region of interest of a surface of a mammalian body part may include a surface of a cavity or lumen of a mammalian body part.

For example, the region of interest 214 of the surface 212 of a mammalian body part 210 may include a surface defining a cavity or lumen of a mammalian body part. For example, the region of interest may include a subsurface region of interest of a mammalian body part. For example, the region of interest may include a wall, membrane, endothelial, or epithelial layer of a surface of a mammalian body part. For example, the region of interest may include a wall, membrane, or epithelial layer defining a cavity or lumen of a mammalian body part. For example, the region of interest may include a region of interest of a surface of an orifice, canal, cavity, or other hollow region of a mammalian body part. For example, the region of interest may include an interior surface of gastrointestinal organ or digestive organ of a mammalian body part. For example, the region of interest may include a region of interest of an interior surface of a colon of the mammal. For example, the region of interest may include a region of interest of an interior surface of an air passageway of a mammalian body part.

In an embodiment, the landmark subsurface feature 216 of the mammalian body part 210 includes a subsurface feature of the cavity or lumen 211 of the mammalian body part that serves as a landmark. For example, the landmark subsurface feature of a cavity or lumen of the mammalian body part may include a subsurface anatomical feature of a cavity or lumen of the mammalian body part. For example, the landmark subsurface feature of a cavity or lumen of the mammalian body part may include a subsurface vascular feature of a cavity or lumen of the mammalian body part. For example, the landmark subsurface feature of a cavity or lumen of the mammalian body part may include a subsurface anomaly of a cavity or lumen of the mammalian body part. For example, the landmark subsurface feature of the mammalian body part may include a subsurface anatomical feature of the mammalian body part. For example, the landmark subsurface feature of the mammalian body part may include a subsurface vascular feature of the mammalian body part. For example, the landmark subsurface feature of the mammalian body part may include a subsurface vessel, blood vessel, vascular structure, or a pattern presented by one or more blood vessels of the mammalian body part. For example, the landmark subsurface feature of the mammalian body part includes blood within a subsurface blood vessel of the mammalian body part. In an embodiment, the landmark subsurface feature of the mammalian body part may include a fluid, or fluid contained within a subsurface feature of the mammalian body part.

For example, the landmark subsurface feature 216 of the mammalian body part 210 may include a physical structure, nerve, void, border, component, tissue, structural feature, or density variation of the mammalian body part. For example, a physical structure may include a duct, a bend or curve in a tubular structure, or an organ such as an appendix or colon. For example, a subsurface feature of the mammalian body part may include a pattern presented by one or more features of the mammalian body part. For example, the landmark subsurface feature of the mammalian body part may include a fiducial formed by one or more junctions between blood vessels, by blood vessel or nerves, by angles between blood vessels at a junction or apparent intersection, relative positions and angles between nearby junctions. For example, the landmark subsurface feature of the mammalian body part may include relative sizes of two or more blood vessels, relative sizes of blood vessels at junctions or nearby junctions, or branching in lungs. For example, a subsurface feature of the mammalian body part may include a normal subsurface feature of the mammalian body part. For example, a normal subsurface feature of the mammalian body part may include a usual, regular, or typical subsurface feature of the mammalian body part. For example, the landmark subsurface feature of the mammalian body part may include an abnormal subsurface feature of the mammalian body part. For example, an abnormal subsurface feature of the mammalian body part may include an unusual, irregular, or disease state subsurface feature of the mammalian body part. For example, an abnormal subsurface feature may include a scar tissue, healed lesion, nodule, or encapsulated foreign object. For example, the landmark subsurface feature of the mammalian body part may include a landmark subsurface feature of the mammalian body part that is machine distinguishable from another landmark subsurface feature of the mammalian body part. For example, the landmark subsurface feature of the mammalian body part may include a landmark subsurface feature of the mammalian body part that is machine differentiable from another landmark subsurface feature of the mammalian body part. For example, a computing machine is able to differentiate between first landmark subsurface feature 216A and second landmark subsurface feature 216B, but may not able to distinguish or discern why they are not the same.

Returning to FIG. 3, the environment 200 includes the system 220. The system includes a receiver circuit 222. The receiver circuit is configured to receive data indicative of a region of interest of the mammalian body part 210, such as the region of interest 214A of FIG. 4.

In an embodiment, the medical image includes a region of interest 214 of a mammalian body part 210. In an embodiment, the medical image includes a selected region of interest of a mammalian body part. In an embodiment, the region of interest may be selected by a health care provider during a colonoscopy, such as by the health care provider activating a selector or a camera during the colonoscopy. The health care provider is illustrated as the person 296. The region of interest may be selected for any reason, including a possible disease state, marking a point of interest to which a health care provider, such as an endoscopist, wants to return in the future, for example, to monitor progression of disease or lack thereof. In an embodiment, the region of interest may be selected by a machine during a virtual colonoscopy, or in response to a virtual colonoscopy.

For example, "a medical image" may include an image created using a technique or process, often for clinical purposes or medical science. For example, "a medical image"

may include an image produced using a technique or process of radiography, magnetic resonance imaging, nuclear medicine, ultrasound, thermography, or tomography. For example, "a medical image" may include a two-dimensional medical image or a three-dimensional medical image. An aspect of a "medical image" may include information or data providing positional information. For example, see GE Healthcare's website "Medcyclopaedia" at "http://www.medcyclopaedia.com/?tt_topic=" includes a library of medical images. (Accessed Aug. 16, 2011.)

For example, "a medical image that includes a region of interest" may include information or data indicative of the region of interest of a surface of a mammalian body part. For example, the "medical image that includes a region of interest" may include information or data indicative of the region of interest of a surface of a cavity or lumen of a mammalian body part. For example, the "medical image that includes a region of interest" may include information or data descriptive of the region of interest of a mammalian body part.

For example, "a reference image" may be created using a technique or process to create an image providing positional information or data related to one or more landmark subsurface features of a mammalian body part. For example, "a reference image" may also provide positional information or data related to one or more regions of interest, but may not provide adequate resolution, definition, or granularity to be considered "a medical image."

In an embodiment, the medical image may include a region of interest 214 of a mammalian body part 210. For example, the medical image may include a two-dimensional medical image or a three-dimensional medical image. For example, the medical image may or may not include a medical image visualizable by the human eye. For example, the medical image may include a medical image indicative of a region of interest of a cavity or lumen of a mammalian body part. For example, the medical image may include a medical image indicative of a region of interest of a surface of a cavity or lumen of a mammalian body part. For example, a single image may include both the medical image and the reference image. For example, the medical image is acquired at substantially a same time as the reference image. For example, the medical image is acquired at substantially different time from the acquisition of the reference image.

In an embodiment, the medical image may include a region of interest 214 of a mammalian body part 210 acquired at substantially a same location as a reference image that includes a landmark subsurface feature of the mammalian body part. In an embodiment, the medical image may include a region of interest of a mammalian body part acquired at substantially a different location as the reference image that includes a landmark subsurface feature of the mammalian body part. In an embodiment, the medical image may include a region of interest of a mammalian body part acquired at substantially same spectra as the reference image that includes a landmark subsurface feature of the mammalian body part. In an embodiment, the medical image may include a region of interest of a mammalian body part acquired at substantially different spectra as the reference image that includes a landmark subsurface feature of the mammalian body part. In an embodiment, the medical image may include a region of interest of a mammalian body part, and have an overlapping field of view with the landmark digital image that includes a subsurface feature of the mammalian body part. For example, the medical image may have been acquired using at least one of a PET, x-ray, CAT, coherence tomography (CT) image, magnetic resonance imaging (MRI) image, fluoroscopy, fluorescence based imaging, or ultrasound based image technology. For example, the medical image may have been acquired using at least one of a visible light, near infrared light, infrared light, ultraviolet light, passive thermal, or active thermal based imaging.

In an embodiment, the receiver circuit 222 configured to receive a medical image that includes region of interest 214 of a mammalian body part 210 may include a receiver circuit configured to facilitate an acquisition of the medical image. In an embodiment, the receiver circuit may facilitate an acquisition of the medical image by sending a signal to an image capture device instructing it to acquire the medical image. The signal may be responsive to a human-user initiated input or a machine initiated input. In an embodiment, the receiver circuit may include a receiver circuit configured to facilitate a capture of the medical image.

In an embodiment, the medical image that includes a region of interest 214 of a mammalian body part 210 may include a user-selected a region of interest of a mammalian body part. In an embodiment, the medical image may include information or data indicative of a region of interest of a mammalian body part. The medical image acquired by a body-insertable device 280 while a portion of the body-insertable device was present in a cavity or lumen of the mammalian body part. For example, the body-insertable device may include a wired or a wireless device. For example, the body-insertable device may include an endoscope, laparoscope, swallowable camera capsule, capsule endoscopic, or pill-type camera apparatus. For example, RF Systems Lab Ltd. located in Nagano, Japan announced a capsule endoscope branded as Sayaka. The Sayaka is marketed as configured to capture medical images of the whole inner surface of the digestive tract. http://www.rfamerica.com/sayaka/index.html (accessed Aug. 16, 2011). For example, Given Imaging Ltd. of Yoqneam, Israel, markets PillCam® for capsule endoscopy of the esophagus and small bowel. For example, a body-insertable device may include an ingestible device. For example, a body-insertable device may include an injectable, implantable, or insertable device.

In an embodiment, a medical image may include a medical image acquired by a body-insertable device while a portion of the body-insertable device is present in a cavity or lumen of the mammalian body part 210. In an embodiment, the medical image may include a medical image acquired by a body-insertable device while a distal end portion of the body-insertable device is present in a cavity or lumen of the mammalian body part. For example, the distal end portion of the body-insertable device may include a camera, effector, scalpel, biopsy device (such as rotational tissue-cutting razor, or ablation device.

In an embodiment, the medical image may be acquired by an ex vivo device 290. In an embodiment, the ex vivo device may include a wired or a wireless device. In an embodiment, the ex vivo device may include an x-ray, fluoroscope, near infrared (NIR), or ultrasound device. In an embodiment, the medical image may include a digital medical image that includes a region of interest of the mammalian body part. In an embodiment, the medical image may include an analog medical image that includes a region of interest of the mammalian body part.

In an embodiment, the receiver circuit 222 is configured to receive a reference image that includes a landmark subsurface feature 216 of the mammalian body part, such as the landmark subsurface feature 216A. The landmark subsurface feature 216 has a spatial relationship to the region of interest 217, such as the spatial relationship 217A. The landmark subsurface feature is of the body part 210 and not of a subsurface feature of another proximate mammalian body part. For example, if the body part is a kidney, the landmark subsurface feature is a subsurface feature of the kidney and not of a feature of another body part, such as a spinal column. For example, the landmark subsurface feature may include a landmark subsurface feature imageable by x-ray, fluoroscope, NIR, or ultrasound. For example, the landmark subsurface feature may include a landmark subsurface feature distinguishable or unique from another landmark subsurface feature of the body part.

In an embodiment, the reference image may include a two-dimensional or three-dimensional digital image that includes a landmark subsurface feature 216 of the mammalian body part 210. The landmark subsurface feature has a spatial relationship to the region of interest. For example, the landmark subsurface feature may include a landmark subsurface feature having an indicated, determinable, estimable, or inferable spatial relationship to the region of interest. For example, the reference image of the landmark subsurface feature may include a reference image that was acquired using at least two wavelength energies. For example, the wavelength energies may include visible light, near infrared, infrared, or ultrasound. For example, the reference image may include a selected landmark subsurface feature of the mammalian body part that has a spatial relationship to the region of interest. For example, the landmark subsurface feature may be selected by a health care provider, such as an endoscopist, by a health care provider according to the mammalian body part involved, or by a machine, such as during a virtual colonoscopy.

In an embodiment, the reference image may include a reference digital image that includes a landmark subsurface feature of the mammalian body part. For example, the reference image may include a reference analog image that includes a landmark subsurface feature of the mammalian body part. In an embodiment, the reference image may include (i) a landmark subsurface feature of the mammalian body part, and (ii) data indicative of an environment when the reference image was acquired. The landmark subsurface feature has a spatial relationship to the region of interest. For example, the data indicative of an environment may include at least one of location data, date/time, temperature of the mammalian body part, or an off-set between the imaging device used to view or capture the medical image and the image capture device used to capture the reference image. For example, the data indicative of an environment may include pH of the mammalian body part, such as for example, a pH of the GI tract or a lumen. For example, the landmark subsurface may include a landmark subsurface feature having a location, position, orientation, distance, directional, alignment, or axial relationship to the region of interest. For example, FIG. 4 illustrates an orientation of the landmark subsurface feature 216B with respect to the region of interest 214B. Continuing with FIG. 3, for example, the landmark subsurface feature may include a landmark subsurface feature described by blood carried in a blood vessel of the mammalian body part, the landmark subsurface feature described by blood carried in a blood vessel having a spatial relationship to the region of interest. For example, the landmark subsurface feature may include a landmark subsurface feature described by a pattern formed by a subsurface blood vessel, nerve, void, border, component, tissue, or structural feature of the mammalian body part, the pattern formed having a spatial relationship to the region of interest.

In an embodiment, the reference image may include an electronic signal indicative of a reference image that includes a landmark subsurface feature of the mammalian body part, the landmark subsurface feature having a spatial relationship to the region of interest. For example, the reference image may include a virtual landmark subsurface feature formed by at least two subsurface features of the mammalian body part, the virtual landmark subsurface feature having a spatial relationship to the region of interest. For example, the landmark subsurface feature 216B and the landmark subsurface feature 216C may be combined into a virtual landmark subsurface feature orientated toward the region of interest 214B.

In an embodiment, the reference image may include a landmark subsurface feature having a spatial relationship to the region of interest. The reference image was acquired using at least one of a visible light, near infrared light, infrared light, ultraviolet light, ultrasound energy, passive thermal, or active thermal based imaging. In an embodiment, the reference image may include a landmark subsurface feature of the mammalian body part. The landmark subsurface feature has a spatial relationship to the region of interest. The reference image was acquired using at least one of a PET, x-ray, CAT, coherence tomography (CT) image, magnetic resonance imaging (MRI) image, fluoroscopy, fluorescence based imaging, ultrasound, or microscopy imaging modality. In an embodiment, the reference image may include a landmark subsurface feature of the mammalian body part. The landmark subsurface feature has a spatial relationship to the region of interest. The reference image was acquired using at least two wavelength energies. For example, wavelength energies may include visible light, near infrared, infrared, or ultrasound.

In an embodiment, the reference image may include a landmark subsurface feature of the mammalian body part. The landmark subsurface feature has a spatial relationship to the region of interest. The reference image that includes indicia of the depth of the subsurface feature below a surface of the mammalian body part. In an embodiment, the reference image may be acquired by a body-insertable device while a portion of the body-insertable device was present in a cavity or lumen of the mammalian body part. The reference image that includes a landmark subsurface feature of the cavity or lumen of the mammalian body part having a spatial relationship to the region of interest. In an embodiment, the reference image may include a landmark subsurface feature of the mammalian body part. The landmark subsurface feature has an indicated, determinable, estimable, or inferable spatial relationship to the region of interest.

In an embodiment, the system 220 includes the registration circuit 224 configured to register a location, position, orientation, distance, directional, alignment, or axial relationship of the region of interest relative to the landmark subsurface feature of the mammalian body part. In an embodiment, the registration circuit may be configured to (i) extract the landmark subsurface feature from the reference image, and (ii) register a spatial relationship of the region of interest relative to the extracted landmark subsurface feature. In an embodiment, the registration circuit may be configured to (i) classify the landmark subsurface feature, and (ii) register a spatial relationship of the region of interest relative to the classified landmark subsurface feature. In an embodiment, the registration circuit may be configured to (i) recognize a pattern evidenced by the landmark subsurface feature, and (ii) register a spatial relationship of the region of interest relative to the recognized pattern evidenced by the landmark subsurface feature. In an embodiment, the registration circuit may be configured to (i) select a pattern presented by the landmark subsurface feature as substantially suitable for image registration, and (ii) register a spatial relationship of the region of interest relative to the selected pattern presented by the landmark subsurface feature. In an embodiment, the registration circuit may be configured to register a spatial relationship of the region of interest relative to at least two landmark subsurface features of the mammalian body part. In an embodiment, the registration circuit may be configured to register a spatial relationship including an orientation of the region of interest relative to the landmark subsurface feature of the mammalian body part. In an embodiment, the registration circuit may be configured to register a spatial relationship including an orientation of the landmark subsurface feature of the mammalian body part relative to the region of interest. In an embodiment, the registration circuit may be configured to register a spatial relationship of the landmark subsurface feature relative to the region of interest. The registration includes an orientation of the landmark subsurface feature and an orientation of the region of interest.

For example, "register" or "registration" may include systematically placing separate images in a common frame of reference so that the information they contain can be optimally integrated or compared. *Medical Image Registration*, §1.1 (Joseph V. Hajnal and Derek L. G. Hill, editors (2001). For example, a registration of the region of interest and the landmark subsurface feature of the mammalian body part may include registering a polyp of a colon to landmark blood vessel subsurface feature. For example, a registration the region of interest and the landmark subsurface feature of the mammalian body part may include registering the region of interest in reference, relative to, or with regard to the landmark subsurface feature of the mammalian body part. For example, a registration of the region of interest and the landmark subsurface feature of the mammalian body part may include transforming them into one coordinate system. For example, a registration of the region of interest and the landmark subsurface feature of the mammalian body part may include spatially relating the region of interest in reference to the landmark subsurface feature of the mammalian body part. For example, the registering the region of interest 214A and the landmark subsurface feature 216A of the mammalian body part 210 may indicate the spatial relationship 217A expressed as a distance, such as 2 mm, between a polyp of a colon and a landmark blood vessel feature. In another example, a registration of the region of interest 214A and the landmark subsurface feature 216A of the mammalian body part may indicate a spatial relationship 217A expressed in x, y, and z coordinates based upon a common point of reference. The common point of reference may be the region of interest, the landmark subsurface feature, or a third point of reference. In another example, a registration of the region of interest 214A and the landmark subsurface feature 216A of the mammalian body part may indicate a spatial relationship 217A expressed in x, y, and z coordinates. In an example, a registration may include registering the region of interest 214A and the landmark subsurface feature 216A of the mammalian body part in one coordinate system.

The system 220 includes a computer-readable media 235 configured to maintain informational data corresponding to the registration of the region of interest and the landmark subsurface feature of the mammalian body part 210. In an embodiment, the computer-readable media may be managed by a computer storage device 234. In an embodiment, the computer-readable media may include a computer-readable media configured to maintain and to provide access to informational data corresponding to the registration of the relationship of the region of interest relative to the landmark subsurface feature of the mammalian body part. In an embodiment, the computer-readable media may include a tangible computer-readable media. In an embodiment, the computer-readable media may include a communications media.

In an embodiment, the system 220 may further include an extraction engine 238 configured to extract the landmark subsurface feature from the reference image. An example of an extraction engine is described by Datacraft Co., Ltd. & Hokkaido University, *Image Feature Extraction Engine*, http://www.igvpj.jp/cp2_en/common/rc/category00/image-feature-extraction-engin-1.html (last accessed Feb. 23, 2010). For example, the extraction engine may be configured to use a pattern recognition technique to extract information from images. In an embodiment, the extraction engine may be configured to use an artificial intelligence technique to extract information from images.

In an embodiment, the system 220 may include a communication circuit 242 configured to output the informational data. In an embodiment, the communication circuit 242 may be configured to provide a notification to at least one of humans (such as the person 296), computers (such as the computing device 292), or systems (not illustrated). The notification is indicative of the registration of the spatial relationship of the region of interest relative to the landmark subsurface feature of the mammalian body part. For example, the system may include a processor 232. For example, the processor may perform or assist a performance of one or more operations performed by the system. For example, the processor may be implemented using the processing unit 21 described in conjunction with FIG. 1, or using the processor 120 described in conjunction with FIG. 2. For example, the system may include a thin computing device, such as the thin computing device 20 described in conjunction with FIG. 1, or using the computing device 110 described in conjunction with FIG. 2. For example, the thin computing device 20 or the computing device 110 may implement one or more of the circuits of the system 220.

Returning to the environment 200 illustrated by FIGS. 3 and 4. In an alternative embodiment, the system 220 includes the registration circuit 224. The registration circuit is configured to register the region of interest 214 of the mammalian body part 210 and the landmark subsurface feature 216 of the mammalian body part. The registration is at least partially based on a spatial relationship 217 between the landmark subsurface feature and the region of interest. In an embodiment, the landmark subsurface feature has an indicated, known, determinable, estimable, or inferable spatial relationship to the region of interest.

The system 220 also includes the computer-readable media 235 configured to maintain informational data corresponding to the registration of the region of interest and the landmark subsurface feature of the mammalian body part. In an embodiment, the system further includes the communication circuit 242 configured to output the informational data corresponding to the registration of the spatial relationship of the region of interest and the landmark subsurface feature of the mammalian body part.

FIG. 5 illustrates an example operational flow 300. After a start operation, the operation flow includes a medical image receiving operation 310. The medical image receiving operation includes receiving a medical image that includes a region of interest of a mammalian body part. In an embodiment, the medical image receiving operation may be implemented using the receiver circuit 222 described in conjunction with FIG. 3. In an alternative embodiment, the medical image receiving operation may be implemented using the thin computing device 20 described in conjunction with FIG. 1 or the computing device 110 described in conjunction with FIG. 2.

A reference image receiving operation 350 includes receiving a reference image that includes a landmark subsurface feature of the mammalian body part. The landmark subsurface feature has a spatial relationship to the region of interest. In an embodiment, the reference image receiving operation may be implemented using the receiver circuit 222 described in conjunction with FIG. 3. In an alternative embodiment, the reference image receiving operation may be implemented using the thin computing device 20 described in conjunction with FIG. 1 or the computing device 110 described in conjunction with FIG. 2. A registration operation 410 includes registering the spatial relationship of the region of interest and the landmark subsurface feature of the mammalian body part. In an embodiment, the registration operation may be implemented using the registration circuit 224 described in conjunction with FIG. 3. In an alternative embodiment, the registration operation may be implemented using the thin computing device 20 described in conjunction with FIG. 1 or the computing device 110 described in conjunction with FIG. 2. A storage operation 440 includes maintaining in a computer-readable media informational data corresponding to the registration of the spatial relationship of the region of interest and the landmark subsurface feature of the mammalian body part. In an embodiment, the storage operation may be implemented using the computer-readable media 235 described in conjunction with FIG. 3. In an alternative embodiment, the storage operation may be implemented using a computer-readable media associated with the thin computing device 20 described in conjunction with FIG. 1 or a computer-readable media associated with the computing device 110 described in conjunction with FIG. 2. The operational flow includes an end operation.

FIG. 6 illustrates alternative embodiments of the medical image receiving operation 310 of FIG. 5. The medical image receiving operation 310 may include at least one additional embodiment. The at least one additional embodiment may include an operation 312, an operation 314, an operation 316, an operation 318, an operation 322, an operation 324, an operation 326, or an operation 328. The operation 312 includes receiving a medical image that includes a region of interest of a cavity or lumen of a mammalian body part. The operation 314 includes receiving a medical image that includes a region of interest of a surface of a cavity or lumen of a mammalian body part. The operation 316 includes receiving a medical image that includes a region of interest of a wall, membrane, or epithelial layer of a mammalian body part. The operation 318 includes receiving a medical image that includes a region of interest of an orifice, canal, cavity, or hollow region of a mammalian body part. The operation 322 includes receiving a medical image that includes information or data indicative of a region of interest of a mammalian body part. The operation 324 includes receiving a medical image that includes a region of interest of a mammalian body part, the medical image acquired using at least one of a PET, x-ray, CAT, coherence tomography (CT) image, magnetic resonance imaging (MRI) image, fluoroscopy, fluorescence based imaging, or ultrasound imaging modality. The operation 326 includes receiving a medical image that includes a region of interest of a mammalian body part and that was acquired using at least one of a visible light, near infrared light, infrared light, passive thermal, or active thermal imaging modality. The operation 328 includes facilitating an acquisition of a medical image of a region of interest of a mammalian body part.

FIG. 7 illustrates alternative embodiments of the medical image receiving operation 310 of FIG. 5. The medical image receiving operation 310 may include at least one additional embodiment. The at least one additional embodiment may include an operation 332, an operation 334, or an operation 336. The operation 332 includes acquiring a medical image that includes a region of interest of a mammalian body part. The operation 334 includes receiving a medical image that includes a selected region of interest of a mammalian body part. In an additional operation, both the medical image and the reference image are received from a single device (not illustrated). In an additional operation, the medical image is received from a first device and the reference image is received from a second device (not illustrated). In an embodiment, the operation 336 includes receiving information or data indicative of a region of interest of a mammalian body part that includes a landmark subsurface feature of the mammalian body part, the landmark subsurface feature having a spatial relationship to the region of interest.

Figure 8:
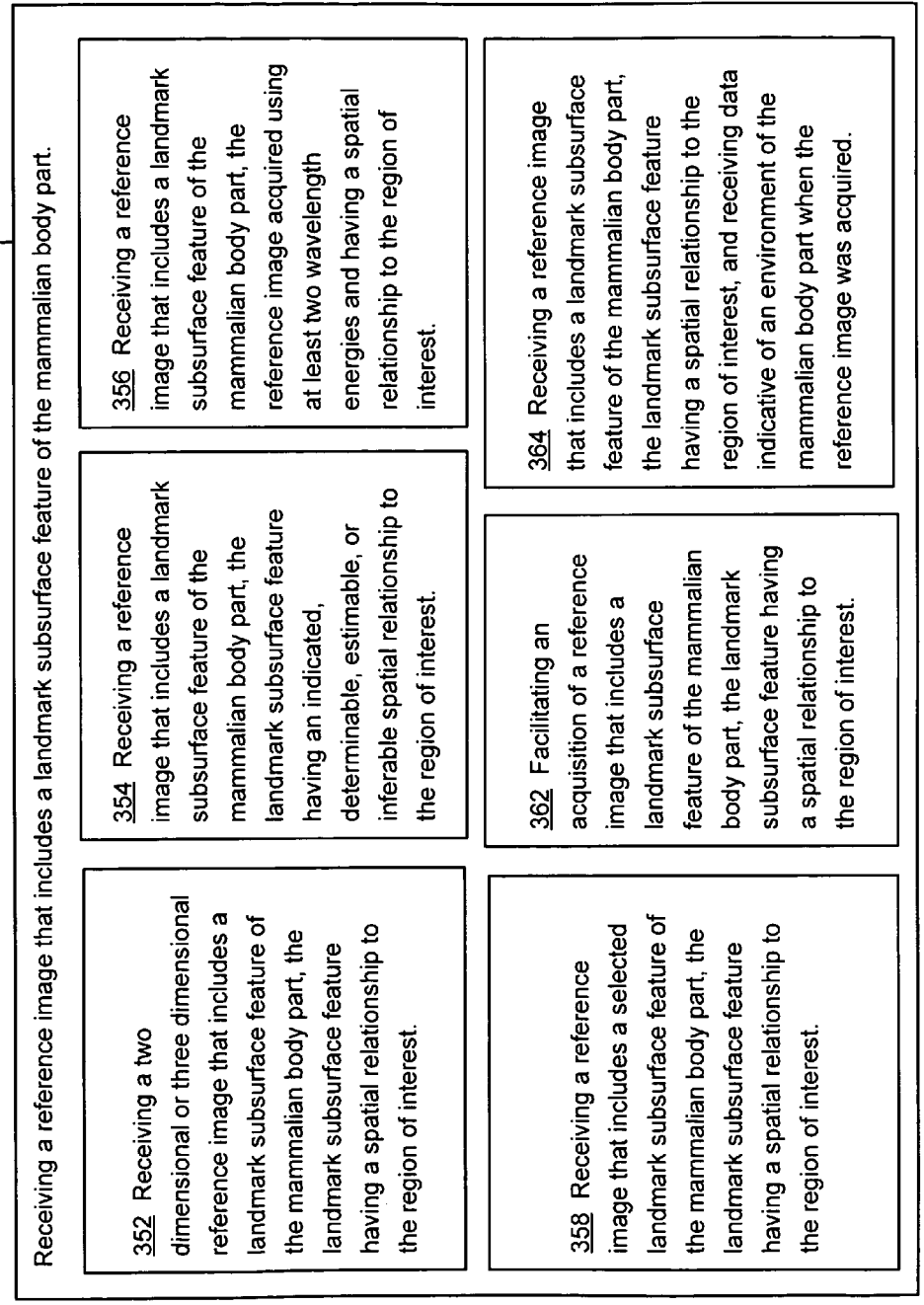
FIG. 8 illustrates alternative embodiments of the reference image receiving operation 350 of FIG. 5.

FIG. 8 illustrates alternative embodiments of the reference image receiving operation 350 of FIG. 5. The reference image receiving operation 350 may include at least one additional embodiment. The at least one additional embodiment may include an operation 352, an operation 354, an operation 356, an operation 358, an operation 362, or an operation 364. The operation 352 includes receiving a two dimensional or three dimensional reference image that includes a landmark subsurface feature of the mammalian body part. The landmark subsurface feature has a spatial relationship to the region of interest. The operation 354 includes receiving a reference image that includes a landmark subsurface feature of the mammalian body part. The landmark subsurface feature has an indicated, determinable, estimable, or inferable spatial relationship to the region of interest. The operation 356 includes receiving a reference image that includes a landmark subsurface feature of the mammalian body part. The reference image acquired using at least two wavelength energies and having a spatial relationship to the region of interest. The operation 358 includes receiving a reference image that includes a selected landmark subsurface feature of the mammalian body part. The landmark subsurface feature has a spatial relationship to the region of interest. The operation 362 includes facilitating an acquisition of a reference image that includes a landmark subsurface feature of the mammalian body part. The landmark subsurface feature has a spatial relationship to the region of interest. In an embodiment, the facilitating an acquisition includes capturing a reference image that includes a landmark subsurface feature of the mammalian body part. The operation 364 includes receiving a reference image that includes a landmark subsurface feature of the mammalian body part, and receiving data indicative of an environment when the reference image was acquired. The landmark subsurface feature has a spatial relationship to the region of interest.

Figure 9:
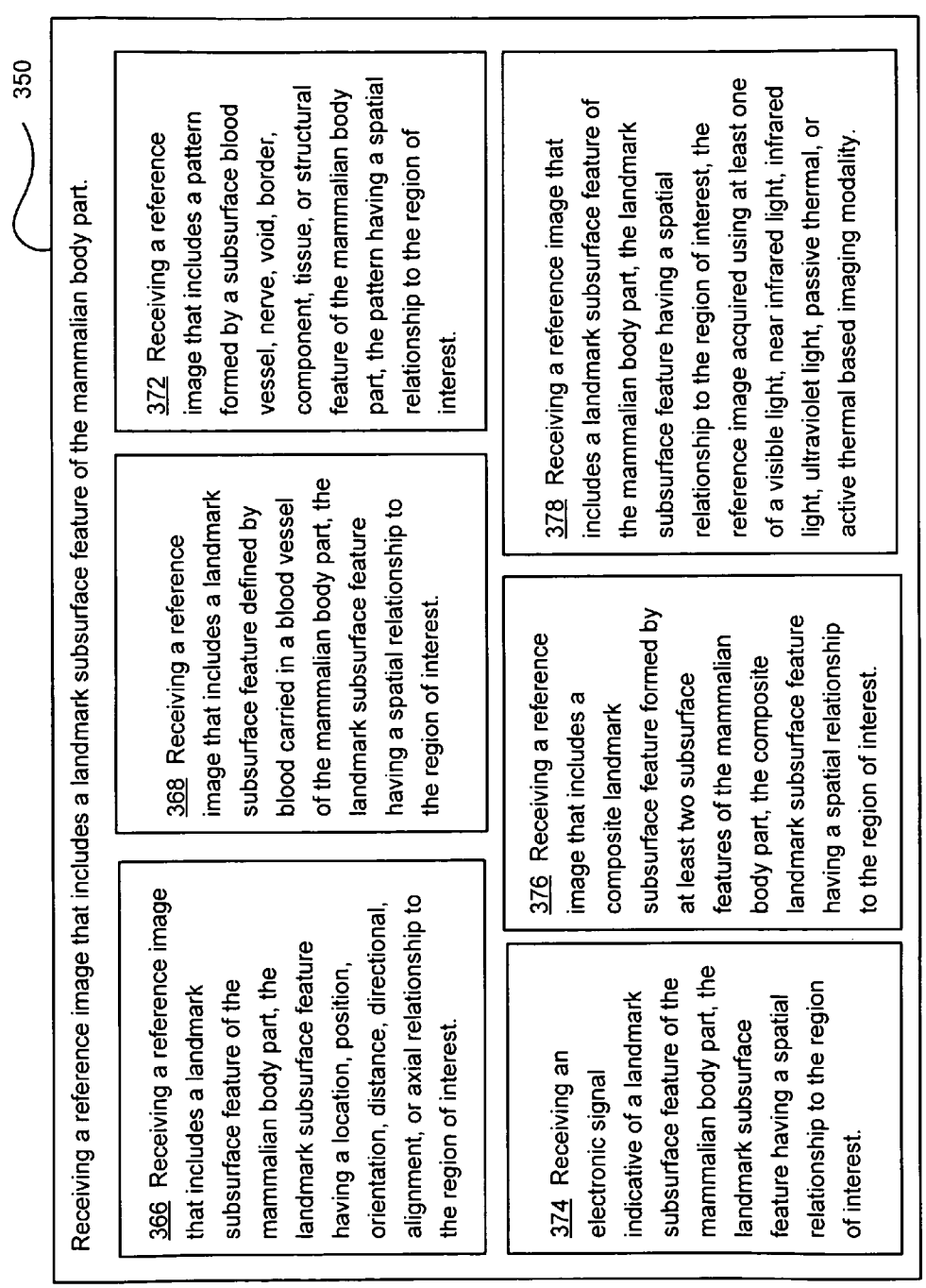
FIG. 9 illustrates alternative embodiments of the reference image receiving operation 350 of FIG. 5.

FIG. 9 illustrates alternative embodiments of the reference image receiving operation 350 of FIG. 5. The reference image receiving operation may include at least one additional embodiment. The at least one additional embodiment may include an operation 366, an operation 368, an operation 372, an operation 374, an operation 376, or an operation 378. The operation 366 includes receiving a reference image that includes a landmark subsurface feature of the mammalian body part. The landmark subsurface feature has a location, position, orientation, distance, directional, alignment, or axial relationship to the region of interest. The operation 368 includes receiving a reference image that includes a landmark subsurface feature defined by blood carried in a blood vessel of the mammalian body part. The landmark subsurface feature has a spatial relationship to the region of interest. In an embodiment, the operation 372 includes receiving a reference image that includes a pattern formed by a subsurface blood vessel, nerve, void, border, component, tissue, or structural feature of the mammalian body part, the pattern having a spatial relationship to the region of interest. In an embodiment, the operation 374 includes receiving an electronic signal indicative of a landmark subsurface feature of the mammalian body part. The landmark subsurface feature has a spatial relationship to the region of interest. In an embodiment, the operation 376 includes a reference image that includes a composite landmark subsurface feature formed by at least two subsurface features of the mammalian body part. The composite landmark subsurface feature has a spatial relationship to the region of interest. In an embodiment, the operation 378 includes receiving a reference image that includes a landmark subsurface feature of the mammalian body part. The landmark subsurface feature has a spatial relationship to the region of interest. The reference image was acquired using at least one of a visible light, near infrared light, infrared light, ultraviolet light, ultrasound energy, passive thermal, or active thermal based imaging.

Figure 10:
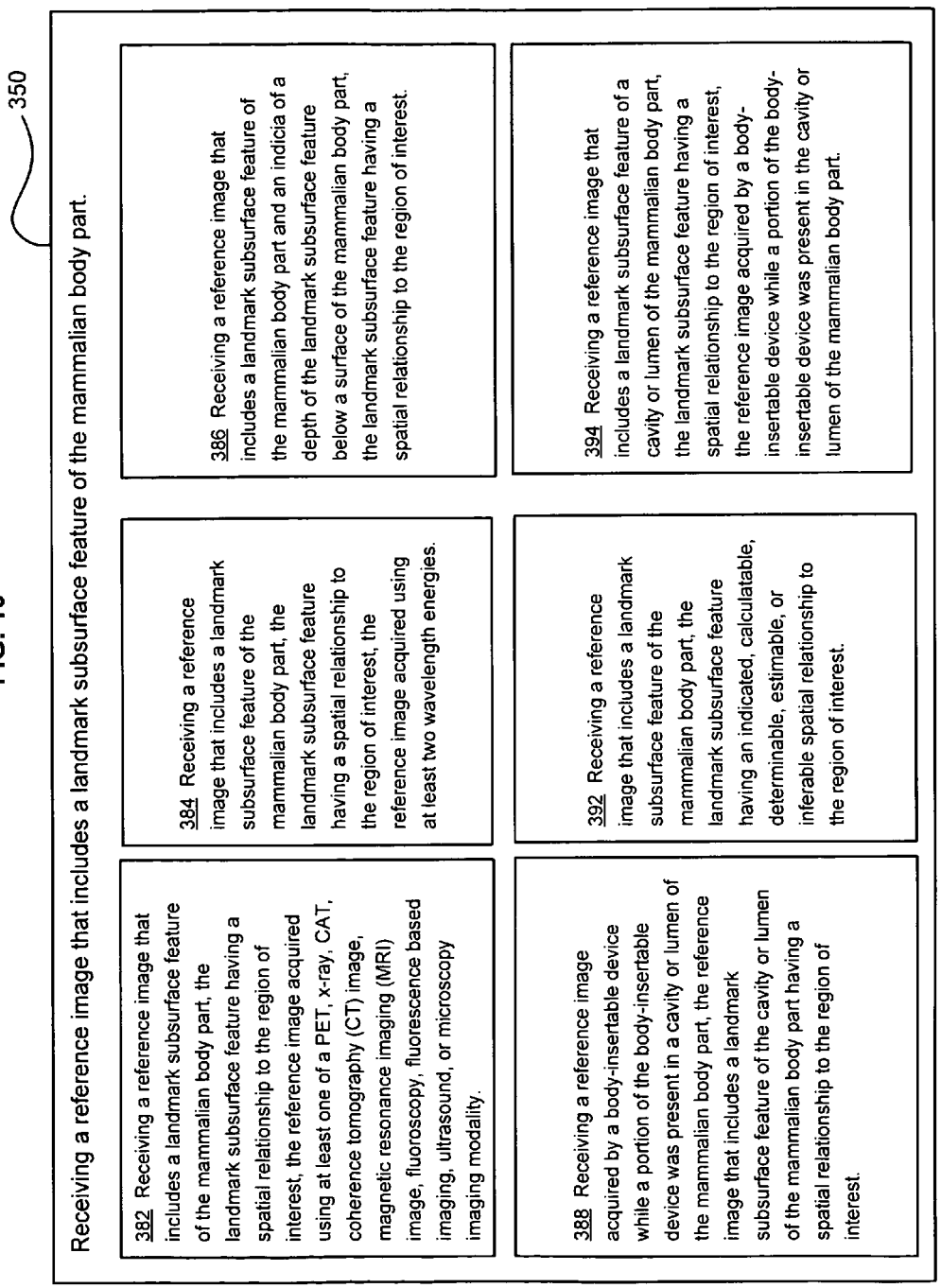
FIG. 10 illustrates alternative embodiments of the reference image receiving operation 350 of FIG. 5.

FIG. 10 illustrates alternative embodiments of the reference image receiving operation 350 of FIG. 5. The reference image receiving operation may include at least one additional embodiment. The at least one additional embodiment may include an operation 382, an operation 384, an operation 386, an operation 388, an operation 392, or an operation 394. The operation 382 includes receiving a reference image that includes a landmark subsurface feature of the mammalian body part. The landmark subsurface feature has a spatial relationship to the region of interest. The reference image was acquired using at least one of a PET, x-ray, CAT, coherence tomography (CT) image, magnetic resonance imaging (MRI) image, fluoroscopy, fluorescence based imaging, ultrasound, or microscopy imaging modality. The operation 384 includes receiving a reference image that includes a landmark subsurface feature of the mammalian body part. The landmark subsurface feature has a spatial relationship to the region of interest. The reference image was acquired using at least two wavelength energies. The operation 386 includes receiving a reference image that includes a landmark subsurface feature of the mammalian body part. The reference image further includes indicia of a depth of the landmark subsurface feature below a surface of the mammalian body part. The landmark subsurface feature has a spatial relationship to the region of interest. The operation 388 includes receiving a reference image acquired by a body-insertable device while a portion of the body-insertable device was present in a cavity or lumen of the mammalian body part. The reference image includes a landmark subsurface feature of the cavity or lumen of the mammalian body part has a spatial relationship to the region of interest. The operation 392 includes receiving a reference image that includes a landmark subsurface feature of the mammalian body part. The landmark subsurface feature an indicated, calculatable, determinable, estimable, or inferable spatial relationship to the region of interest. The operation 394 includes receiving a reference image that includes a landmark subsurface feature of a cavity or lumen of the mammalian body part. The landmark subsurface feature has a spatial relationship to the region of interest, and the reference image was acquired by a body-insertable device while a portion of the body-insertable device was present in the cavity or lumen of the mammalian body part.

Figure 11:
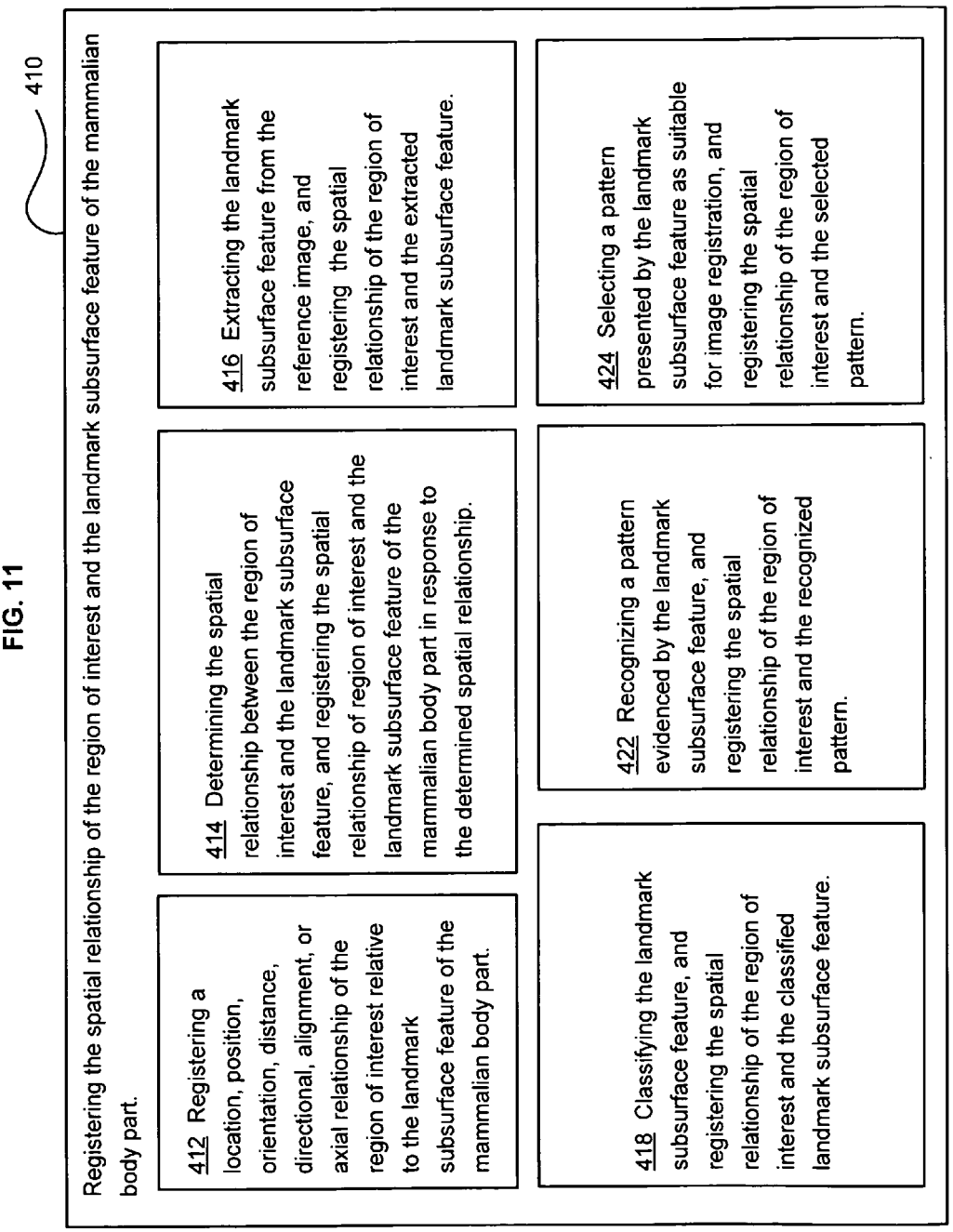
FIG. 11 illustrates alternative embodiments of the registration operation 410 of FIG. 5.

FIG. 11 illustrates alternative embodiments of the registration operation 410 of FIG. 5. The registration operation may include at least one additional embodiment. The at least one additional embodiment may include an operation 412, an operation 414, an operation 416, an operation 418, an operation 422, or an operation 424. The operation 412 includes registering a location, position, orientation, distance, directional, alignment, or axial relationship of the region of interest relative to the landmark subsurface feature of the mammalian body part. The operation 414 includes the spatial relationship between the region of interest and the landmark subsurface feature, and registering the spatial relationship of region of interest and the landmark subsurface feature of the mammalian body part in response to the determined spatial relationship. The spatial relationship may include a two-dimensional or a three-dimensional spatial relationship. The operation 416 includes extracting the landmark subsurface feature from the reference image, and registering the spatial relationship of the region of interest and the extracted landmark subsurface feature. The operation 418 includes classifying the landmark subsurface feature, and registering the spatial relationship of the region of interest and the classified landmark subsurface feature. For example, the landmark subsurface feature may be classified as a blood vessel, a component, or a structural feature. The operation 422 includes recognizing a pattern evidenced by the landmark subsurface feature, and registering the spatial relationship of the region of interest and the recognized pattern. The operation 424 includes selecting a pattern presented by the landmark subsurface feature as suitable for image registration, and registering the spatial relationship of the region of interest and the selected pattern.

FIG. 12 illustrates alternative embodiments of the registration operation 410 of FIG. 5. The registration operation may include at least one additional embodiment. The at least one additional embodiment may include an operation 426, an operation 428, an operation 432, or an operation 434. The operation 426 includes registering the spatial relationship of the region of interest relative to at least two landmark subsurface features of the mammalian body part. The operation 428 includes registering the spatial relationship including an orientation of the region of interest relative to the landmark subsurface feature of the mammalian body part. The operation 432 includes registering the spatial relationship including an orientation of the landmark subsurface feature of the mammalian body part and the region of interest. The operation 434 includes registering the spatial relationship including an orientation of the landmark subsurface feature of the mammalian body part and including an orientation of the region of interest.

FIG. 13 illustrates alternative embodiments of the operational flow 300 of FIG. 5. The operational flow may include at least one additional embodiment, such as an extraction operation 450. The extraction operation includes extracting the landmark subsurface feature from the reference image. The extraction operation may include at least one additional embodiment. The at least one additional embodiment may include an operation 452 or an operation 454. The operation 452 includes extracting the landmark subsurface feature from the reference image using a pattern recognition technique. The operation 454 includes extracting the landmark subsurface feature from the reference image using an artificial intelligence technique.

FIG. 14 illustrates alternative embodiments of the operational flow 300 of FIG. 5. The operational flow may include at least one additional embodiment 460. The at least one additional embodiment 460 may include an operation 462, an operation 464, an operation 466, or an operation 468. The operation 462 includes providing electronic access to the informational data. The operation 464 includes transforming the informational data corresponding into a particular visual depiction of the registration of the spatial relationship of the region of interest and the landmark subsurface feature of the mammalian body part. The operation 466 includes outputting the informational data. The operation 468 includes providing a notification that is at least partially based on the informational data to at least one of a human, computer, or system.

FIG. 15 illustrates a computer program product 500. The computer program product includes a computer-readable media 510 bearing program instructions 520. The program instructions, when executed by a processor of a computing device, cause the computing device to perform a process. The process includes receiving a medical image that includes a region of interest of a mammalian body part. The process includes receiving a reference image that includes a landmark subsurface feature of the mammalian body part. The landmark subsurface feature has a spatial relationship to the region of interest. The process includes registering the region of interest and the landmark subsurface feature of the mammalian body part. The process includes storing in another computer-readable media operably coupled with the processor informational data corresponding to the registration of the region of interest and the landmark subsurface feature of the mammalian body part.

In an embodiment, the process of the program instructions 520 may include at least one additional process. The at least one additional process may include a process 522 or a process 524. The process 522 includes transforming the informational data into data useable in providing a particular visual depiction of the region of interest relative to the landmark subsurface feature of the mammalian body part. The process 524 includes providing a notification that is at least partially based on the informational data to at least one of a human, computer, or system. In an embodiment, the computer-readable media 510 includes a tangible computer-readable media 526. In an embodiment, the computer-readable media includes a communications medium 528.

Figure 16:
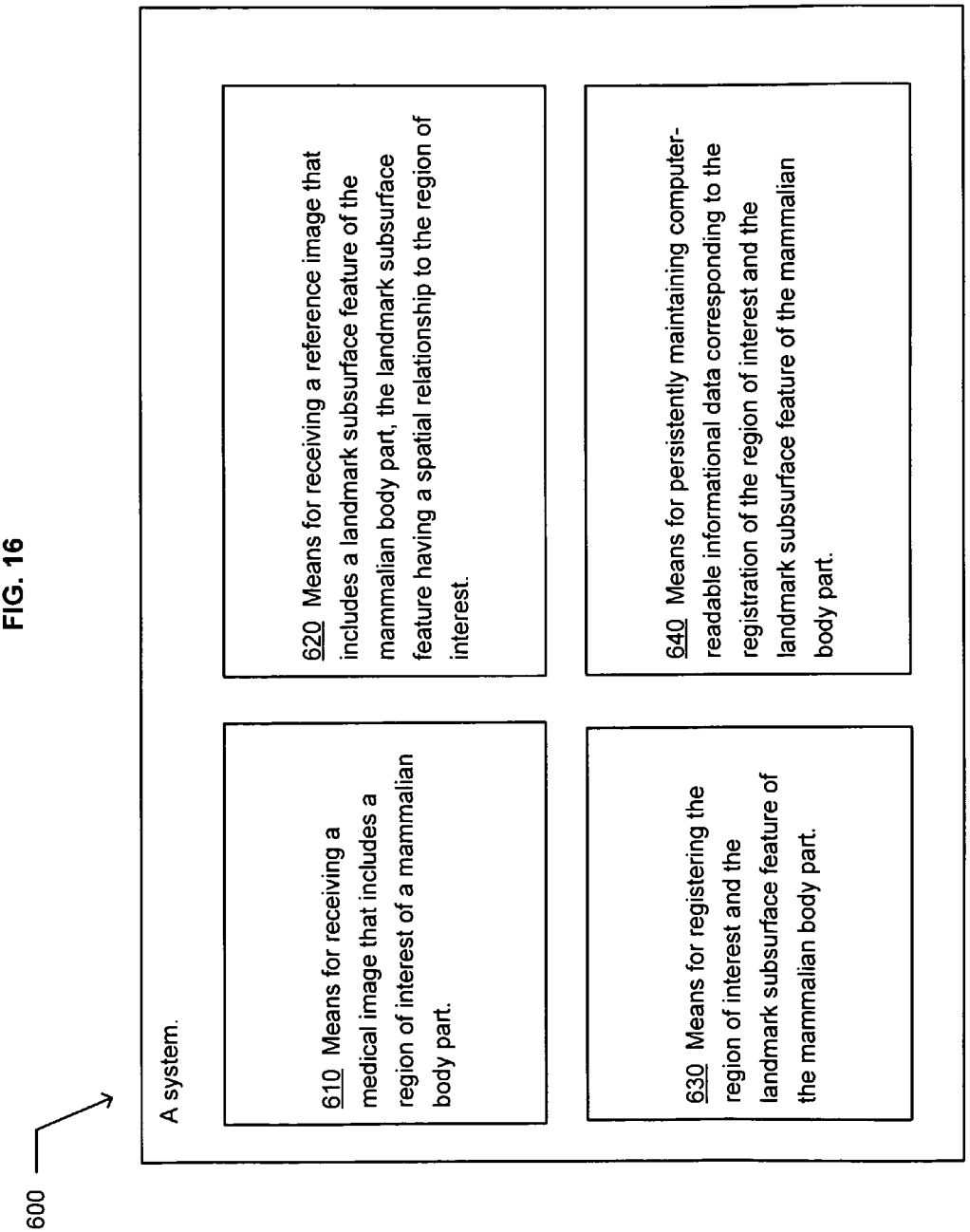
FIG. 16 illustrates an example system.

FIG. 16 illustrates an example system 600. The system includes means 610 for receiving a medical image that includes a region of interest of a mammalian body part. The system also includes means 620 for receiving a reference image that includes a landmark subsurface feature of the mammalian body part. The landmark subsurface feature has a spatial relationship to the region of interest. The system further includes means 630 for registering the region of interest and the landmark subsurface feature of the mammalian body part. The system also includes means 640 for persistently maintaining computer-readable informational data corresponding to the registration of the region of interest and the landmark subsurface feature of the mammalian body part.

Figure 17:
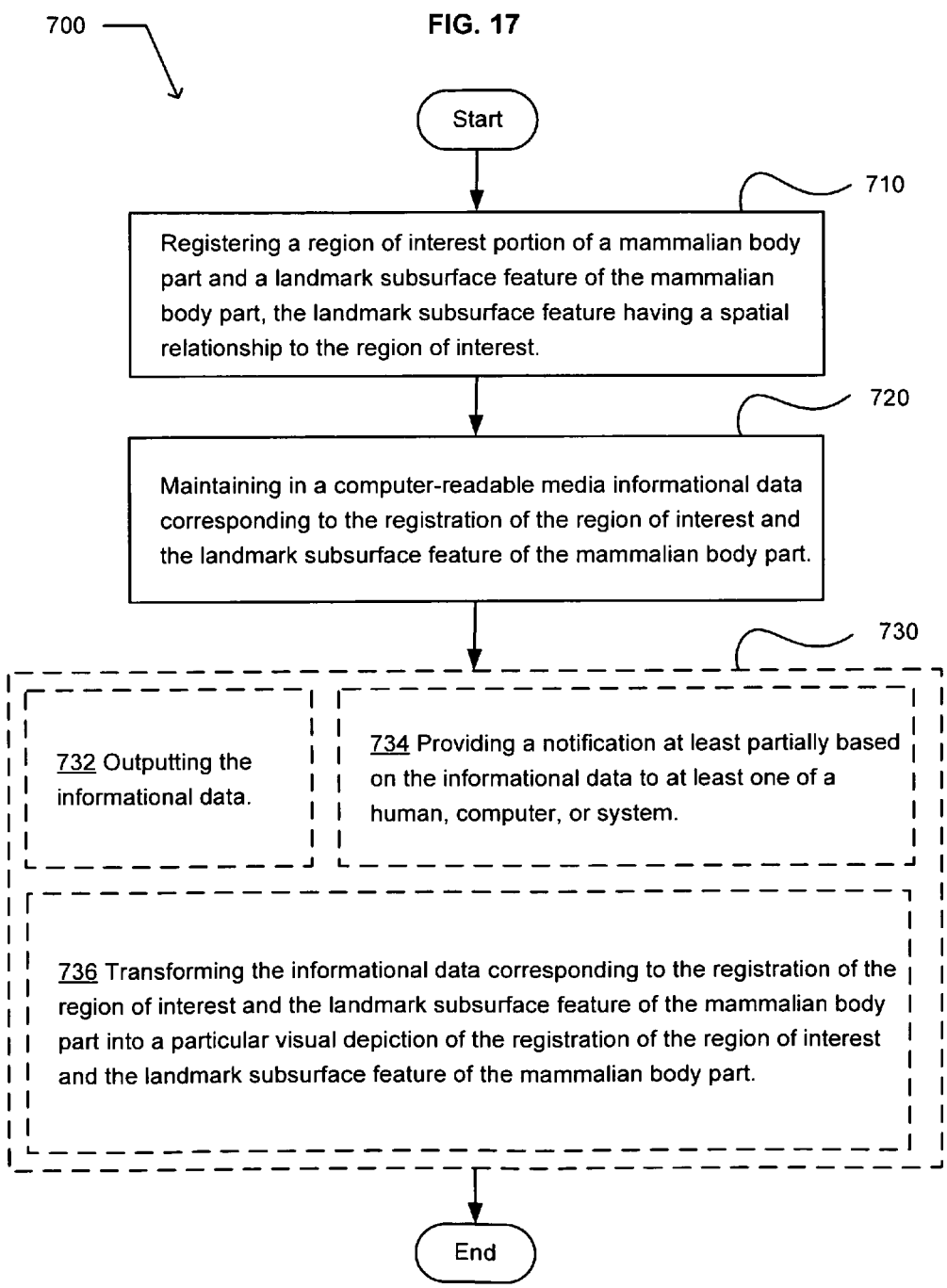
FIG. 17 illustrates an example operational flow.

FIG. 17 illustrates an example operational flow 700. After a start operation, the operational flow includes a registration operation 710. The registration operation includes registering a region of interest of a mammalian body part and a landmark subsurface feature of the mammalian body part. The registration is at least partially based on a spatial relationship between the landmark subsurface feature and the region of interest. In an embodiment, the landmark subsurface has an indicated, known, determinable, estimable, or inferable spatial relationship to the region of interest. For example, the registration operation may be implemented using the registration circuit 224 described in conjunction with FIG. 3. For example, the registration operation may be implemented using the thin computing device 20 described in conjunction with FIG. 1 or the computing device 110 described in conjunction with FIG. 2. A storage operation 720 includes maintaining in a computer-readable media informational data corresponding to the registration of the region of interest and the landmark subsurface feature of the mammalian body part. For example, the storage operation may be implemented using the computer-readable media 235 described in conjunction with FIG. 3. For example, the registration operation may be implemented using a computer-readable media associated with the thin computing device 20 described in conjunction with FIG. 1 or a computer-readable media associated with the computing device 110 described in conjunction with FIG. 2. The operational flow includes an end operation.

In an embodiment, the operational flow may include at least one additional embodiment 730. The at least one additional embodiment may include an operation 732, an operation 734, or an operation 736. The operation 732 includes outputting the informational data. The operation 734 includes providing a notification that is at least partially based on the informational data to at least one of a human, computer, or system. The operation 736 includes transforming the informational data into a particular visual depiction of the registration of the region of interest and the landmark subsurface feature.

Figure 18:
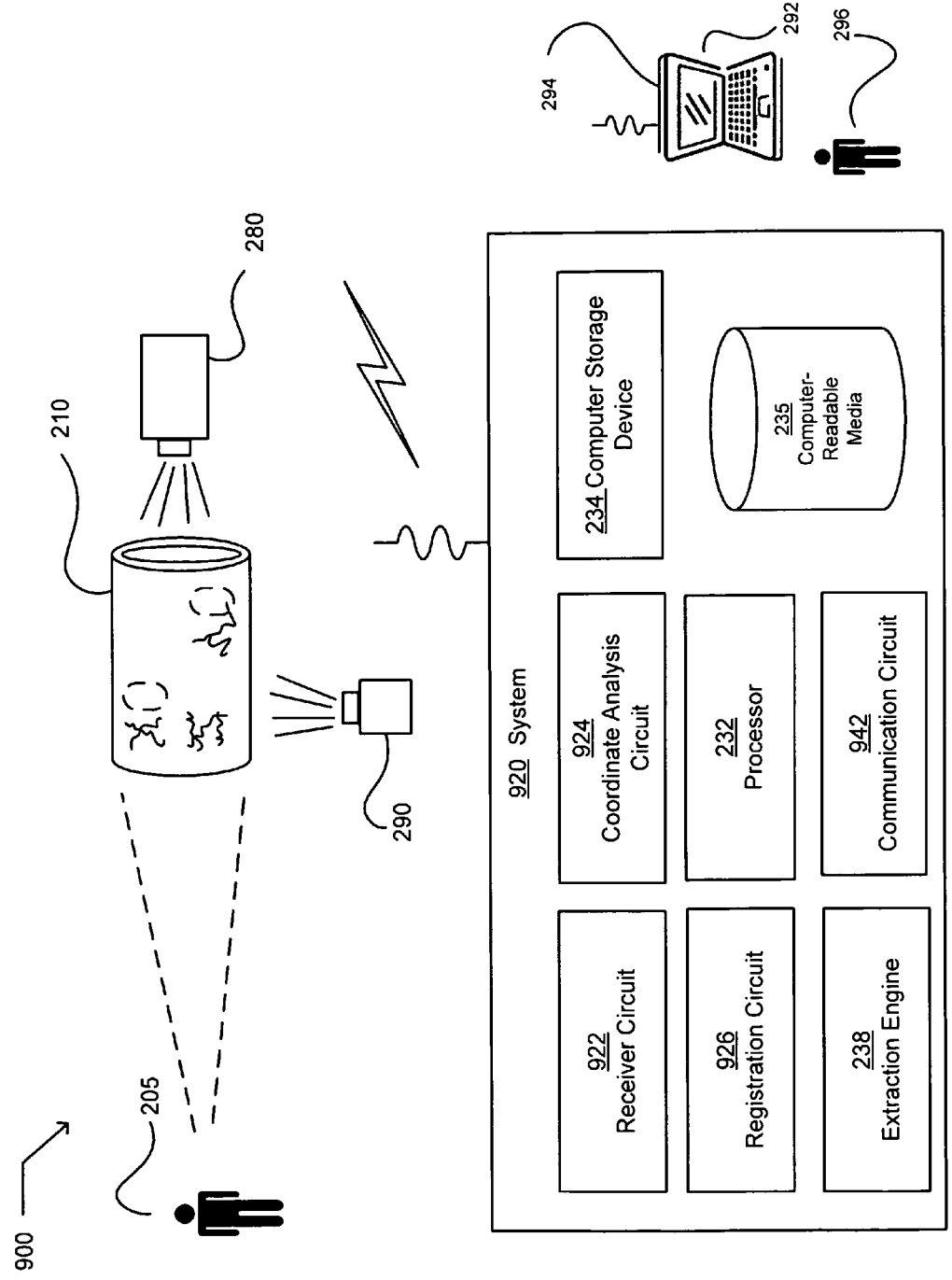
FIG. 18 illustrates an example environment.

FIG. 18 illustrates an example environment 900. The example environment includes the mammal 205, illustrated by the human profile, the mammalian body part 210, illustrated as tubular structure, and a system 920. The environment may also include the body-insertable device 280, or the ex vivo device 290.

The system includes a receiver circuit 922. The receiver circuit is configured to receive (i) a first medical image that includes a first region of interest of a mammalian body part, and (ii) a second medical image that includes a second region of interest of the mammalian body part. The receiver circuit is configured to receive (iii) a first reference image that includes a first landmark subsurface feature of the mammalian body part. The first landmark subsurface feature has a first spatial relationship to the first region of interest. The receiver circuit is configured to receive (iv) a second reference image that includes a second landmark subsurface feature of the mammalian body part. The second landmark subsurface feature has a second spatial relationship to the second region of interest. In an embodiment, the receiver circuit may include at least two sub-circuits (not illustrated). For example, a first sub-circuit may be configured to receive the first medical image and the second medical image. A second sub-circuit may be configured to receive the first reference image and the second reference image.

The system 920 includes a coordinate analysis circuit 924. The coordinate analysis circuit is configured to determine a common frame of reference that is at least partially based on the first landmark subsurface feature of the mammalian body part or the second landmark subsurface feature of the mammalian body part. The word "or" as used in this document should be understood to contemplate the possibilities of including one of the terms, either of the terms, or both terms. For example, the phrase "A or B" will be understood to include the possibilities of "A" or "B," or "A and B." For example, the coordinate analysis circuit may be configured to determine a common frame of reference that is at least partially based on the first landmark subsurface feature of the mammalian body part. For example, the coordinate analysis circuit may be configured to determine a common frame of reference that is at least partially based on both the first landmark subsurface feature of the mammalian body part and the second landmark subsurface feature of the mammalian body part. For example, a common frame of reference may include a Cartesian coordinate system that will serve to orient and locate objects in space, such as landmark subsurface features or regions of interest. For example, a common frame of reference may relate to a physical or virtual object. For example, a common frame of reference may use a parameter or set of parameters to determine a location of the origin of a coordinate reference system.

The system 920 includes a registration circuit 926. The registration circuit is configured to register the first region of interest and the second region of interest at least partially based on the common frame of reference. For example, "registration" or image "registration" may include systematically placing separate images in a common frame of reference so that the information they contain can be optimally integrated or compared. See, *Medical Image Registration*, section 1.1, Joseph V. Hajnal & Derek L. G. Hill eds., (2001). For example, with reference to FIG. 4, the origin or zero point of the common frame of reference determined by the coordinate analysis circuit 924 may be used to register the region of interest 214A and the region of interest 214B. In an example, the origin or zero point of the common frame of reference may be the region of interest 214A, and the region of interest 214B may be registered by a coordinate system with reference to the region of interest 214A. For example, the common frame of reference determined by the coordinate analysis circuit 924 may be a third point, such as the landmark subsurface feature 216C. Continuing with reference to FIG. 18, the system 920 includes the computer-readable media 235 configured to maintain informational data corresponding to the registration of the first region of interest and the second region of interest.

For example, the first landmark subsurface feature of the mammalian body part may be the same landmark subsurface feature as the second landmark subsurface feature of the mammalian body part. For example, the first landmark subsurface feature and the second landmark subsurface feature may be illustrated by the landmark subsurface feature 216A of FIG. 4. For example, the first landmark subsurface feature of the mammalian body part may be a substantially different subsurface feature than the second landmark subsurface feature of the mammalian body part. For example, the first landmark subsurface feature may be illustrated by the landmark subsurface feature 216A and the second landmark subsurface feature may be illustrated by the landmark subsurface feature 216B of FIG. 4.

In an embodiment, the first medical image may include a region of interest acquired by a body-insertable device while a portion of the body-insertable device is present in a cavity or lumen of the mammalian body part. For example, the first region of interest may include the region of interest 214A of the cavity or lumen 211 of the mammalian body part 210, and the body-insertable device may include the body-insertable device 280. In an embodiment, the first medical image may include a first region of interest acquired by a body-insertable device configured for examination or inspection of a cavity or lumen of a mammalian body part. The first medical image was acquired while a portion of the body-insertable device was present in a cavity or lumen of the mammalian body part. In an embodiment, the first medical image may include a first medical image that includes a first region of interest of a cavity or lumen of a mammalian body part. In an embodiment, the second medical image may include a second region of interest of the cavity or lumen of the mammalian body part. For example, the first region of interest may include the region of interest 214A and the second region of interest may include the region of interest 214B. In an embodiment, the first medical image may include a first region of interest of a surface of a cavity or lumen of a mammalian body part. In an embodiment, the second medical image may include a second region of interest of the surface of the cavity or lumen of the mammalian body part. In an embodiment, the first medical image may include a first medical image acquired by an ex vivo device and indicative of a first region of interest of a surface of a cavity or lumen of a mammalian body part. For example, the ex vivo device may include the ex vivo device 290. In an embodiment, the second medical image may be acquired by the ex vivo device and include a second region of interest of the surface of the cavity or lumen of the mammalian body part. In an embodiment, the first medical image may include a first medical image acquired by an ex vivo device and indicative of a first region of interest of a surface of a cavity or lumen of a mammalian body part. In an embodiment, the second medical image may include a second medical image acquired by the ex vivo device and indicative of a second region of interest of the surface of the cavity or lumen of the mammalian body part.

In an embodiment, the first reference image includes a first reference image acquired by a body-insertable device and that includes a first landmark subsurface feature of the mammalian body part. The first landmark subsurface feature has a first spatial relationship to the first region of interest. In an embodiment, the body-insertable device may include a body-insertable device 280 configured for examination or inspection of a cavity or lumen of a mammalian body part. In an embodiment, the second reference image includes a second reference image acquired by the body-insertable device and includes a second landmark subsurface feature of the mammalian body part. The second landmark subsurface feature has a second spatial relationship to the second region of interest. In an embodiment, the first reference image includes a first reference image acquired by an ex vivo device and that includes a first landmark subsurface feature of the mammalian body part. The first landmark subsurface feature has a first spatial relationship to the first region of interest. In an embodiment, the second reference image includes a second reference image acquired by the ex vivo device and that includes a second landmark subsurface feature of the mammalian body part. The second landmark subsurface feature has a second spatial relationship to the second region of interest.

In an embodiment, the receiver circuit 922 includes a receiver circuit configured to receive (i) a first digital image representative of a first region of interest of a mammalian body part, and (ii) a second digital image representative of a second region of interest of the mammalian body part. The receiver circuit is configured to receive (iii) a first reference image representative of a first landmark subsurface feature of the mammalian body part, the first landmark subsurface feature having a first spatial relationship to the first region of interest, and (iv) a second reference image representative of a second landmark subsurface feature of the mammalian body part, the second landmark subsurface feature having a second spatial relationship to the second region of interest.

In an embodiment, the second reference image includes a second landmark subsurface feature of the mammalian body part. The second landmark subsurface feature has a second spatial relationship to the second region of interest, and the second landmark subsurface feature has another spatial relationship to the first landmark subsurface feature. For example and with reference to FIG. 4, the landmark subsurface feature 216B of the mammalian body part 210 has the spatial relationship 217B to the region of interest 214B. The landmark subsurface feature 216B also has a spatial relationship 213C to the landmark subsurface feature 216A.

In an embodiment, the coordinate analysis circuit 924 may be configured to determine a common frame of reference and a coordinate system that is at least partially based on the first landmark subsurface feature or the second landmark subsurface feature. For example, the coordinate analysis circuit may be configured to determine a common frame of reference anchored in the first landmark subsurface feature or the second landmark subsurface feature. For example, the coordinate analysis circuit may be configured to determine a coordinate reference system that is at least partially based on the first landmark subsurface feature or the second landmark subsurface feature.

In an embodiment, the registration circuit 926 may be configured to register the first region of interest and the second region of interest. The registration is at least partially based on the determined common frame of reference and on a spatial relationship between the first landmark subsurface feature and the second landmark subsurface feature. In an embodiment, the registration circuit may be configured to register a spatial relationship of the first region of interest relative to the second region of interest. The registration is at least partially based on the determined common frame of reference. In an embodiment, the registration circuit may be configured to register the first region of interest and the second region of interest in response to a coordinate reference system. The registration is at least partially based on the common frame of reference. In an embodiment, the registration circuit may include a registration circuit configured to register the first region of interest and the second region of interest. The registration is at least partially based on the common frame of reference, and the registration includes an orientation of the first region of interest relative to the second region of interest. In an embodiment, the registration circuit may be configured to register the first region of interest and the second region of interest. The registration is at least partially based on the common frame of reference. The registration includes an orientation of the first region of interest relative to the second region of interest.

In an embodiment, the computer-readable media 235 includes a computer-readable media configured to maintain and to provide electronic access to informational data corresponding to the registration of the first region of interest and the second region of interest. In an embodiment, the computer-readable media may include a computer-readable media configured to maintain informational data corresponding to the registration, and informational data corresponding to the determined common frame of reference. In an embodiment, the computer-readable media may include a computer storage device 234 having the computer-readable media 235, and configured to maintain informational data corresponding to the registration of the first region of interest and the second region of interest.

In an embodiment, the system 920 includes a communication circuit 942 configured to output the informational data. In an embodiment, the communication circuit may be configured to provide a notification that is at least partially based on the informational data to at least one of a human, computer, or system. In an embodiment, the system includes the processor 232.

Figure 19:
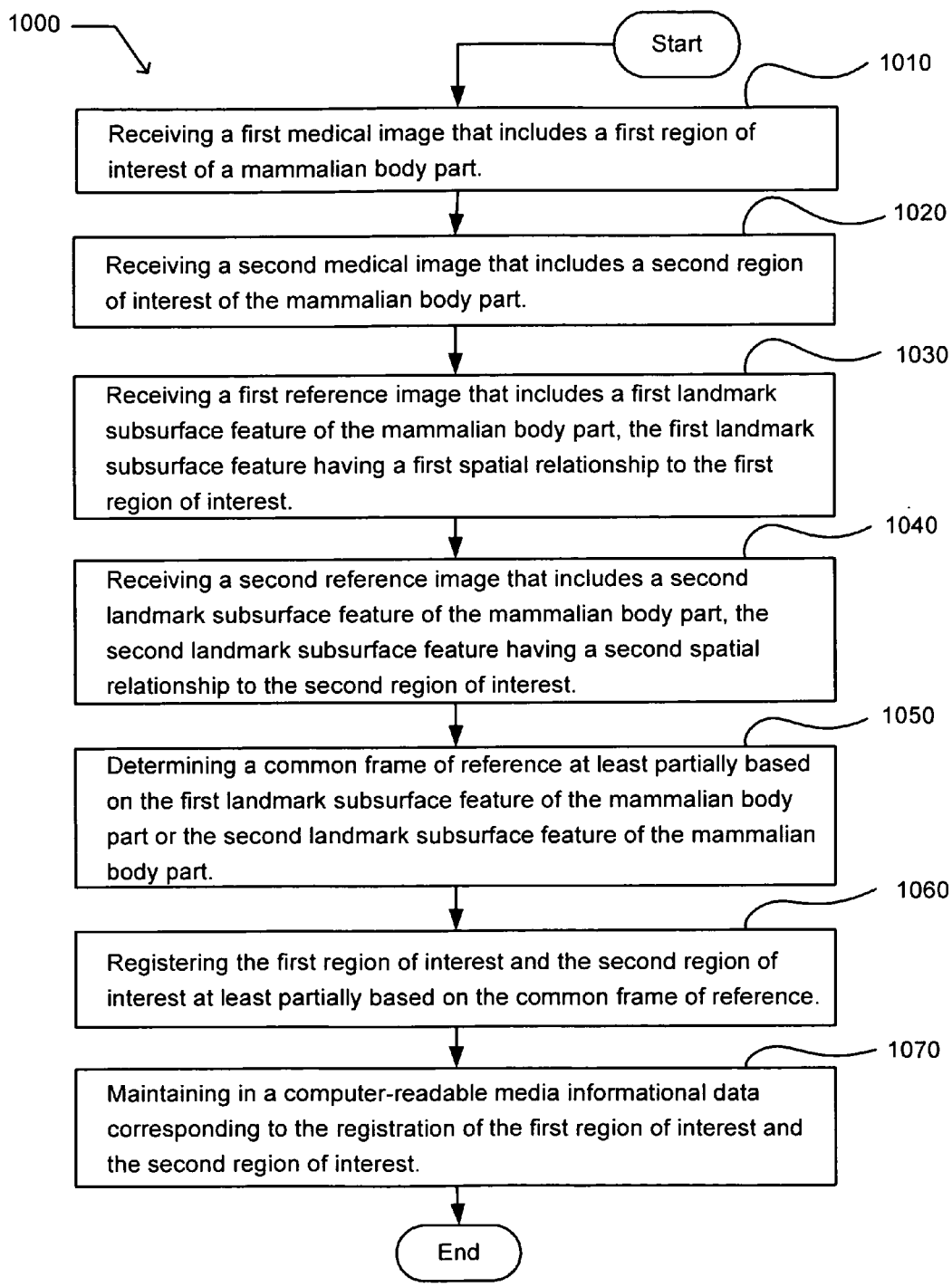
FIG. 19 illustrates an example operational flow.

FIG. 19 illustrates an example operational flow 1000. After a start operation, the operational flow includes a first reception operation 1010. The first reception operation includes receiving a first medical image that includes a first region of interest of a mammalian body part. A second reception operation 1020 includes receiving a second medical image that includes a second region of interest of the mammalian body part. A third reception operation 1030 includes receiving a first reference image that includes a first landmark subsurface feature of the mammalian body part. The first landmark subsurface feature has a first spatial relationship to the first region of interest. A fourth reception operation 1040 includes receiving a second reference image that includes a second landmark subsurface feature of the mammalian body part. The second landmark subsurface feature has a second spatial relationship to the second region of interest. For example, at least one of the first, second, third, or fourth reception operations may be implemented using the receiver circuit 922 described in conjunction with FIG. 18. A reference operation 1050 includes determining a common frame of reference that is at least partially based on the first landmark subsurface feature of the mammalian body part or the second landmark subsurface feature of the mammalian body part. For example, the reference operation may be implemented using the coordinate analysis circuit 924 described in conjunction with FIG. 18. A registration operation 1060 includes registering the first region of interest and the second region of interest at least partially based on the common frame of reference. For example, the registration operation may be implemented using the registration circuit 926 described in conjunction with FIG. 18. A storage operation 1070 includes maintaining in a computer-readable media informational data corresponding to the registration of the first region of interest and the second region of interest. For example, the storage operation may be implemented using the computer-readable media 235 described in conjunction with FIG. 18. The operational flow includes an end operation.

Figure 20:
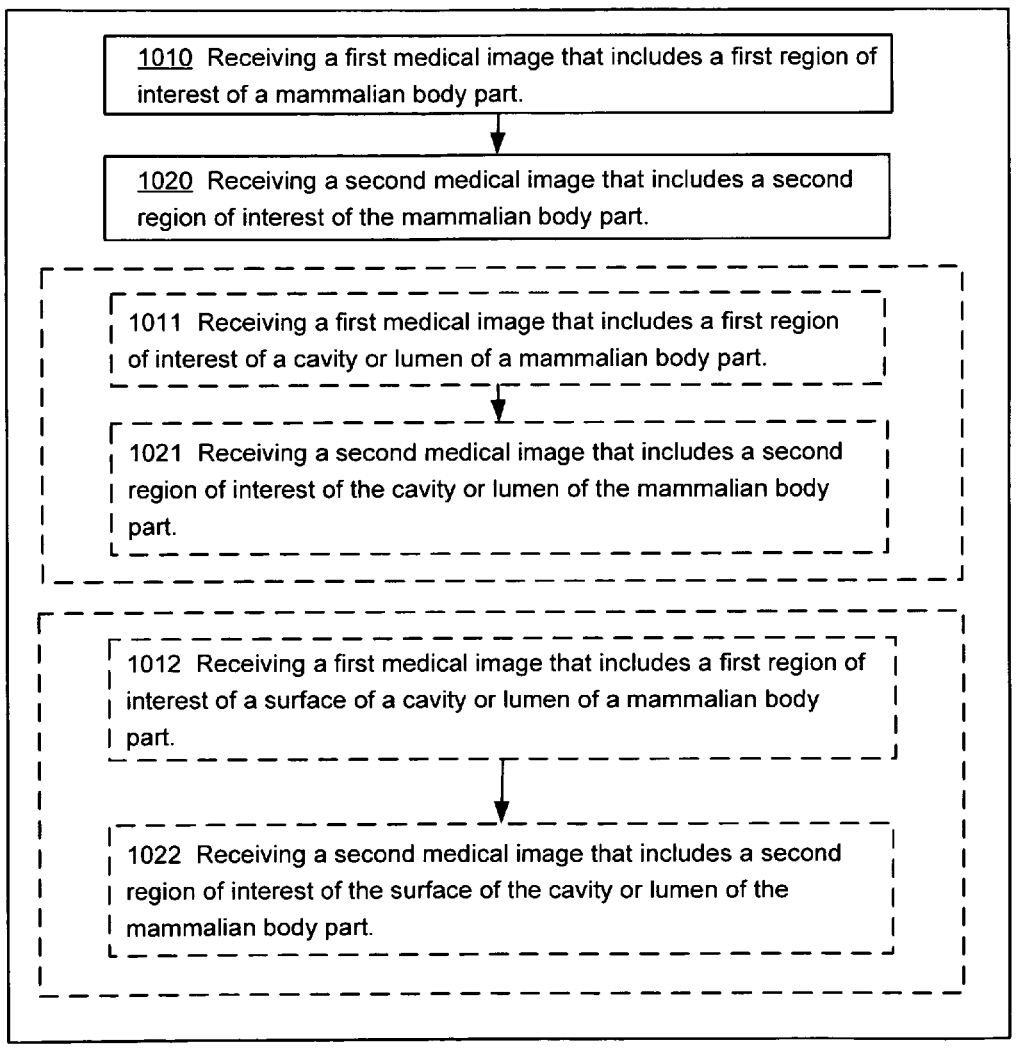
FIG. 20 illustrates an alternative embodiment of the operational flow of FIG. 19.

FIG. 20 illustrates an alternative embodiment of the operational flow 1000 of FIG. 19. In an embodiment, the first reception operation 1010 includes a first reception operation 1011 and the second reception operation 1020 includes a second reception operation 1021. The first reception operation 1011 includes receiving a first medical image that includes a first region of interest of a cavity or lumen of a mammalian body part. The second reception operation 1021 includes receiving a second medical image that includes a second region of interest of the cavity or lumen of the mammalian body part. In an embodiment, the first reception operation 1010 includes a first reception operation 1012 and the second reception operation 1020 includes a second reception operation 1022. The first reception operation 1012 includes receiving a first medical image that includes a first region of interest of a surface of a cavity or lumen of a mammalian body part. The second reception operation 1022 includes receiving a second medical image that includes a second region of interest of the surface of the cavity or lumen of the mammalian body part.

Figure 21:
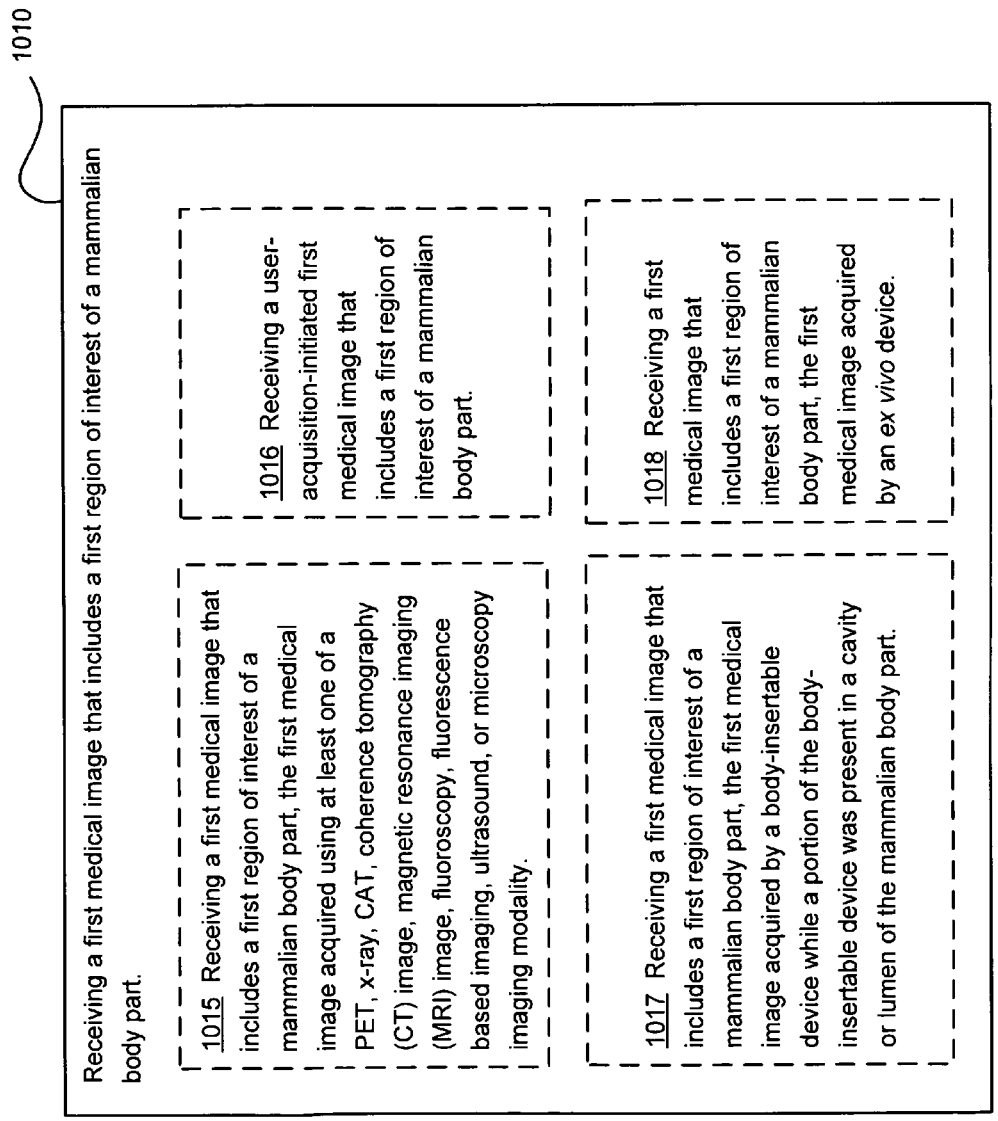
FIG. 21 illustrates an alternative embodiment of the first reception operation 1010 of FIG. 19.

FIG. 21 illustrates an alternative embodiment of the first reception operation 1010 of FIG. 19. The first reception operation may include at least one additional embodiment. The at least one additional embodiment includes an operation 1015, an operation 1016, an operation 1017, or an operation 1018. The operation 1015 includes receiving a first medical image that includes a first region of interest of a mammalian body part, the first medical image acquired using at least one of a PET, x-ray, CAT, coherence tomography (CT) image, magnetic resonance imaging (MRI) image, fluoroscopy, fluorescence based imaging, ultrasound, or microscopy imaging modality. The operation 1016 includes receiving a user-acquisition-initiated first medical image that includes a first region of interest of a mammalian body part. For example, the user may include a human user, such as the person 296 illustrated in FIG. 18, or a machine user (not illustrated). The operation 1017 includes receiving a first medical image that includes a first region of interest of a mammalian body part. The first medical image was acquired by a body-insertable device while a portion of the body-insertable device was present in a cavity or lumen of the mammalian body part. The operation 1018 includes receiving a first medical image that includes a first region of interest of a mammalian body part. The first medical image was acquired by an ex vivo device.

FIG. 22 illustrates an alternative embodiment of the operational flow 1000 of FIG. 19. In an embodiment, the third reception operation 1030 may include at least one additional embodiment. The at least one additional embodiment includes an operation 1015, an operation 1016, an operation 1017, or an operation 1018. The at least one additional embodiment may include an operation 1031, an operation 1032, an operation 1033, an operation 1034, or an operation 1035. The operation 1031 includes receiving a first two-dimensional or three-dimensional reference image that includes a first landmark subsurface feature of the mammalian body part. The first landmark subsurface feature has a first spatial relationship to the first region of interest. The operation 1032 includes receiving a first reference image that includes a first landmark subsurface feature of the mammalian body part. The first landmark subsurface feature has an indicated, determinable, estimable, or inferable first spatial relationship to the first region of interest. The operation 1033 includes receiving a first reference image that includes a first landmark subsurface feature of the mammalian body part, and receiving data indicative of an environment when the first reference image was acquired. The first landmark subsurface feature has a first spatial relationship to the first region of interest. The operation 1034 includes receiving a first reference image that includes a first landmark subsurface feature of the mammalian body part. The first landmark subsurface feature has a first spatial relationship to the first region of interest, and the first reference image was acquired by a body-insertable device while a portion of the body-insertable device was present in a cavity or lumen of the mammalian body part. The operation 1035 includes receiving a first reference image that includes a first landmark subsurface feature of the mammalian body part. The first landmark subsurface feature has a first spatial relationship to the first region of interest, and the first reference image was acquired by an ex vivo device.

Figure 23:
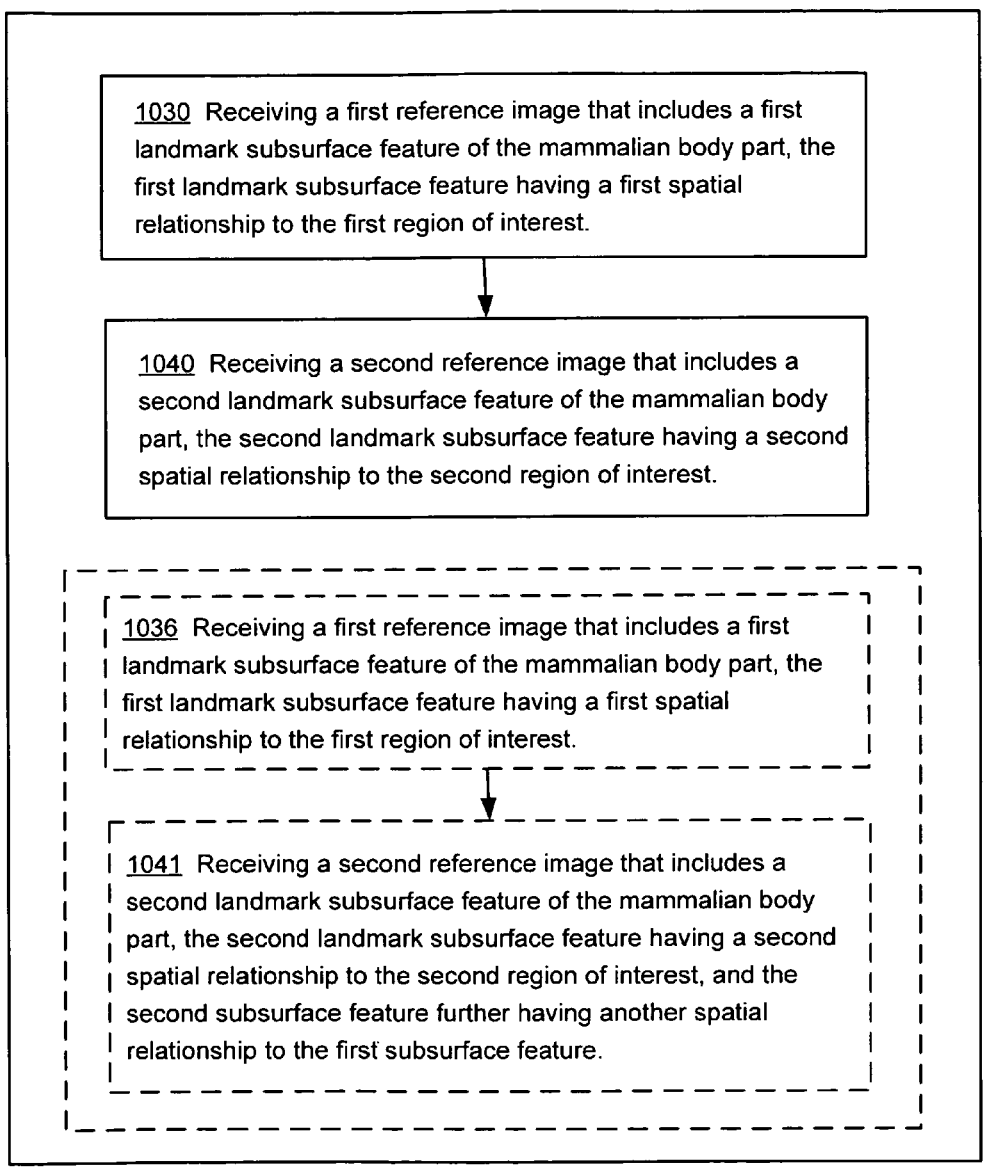
FIG. 23 illustrates an alternative embodiment of the operational flow 1000 of FIG. 19.

FIG. 23 illustrates an alternative embodiment of the operational flow 1000 of FIG. 19. In an embodiment, the third reception operation 1030 includes a third reception operation 1036 and the fourth reception operation 1040 includes a fourth reception operation 1041. The third reception operation 1036 includes receiving a first reference image that includes a first landmark subsurface feature of the mammalian body part. The first landmark subsurface feature has a first spatial relationship to the first region of interest. The fourth reception operation 1041 includes receiving a second reference image that includes a second landmark subsurface feature of the mammalian body part. The second landmark subsurface feature has a second spatial relationship to the second region of interest, and the second subsurface feature further has another spatial relationship to the first subsurface feature.

FIG. 24 illustrates an alternative embodiment of the reference operation 1050 of FIG. 19. The reference operation may include at least one additional embodiment. The at least one additional embodiment may include an operation 1051, an operation 1052, or an operation 1053. The operation 1051 includes determining a common frame of reference and a coordinate system that is at least partially based on the first landmark subsurface feature of the mammalian body part or the second landmark subsurface feature of the mammalian body part. The operation 1052 includes determining a common frame of reference that is at least partially anchored in the first landmark subsurface feature of the mammalian body part or the second landmark subsurface feature of the mammalian body part. The operation 1053 includes determining a coordinate reference system that is at least partially based on the first landmark subsurface feature of the mammalian body part or the second landmark subsurface feature of the mammalian body part.

FIG. 25 illustrates an alternative embodiment of the registration operation 1060 of FIG. 19. The registration operation may include at least one additional embodiment. The at least one additional embodiment may include an operation 1061, an operation 1062, an operation 1063, an operation 1064, an operation 1065, or an operation 1066. The operation 1061 includes registering the first region of interest and the second region of interest. The registering is at least partially based on the determined common frame of reference and on a spatial relationship of the first landmark subsurface feature and the second landmark subsurface feature. The operation 1062 includes registering the first region of interest relative to the second region of interest. The registering is at least partially based on the common frame of reference. The operation 1063 includes registering a spatial relationship of the first region of interest relative to the second region of interest. The registering is at least partially based on the common frame of reference. The operation 1064 includes registering a location, position, orientation, distance, directional, alignment, or axial relationship. The registering is at least partially based on the common frame of reference. The operation 1065 includes determining a spatial relationship between the first region of interest and the second region of interest. The operation 1065 also includes registering the first region of interest and the second region of interest at least partially based on the common frame of reference. In an embodiment, the determined spatial relationship may include a determined two-dimension or a determined three-dimensional relationship. The operation 1066 includes registering an orientation of the first region of interest relative to the first landmark subsurface feature, registering an orientation of the second region of interest relative to the second landmark subsurface feature, and registering the first region of interest and the second region of interest. The registering is at least partially based on the common frame of reference.

FIG. 26 illustrates an alternative embodiment of the storage operation 1070 of FIG. 19. The storage operation may include at least one additional embodiment, such as an operation 1071. The operation 1071 includes maintaining in a computer-readable media informational data corresponding to the registration of the first region of interest and the second region of interest, and providing electronic access to the informational data.

Figure 27:
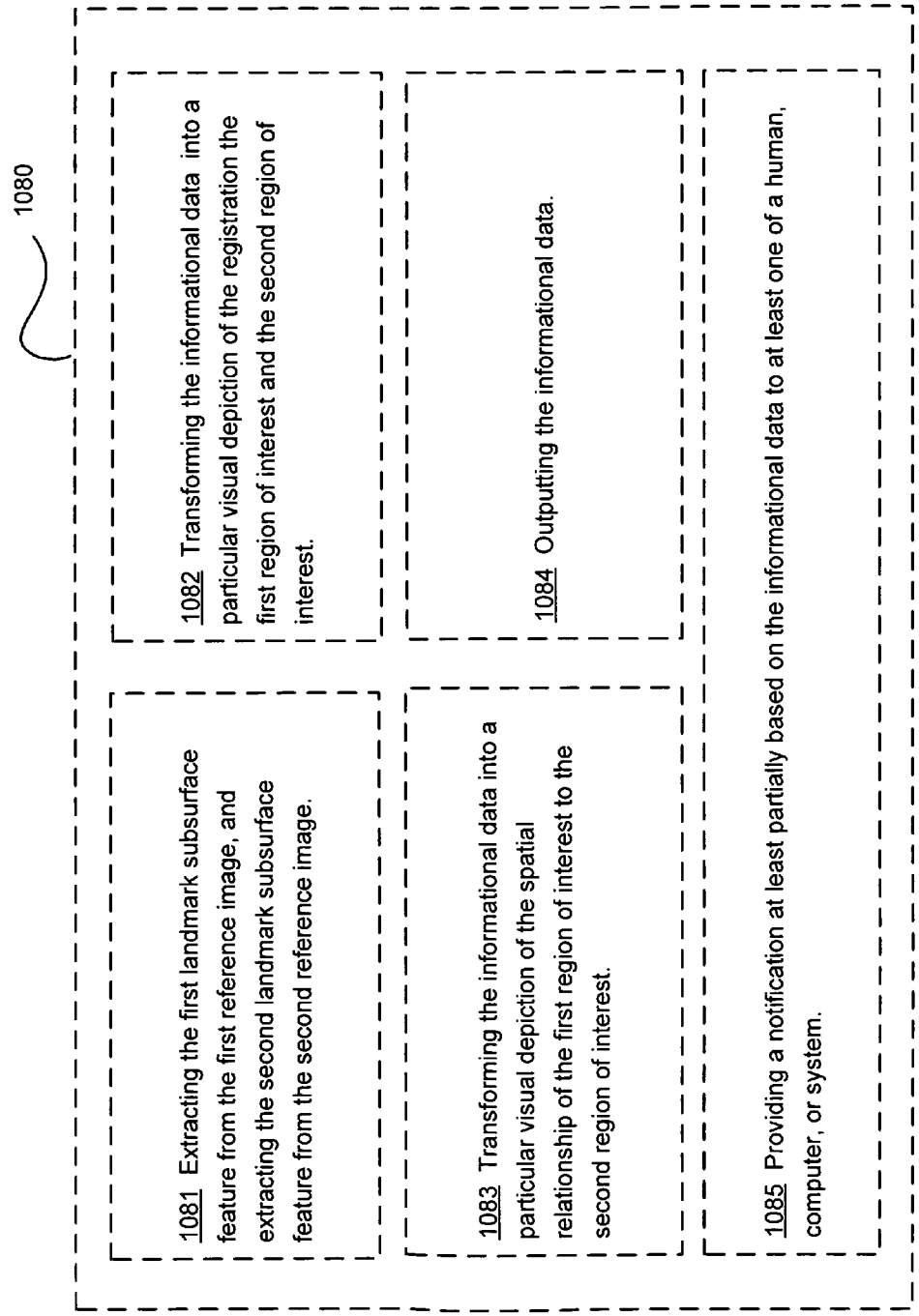
FIG. 27 illustrates an alternative embodiment of the operational flow 1000 of FIG. 19.

FIG. 27 illustrates an alternative embodiment of the operational flow 1000 of FIG. 19. In an embodiment, the operational flow may include at least one additional embodiment 1080. The at least one additional embodiment may include an operation 1081, an operation 1082, an operation 1083, an operation 1084, or an operation 1085. The operation 1081 includes extracting the first landmark subsurface feature from the first reference image, and extracting the second landmark subsurface feature from the second reference image. In an embodiment, the operation 1081 may be implemented using the extraction engine 238 described in conjunction with FIG. 3. The operation 1082 includes transforming the informational data into a particular visual depiction of the registration the first region of interest and the second region of interest. For example, the operation 1082 may be implemented using the communication circuit 242, and the particular visual depiction may be displayed on the screen 294 of the computing device 292 to the person 296 as described in conjunction with FIG. 3. The operation 1083 includes transforming the informational data into a particular visual depiction of the spatial relationship of the first region of interest to the second region of interest. For example, the operation 1083 may be implemented using the communication circuit 242 described in conjunction with FIG. 3. In an embodiment, the operation 1084 includes outputting the informational data. For example, the operation 1084 may be implemented using the communication circuit 242 described in conjunction with FIG. 3. In an embodiment, the operation 1085 includes providing a notification that is at least partially based on the informational data to at least one of a human, computer, or system. For example, the operation 1085 may be implemented using the communication circuit 242, and the notification may be displayed on the screen 294 of the computing device 292 to the person 296 as described in conjunction with FIG. 3.

Figure 28:
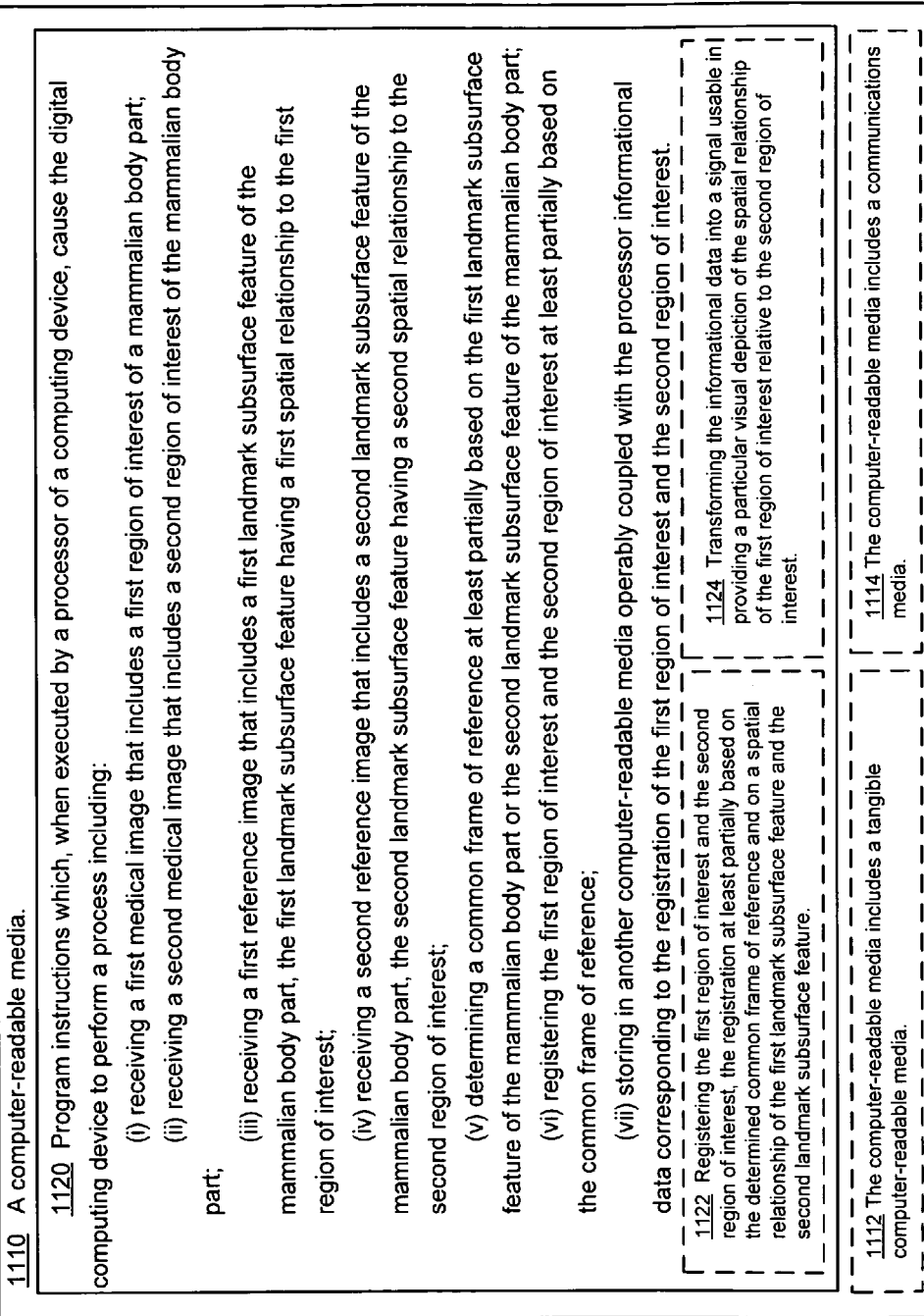
FIG. 28 illustrates an example computer program product.

FIG. 28 illustrates an example computer program product 1100. The computer program product includes computer-readable media 1110 bearing program instructions 1120 which, when executed by a processor of a computing device, cause the computing device to perform a process. The process includes receiving a first medical image that includes a first region of interest of a mammalian body part. The process includes receiving a second medical image that includes a second region of interest of the mammalian body part. The process includes receiving a first reference image that includes a first landmark subsurface feature of the mammalian body part. The first landmark subsurface feature has a first spatial relationship to the first region of interest. The process includes receiving a second reference image that includes a second landmark subsurface feature of the mammalian body part. The second landmark subsurface feature has a second spatial relationship to the second region of interest. The process includes determining a common frame of reference at least partially based on the first landmark subsurface feature of the mammalian body part or the second landmark subsurface feature of the mammalian body part. The process includes registering the first region of interest and the second region of interest at least partially based on the common frame of reference. The process includes storing informational data corresponding to the registration of the first region of interest and the second region of interest in another computer-readable media operably coupled with the processor.

In an embodiment, the registering process includes 1122 registering the first region of interest and the second region of interest. The registration is at least partially based on the determined common frame of reference and on a spatial relationship of the first landmark subsurface feature and the second landmark subsurface feature. In an embodiment, the process includes 1124 transforming the informational data into a signal usable in providing a particular visual depiction of the spatial relationship of the first region of interest relative to the second region of interest.

In an embodiment, the computer-readable media 1110 includes a tangible computer-readable media 1112. In an embodiment, the computer-readable media includes a communications medium 1114.

Figure 29:
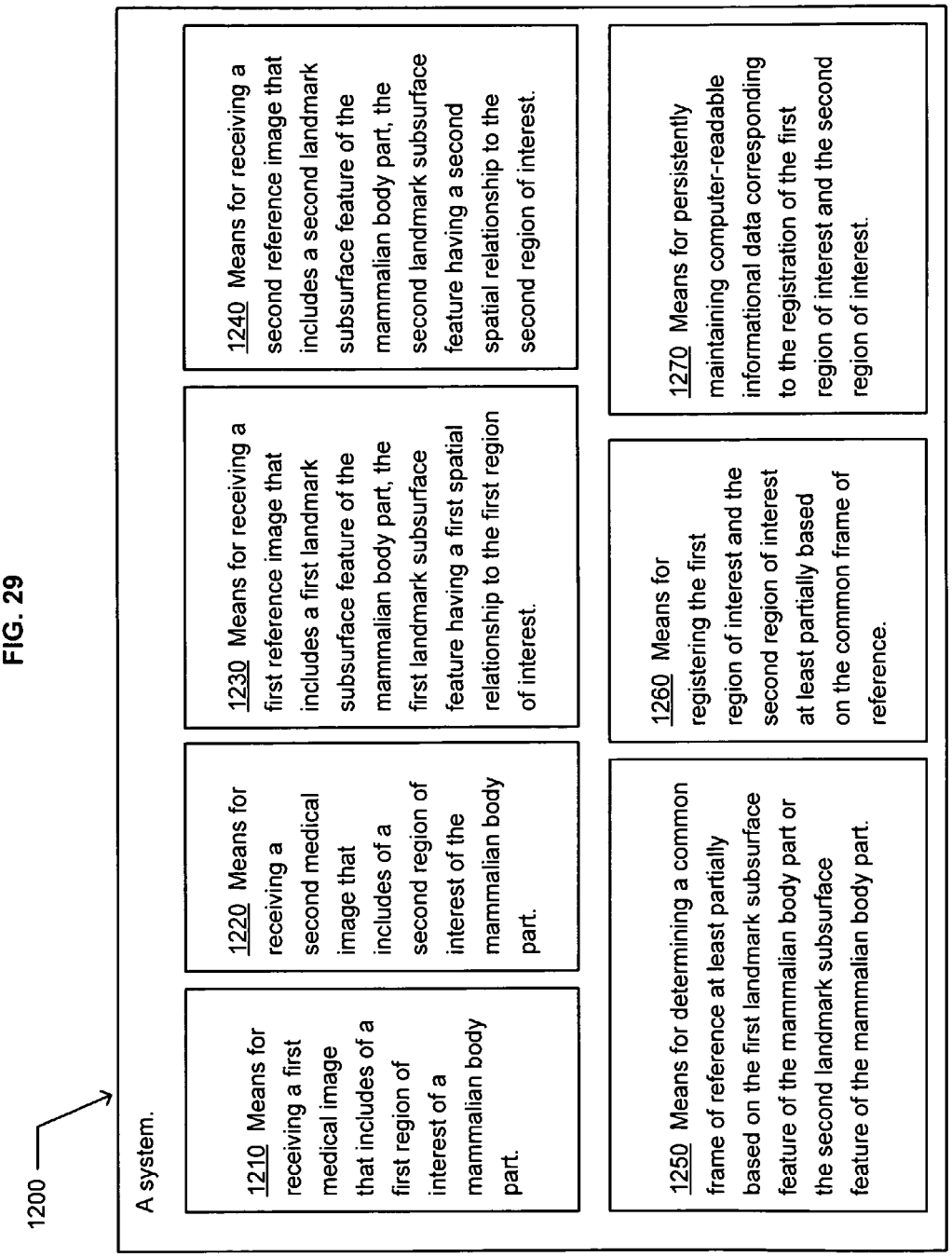
FIG. 29 illustrates an example system.

FIG. 29 illustrates an example system 1200. The system includes means 1210 for receiving a first medical image that includes a first region of interest of a mammalian body part. The system includes means 1220 for receiving a second medical image that includes a second region of interest of the mammalian body part. The system includes means 1230 for receiving a first reference image that includes a first landmark subsurface feature of the mammalian body part. The first landmark subsurface feature has a first spatial relationship to the first region of interest. The system includes means 1240 for receiving a second reference image that includes a second landmark subsurface feature of the mammalian body part. The second landmark subsurface feature has a second spatial relationship to the second region of interest. The system includes means 1250 for determining a common frame of reference that is at least partially based on the first landmark subsurface feature of the mammalian body part or the second landmark subsurface feature of the mammalian body part. The system includes means 1260 for registering the first region of interest and the second region of interest that is at least partially based on the common frame of reference. The system includes means 1270 for persistently maintaining computer-readable informational data corresponding to the registration of the first region of interest and the second region of interest.

Returning to FIG. 18, an alternative embodiment of the example system 920 is also illustrated by FIG. 18. In the alternative embodiment, the example system includes the coordinate analysis circuit 924 configured to determine a common frame of reference. The common frame of reference is determined at least partially based on a first landmark subsurface feature of the mammalian body part 210 or a second landmark subsurface feature of the mammalian body part. The first landmark subsurface feature has a first spatial relationship to a first region of interest of the mammalian body part, and the second landmark subsurface feature has a second spatial relationship to a second region of interest of the mammalian body part. In an embodiment, the system may include the registration circuit 926 configured to register the first region of interest and the second region of interest at least partially based on the common frame of reference. In an embodiment, the system may include the computer-readable media 235 configured to maintain informational data corresponding to the registration of the first region of interest relative to the second region of interest.

In an embodiment of the alternative embodiment, the coordinate analysis circuit 924 is configured to determine a common frame of reference at least partially based on a first landmark subsurface feature of a mammalian body part or a second landmark subsurface feature of the mammalian body part. The first landmark subsurface feature has a first spatial relationship to a first region of interest of a cavity or lumen of the mammalian body part, and the second landmark subsurface feature has a second spatial relationship to a second region of interest of the cavity or lumen of the mammalian body part. In an embodiment of the alternative embodiment, the coordinate analysis circuit is configured to determine a common frame of reference at least partially based on a first landmark subsurface feature of a cavity or lumen of a mammalian body part or a second landmark subsurface feature of the cavity or lumen of the mammalian body part. The first landmark subsurface feature has a first spatial relationship to a first region of interest of a surface of the cavity or lumen of the mammalian body part, and the second landmark subsurface feature has a second spatial relationship to the second region of interest of the surface of the cavity or lumen of the mammalian body part.

In an embodiment of the alternative embodiment, the registration circuit 926 is configured to register the first region of interest and the second region of interest. The registration is at least partially based on the determined common frame of reference and on a spatial relationship of the first landmark subsurface feature and the second landmark subsurface feature.

In an embodiment of the alternative embodiment, the system includes the communication circuit 942. The communication circuit is configured to output the informational data. For example, the communication circuit may be configured to provide a notification that is at least partially based on the informational data to at least one of a human, computer, or system.

In an embodiment of the alternative embodiment, the system includes the receiver circuit 922. The receiver circuit is configured to receive a first medical image that includes the first region of interest of the mammalian body part, and a second medical image that includes the second region of interest of the mammalian body part. In an embodiment, the receiver circuit is configured to receive a first reference image that includes the first landmark subsurface feature of the mammalian body part, and a second reference image that includes the second landmark subsurface feature of the mammalian body part.

Figure 30:
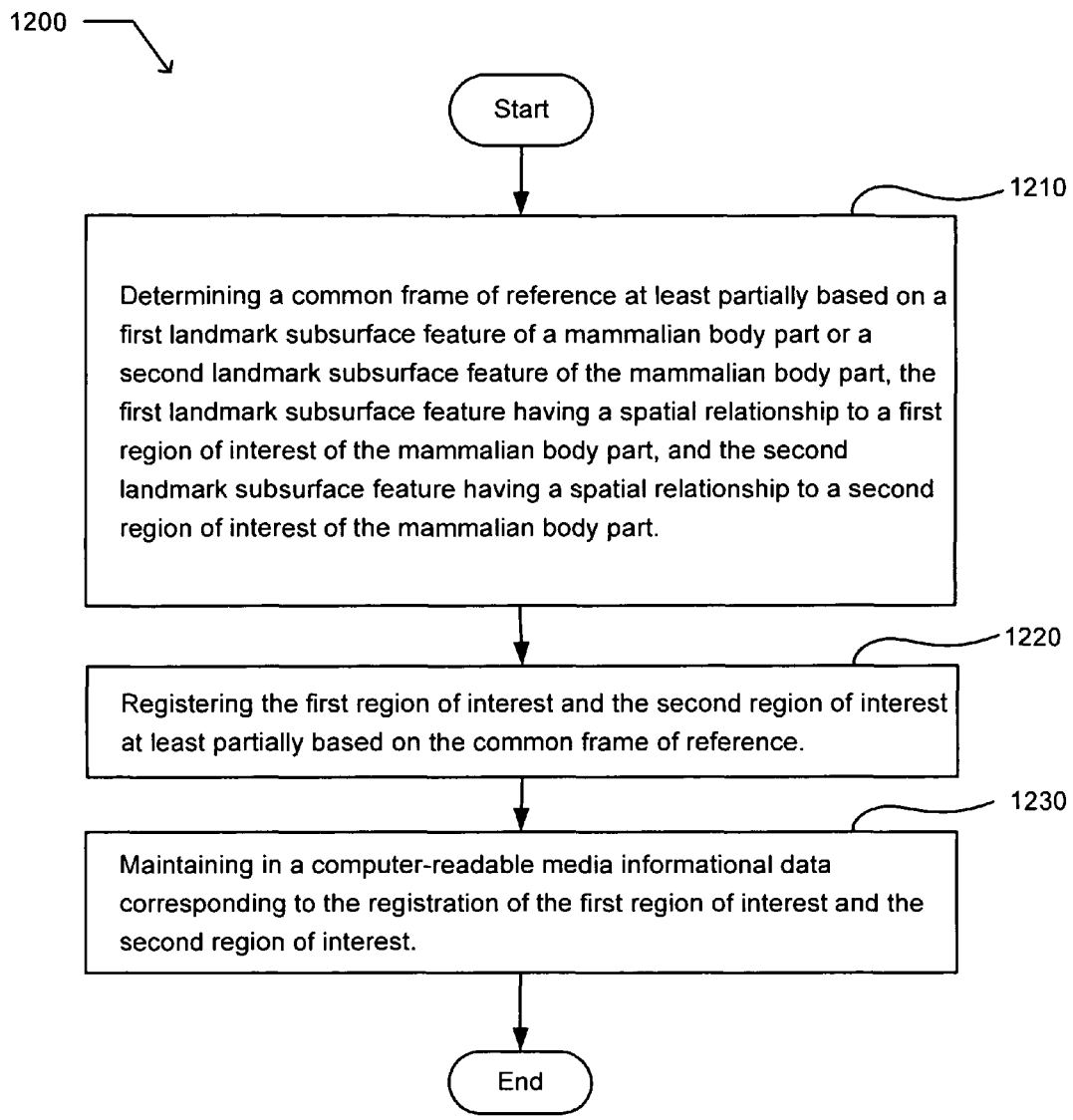
FIG. 30 illustrates an example operational flow 1200.

FIG. 30 illustrates an example operational flow 1200. The operational flow includes a start operation. The operational flow includes a reference operation 1210. The reference operation includes determining a common frame of reference at least partially based on a first landmark subsurface feature of a mammalian body part or a second landmark subsurface feature of the mammalian body part. The first landmark subsurface feature has a first spatial relationship to a first region of interest of the mammalian body part, and the second landmark subsurface feature has a second spatial relationship to a second region of interest of the mammalian body part. For example, the reference operation may be implemented using the coordinate analysis circuit 924 described in conjunction with FIG. 18. The operational flow includes a registration operation 1220. The registration operation includes registering the first region of interest and the second region of interest at least partially based on the common frame of reference. In an embodiment, the registration operation may be implemented using the registration circuit 926 described in conjunction with FIG. 18. For example, the registration operation may be implemented using the thin computing device 20 described in conjunction with FIG. 1 or the computing device 110 described in conjunction with FIG. 2. The operational flow includes a storage operation 1230. The storage operation includes maintaining in a computer-readable media informational data corresponding to the registration of the first region of interest and the second region of interest at least. For example, the storage operation may be implemented using the computer-readable media 235 described in conjunction with FIG. 3. For example, the storage operation may be implemented using a computer-readable media associated with the thin computing device 20 described in conjunction with FIG. 1 or a computer-readable media associated with the computing device 110 described in conjunction with FIG. 2. The operational flow includes an end operation.

Figure 31:
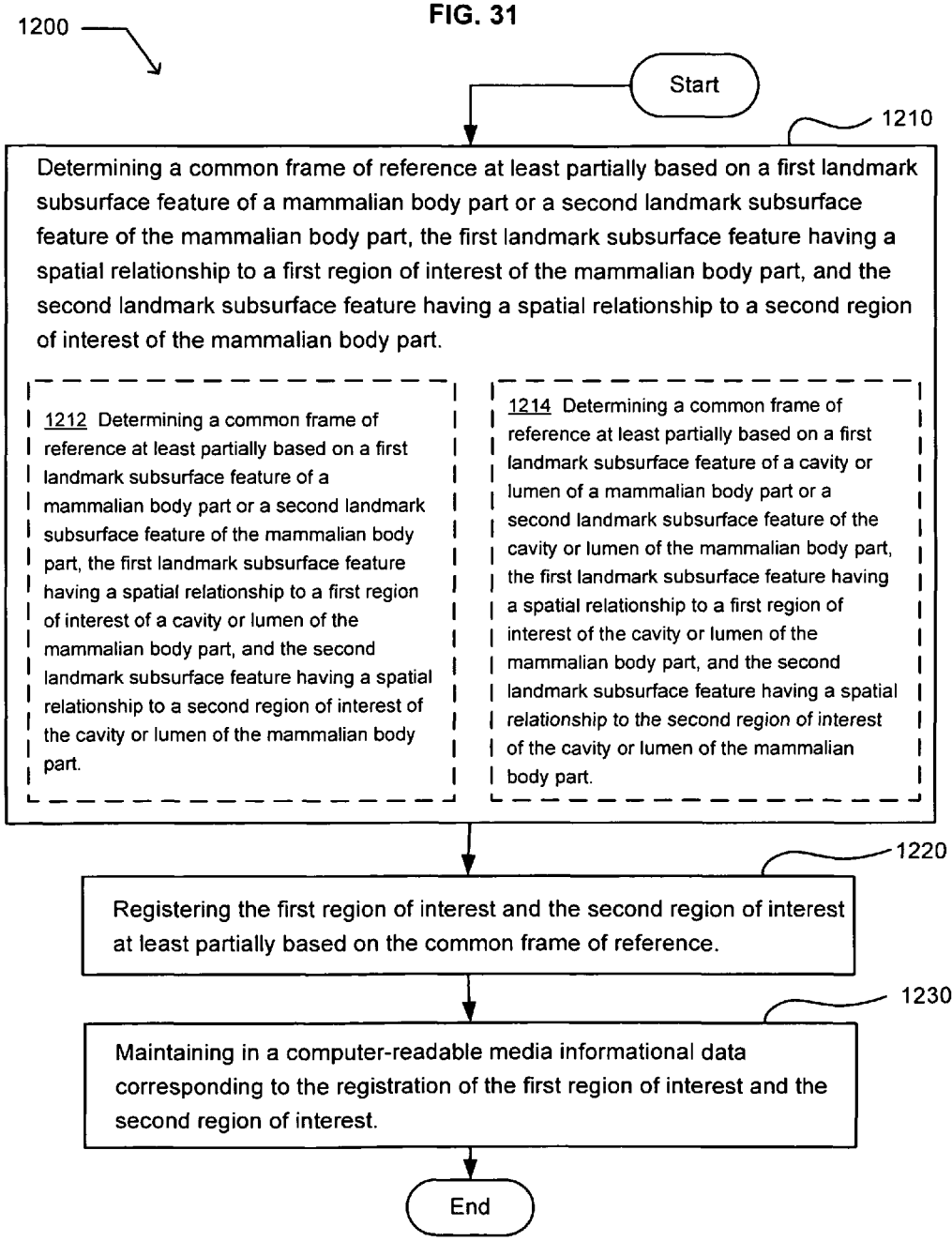
FIG. 31 illustrates an alternative embodiment of the reference operation 1210 described in conjunction with FIG. 30.

FIG. 31 illustrates an alternative embodiment of the reference operation 1210 described in conjunction with FIG. 30. In an alternative embodiment, the reference operation may include at least one additional embodiment. The at least one additional embodiment may include an operation 1212 or an operation 1214. The operation 1212 includes determining a common frame of reference that is at least partially based on a first landmark subsurface feature of a mammalian body part or a second landmark subsurface feature of the mammalian body part. The first landmark subsurface feature has a first spatial relationship to a first region of interest of a cavity or lumen of the mammalian body part. The second landmark subsurface feature has a second spatial relationship to a second region of interest of the cavity or lumen of the mammalian body part. The operation 1214 includes determining a common frame of reference that is at least partially based on a first landmark subsurface feature of a cavity or lumen of a mammalian body part or a second landmark subsurface feature of the cavity or lumen of the mammalian body part. The first landmark subsurface feature has a first spatial relationship to a first region of interest of the cavity or lumen of the mammalian body part. The second landmark subsurface feature has a second spatial relationship to the second region of interest of the cavity or lumen of the mammalian body part.

Figure 32:
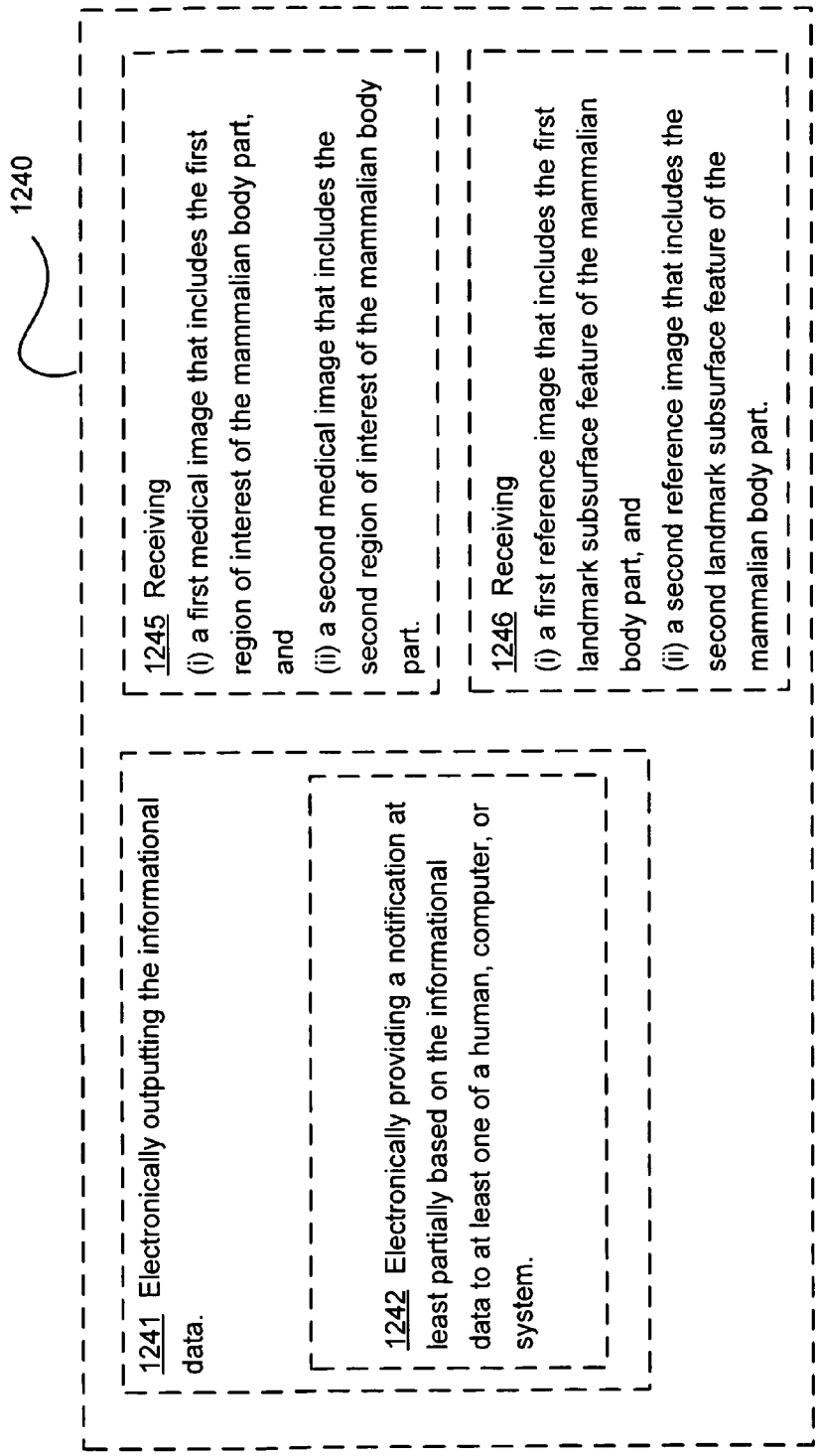
FIG. 32 illustrates an alternative embodiment of the operational flow 1200 described in conjunction with FIG. 30.

FIG. 32 illustrates an alternative embodiment of the operational flow 1200 described in conjunction with FIG. 30. In an alternative embodiment, the operational flow may include at least one additional embodiment. The at least one additional embodiment may include an operation 1241, an operation 1245, or an operation 1246. The operational flow 1241 includes electronically outputting the informational data. In an embodiment, the operational flow 1241 may include at least one additional embodiment, such as an operation 1242. The operation 1242 includes electronically providing a notification that is at least partially based on the informational data to at least one of a human, computer, or system. The operation 1245 includes receiving a first medical image that includes the first region of interest of the mammalian body part, and a second medical image that includes the second region of interest of the mammalian body part. The operation 1246 includes receiving a first reference image that includes the first landmark subsurface feature of the mammalian body part, and a second reference image that includes the second landmark subsurface feature of the mammalian body part.

FIG. 33 illustrates an example computer program product 1300. The computer program product includes a computer-readable media 1310 bearing program instructions 1320 which, when executed by a processor of a computing device, cause the computing device to perform a process. The process includes determining a common frame of reference that is at least partially based on a first landmark subsurface feature of a mammalian body part or a second landmark subsurface feature of the mammalian body part. The first landmark subsurface feature has a first spatial relationship to a first region of interest of the mammalian body part. The second landmark subsurface feature has a second spatial relationship to a second region of interest of the mammalian body part. The process includes registering the first region of interest and the second region of interest at least partially based on the common frame of reference. The process includes storing in another computer-readable media operably coupled with the processor informational data corresponding to the registration of the first region of interest and the second region of interest. In an embodiment, the registering may include 1322 registering the first region of interest and the second region of interest. The registration is at least partially based on the determined common frame of reference and on a spatial relationship of the first landmark subsurface feature relative to the second landmark subsurface feature. In an embodiment, the process may include 1330 transforming the informational data into signal usable in providing a particular visual depiction of the registration of the first region of interest and the second region of interest.

In an embodiment, the computer-readable media 1310 includes a tangible computer-readable media 1312. In an embodiment, the computer-readable media includes a communications medium 1314.

FIG. 34 illustrates an example system 1400. The system includes means 1410 for determining a common frame of reference at least partially based on a first landmark subsurface feature of a mammalian body part or a second landmark subsurface feature of the mammalian body part. The first landmark subsurface feature has a first spatial relationship to a first region of interest of the mammalian body part, and the second landmark subsurface feature has a second spatial relationship to a second region of interest of the mammalian body part. The system includes means 1420 for registering the first region of interest relative to the second region of interest that is at least partially based on the common frame of reference. The system includes means 1430 for persistently maintaining computer-readable informational data corresponding to the registration of the first region of interest and the second region of interest.

Figure 35:
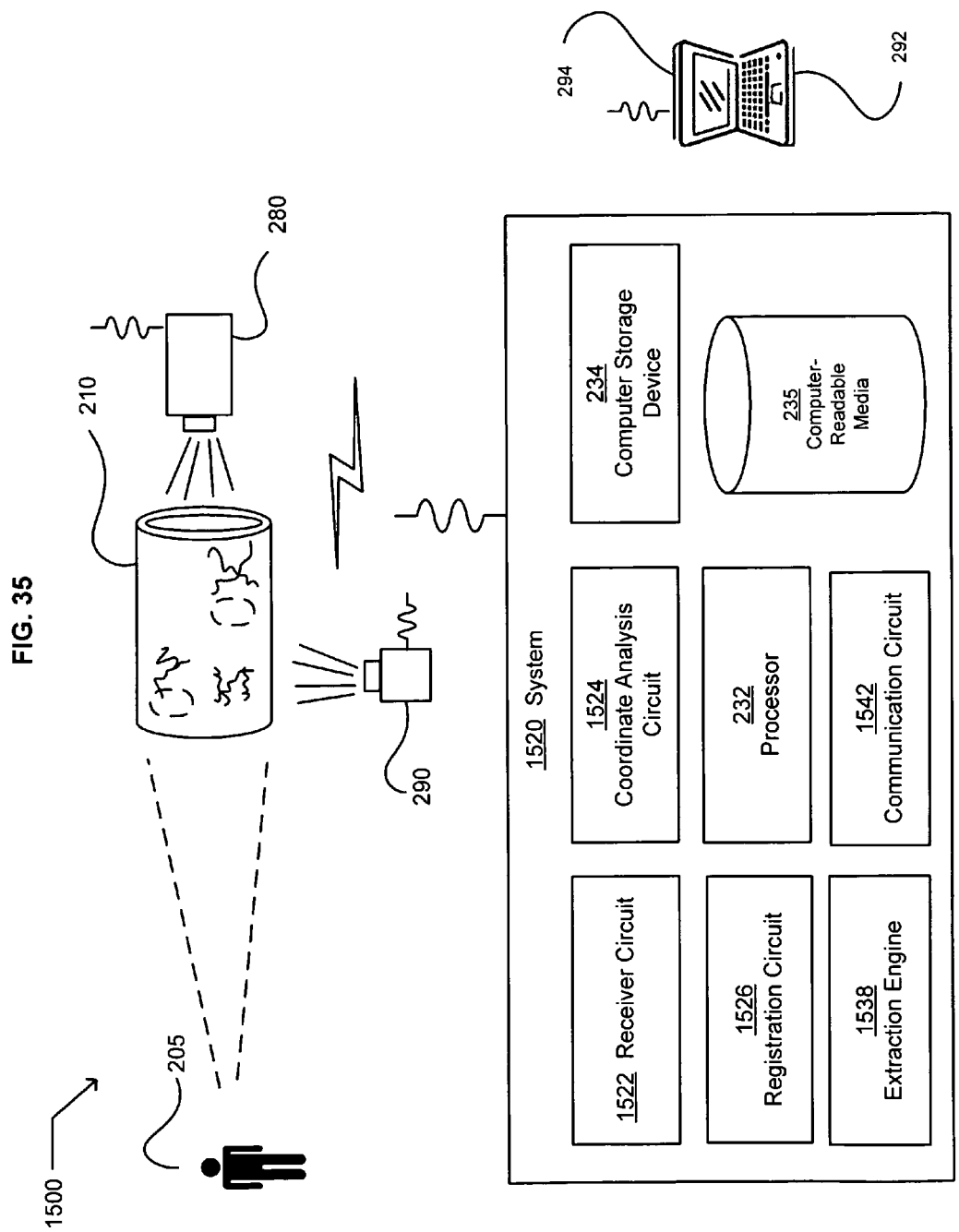
FIG. 35 illustrates an example environment.

FIG. 35 illustrates an example environment 1500. The environment includes the mammalian body part 210 of the mammal 205. A system 1520 includes a coordinate analysis circuit 1524 configured to determine a common frame of reference at least partially based on a landmark subsurface feature of a mammalian body part has at least two landmark subsurface features and at least two regions of interest. Each landmark subsurface feature of at least two landmark subsurface features has a respective spatial relationship to a respective region of interest of the at least two regions of interest. The system includes a registration circuit 1526 configured to register the respective regions of interest of a mammalian body part. The registration is at least partially based on the common frame of reference. The system includes the computer-readable media 235 configured to maintain informational data corresponding to the respective registered regions of interest.

In an embodiment of the system 1520, the coordinate analysis circuit 1524 may include a coordinate analysis circuit configured to determine a common frame of reference at least partially based on a landmark subsurface feature of a cavity or lumen of a mammalian body part. The cavity or lumen of the mammalian body part has at least two landmark subsurface features and at least two regions of interest. Each landmark subsurface feature of at least two landmark subsurface features has a respective spatial relationship to a respective region of interest of the at least two regions of interest. In an embodiment, the coordinate analysis circuit 1524 may include a coordinate analysis circuit configured to determine a common frame of reference at least partially based on a landmark subsurface feature of a cavity or lumen of a mammalian body part. The cavity or lumen of the mammalian body part has at least two landmark subsurface features and at least two regions of interest of a surface of the cavity or lumen. Each landmark subsurface feature of at least two landmark subsurface features has a respective spatial relationship to a respective region of interest of the at least two regions of interest. In an embodiment, the coordinate analysis circuit may include a coordinate analysis circuit configured to determine a common frame of reference and a coordinate system at least partially based on a landmark subsurface feature of a mammalian body part. The mammalian body part has at least two landmark subsurface features and at least two regions of interest. Each landmark subsurface feature of at least two landmark subsurface features has a respective spatial relationship to a respective region of interest of the at least two regions of interest. In an embodiment, the coordinate analysis circuit may include a coordinate analysis circuit configured to determine a common frame of reference anchored in a landmark subsurface feature of a mammalian body part has at least two landmark subsurface features and at least two regions of interest. Each landmark subsurface feature of at least two landmark subsurface features has a respective spatial relationship to a respective region of interest of the at least two regions of interest.

In an embodiment, the registration circuit 1526 may include a registration circuit configured to register the respective regions of interest of a mammalian body part. The registration is at least partially based on the determined common frame of reference and on a spatial relationship among each landmark subsurface feature of at least two landmark subsurface features. In an embodiment, the registration circuit may include a registration circuit configured to register a spatial relationship of the respective regions of interest of a mammalian body part with respect to each other region of interest of the at least two regions of interest. The registration is at least partially based on the common frame of reference. In an embodiment, the registration circuit may include a registration circuit configured to register the respective regions of interest of a mammalian body part. The registration includes an orientation of the respective regions of interest. The registration is at least partially based on the common frame of reference.

In an embodiment, the computer-readable media 235 may include a computer-readable media configured to maintain informational data corresponding to the respective registered regions of interest, and corresponding to the determined common frame of reference.

In an embodiment, the system 1520 may include the communication circuit 1542 configured to output the informational data. In an embodiment, the system may include a communication circuit configured to provide a notification that is at least partially based on the informational data to at least one of a human, computer, or system. In an embodiment, the system may include the processor 232. In an embodiment, the system may include an extraction engine 1538. The extraction engine is configured to extract a landmark subsurface feature or a region of interest from a digital image. In an embodiment, the system may include a receiver circuit 1522 configured to receive at least two medical images. Each medical image of the at least two medical images includes a respective region of interest of the mammalian body part. In an embodiment, the system may include a receiver circuit configured to receive at least two reference images. Each reference image of the at least two reference images includes a respective landmark subsurface feature of the mammalian body part. Each landmark subsurface feature has a spatial relationship to a respective region of interest included in a medical image of the at least two medical images.

FIG. 36 illustrates an example operational flow 1600. The operational flow includes a start operation. The operational flow includes a reference operation 1610. The reference operation includes determining a common frame of reference that is at least partially based on a landmark subsurface feature of a mammalian body part has at least two landmark subsurface features and at least two regions of interest. Each landmark subsurface feature of at least two landmark subsurface features has a respective spatial relationship to a respective region of interest of the at least two regions of interest. For example, the reference operation may be implemented using the coordinate analysis circuit 1524 described in conjunction with FIG. 35. A registration operation 1620 includes registering the respective regions of interest of a mammalian body part. The registration is at least partially based on the common frame of reference. For example, the registration operation may be implemented at least in part using the registration circuit 1526 described in conjunction with FIG. 35. A storage operation 1630 includes maintaining in a computer-readable media informational data corresponding to the respective registered regions of interest. For example, the storage operation may be implemented at least in part using the computer-readable media 235 described in conjunction with FIG. 3.

FIG. 37 illustrates an alternative embodiment of the operational flow 1600 of FIG. 36. In an embodiment, the reference operation 1610 may include at least one additional embodiment. The at least one additional embodiment may include an operation 1611 or an operation 1612. The operation 1611 includes determining a common frame of reference that is at least partially based on a landmark subsurface feature of a cavity or lumen of a mammalian body part. The cavity or lumen of the mammalian body part has at least two landmark subsurface features and at least two regions of interest. Each landmark subsurface feature of at least two landmark subsurface features has a respective spatial relationship to a respective region of interest of the at least two regions of interest. The operation 1612 includes determining a common frame of reference that is at least partially based on a landmark subsurface feature of a cavity or lumen of a mammalian body part. The cavity or lumen of the mammalian body part has at least two landmark subsurface features and at least two regions of interest of a surface of the cavity or lumen. Each landmark subsurface feature of at least two landmark subsurface features has a respective spatial relationship to a respective region of interest of the at least two regions of interest.

In an embodiment, the registration operation 1620 may include at least one additional embodiment, such as the operation 1621. The operation 1621 includes registering the respective regions of interest of a mammalian body part. The registration is at least partially based on the determined common frame of reference and on a spatial relationship among each landmark subsurface feature of at least two landmark subsurface features.

In an embodiment, the storage operation 1630 may include at least one additional embodiment, such as the operation 1631. The operation 1631 includes maintaining in a computer-readable media informational data corresponding to the respective registered regions of interest, and providing electronic access to the informational data.

FIG. 38 illustrates an alternative embodiment of the operational flow 1610 of FIG. 36. The operational flow may include at least on additional operation 1640. The at least one additional operation may include an operation 1641, an operation 1642, an operation 1643, or an operation 1644. The operation 1641 includes transforming the informational data into a particular visual depiction of the respective registered regions of interest. The operation 1642 includes transforming the informational data into a particular visual depiction of a spatial relationship among the respective registered regions of interest. The operation 1643 includes outputting the informational data. The operation 1644 includes providing a notification that is at least partially based on the informational data to at least one of a human, computer, or system. In an embodiment, the operational flow may include receiving at least two medical images (not illustrated). Each medical image of the received at least two medical images includes a respective region of interest of the mammalian body part.

FIG. 39 illustrates an example computer program product 1700. The computer program product includes a computer-readable media 1710 bearing program instructions 1720. The program instructions, when executed by a processor of a computing device, cause the computing device to perform a process. The process includes determining a common frame of reference at least partially based on a landmark subsurface feature of a mammalian body part having at least two landmark subsurface features and at least two regions of interest. Each landmark subsurface feature of at least two landmark subsurface features has a respective spatial relationship to a respective region of interest of the at least two regions of interest. The process includes registering the respective regions of interest of a mammalian body part. The registration is at least partially based on the common frame of reference. The process includes storing in another computer-readable media operably coupled with the processor informational data corresponding to the respective registered regions of interest.

In an embodiment, the process further includes 1732 transforming the informational data into a signal useable in providing a particular visual depiction of the respective registered regions of interest. In an embodiment, the process further includes 1734 providing a notification to at least one of humans, computers, or systems indicative of the respective registered regions of interest.

In an embodiment, the computer-readable media 1710 includes a tangible computer-readable media 1712. In an embodiment, the computer-readable media includes a communications media 1714.

Figure 40:
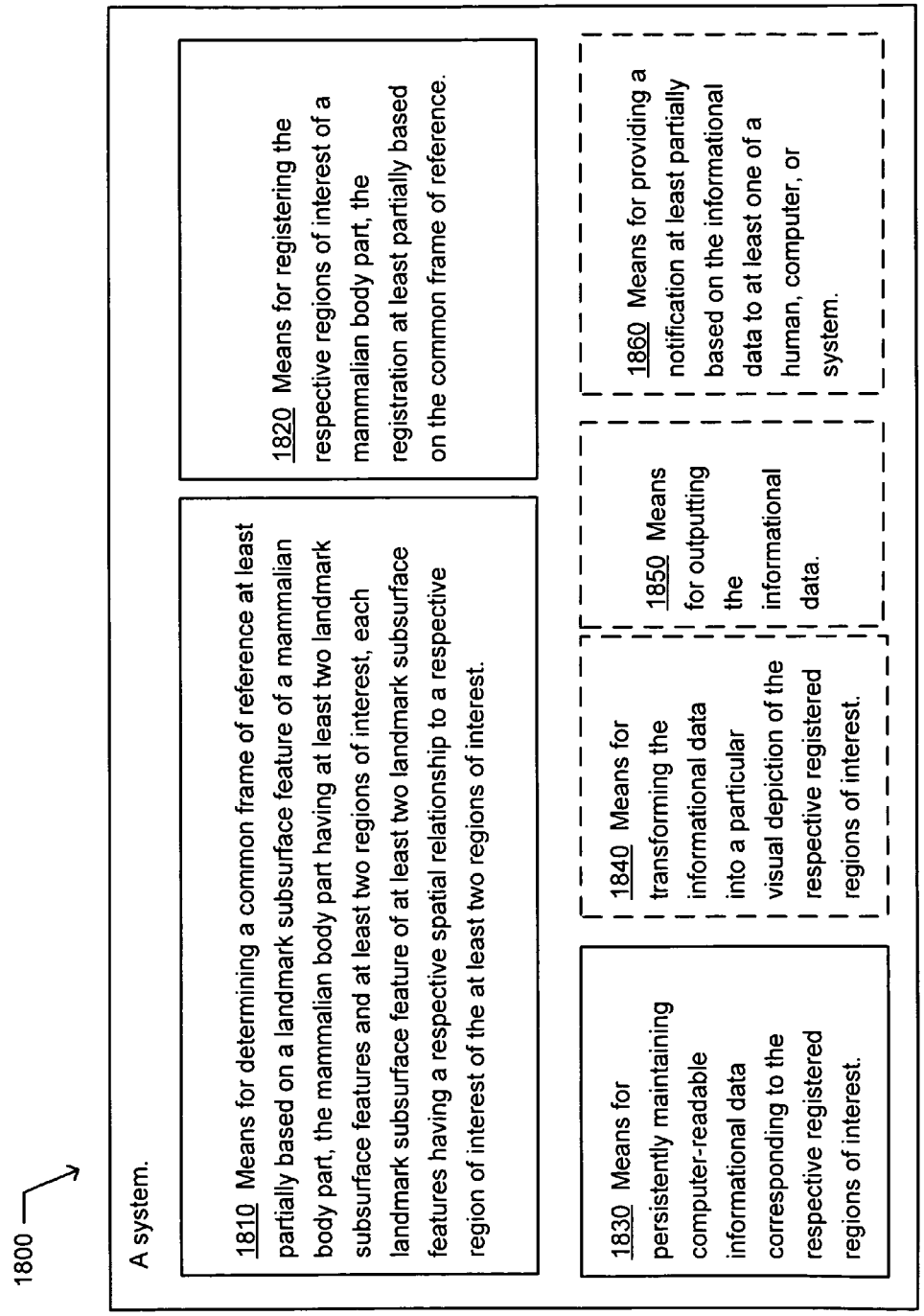
FIG. 40 illustrates an example system.

FIG. 40 illustrates an example system 1800. The system includes means 1810 for determining a common frame of reference that is at least partially based on a landmark subsurface feature of a mammalian body part. The mammalian body part has at least two landmark subsurface features and at least two regions of interest. Each landmark subsurface feature of at least two landmark subsurface features has a respective spatial relationship to a respective region of interest of the at least two regions of interest. The system includes means 1820 for registering the respective regions of interest of a mammalian body part. The registration is at least partially based on the common frame of reference. The system includes means 1830 for persistently maintaining computer-readable informational data corresponding to the respective registered regions of interest.

In an embodiment, the system 1800 may include means 1840 for transforming the informational data into a particular visual depiction of the respective registered regions of interest. In an embodiment, the system may include means 1850 for outputting the informational data. In an embodiment, the system may include means 1860 for providing a notification that is at least partially based on the informational data to at least one of a human, computer, or system.

Figure 41:
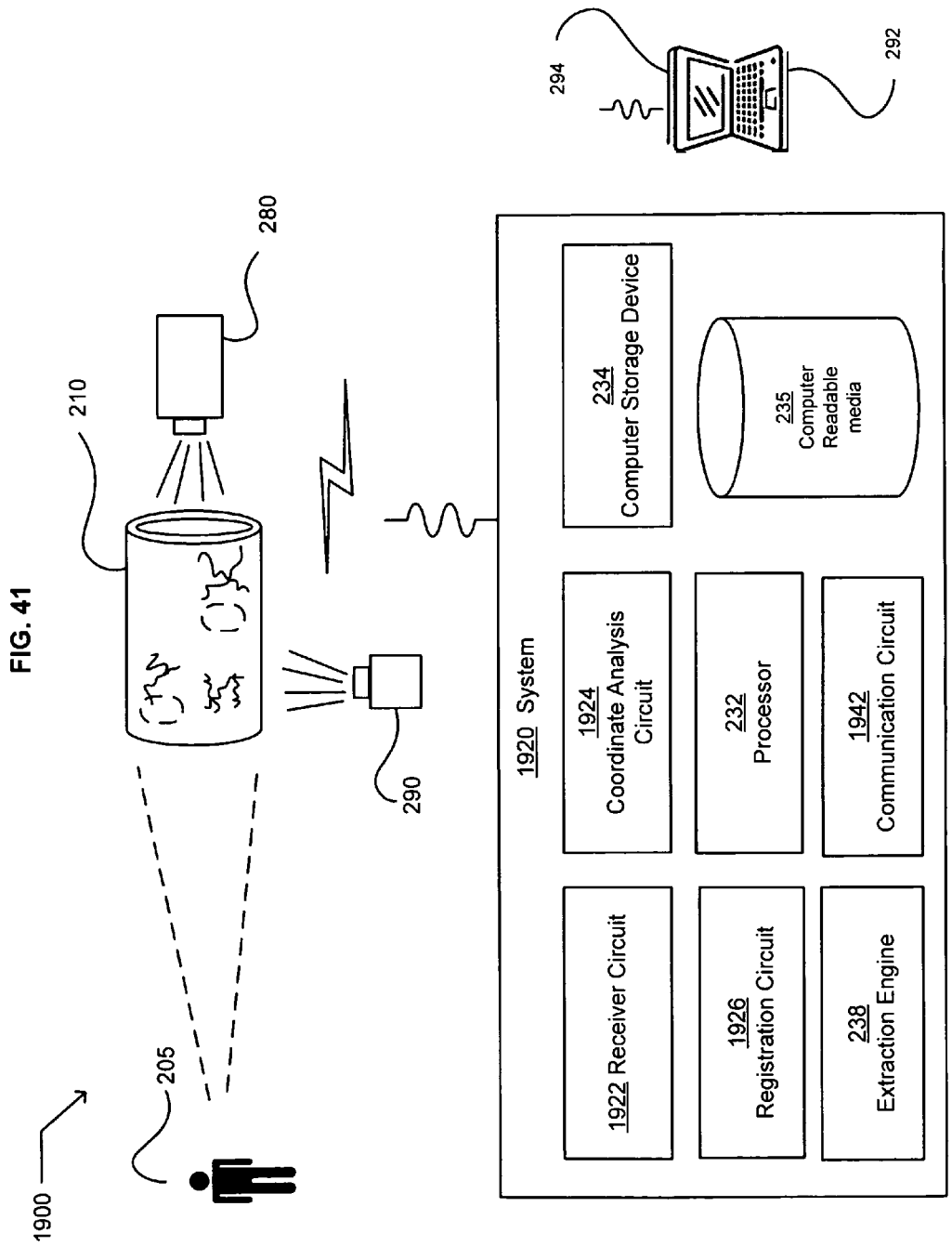
FIG. 41 illustrates an example environment.

FIG. 41 illustrates an example environment 1900. The environment includes the mammalian body part 210 of the mammal 205, and a system 1920. The system includes a receiver circuit 1922 configured to receive at least two medical images. Each medical image of the at least two medical images includes a respective region of interest of a mammalian body part. The receiver circuit is also configured to receive at least two reference images. Each reference image of the at least two reference images includes a respective landmark subsurface feature of the mammalian body part. Each landmark subsurface feature has a respective spatial relationship to a respective region of interest included in a medical image of the at least two medical images. For example, FIG. 4 illustrates regions of interest 214A and 214B of the mammalian body part 210. These regions of interest may be respectively included in two medical images, one medical image for each region of interest.

Figure 42:
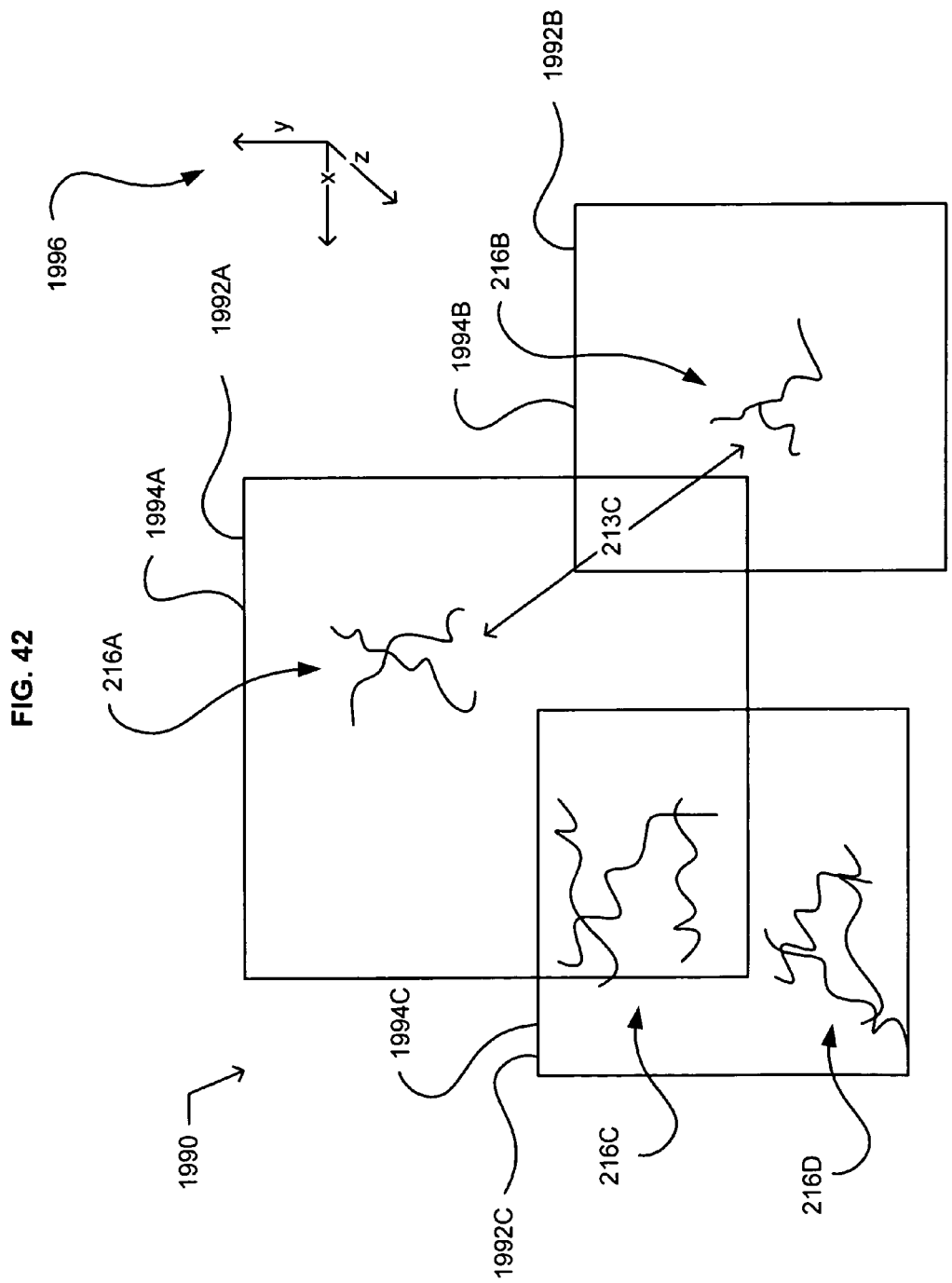
FIG. 42 illustrates three example reference images having respective fields of view that respectively include landmark subsurface features.

FIG. 42 illustrates three example reference images 1992A-1992C that have respective fields of view 1994A-1994C. These fields of view respectively include the landmark subsurface features 216A-216C. The respective landmark subsurface features 216A-216C are also illustrated in FIG. 4. Landmark subsurface features 216A and 216B have respective spatial relationships 217A and 217B respectively to the regions of interest 214A and 214B. In addition, landmark subsurface feature 216C has the spatial relationship 213B to landmark subsurface feature 216B.

Continuing with FIG. 41, the system 1920 includes a coordinate analysis circuit 1924 configured to determine a common frame of reference that is at least partially based on a landmark subsurface feature included in a reference image of the at least two reference images. The system includes a registration circuit 1926 configured to register the respective regions of interest included in the at least two medical images. The registration is at least partially based on the determined common frame of reference. The system includes the computer-readable media 235 configured to maintain informational data corresponding to the respective registered regions of interest included in the at least two medical images.

In an embodiment, a first landmark subsurface feature of the mammalian body part of a first digital image of at least two digital images and a second landmark subsurface feature of the mammalian body part of a second reference image of the at least two reference images are the same landmark subsurface feature. For example, FIG. 42 illustrates the landmark subsurface feature 216C of the reference image 1992C as being the same landmark subsurface feature as the landmark subsurface feature 216C of the reference image 1992A. Please note that in an embodiment, while the field of view 1994A of the reference image 1992A includes the two landmark subsurface features 216A and 216C, neither landmark subsurface feature 216A or 216B of landmark subsurface feature 216A is necessarily a "second landmark subsurface feature." In an embodiment, first landmark subsurface feature of the mammalian body part of a first reference image of the at least two reference images and a second landmark subsurface feature of the mammalian body part of a second reference image of the at least two reference images are different landmark subsurface features. For example, FIG. 42 illustrates the landmark subsurface feature 216C of reference image 1992C as being a different landmark subsurface feature than the landmark subsurface feature 216B of the reference image 1992B.

Continuing with FIG. 41, in an embodiment, the least two medical images may have been acquired by a body-insertable device, such as the body insertable device 280, while a portion of the body-insertable device was present in a cavity or lumen of a mammalian body part 210. Each medical image of the at least two medical images include a respective region of interest of the mammalian body part. In an embodiment, the body-insertable device may be configured for examination or inspection of a cavity or lumen of a mammalian body part. In an embodiment, each medical image of the at least two medical images may include a respective region of interest of a cavity or lumen of a mammalian body part. Referring to FIG. 4 for example, a first medical image may include the region of interest 214A, a second medical image may include the region of interest 214B, and a third medical image may include the region of interest 214C, all of the cavity or lumen 212 of the mammalian body part 210. In an embodiment, each medical image of the at least two medical images may include a respective region of interest of a surface of a cavity or lumen of a mammalian body part. Referring to FIG. 4 for example, a first medical image may include the region of interest 214A, a second medical image may include the region of interest 214B, and a third medical image may include the region of interest 214C of the surface 212, all of the cavity or lumen 211 of the mammalian body part 210.

Continuing with FIG. 41, in an embodiment, the at least two medical images may have been acquired by an ex vivo device, such as the device 290. Each medical image of the at least two medical images includes a respective region of interest of the mammalian body part. In an embodiment, the at least two reference images may have been acquired by an ex vivo device. Each reference image of the at least two reference images includes a respective landmark subsurface feature of the mammalian body part. Each landmark subsurface feature has a respective spatial relationship to a respective region of interest included in a medical image of the at least two medical images. For example, each reference image of the at least two reference images is representative of a respective landmark subsurface feature of the mammalian body part. Each landmark subsurface feature has a spatial relationship to a respective region of interest included in a medical image of the at least two medical images. For example, each reference image of the at least two reference images may include a respective landmark subsurface feature of the cavity or lumen of the mammalian body part. Each landmark subsurface feature has a spatial relationship to a respective region of interest of the cavity or lumen of the mammalian body part is included in a medical image of the at least two medical images. For example, each reference image of the at least two reference images may include a respective landmark subsurface feature of the mammalian body part. Each landmark subsurface feature has a spatial relationship to a respective region of interest of the mammalian body part included in a medical image of the at least two medical images. A first reference image includes a first landmark subsurface feature of the mammalian body part having a first spatial relationship to the first region of interest. A second reference image includes a second landmark subsurface feature having a second spatial relationship to a second region of interest. The second landmark subsurface feature also includes a third spatial relationship to the first subsurface feature. For example, FIG. 4 illustrates the landmark subsurface feature 216B having a spatial relation 217B to the region of interest 214B, and having a spatial relationship 213D to the region of interest 214A.

Continuing with FIG. 41, in an embodiment, the coordinate analysis circuit 1924 may be configured to determine a common frame of reference and a coordinate reference system. The determination is at least partially based on a landmark subsurface feature included in a reference image of the at least two reference images. In an embodiment, the coordinate analysis circuit may be configured to determine a common frame of reference anchored in a landmark subsurface feature that is included in a reference image of the at least two reference images. In an embodiment, the coordinate analysis circuit may be configured to determine a coordinate reference system at least partially based on a landmark subsurface feature included in a reference image of the at least two reference images.

In an embodiment, the registration circuit 1926 may be configured to register the respective regions of interest included in the at least two medical images. The registration is at least partially based on the determined common frame of reference and on a spatial relationship among each respective landmark subsurface feature of the at least two reference images. In an embodiment, the registration circuit may be configured to register a spatial relationship of the respective regions of interest included in the at least two medical images. The registration is at least partially based on the determined common frame of reference. In an embodiment, the registration circuit may be configured to register the respective regions of interest included in the at least two medical images. The registration is at least partially based on the determined common frame of reference and includes an orientation of the respective regions of interest.

In an embodiment, the computer-readable media 235 may be configured to maintain and to provide electronic access to informational data corresponding to the registration of the respective regions of interest included in the at least two medical images. In an embodiment, the computer-readable media may be configured to maintain informational data corresponding to the respective registered regions of interest included in the at least two medical images, and to maintain informational data corresponding to the determined common frame of reference. In an embodiment, a computer storage device includes the computer-readable media, which may be configured to maintain informational data corresponding to the respective registered regions of interest included in the at least two medical images.

In an embodiment, the system 1920 may include a communication circuit, such as for example the communication circuit 1942, configured to output the informational data. In an embodiment, the system may be configured to provide a notification that is at least partially based on the informational data to at least one of a human, computer, or system.

Figure 43:
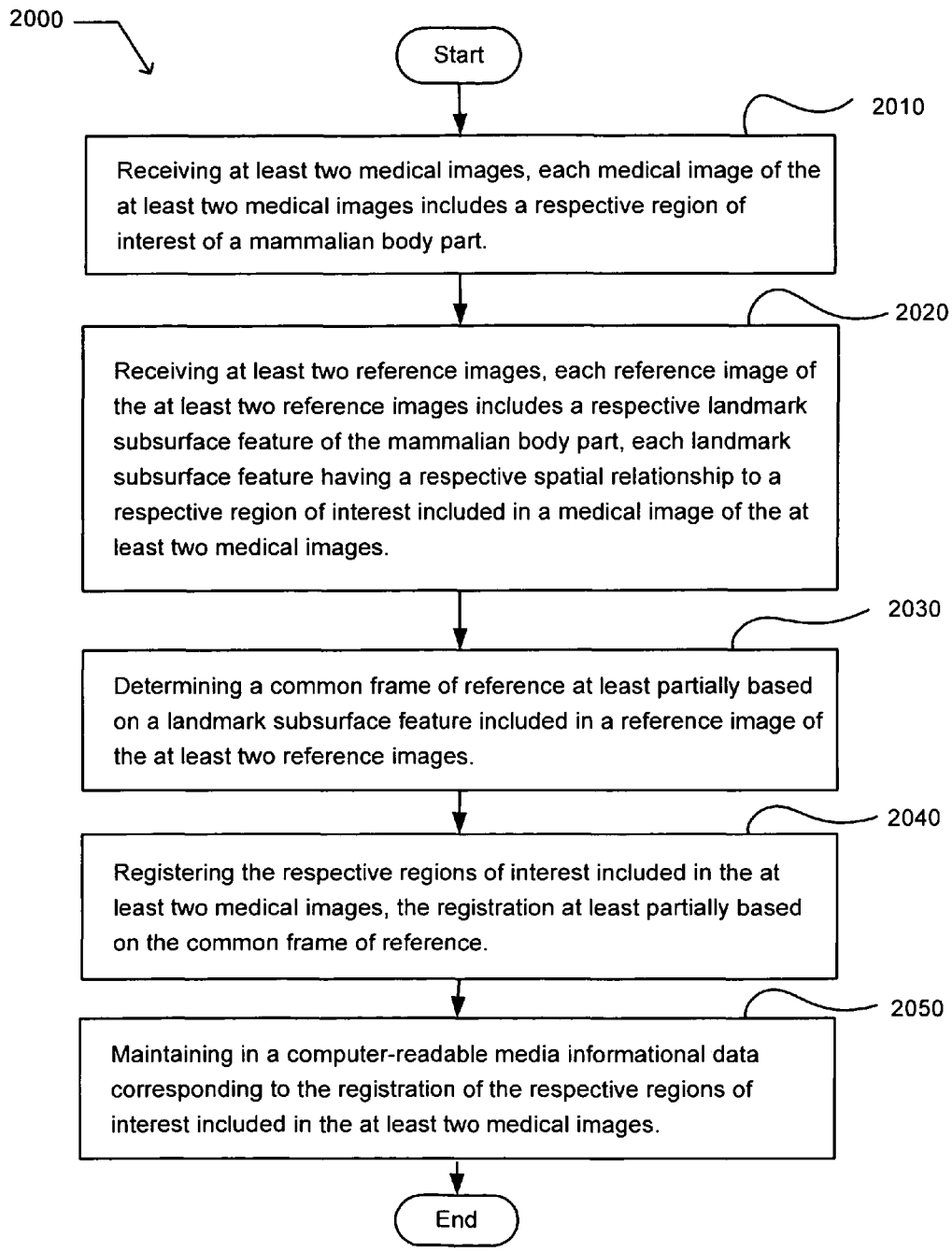
FIG. 43 illustrates an example operational flow.

FIG. 43 illustrates an example operational flow 2000. The operational flow includes a start operation. A first reception operation 2010 includes receiving at least two medical images. Each medical image of the at least two medical images includes a respective region of interest of a mammalian body part. For example, the first reception operation may be implemented using the receiver circuit 1922 described in conjunction with FIG. 41. A second reception operation 2020 includes receiving at least two reference images. Each reference image of the at least two reference images includes a respective landmark subsurface feature of the mammalian body part. Each landmark subsurface feature has a respective spatial relationship to a respective region of interest included in a medical image of the at least two medical images. For example, the second reception operation may be implemented using the receiver circuit 1922 described in conjunction with FIG. 41. A reference operation 2030 includes determining a common frame of reference. The determination is at least partially based on a landmark subsurface feature included in a reference image of the at least two reference images. For example, the reference operation may be implemented using the coordinate analysis circuit 1924 described in conjunction with FIG. 41. A registration operation 2040 includes registering the respective regions of interest included in the at least two medical images. The registration is at least partially based on the common frame of reference. For example, the registration operation may be implemented using the registration circuit 1926 described in conjunction with FIG. 41. A storage operation 2050 includes maintaining in a computer-readable media informational data corresponding to the registration of the respective regions of interest included in the at least two medical images. For example, the storage operation may be implemented using the computer-readable media 235 described in conjunction with FIG. 3. The operational flow includes an end operation.

Figure 44:
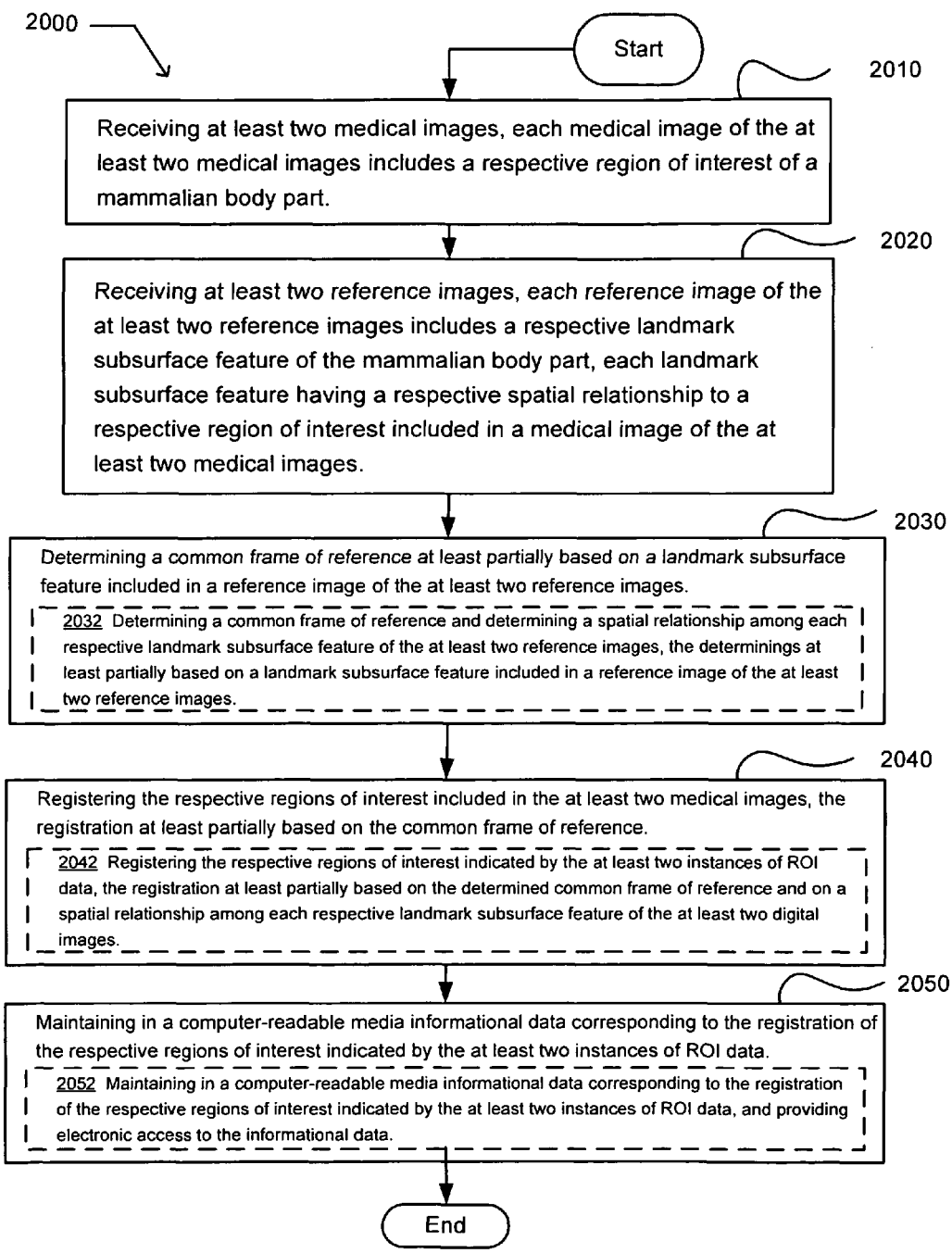
FIG. 44 illustrates an alternative embodiment of the operational flow 2000 described in FIG. 43.

FIG. 44 illustrates an alternative embodiment of the operational flow 2000 described in FIG. 43. The reference operation 2030 may include at least one additional operation, such as the operation 2032. The operation 2032 includes determining a common frame of reference and determining a spatial relationship among each respective landmark subsurface feature of the at least two reference images. The determining a common frame of reference and determining a spatial relationship are at least partially based on a landmark subsurface feature included in a reference image of the at least two reference images. The registration operation 2040 may include at least one additional embodiment, such as the operation 2042. The operation 2042 includes registering the respective regions of interest included in the at least two medical images. The registration is at least partially based on the common frame of reference and on a spatial relationship among each respective landmark subsurface feature of the at least two reference images. In an embodiment, the storage operation 2050 may include at least one additional embodiment, such as the operation 2052. The operation 2052 includes maintaining in a computer-readable media informational data corresponding to the registration of the respective regions of interest. The operation 2052 also includes providing electronic access to the informational data.

Figure 45:
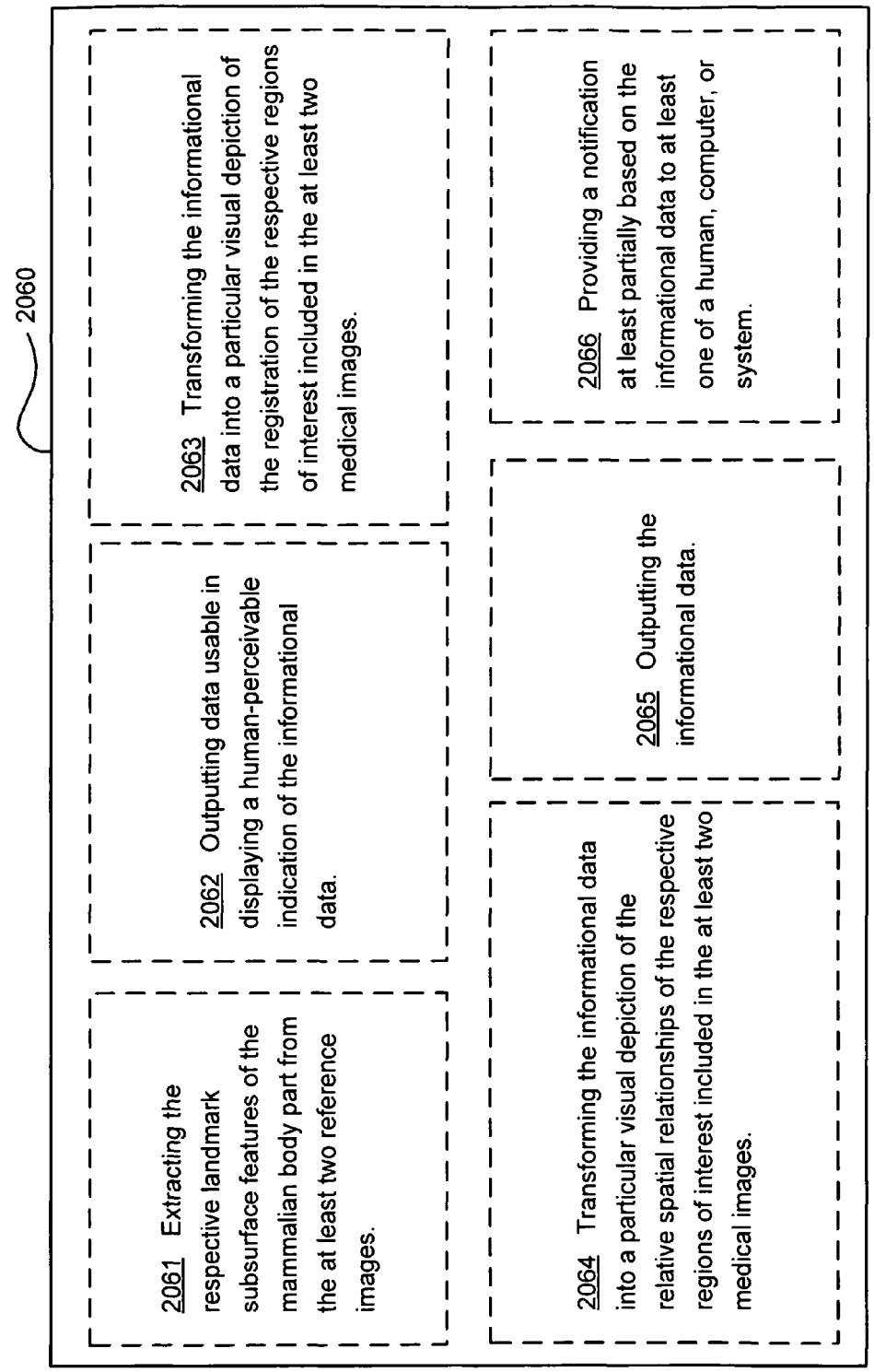
FIG. 45 illustrates an alternative embodiment of the operational flow 2000.

FIG. 45 illustrates an alternative embodiment of the operational flow 2000 described in FIG. 43. The operational flow may include at least one additional embodiment, illustrated as additional operation 2060. The additional operation may include an operation 2061, an operation 2062, an operation 2063, an operation 2064, an operation 2065, or an operation 2066. The operation 2061 includes extracting the respective landmark subsurface features of the mammalian body part from the at least two reference images. The operation 2062 includes outputting data usable in displaying a human-perceivable indication of the informational data. The operation 2063 includes transforming the informational data into a particular visual depiction of the registration of the respective regions of interest included in the at least two medical images. The operation 2064 includes transforming the informational data into a particular visual depiction of the relative spatial relationships of the respective regions of interest included in the at least two medical images. The operation 2065 includes outputting the informational data. The operation 2066 includes providing a notification that is at least partially based on the informational data to at least one of a human, computer, or system.

FIG. 46 illustrates a computer program product 2100. The computer program product includes a computer-readable media 2110 bearing program instructions 2120. The program instructions, when executed by a processor of a computing device, cause the computing device to perform a process. The process includes receiving at least two medical images. Each medical image of the at least two medical images includes a respective region of interest of a mammalian body part. The process includes receiving at least two reference images. Each reference image of the at least two reference images includes a respective landmark subsurface feature of the mammalian body part. Each landmark subsurface feature has a respective spatial relationship to a respective region of interest included in a medical image of the at least two medical images. The process includes determining a common frame of reference. The common frame of reference is determined that is at least partially based on a landmark subsurface feature included in a reference image of the at least two reference images. The process includes registering the respective regions of interest included in the at least two medical images. The registration is at least partially based on the common frame of reference. The process includes storing in another computer-readable media operably coupled with the processor informational data corresponding to the registration of the respective regions of interest included in the at least two medical images.

In an embodiment, the determining may include 2121 determining a common frame of reference and determining a spatial relationship among each respective landmark subsurface feature of the at least two reference images. The determining a common frame of reference and determining a spatial relationship are at least partially based on a landmark subsurface feature included in a reference image of the at least two reference images. In an embodiment, the registering may include 2122 registering the respective regions of interest included in the at least two medical images. The registration is at least partially based on the determined common frame of reference and on a spatial relationship among each respective landmark subsurface feature of the at least two reference images. In an embodiment, the computer-readable media 2110 may include a tangible computer-readable media 2112. In an embodiment, the computer-readable media may include a communications media 2114.

Figure 47:
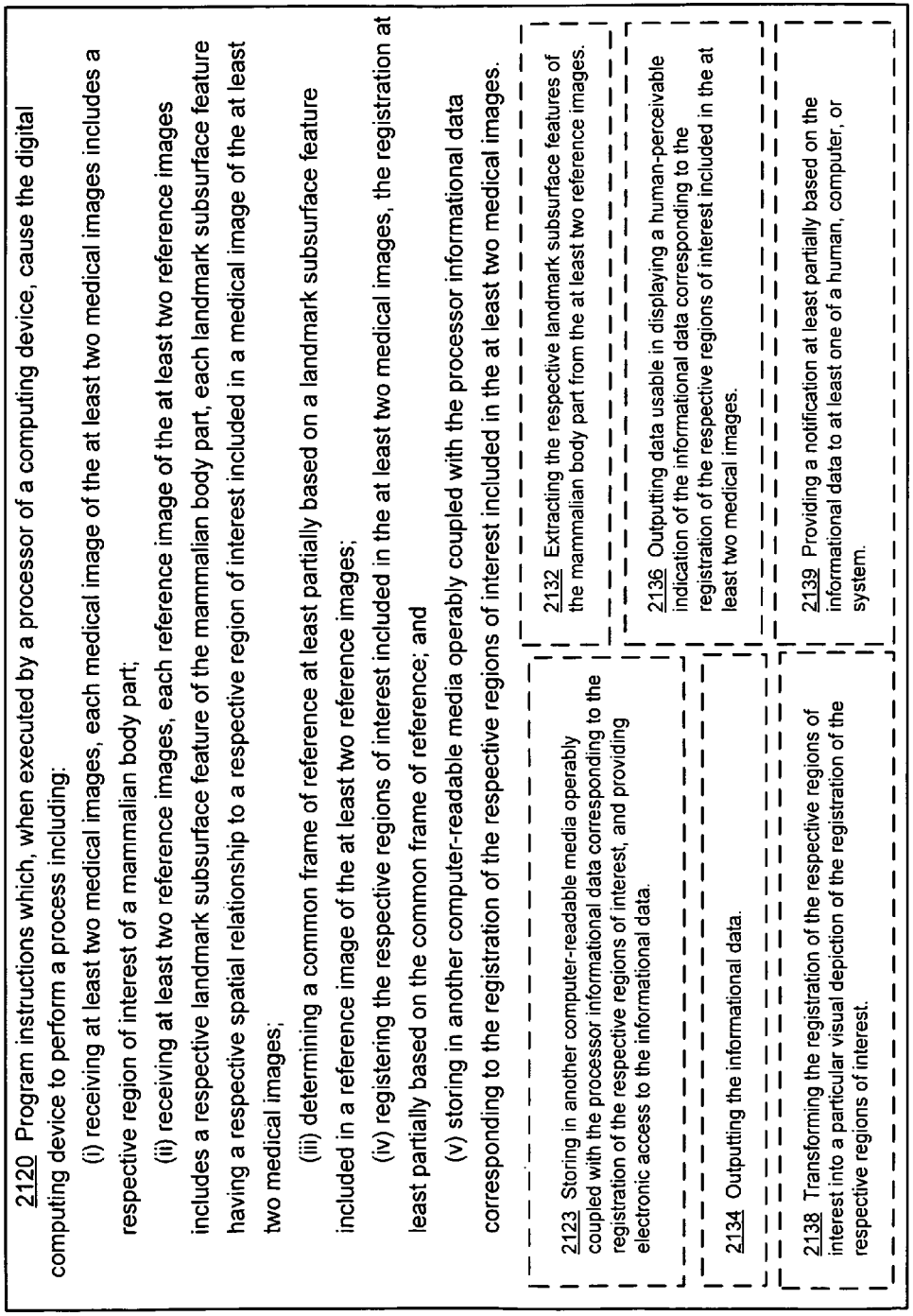
FIG. 47 illustrates an alternative embodiment of the computer program product 2100 of FIG. 46.

FIG. 47 illustrates an alternative embodiment of the computer program product 2100 of FIG. 46. In an embodiment, the storing may include 2123 storing in another computer-readable media operably coupled with the processor informational data corresponding to the registration of the respective regions of interest, and providing electronic access to the informational data. In an embodiment, the process 2120 may include 2132 extracting the respective landmark subsurface features of the mammalian body part from the at least two reference images. In an embodiment, the process may include 2134 outputting the informational data. In an embodiment, the process may include 2136 outputting data usable in displaying a human-perceivable indication of the informational data corresponding to the registration of the respective regions of interest included in the at least two medical images. In an embodiment, the process may include 2138 transforming the registration of the respective regions of interest into a particular visual depiction of the registration of the respective regions of interest. In an embodiment, the process may include transforming the registration of the respective regions of interest into a particular visual depiction of the relative spatial relationships of the respective regions of interest [not illustrated]. In an embodiment, the process may include 2139 providing a notification that is at least partially based on the informational data to at least one of a human, computer, or system.

Figure 48:
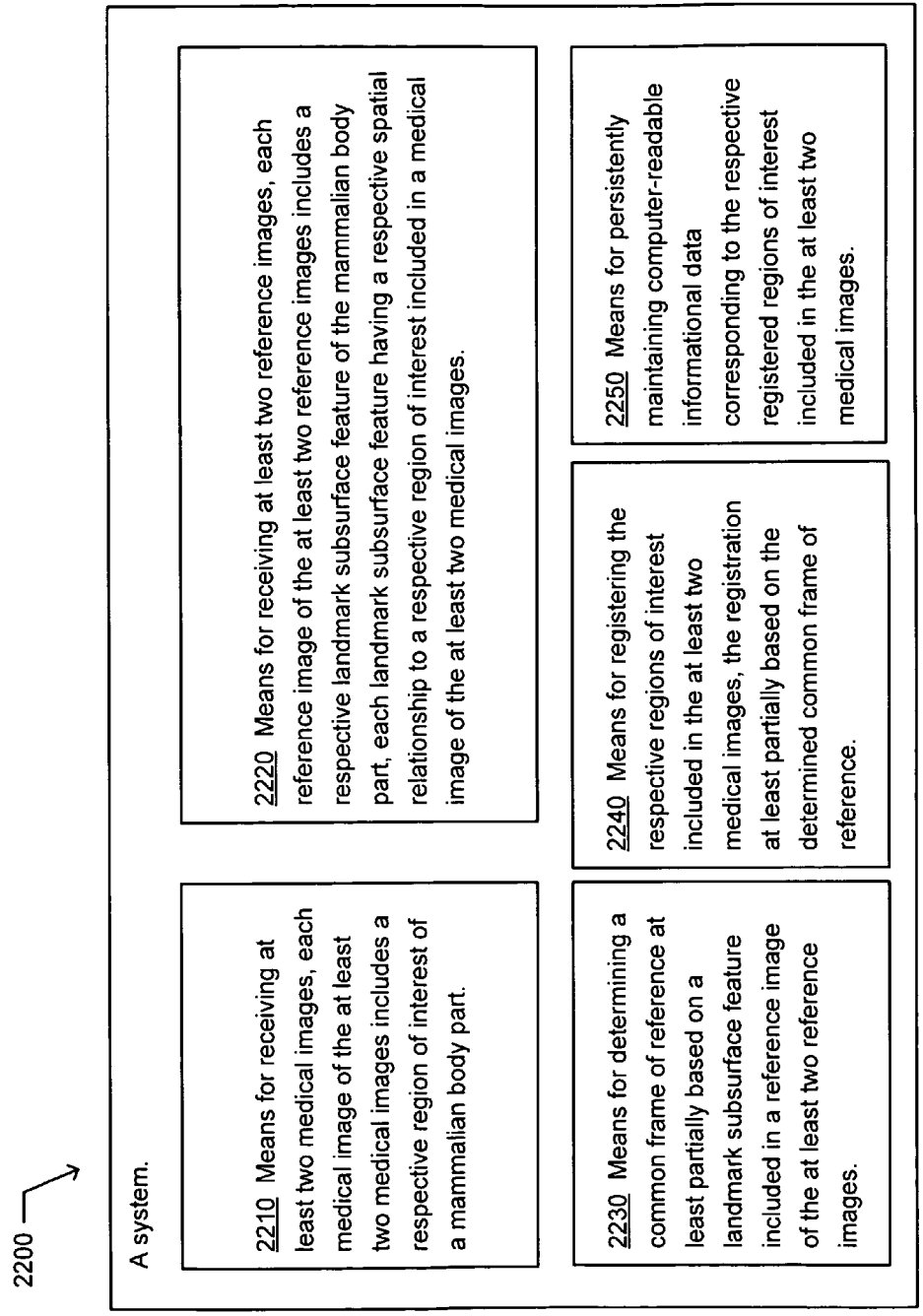
FIG. 48 illustrates an example system.

FIG. 48 illustrates an example system 2200. The system includes means 2210 for receiving at least two medical images. Each medical image of the at least two medical images includes a respective region of interest of a mammalian body part. The system includes means 2220 for receiving at least two reference images. Each reference image of the at least two reference images includes a respective landmark subsurface feature of the mammalian body part. Each landmark subsurface feature has a respective spatial relationship to a respective region of interest included in a medical image of the at least two medical images. The system includes means 2230 for determining a common frame of reference that is at least partially based on a landmark subsurface feature included in a reference image of the at least two reference images. The system includes means 2240 for registering the respective regions of interest included in the at least two medical images. The registration is at least partially based on the determined common frame of reference. The system includes means 2250 for persistently maintaining computer-readable informational data corresponding to the respective registered regions of interest included in the at least two medical images.

Figure 49:
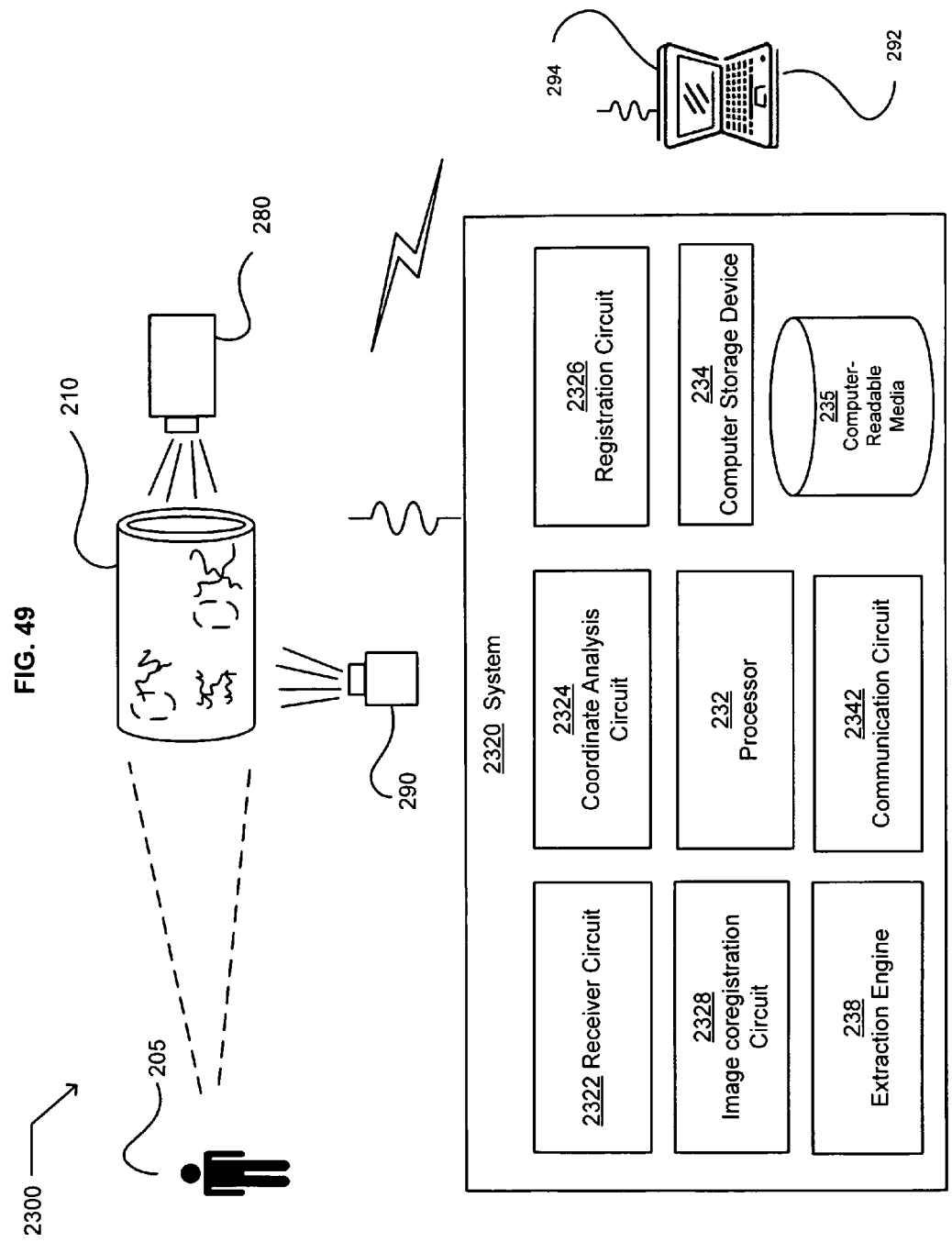
FIG. 49 illustrates an example environment.
Figure 50:
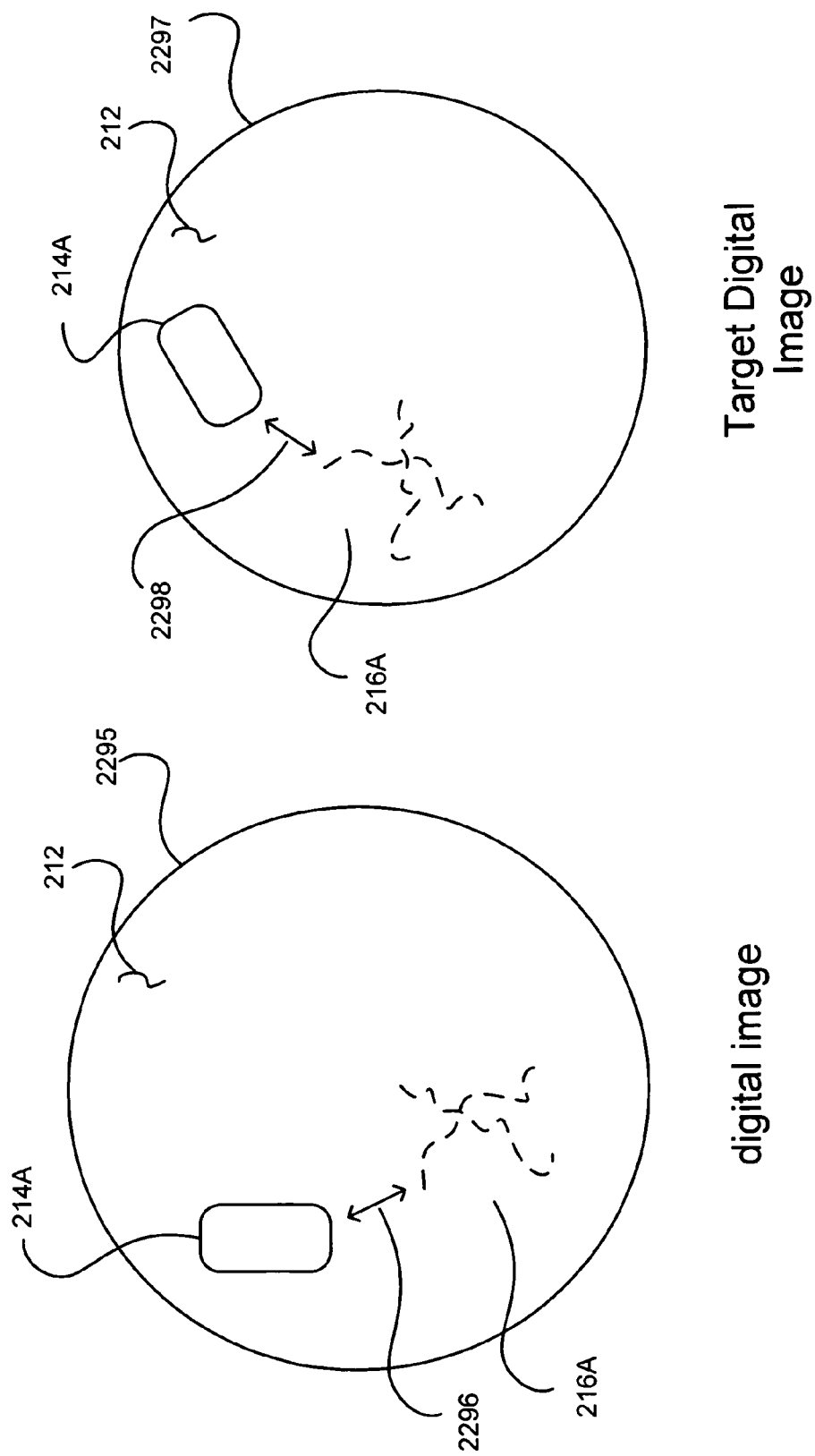
FIG. 50 illustrates an embodiment with a reference image having a field of view of the lumen or cavity of the mammalian body part.

FIG. 49 illustrates an example environment 2300. The environment includes the mammalian body part 210 of the mammal 205, and a system 2320. The system includes an image coregistration circuit 2328. The image coregistration circuit is configured to coregister a first depiction by a reference medical image of a region of interest of a mammalian body part and a second depiction by a target medical image of the region of interest of the mammalian body part. The first depiction of the region of interest has a first spatial relationship to a landmark subsurface feature of the mammalian body part during a first condition. The second depiction of the region of interest has a second spatial relationship to the landmark subsurface feature of the mammalian body part during a second condition. The coregistration of the first depiction of the region of interest and the second depiction of the region of interest is at least partially based on the first spatial relationship and on the second spatial relationship. For example, FIG. 50 illustrates an embodiment with a reference image having a field of view 2295 of the lumen or cavity 212 of the mammalian body part 210. The field of view 2295 includes the landmark subsurface feature 216A having a first spatial relationship 2996 to a first depiction of the region of interest 214A. FIG. 50 also illustrates an embodiment with a target digital image having a field of view 2297 of the lumen or cavity of the mammalian body part. The field of view 2297 includes the landmark subsurface feature 216A having a second spatial relationship 2298 to a second depiction of the region of interest 214A.

In an embodiment, "coregister" or "coregistration" of depictions of a region of interest or of images depicting a region of interest includes transforming corresponding different sets of data each representing the depiction of the region of interest into one coordinate system. Once co-registered, the different depictions of the region of interest or of images depicting the region of interest can be compared or integrated. In an embodiment, "coregister" or "coregistration" of different depictions of the region of interest or of images depicting the region of interest includes bringing the different depictions into an alignment. In an embodiment, "coregister" or "coregistration" of different depictions includes aligning depictions by two different modalities, such as a PET image and an MRI image. In an embodiment, "coregister" or "coregistration" of different depictions includes overlaying the depictions with a correct orientation and geometry so that corresponding internal features align.

In an embodiment, "coregister" or "coregistration" of images representing a scene or object, such as a region of interest or a landmark subsurface feature, includes transforming corresponding different sets of data each representing the scene or object into one coordinate system. Once co-registered, the different images can be compared or integrated. In an embodiment, "coregister" or "coregistration" of different images representing a scene or object includes bringing the different images into an alignment. In an embodiment, "coregister" or "coregistration" of different images representing a scene or object includes aligning images of two different modalities, such as a PET image and an MRI image. In an embodiment, "coregister" or "coregistration" of different images representing a scene or object includes overlaying the images with a correct orientation and geometry so that corresponding internal features align.

Returning to FIG. 49, the system also includes the computer-readable media 235. The computer-readable media configured to maintain informational data corresponding to the coregistration of the first depiction of the region of interest and the second depiction of the region of interest.

In an embodiment, the first condition may include a first surgical state and the second condition includes a second surgical state. For example, the first surgical state may include a pre-surgical state of a surface of a colon and the second surgical state may include post surgical state of the surface of the colon. In an embodiment, the first condition may include a first disease state of the mammalian body part and the second condition includes a second disease state of the mammalian body part. For example, a progression of a lesion on a surface of a colon over time may be illustrated by the first condition and the second condition. In an embodiment, the first condition includes a first time and the second condition includes a second time, wherein the first time and the second time are close in time. For example, the first condition and the second condition may be relative to seconds, minutes or a few hours of each other. For example, as during a single endoscopic examination procedure of a colon. For example, a first disease state may be a state of no apparent pathology, and a second disease state may be a state of an apparent pathology. For example, a first disease state may be a first stage of an apparent pathology, and a second disease state may be a second state of the apparent pathology. For example, a first disease state may be a disease state of the region interest before administration of a therapeutic substance to mammal and a second disease state may be a disease state of the region of interest after administration of the therapeutic substance to mammal. This would allow a heath care provider to monitor the effect of the administration of the therapeutic substance to mammal, and possible form a basis for future treatment of the mammal using the coregistered first depiction of the region of interest and the second depiction of the region of interest. In an embodiment, the first condition includes first time and the second condition includes second time, wherein the first time and the second time are substantially different times. For example, such as more than 12 hours from each other. For example, as during different endoscopic examination procedures of a colon occurring several weeks, months, or years apart.

In an embodiment, the second spatial relationship is substantially the same as the first spatial relationship. For example, when there has not been movement within the body part. In an embodiment, the second spatial relationship is substantially different from the first spatial relationship. For example, where there has been movement within the body part, such as the patient breathed or shifted position, or some temporal change.

In an embodiment, the image coregistration circuit 2328 includes an image coregistration circuit configured to coregister a first depiction by a reference medical image of a region of interest of a cavity or lumen of a mammalian body part during a first condition and a second depiction by a target medical image of the region of interest of the cavity or lumen of the mammalian body part during a second condition. The region of interest has a first spatial relationship to a landmark subsurface feature of the cavity or lumen of the mammalian body part during the first condition. The region of interest has a second spatial relationship to the landmark subsurface feature of the cavity or lumen of the mammalian body part during the second condition. The coregistration of the first depiction of the region of interest and the second depiction of the region of interest is at least partially based on the first spatial relationship and on the second spatial relationship. In an embodiment, the image coregistration circuit includes an image coregistration circuit configured to coregister a first depiction by a reference medical image of a region of interest of a surface of a cavity or lumen of a mammalian body part, during the first condition the region of interest has a first spatial relationship to a landmark subsurface feature of the cavity or lumen of the mammalian body part during a first condition, and a second depiction by a target medical image of the region of interest of the surface of the cavity or lumen of the mammalian body part during a second condition, the region of interest has a second spatial relationship to the landmark subsurface feature of the cavity or lumen of the mammalian body part during the second condition. The coregistration of the first depiction of the region of interest and the second depiction of the region of interest is at least partially based on the first spatial relationship and on the second spatial relationship.

In an embodiment, the image coregistration circuit 2328 includes an image coregistration circuit configured to coregister relative locations of a first depiction by a reference medical image of a region of interest of a mammalian body part during a first condition, the region of interest has a first spatial relationship to a landmark subsurface feature of the mammalian body part during the first condition, and a second depiction by a target medical image of the region of interest of the mammalian body part during a second condition, the region of interest has a second spatial relationship to the landmark subsurface feature of the mammalian body part during the second condition. The coregistration of the first depiction of the region of interest and the second depiction of the region of interest is at least partially based on the first spatial relationship and on the second spatial relationship. In an embodiment, the image coregistration circuit includes an image coregistration circuit configured to coregister relative locations and orientations of a first depiction by a reference medical image of a region of interest of a mammalian body part during a first condition, the region of interest has a first spatial relationship to a landmark subsurface feature of the mammalian body part during the first condition, and a second depiction by a target medical image of the region of interest of the mammalian body part during a second condition, the region of interest has a second spatial relationship to the landmark subsurface feature of the mammalian body part during the second condition. The coregistration of the first depiction of the region of interest and the second depiction of the region of interest is at least partially based on the first spatial relationship and on the second spatial relationship.

In an embodiment, the computer-readable media 235 includes a computer-readable media configured to maintain and provide access to informational data corresponding to the coregistration of the first depiction of the region of interest and the second depiction of the region of interest.

In an embodiment, the system 2320 includes a communication circuit 2342 configured to output a signal usable in displaying a human-perceivable indication of the coregistration of the first depiction of the region of interest and the second depiction of the region of interest. In an embodiment, the system 2320 may include a receiver circuit 2322 configured to receive the first depiction and the second depiction. In an embodiment, the system may include the registration circuit 2326. In an embodiment, the system may include the processor 232. In an embodiment, the system may include the computer storage device 234. In an embodiment, the system may include the extraction engine 238.

In an embodiment, the system 2320 includes a comparative-analysis circuit (not shown) configured to detect a change in the region of interest of the mammalian body part at least partially based on the coregistered first depiction of the region of interest and second depiction of the region. For example, the comparative-analysis circuit (not shown) may be configured to detect a change in the region of interest of the mammalian body part using a pattern recognition methodology, or an artificial intelligence methodology. For example, the detected change may include a change in one or more blood vessels in the region of interest, such as number of blood vessels, size of one or more blood vessels, or a pattern formed by blood vessels. In an example, a detected change may include a new pattern of blood vessels, which may indicate a tumor disease state in the region of interest. Such "neo-angiogenesis" can be apparent even at the microscopic level quite early on. In another example, a detected change in a presence of capillary buds or other angiogenesis may indicate inflammation in the region of interest. In a further example, a detected change may include a detected change in a size, color, or border of a lesion in the region of interest. In an example, a detected change may include a change in a pattern of surface topology, which could indicate tumor, polyps, inflammatory bowel disease, ulcerations, or the like. In an embodiment, the comparative-analysis circuit may be configured to compare the coregistered first depiction of the region of interest and second depiction of the region of interest and detect a change in the region of interest over time. This is expected to be of assistance to health care providers in diagnosis and treatment of disease.

For example, in use, a change in the region of interest detected by the comparative-analysis circuit may include a change in GI tract (stomach, intestine, colon, rectum, etc.), in lungs, or in blood vessels. The first depiction of the region of interest and the second depiction of the region of interest may be acquired during endoscopic examination the (using capsule endoscopy and traditional colonoscopy) of the body part. The first depiction of the region of interest and the second depiction of the region of interest may be used in comparing images of the same region at two different times to look for a change in disease state or condition and report change, or may be used reporting a "questionable site" that should be looked at in further detail or providing information on the actual change. For example, in use, a change in the region of interest detected by the comparative-analysis circuit may include a change between in an image taken of a region or interest at one time, e.g. in a state/condition of no apparent disease, then an image taken of a region or interest taken at a second time, e.g. in a follow-up colonoscopy, comparing a second image of the region and determining the change in state/condition with no prior knowledge of the state/condition. The comparison could include a change in a pattern. Information from comparisons can be added to provide more specificity and sensitivity. For example, if there is a change in blood vessels, the information may include a look at topology, or add results of the comparison to a list or report. Another example would be the absence of a disease state, e.g. after treatment with a therapeutic, especially an anti-angiogenic, the tumor or aberrant vascularization will be lessened and even absent. One example would be that a detected new pattern of blood vessels could indicate the onset of a tumor disease state. Such "neo-angiogenesis" may be apparent even at the microscopic level quite early on. Similarly, a detected presence of capillary buds or other angiogenesis may indicate onset of inflammation. Detected changes in patterns of surface topology may indicate tumor, polyps, inflammatory bowel disease, ulcerations. For example, in use, a detected change in the region of interest by the comparative-analysis circuit may be used for example in people at risk for certain diseases, in patients to follow progression of a disease state, in patients to assess therapeutic response, post-surgery or other intervention to monitor for relapse. For example, a change in the region of interest detected by the comparative-analysis circuit may include a change in a pattern in a portion of a larger field, where the larger field is used to align the imager.

Further, the system 2320 may include a decision circuit (not shown) operable to recommend or initiate acquisition of additional depictions of the region of interest, acquisition of a higher resolution depiction of the region of interest, acquisition of a depiction of the region of interest at a different wavelength or modality, or acquisition of an enhanced depiction of the region of interest, such with a contrast agent.

Figure 51:
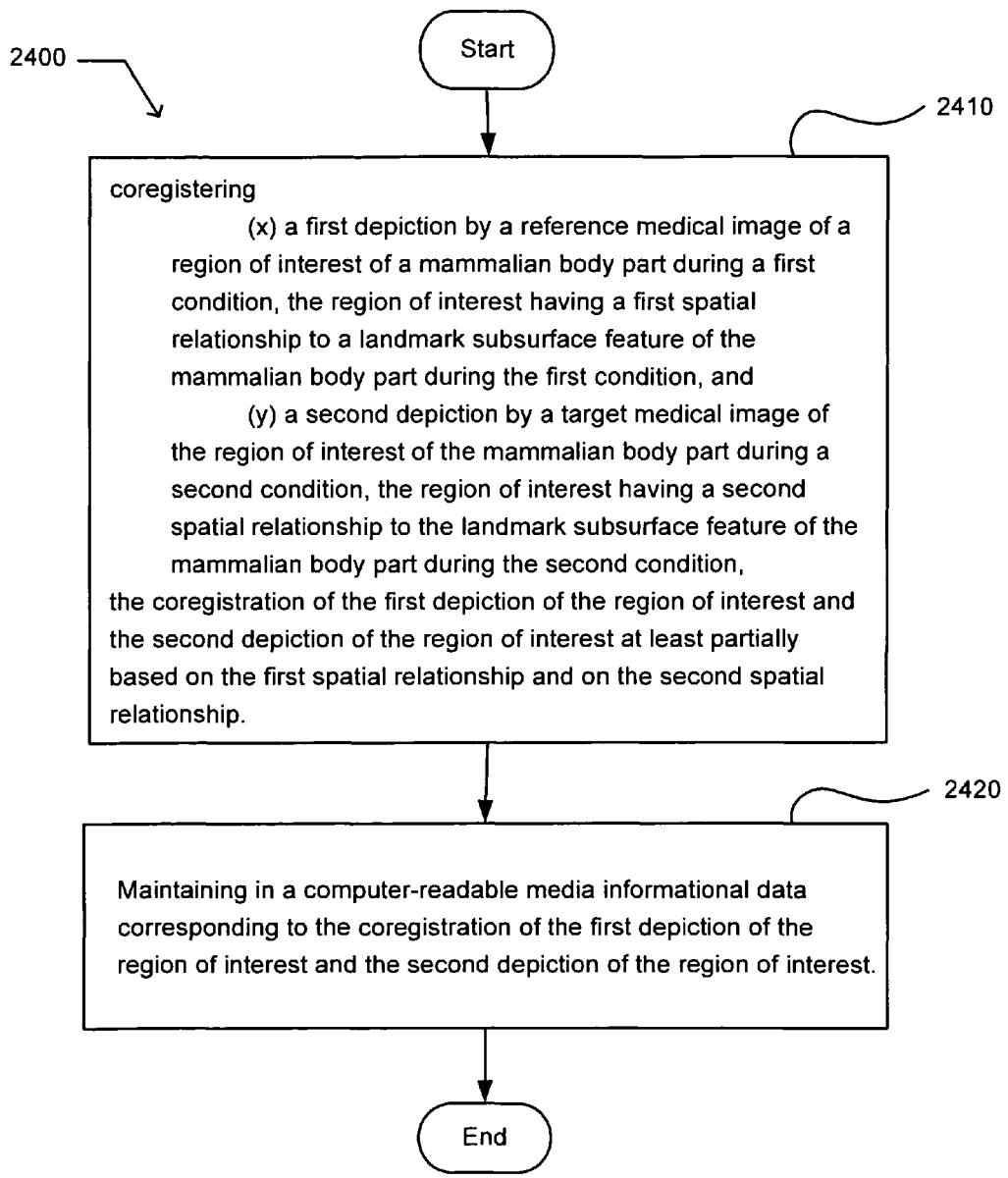
FIG. 51 illustrates an example operational flow.

FIG. 51 illustrates an example operational flow 2400. The operational flow includes a start operation. The operational flow includes a coregistration operation 2410. The coregistration operation includes coregistering a first depiction by a reference medical image of a region of interest of a mammalian body part during a first condition and a second depiction by a target medical image of the region of interest of the mammalian body part during a second condition. The region of interest has a first spatial relationship to a landmark subsurface feature of the mammalian body part during the first condition. The region of interest has a second spatial relationship to the landmark subsurface feature of the mammalian body part during the second condition. The coregistration of the first depiction of the region of interest and the second depiction of the region of interest is at least partially based on the first spatial relationship and on the second spatial relationship. In an embodiment, the coregistration operation may be implemented using the image coregistration circuit 2328 of FIG. 49. The operational flow includes a storage operation 2420. The storage operation includes maintaining in a computer-readable media informational data corresponding to the coregistration of the first depiction of the region of interest and the second depiction of the region of interest. In an embodiment, the storage operation may be implemented using the computer-readable media 235 described in conjunction with FIG. 49. The operational flow includes an end operation.

Figure 52:
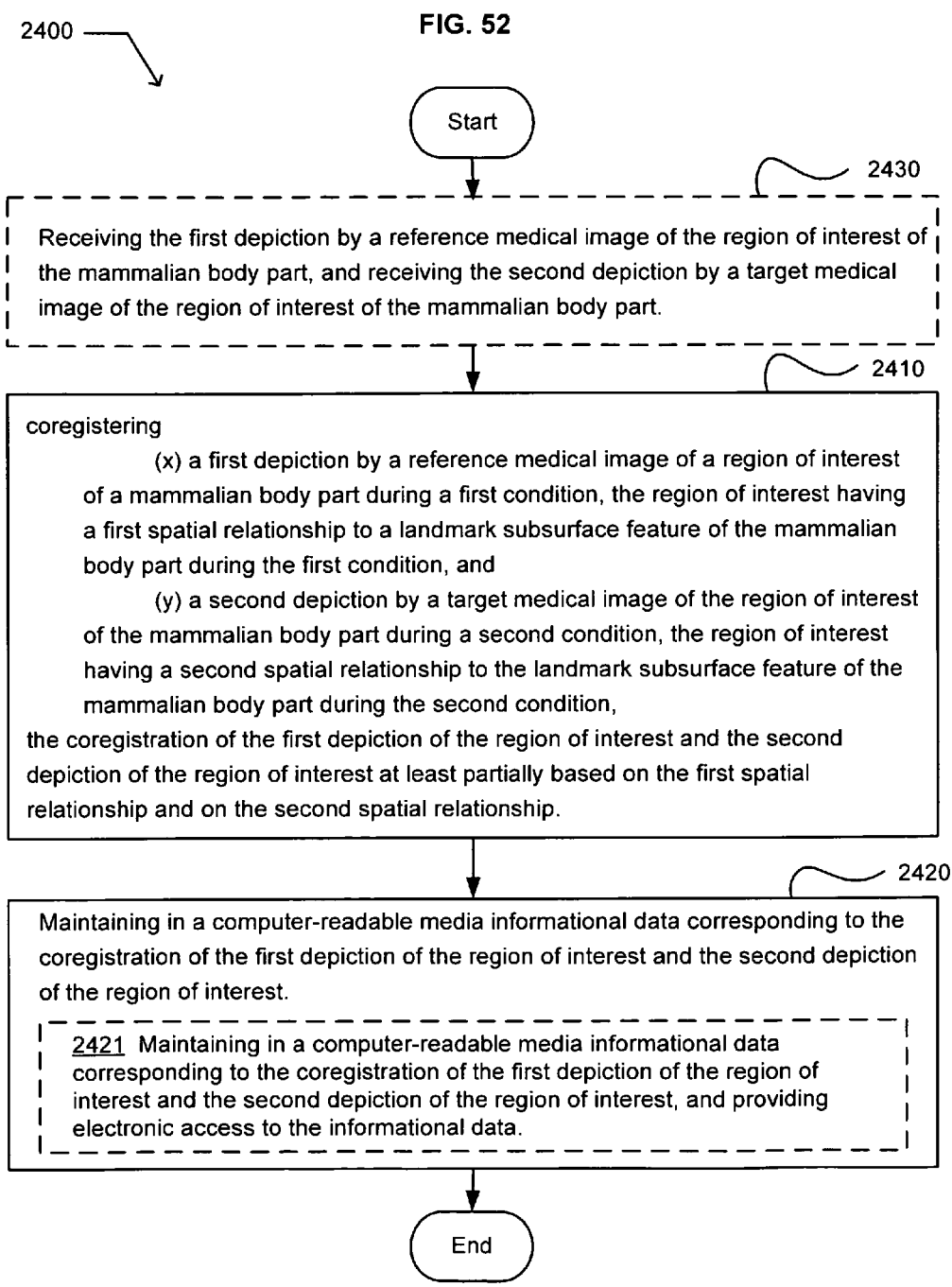
FIG. 52 illustrates an alternative embodiment of the operational flow 2400 of FIG. 51.

FIG. 52 illustrates an alternative embodiment of the operational flow 2400 of FIG. 51. The operational flow may include at least one additional embodiment, such as an operation 2430. The operation 2430 includes receiving the first depiction by a reference medical image of the region of interest of the mammalian body part, and receiving the second depiction by a target medical image of the region of interest of the mammalian body part. In an embodiment, the storage operation 2420 may include at least one additional embodiment, such as the operation 2421. The at least one additional embodiment includes maintaining in a computer-readable media informational data corresponding to the coregistration of the first depiction of the region of interest and the second depiction of the region of interest, and providing electronic access to the informational data.

Figure 53:
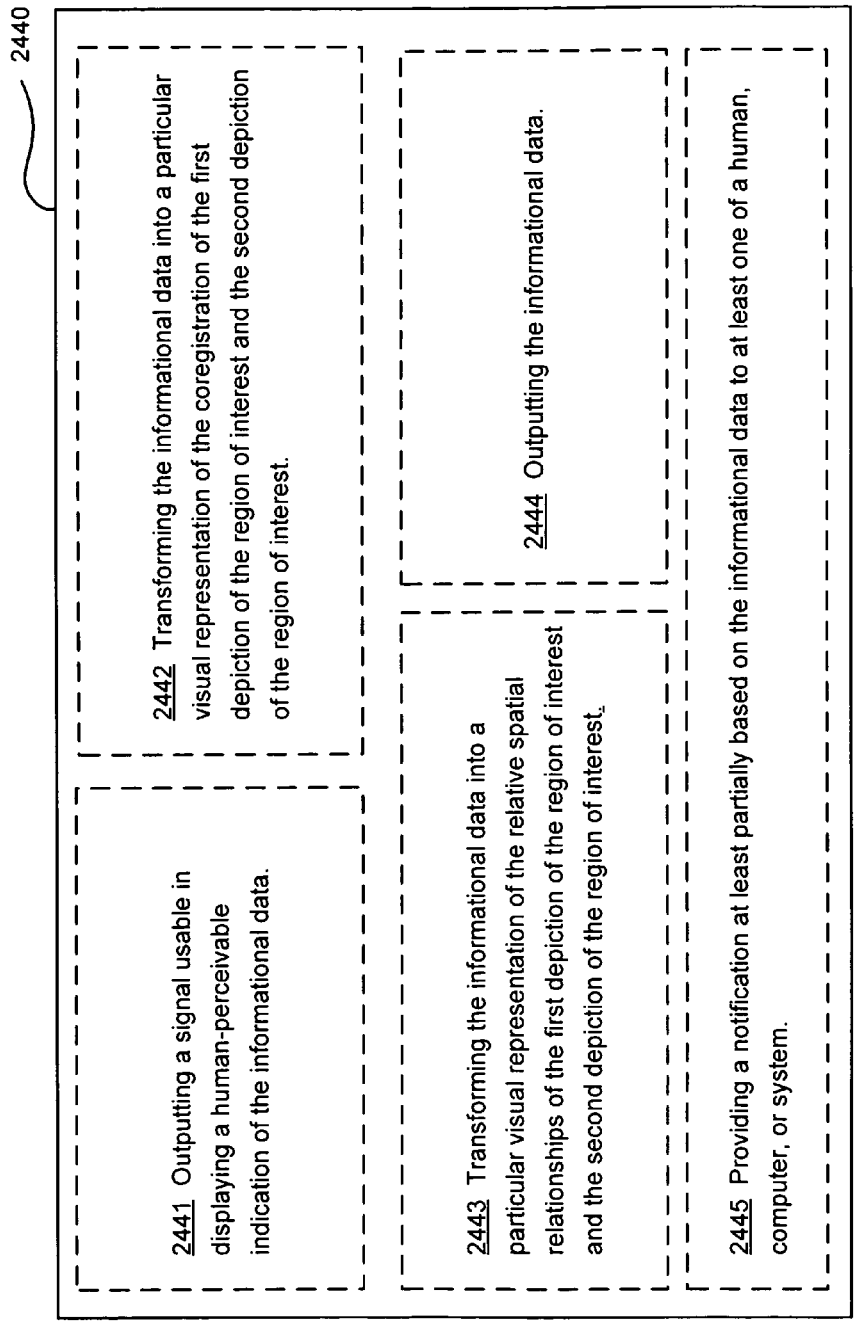
FIG. 53 illustrates an alternative embodiment of the operational flow 2400 of FIG. 51.

FIG. 53 illustrates an alternative embodiment of the operational flow 2400 of FIG. 51. The operational flow may include at least one additional embodiment illustrated as operation 2440. The operation 2400 includes an operation 2441, an operation 2442, an operation 2443, an operation 2444, or an operation 2445. The operation 2441 includes outputting a signal usable in displaying a human-perceivable indication of the informational data. The operation 2442 includes transforming the informational data into a particular visual representation of the coregistration of the first depiction of the region of interest and the second depiction of the region of interest. The operation 2443 includes transforming the informational data into a particular visual representation of the relative spatial relationships of the first depiction of the region of interest and the second depiction of the region of interest. The operation 2444 includes outputting the informational data. The operation 2445 includes providing a notification that is at least partially based on the informational data to at least one of a human, computer, or system.

FIG. 54 illustrates a computer program product 2500. The computer program product includes a computer-readable media 2510 bearing program instructions 2520. The program instructions, when executed by a processor of a computing device, cause the computing device to perform a process. The process includes coregistering a first depiction by a reference medical image of a region of interest of a mammalian body part during a first condition and a second depiction by a target medical image of the region of interest of the mammalian body part during a second condition. The region of interest has a first spatial relationship to a landmark subsurface feature of the mammalian body part during the first condition. The region of interest has a second spatial relationship to the landmark subsurface feature of the mammalian body part during the second condition. The coregistering of the first depiction and the second depiction is at least partially based on the first spatial relationship and on the second spatial relationship. The process includes storing in another computer-readable media operably coupled with the processor informational data corresponding to the coregistration of the first depiction of the region of interest and the second depiction of the region of interest.

In an embodiment, the computer-readable media 2510 includes a tangible computer-readable media 2512. In an embodiment, the computer-readable media includes a communications media 2514.

In an embodiment, the storing process includes 2522 storing in another computer-readable medium operably coupled with the processor informational data corresponding to the coregistration of the first depiction of the region of interest and the second depiction of the region of interest, and providing electronic access to the informational data.

FIG. 55 illustrates an alternative embodiment of the program instructions 2520 which cause the computing device to perform a process. In an embodiment, the process further includes 2531 outputting the informational data. In an embodiment, the process further includes 2532 outputting a signal usable in displaying a human-perceivable indication of the coregistration of the first depiction of the region of interest and the second depiction of the region of interest. In an embodiment, the process further includes 2533 transforming the informational data into a particular visual depiction of the coregistration of the first depiction of the region of interest and the second depiction of the region of interest. In an embodiment, the process further includes 2534 providing a notification that is at least partially based on the informational data to at least one of a human, computer, or system.

FIG. 56 illustrates an example system 2600. The system includes means 2610 for coregistering a first depiction by a reference medical image of a region of interest of a mammalian body part during a first condition, the region of interest has a first spatial relationship to a landmark subsurface feature of the mammalian body part during the first condition, and a second depiction by a target medical image of the region of interest of the mammalian body part during a second condition, the region of interest has a second spatial relationship to the landmark subsurface feature of the mammalian body part during the second condition. The coregistration of the first depiction of the region of interest and the second depiction of the region of interest is at least partially based on the first spatial relationship and on the second spatial relationship. The system includes means 2620 for persistently maintaining computer-readable informational data corresponding to the coregistration of the first depiction of the region of interest and the second depiction of the region of interest. In an embodiment, the system includes means for receiving the reference medical image; means for receiving the target medical image; means for receiving the first data indicative of a first spatial relationship; and means for receiving the second data indicative of a second spatial relationship. [not illustrated]

Returning to FIG. 49, which illustrates an alternative embodiment of the system 2320. The alternative embodiment of the system 2320 includes the receiver circuit 2322 configured to receive (i) a reference image that includes a first depiction of a region of interest of a mammalian body part during a first condition, and (ii) a target digital image that includes a second depiction the region of interest of the mammalian body part during a second condition. The receiver circuit is also configured to receive (iii) a first data indicative of a first spatial relationship between a landmark subsurface feature of the mammalian body part and the region of interest during the first condition, and (iv) a second data indicative of a second spatial relationship between the landmark subsurface feature of the mammalian body part and the region of interest during the second condition. In an embodiment, the first digital image includes the first data indicative of a first spatial relationship between a landmark subsurface feature of the mammalian body part and the region of interest during the first condition. For example, the first digital image may include the reference image. For example, the first digital image may be an image other than the reference image. In an embodiment, the second first digital image includes the second data indicative of a first spatial relationship between a landmark subsurface feature of the mammalian body part and the region of interest during the first condition. For example, the second digital image may include the target image. For example, the second digital image may be an image other than the target image.

The image coregistration circuit 2328 is configured to coregister the first depiction of the region of interest and the second depiction of the region of interest. The coregistration is at least partially based on the first spatial relationship and on the second spatial relationship. The computer-readable media 235 is configured to maintain informational data corresponding to the coregistration of the first depiction of the region of interest and the second depiction of the region of interest.

In an embodiment of the alternative embodiment, the receiver circuit 2322 is configured to receive (i) a reference medical image that includes a first depiction of a region of interest of a cavity or lumen of a mammalian body part during a first condition, (ii) a target medical image that includes a second depiction the region of interest of the cavity or lumen of the mammalian body part during a second condition. The receiver circuit is also configured to receive (iii) a first data indicative of a first spatial relationship between a landmark subsurface feature of the cavity or lumen of the mammalian body part and the region of interest during the first condition, and (iv) a second data indicative of a second spatial relationship between the landmark subsurface feature of the cavity or lumen of the mammalian body, part and the region of interest during the second condition. In an embodiment, the receiver circuit is configured to receive (i) a reference medical image that includes a first depiction of a region of interest of a surface of a cavity or lumen of a mammalian body part during a first condition, (ii) a target medical image that includes a second depiction the region of interest of the surface of the cavity or lumen of the mammalian body part during a second condition. The receiver circuit is also configured to receive (iii) a first data indicative of a first spatial relationship between a landmark subsurface feature of the surface of the cavity or lumen of the mammalian body part and the region of interest during the first condition, and (iv) a second data indicative of a second spatial relationship between the landmark subsurface feature of the surface of the cavity or lumen of the mammalian body part and the region of interest during the second condition.

In an embodiment of the alternative embodiment, the receiver circuit 2322 is configured to receive (i) a reference medical image that was acquired by a first device and includes a first depiction of a region of interest of a mammalian body part during a first condition, and (ii) a target medical image that was acquired by a second device and includes a second depiction the region of interest of the mammalian body part during a second condition. The receiver circuit is also configured to receive (iii) a first data was acquired by a third device and indicative of a first spatial relationship between a landmark subsurface feature of the mammalian body part and the region of interest during the first condition, and (iv) a second data acquired by a fourth device and indicative of a second spatial relationship between the landmark subsurface feature of the mammalian body part and the region of interest during the second condition. In an embodiment, the first device includes a body-insertable device. In an embodiment, the first device includes an ex vivo device. In an embodiment, the second device includes a device substantially similar to the first device. In an embodiment, the second device includes a device substantially dissimilar to the first device. In an embodiment, the third device includes a device substantially similar to the first device. In an embodiment, the third device includes a device substantially different from the first device. In an embodiment, the fourth device includes a device substantially similar to the first device. In an embodiment, the fourth device includes a device substantially different from to the first device.

In an embodiment of the alternative embodiment, the image coregistration circuit 2328 is configured to coregister the location of the first depiction of the region of interest relative to the second depiction of the region of interest, the coregistration is at least partially based on the first spatial relationship and the second spatial relationship. In an embodiment, the image coregistration circuit is configured to coregister the first depiction of the region of interest and the second depiction of the region of interest. The coregistration includes relative orientations of the first depiction of the region of interest and the second depiction of the region of interest. The registration is at least partially based on the first spatial relationship and the second spatial relationship. In an embodiment, the image coregistration circuit is configured to coregister the first depiction of the region of interest and the second depiction of the region of interest. The coregistration includes a registration of relative distortions of the region of interest between the first depiction of the region of interest and the second depiction of the region of interest. In an embodiment, the image coregistration circuit is configured to coregister the first depiction of the region of interest and the second depiction of the region of interest. The coregistration includes a spatial translation of the second depiction of the region of interest to substantially align with the first depiction of the region of interest. The coregistration is at least partially based on the first spatial relationship and the second spatial relationship.

In an embodiment of the alternative embodiment, the system 2320 includes a registration circuit 2326 configured to register the first depiction of the region of interest relative to the landmark subsurface feature of the mammalian body part at least partially based on the first spatial relationship, and to register the second depiction of the region of interest relative to the landmark subsurface feature of the mammalian body part at least partially based on the second spatial relationship. In an embodiment, the image coregistration circuit 2328 is configured to coregister the first depiction of the region of interest and the second depiction of the region of interest. The coregistration is at least partially based on the registration of the first depiction of the region of interest relative to the landmark subsurface feature of the mammalian body part and on the registration of the second depiction of the region of interest relative to the landmark subsurface feature of the mammalian body part.

In an embodiment of the alternative embodiment, the system 2320 includes the coordinate analysis circuit 2324 configured to determine a spatial relationship of the first depiction of the region of interest relative to the landmark subsurface feature of the mammalian body part, and to determine a spatial relationship of the second depiction of the region of interest to the landmark subsurface feature of the mammalian body part. In an embodiment, the image coregistration circuit 2328 is configured to coregister the first depiction of the region of interest and the second depiction of the region of interest, the coregistration is at least partially based on the determined spatial relationship of the first depiction of the region of interest relative to the landmark subsurface feature of the mammalian body part, and the determined spatial relationship of the second depiction of the region of interest to the landmark subsurface feature of the mammalian body part.

In an embodiment of the alternative embodiment, the computer-readable media 235 is configured to maintain and provide access to informational data corresponding to the coregistration of the first depiction of the region of interest and the second depiction of the region of interest. In an embodiment, the alternative embodiment of the system 2320 includes a communication circuit 2342 configured to output a signal usable in displaying a human-perceivable indication of the informational data.

FIG. 57 illustrates an example operational flow 2700. The operational flow includes a start operation. A first reception operation 2710 includes receiving a reference medical image that includes a first depiction of a region of interest of a mammalian body part during a first condition. A second reception operation 2720 includes receiving a target medical image that includes a second depiction the region of interest of the mammalian body part during a second condition. A third reception operation 2730 includes receiving a first data indicative of a first spatial relationship between a landmark subsurface feature of the mammalian body part and the region of interest during the first condition. A fourth reception operation 2740 includes receiving a second data indicative of a second spatial relationship between the landmark subsurface feature of the mammalian body part and the region of interest during the second condition. In an embodiment, at least one of the first reception operation, the second reception operation, the third reception operation, or the fourth reception operation may be implemented using the receiver circuit 2322 of FIG. 49. A coregistration operation 2750 includes coregistering the first depiction of the region of interest and the second depiction of the region of interest, the coregistration is at least partially based on the first spatial relationship and the second spatial relationship. In an embodiment, the coregistration operation may be implemented using the image coregistration circuit 2328 of FIG. 49. A storage operation 2760 includes maintaining in a computer-readable media informational data corresponding to the coregistration of the first depiction of the region of interest and the second depiction of the region of interest. In an embodiment, the storage operation may be implemented using the computer-readable media 235 of FIG. 3. The operational flow includes an end operation.

In an embodiment, the mammalian body part includes a cavity or lumen of a mammalian body part. In an embodiment, the mammalian body part includes a surface of a cavity or lumen of a mammalian body part. In an embodiment, the second spatial relationship is substantially the same as the first spatial relationship. In an embodiment, the second spatial relationship is substantially different from the first spatial relationship.

FIG. 58 illustrates alternative embodiments of the first reception operation 2710 and the second reception operation 2720 of the operational flow 2700 of FIG. 57. In an embodiment, the first reception operation may include at least one additional embodiment, such as an operation 2711 or an operation 2712. The operation 2711 includes receiving a reference medical image that was acquired by a body-insertable device and that includes a first depiction of a region of interest of a mammalian body part during a first condition. The operation 2712 includes receiving a reference medical image that was acquired by an ex vivo device and that includes a first depiction of a region of interest of a mammalian body part during a first condition.

In an embodiment, the second reception operation may include at least one additional embodiment, such as an operation 2721 or an operation 2722. The operation 2721 includes receiving a target medical image acquired by a body-insertable device and includes a second depiction the region of interest of the mammalian body part during a second condition. The operation 2722 includes receiving a target medical image acquired by an ex vivo device and includes a second depiction the region of interest of the mammalian body part during a second condition.

FIG. 59 illustrates alternative embodiments of the third reception operation 2730 and the fourth reception operation 2740. In an embodiment, the third reception operation may include at least one additional embodiment, such as an operation 2731 or an operation 2732. The operation 2731 includes receiving a first data acquired by a body-insertable device and indicative of a first spatial relationship between a landmark subsurface feature of the mammalian body part and the region of interest during the first condition. The operation 2732 includes receiving a first data acquired by an ex vivo device and indicative of a first spatial relationship between a landmark subsurface feature of the mammalian body part and the region of interest during the first condition.

In an embodiment, the fourth operation may include an operation 2741 or an operation 2742. The operation 2741 includes receiving a second data acquired by a body-insertable device and indicative of a second spatial relationship between the landmark subsurface feature of the mammalian body part and the region of interest during the second condition. The operation 2742 includes receiving a second data acquired by an ex vivo device and indicative of a second spatial relationship between the landmark subsurface feature of the mammalian body part and the region of interest during the second condition.

Figure 60:
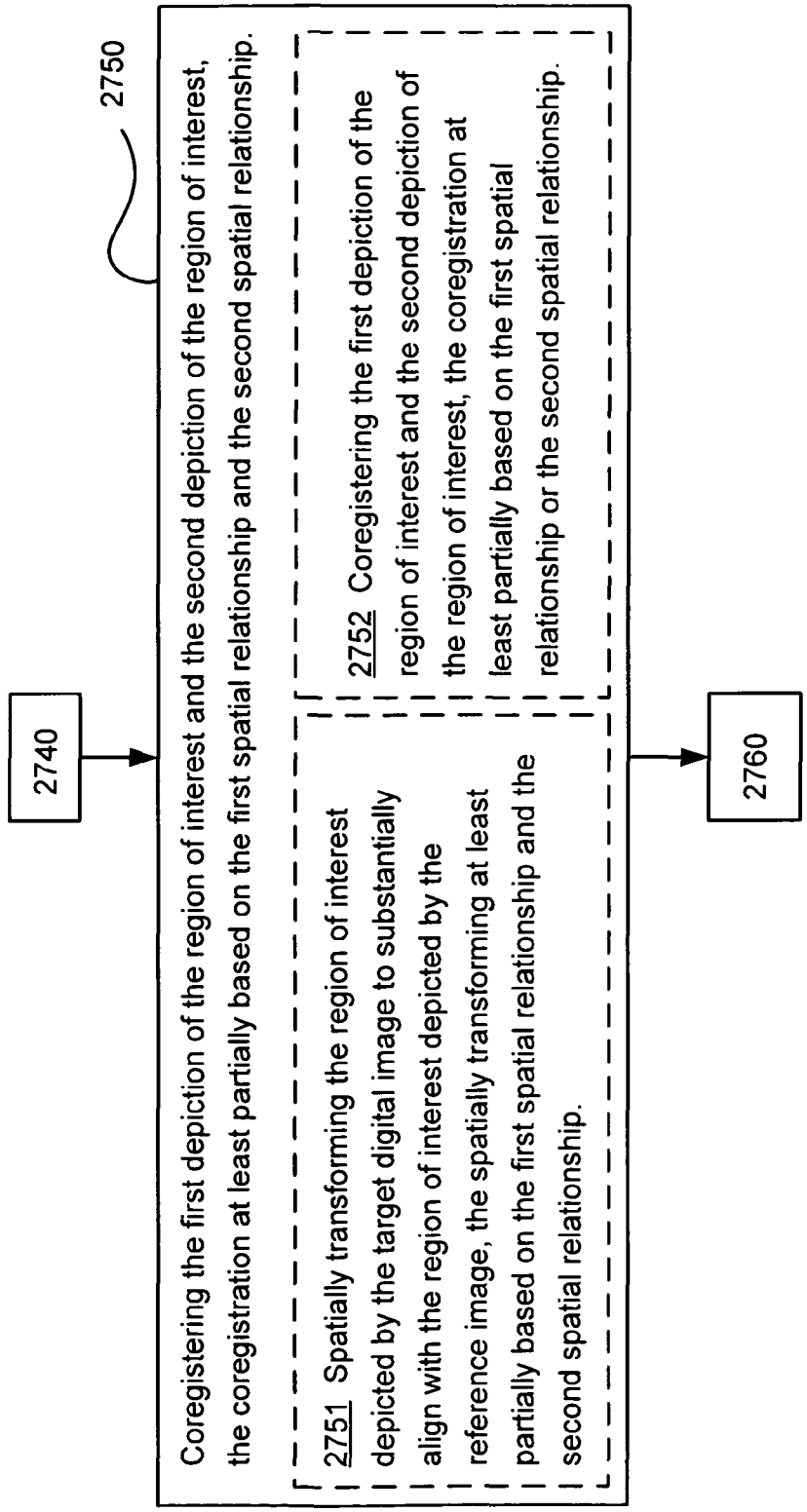
FIG. 60 illustrates an alternative embodiment of the operational flow 2700 of FIG. 57.

FIG. 60 illustrates an alternative embodiment of the coregistration operation 2750. In an embodiment, the coregistration operation may include at least one additional embodiment, such as an operation 2751 or an operation 2752. The operation 2751 includes spatially transforming the region of interest depicted by the target digital image to substantially align with the region of interest depicted by the reference image, the spatially transforming is at least partially based on the first spatial relationship and the second spatial relationship. The operation 2752 includes coregistering the first depiction of the region of interest and the second depiction of the region of interest, the coregistration is at least partially based on the first spatial relationship or the second spatial relationship.

Figure 61:
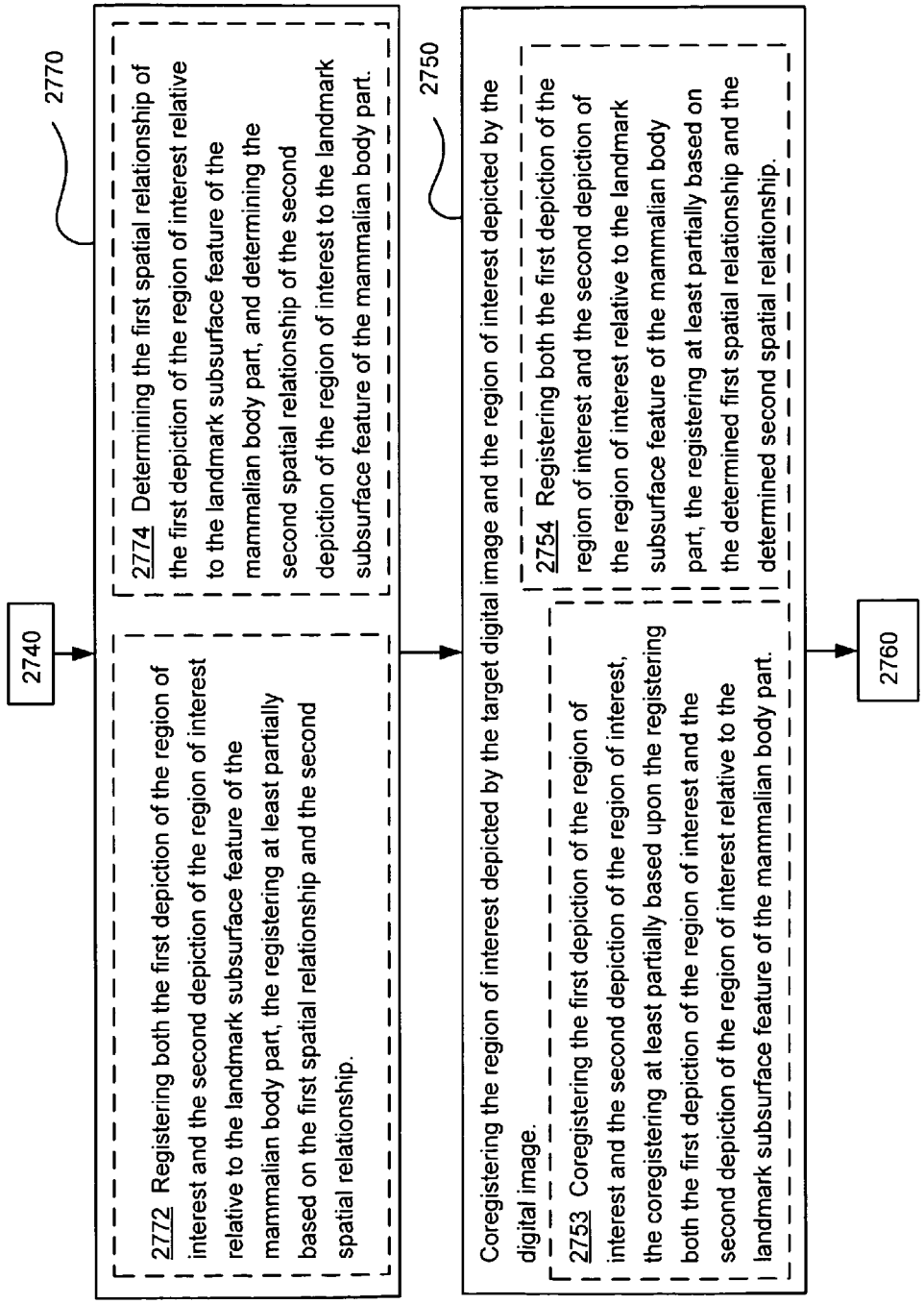
FIG. 61 illustrates an alternative embodiment of the operational flow 2700 of FIG. 57.

FIG. 61 illustrates an alternative embodiment of the operational flow 2700 of FIG. 57. In an embodiment, the operational flow may include at least one additional embodiment 2770. The at least one additional embodiment may include an operation 2772 or an operation 2774. In an embodiment, the coregistration operation 2750 may include at least one additional embodiment, such as an operation 2753 or an operation 2754. The operation 2772 includes registering both the first depiction of the region of interest and the second depiction of the region of interest relative to the landmark subsurface feature of the mammalian body part. The registering is at least partially based on the first spatial relationship and the second spatial relationship. The operation 2753 includes coregistering the first depiction of the region of interest and the second depiction of the region of interest. The coregistering is at least partially based upon the registering both the first depiction of the region of interest and the second depiction of the region of interest relative to the landmark subsurface feature of the mammalian body part. The operation 2774 includes determining the first spatial relationship of the first depiction of the region of interest relative to the landmark subsurface feature of the mammalian body part, and determining the second spatial relationship of the second depiction of the region of interest to the landmark subsurface feature of the mammalian body part. The operation 2754 includes registering both the first depiction of the region of interest and the second depiction of the region of interest relative to the landmark subsurface feature of the mammalian body part. The registering is at least partially based on the determined first spatial relationship and the determined second spatial relationship.

Figure 62:
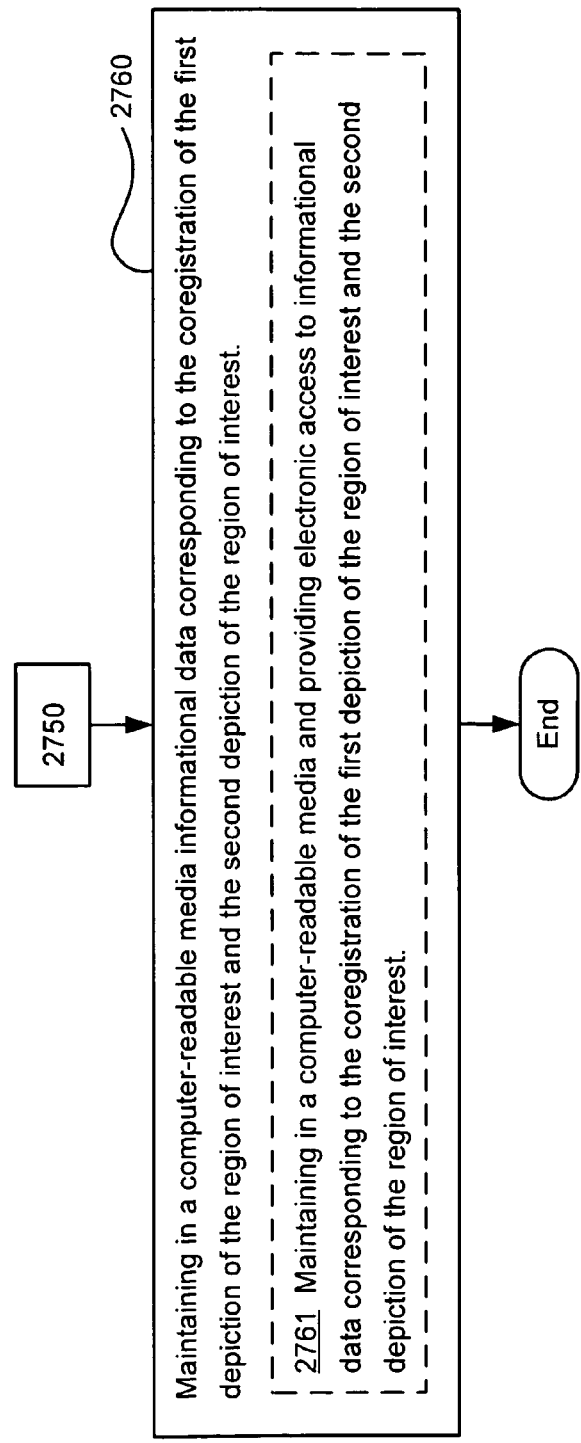
FIG. 62 illustrates an alternative embodiment of the operational flow 2700 of FIG. 57.

FIG. 62 illustrates an alternative embodiment of the storage operation 2760 of FIG. 57. In an embodiment, the storage operation may include at least one additional embodiment, such as an operation 2761. The operation 2761 includes maintaining in a computer-readable media and providing electronic access to informational data corresponding to the coregistration of the first depiction of the region of interest and the second depiction of the region of interest.

Figure 63:
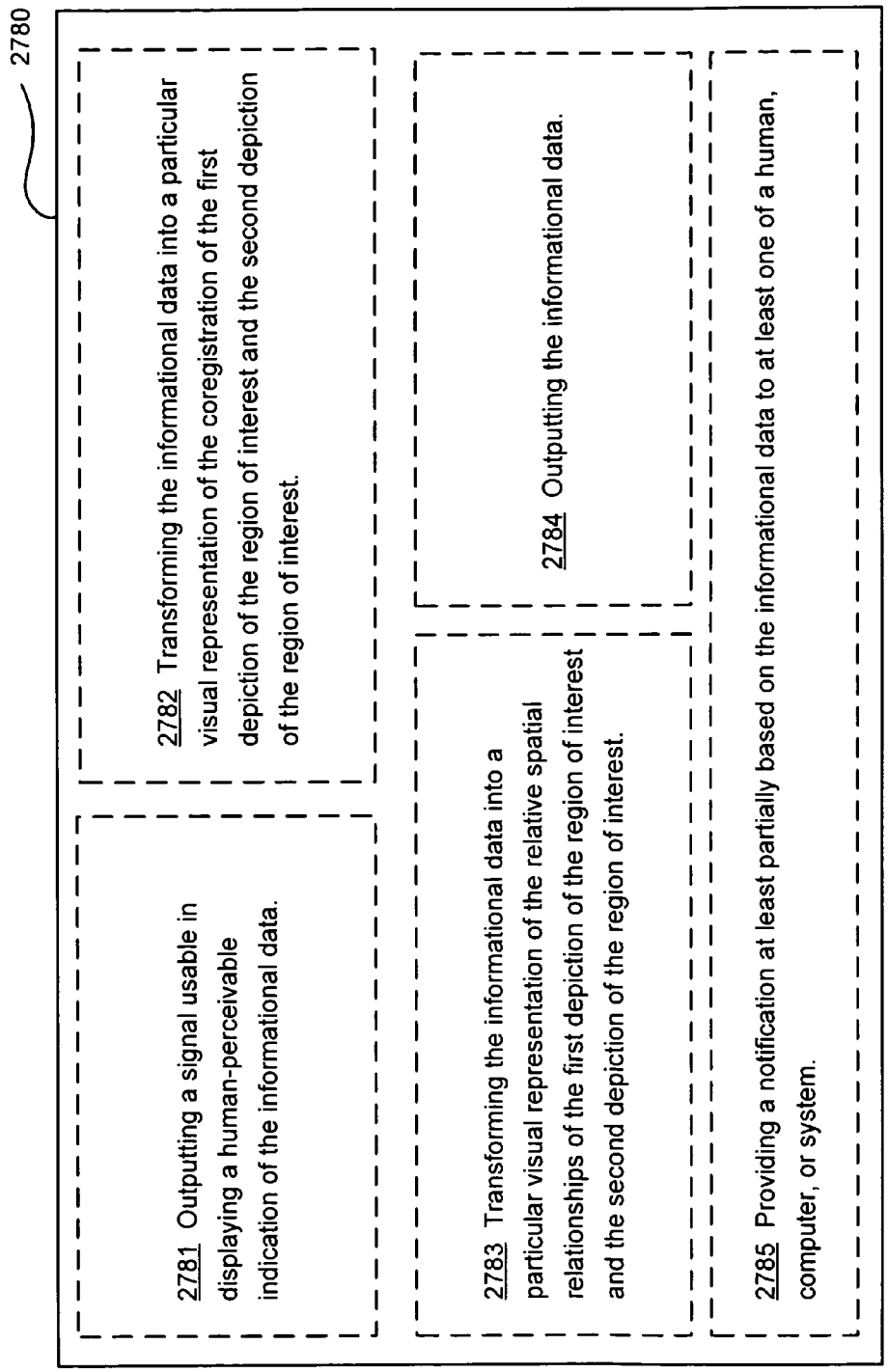
FIG. 63 illustrates an alternative embodiment of the operational flow 2700 of FIG. 57.

FIG. 63 illustrates an alternative embodiment of the operational flow 2700 of FIG. 57. The operational flow may include at least one additional embodiment 2780. The at least one additional embodiment may include an operation 2781, an operation 2782, an operation 2783, an operation 2784, or an operation 2785. The operation 2781 includes outputting a signal usable in displaying a human-perceivable indication of the coregistration of the first depiction of the region of interest and the second depiction of the region of interest. The operation 2782 includes transforming the informational data into a particular visual representation of the coregistration of the first depiction of the region of interest and the second depiction of the region of interest. The operation 2783 includes transforming the informational data into a particular visual representation of the relative spatial relationships of the first depiction of the region of interest and the second depiction of the region of interest. The operation 2784 includes outputting the informational data. The operation 2785 includes providing a notification that is at least partially based on the informational data to at least one of a human, computer, or system.

FIG. 64 illustrates an example computer program product. The computer program product includes a computer-readable media 2810 bearing program instructions 2820. The program instructions, when executed by a processor of a computing device, cause the computing device to perform a process. The process includes receiving a reference medical image that includes a first depiction of a region of interest of a mammalian body part during a first condition. The process includes receiving a target medical image that includes a second depiction the region of interest of the mammalian body part during a second condition. The process includes receiving a first data indicative of a first spatial relationship between a landmark subsurface feature of the mammalian body part and the region of interest during the first condition. The process includes receiving a second data indicative of a second spatial relationship between the landmark subsurface feature of the mammalian body part and the region of interest during the second condition. The process includes coregistering the first depiction of the region of interest and the second depiction of the region of interest. The process includes storing in another computer-readable media operably coupled with the processor informational data corresponding to the coregistration of the first depiction of the region of interest and the second depiction of the region of interest.

In an embodiment, the computer-readable media 2810 includes a tangible computer-readable media 2812. In an embodiment, the computer-readable media includes a communications medium 2814.

FIG. 65 illustrates an alternative embodiment of the program instructions, when executed by a processor of a computing device, cause the computing device to perform a process. In an embodiment, the process further includes 2822 outputting the informational data. In an embodiment, the process further includes 2824 outputting a signal useable in displaying a human-perceivable indication of the coregistration of the first depiction of the region of interest and the second depiction of the region of interest. In an embodiment, the process further includes 2826 transforming the informational data into a particular visual depiction of the coregistration of the first depiction of the region of interest and the second depiction of the region of interest. In an embodiment, the process further includes 2828 providing a notification that is at least partially based on the informational data to at least one of a human, computer, or system.

FIG. 66 illustrates an example system 2900. The system includes 2910 means for receiving a reference medical image that includes a first depiction of a region of interest of a mammalian body part during a first condition. The system includes means 2920 for receiving a target medical image that includes a second depiction the region of interest of the mammalian body part during a second condition. The system includes 2930 means for receiving a first data indicative of a first spatial relationship between a landmark subsurface feature of the mammalian body part and the region of interest during the first condition. The system includes means 2940 for receiving a second data indicative of a second spatial relationship between the landmark subsurface feature of the mammalian body part and the region of interest during the second condition. The system includes means 2950 for coregistering the first depiction of the region of interest and the second depiction of the region of interest. The system includes means 2960 for persistently maintaining computer-readable informational data corresponding to the coregistration of the first depiction of the region of interest and the second depiction of the region of interest.

FIG. 67 illustrates an example environment 3000. The environment includes the mammalian body part 210 of the mammal 205, and a system 3020. The system includes a receiver circuit 3022. The receiver circuit is configured to receive (i) a first reference image that includes a first landmark subsurface feature of a mammalian body part, (ii) a second reference image that includes a second landmark subsurface feature of the mammalian body part, and (iii) data indicative of a spatial relationship between the first landmark subsurface feature and the second landmark subsurface feature. At least one of the first reference image, the second reference image, and the data may be acquired using an ex vivo imaging system, such as an MRI, CAT scan, fluoroscope, or other externally sourced imaging technique operable to acquire digital representation of landmark subsurface features of the mammalian body part. At least one of the first reference image, the second reference image, and the data may be acquired using an internal image acquisition device moved through the cavity or lumen. In an embodiment, for example, the internal image acquisition device may include the body-insertable device 280. In an embodiment, the data may be acquired using an internal image acquisition device having a 3-axis, 4-axis, 5-axis, or 6-axis accelerometers to signal translational and rotational movements by the internal image acquisition device. The system includes a coordinate analysis circuit 3024 configured to determine a common frame of reference that is at least partially based on the first landmark subsurface feature or the second landmark subsurface feature. The system includes the registration circuit 3026 configured to register the first landmark subsurface feature and the second landmark subsurface feature at least partially based on the common frame of reference. The system includes the computer-readable media 235 configured to maintain informational data corresponding to the registration of the first landmark subsurface feature and the second landmark subsurface feature.

In an embodiment, the receiver circuit 3022 is configured to receive (i) a first reference image that includes a first landmark subsurface feature of a cavity or lumen of a mammalian body part, (ii) a second reference image that includes a second landmark subsurface feature of the cavity or lumen of the mammalian body part, and (iii) data indicative of a spatial relationship between the first landmark subsurface feature and the second landmark subsurface feature. In an embodiment, the receiver circuit is configured to receive (i) a first reference image that includes a first machine-discernable landmark subsurface feature of a mammalian body part, (ii) a second reference image that includes a second machine-discernable landmark subsurface feature of the mammalian body part, and (iii) data indicative of a spatial relationship between the first landmark subsurface feature and the second landmark subsurface feature. In an embodiment, the receiver circuit is configured to receive (i) a first reference image that includes a first landmark subsurface feature of a mammalian body part acquired by a first device, (ii) a second reference image that includes a second landmark subsurface feature of the mammalian body part acquired by a second device, and (iii) data indicative of a spatial relationship between the first landmark subsurface feature and the second landmark subsurface feature.

In an embodiment, the first device includes a body-insertable device. In an embodiment, the first device includes an ex vivo device. In an embodiment, the second device includes a device substantially similar to the first device. In an embodiment, the second device includes a device substantially dissimilar to the first device.

In an embodiment, the receiver circuit 3022 is configured to receive (i) a first reference image that includes a first landmark subsurface feature of a mammalian body part, (ii) a second reference image that includes a second landmark subsurface feature of the mammalian body part, and (iii) data indicative of a determinable, estimable, or inferable spatial relationship between the first landmark subsurface feature and the second landmark subsurface feature. In an embodiment the receiver circuit is configured to receive (i) a first reference image that includes a first landmark subsurface feature of a mammalian body part and a third landmark subsurface feature, and (ii) a second reference image that includes a second landmark subsurface feature of the mammalian body part, and the third landmark subsurface feature. For example, FIG. 42 illustrates an example of a common third landmark subsurface feature in a first reference image and a second reference image. In FIG. 42, the reference image 1992C includes within its field of view 1994C the landmark subsurface feature 216D and the landmark subsurface feature 216C. The reference image 1992A includes within its field of view 1994A the landmark subsurface feature 216A and the landmark subsurface feature 216C. In an embodiment, the coordinate analysis circuit 3024 is configured to determine a common frame of reference at least partially based on the first landmark subsurface feature, the second landmark subsurface feature, or the third landmark subsurface feature.

Returning to FIG. 67, in an embodiment, the receiver circuit 3022 is configured to receive (i) a first reference image that includes a first landmark subsurface feature of a mammalian body part, and an anomaly of the mammalian body part, and (ii) a second reference image that includes a second landmark subsurface feature of the mammalian body part, and the anomaly of the mammalian body part. In an embodiment, the receiver circuit is configured to receive (i) a first reference image having a first field of view and including a first landmark subsurface feature of a mammalian body part, and (ii) a second reference image having a second field of view and including a second landmark subsurface feature of the mammalian body part, a portion of the second field of view coextensive with the first field of view. The portion of the second field of view coextensive with the first field of view may include an edge overlap. The portion of the second field of view coextensive with the first field of view may include another feature common to both the first field of view and the second field of view. In an embodiment, the coordinate analysis circuit 3024 is configured to determine a common frame of reference at least partially based on the first landmark subsurface feature, the second landmark subsurface feature, or the portion of the second field of view coextensive with the first field of view. In an embodiment, the receiver circuit is configured to receive (i) a first reference image that includes a first landmark subsurface feature of a mammalian body part, (ii) a second reference image that includes a second landmark subsurface feature of the mammalian body part, and (iii) a third reference image that includes the first landmark subsurface feature and the second landmark subsurface feature. For example, the third reference image may be acquired by fluoroscope or other ex vivo imaging device. In an embodiment, the receiver circuit is configured to receive a reference image that includes a first landmark subsurface feature of a mammalian body part, a second landmark subsurface feature of the mammalian body part, and data indicative of a spatial relationship between the first landmark subsurface feature and the second landmark subsurface feature. In an embodiment, the receiver circuit is configured to determine a common frame of reference at least partially based on the first landmark subsurface feature, the second landmark subsurface feature, or the data indicative of a spatial relationship between the first landmark subsurface feature and the second landmark subsurface feature.

In an embodiment, the coordinate analysis circuit 3024 is configured to determine a common frame of reference and a coordinate system at least partially based on the first landmark subsurface feature or the second landmark subsurface feature. In an embodiment, the coordinate analysis circuit is configured to determine a common frame of reference anchored in the first landmark subsurface feature or the second landmark subsurface feature. In an embodiment, the coordinate analysis circuit is configured to determine a coordinate reference system at least partially based on the first landmark subsurface feature or the second landmark subsurface feature.

In an embodiment, the registration circuit 3026 is configured to register the first landmark subsurface feature the second landmark subsurface feature, the registration is at least partially based on the determined common frame of reference and on a spatial relationship of the first landmark subsurface feature and the second landmark subsurface feature. In an embodiment, the registration circuit is configured to register a spatial relationship of the first landmark subsurface feature relative to the second landmark subsurface feature at least partially based on the common frame of reference. In an embodiment, the registration circuit is configured to register the first landmark subsurface feature relative to the second landmark subsurface feature. The registration includes an orientation of the first landmark subsurface feature relative to the second landmark subsurface feature, and the registration is at least partially based on the common frame of reference.

In an embodiment, the system includes 3020 includes a communication circuit 3042 configured to output the informational data. In an embodiment, the system includes a communication circuit configured to provide a notification that is at least partially based on the informational data to at least one of a human, computer, or system.

In an embodiment, the system 3020 includes an atlas generation circuit 3028 configured to generate a subsurface feature atlas of the mammalian body part. The subsurface feature atlas is at least partially based on the informational data. In an embodiment, the system includes a communication circuit 3042 configured to output informational data corresponding to the subsurface feature atlas of the mammalian body part. In an embodiment, the computer-readable media 235 is configured to maintain informational data corresponding to the subsurface feature atlas of the mammalian body part. In an embodiment, the system includes a communications circuit 3042 configured to output a signal usable in displaying a human-perceivable depiction of the subsurface feature atlas of the mammalian body part. The human-perceivable depiction may include an audio or a visual human-perceivable depiction.

FIG. 68 illustrates an example operational flow 3100. The operational flow includes a start operation. A first reception operation 3110 includes receiving a first reference image that includes a first landmark subsurface feature of a mammalian body part. A second reception operation 3120 includes receiving a second reference image that includes a second landmark subsurface feature of the mammalian body part. A third reception operation 3130 includes receiving data indicative of a spatial relationship between the first landmark subsurface feature and the second landmark subsurface feature. In an embodiment, at least one of the first reception operation, the second reception operation, or the third reception operation may be implemented using the receiver circuit 3022 of FIG. 67. A reference operation 3140 includes determining a common frame of reference is at least partially based on the first landmark subsurface feature or the second landmark subsurface feature. In an embodiment, the reference operation may be implemented using the coordinate analysis circuit 3024 of FIG. 67. A registering operation 3150 includes registering the first landmark subsurface feature and the second landmark subsurface feature at least partially based on the common frame of reference. In an embodiment, the registering operation may be implemented using the registration circuit 3026 of FIG. 67. A storage operation 3160 includes maintaining in a computer-readable media informational data corresponding to the registration of the first landmark subsurface feature and the second landmark subsurface feature. In an embodiment, the storage operation may be implemented using the computer-readable media 235 of FIG. 67. The operational flow includes an end operation. In an embodiment, the operational flow may include a mapping operation 3170 generating a subsurface feature atlas of the mammalian body part that is at least partially based on the registration of the first landmark subsurface feature and the second landmark subsurface feature.

Figure 69:
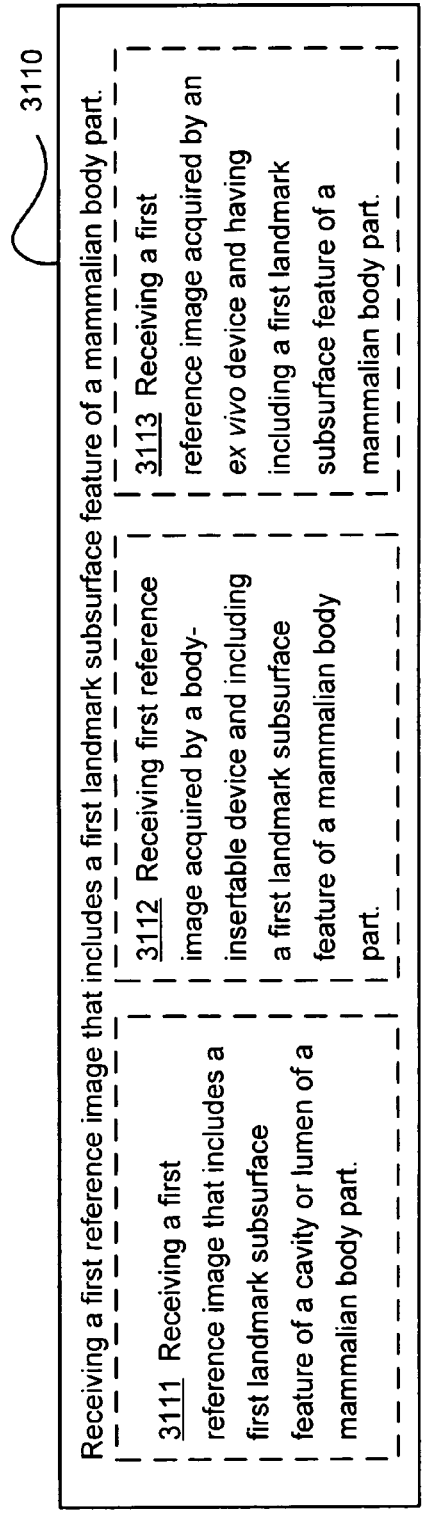
FIG. 69 illustrates an alternative embodiment of the operational flow of FIG. 68.

FIG. 69 illustrates an alternative embodiment of the first reception operation 3110 of FIG. 68. The first reception operation may include at least one additional embodiment.

The at least one additional embodiment may include an operation 3111, an operation 3112, or an operation 3113. The operation 3111 includes receiving a first reference image that includes a first landmark subsurface feature of a cavity or lumen of a mammalian body part. The operation 3112 includes receiving first reference image that was acquired by a body-insertable device and includes a first landmark subsurface feature of a mammalian body part. The operation 3113 includes receiving first reference image that was acquired by an ex vivo device and includes a first landmark subsurface feature of a mammalian body part.

Figure 70:
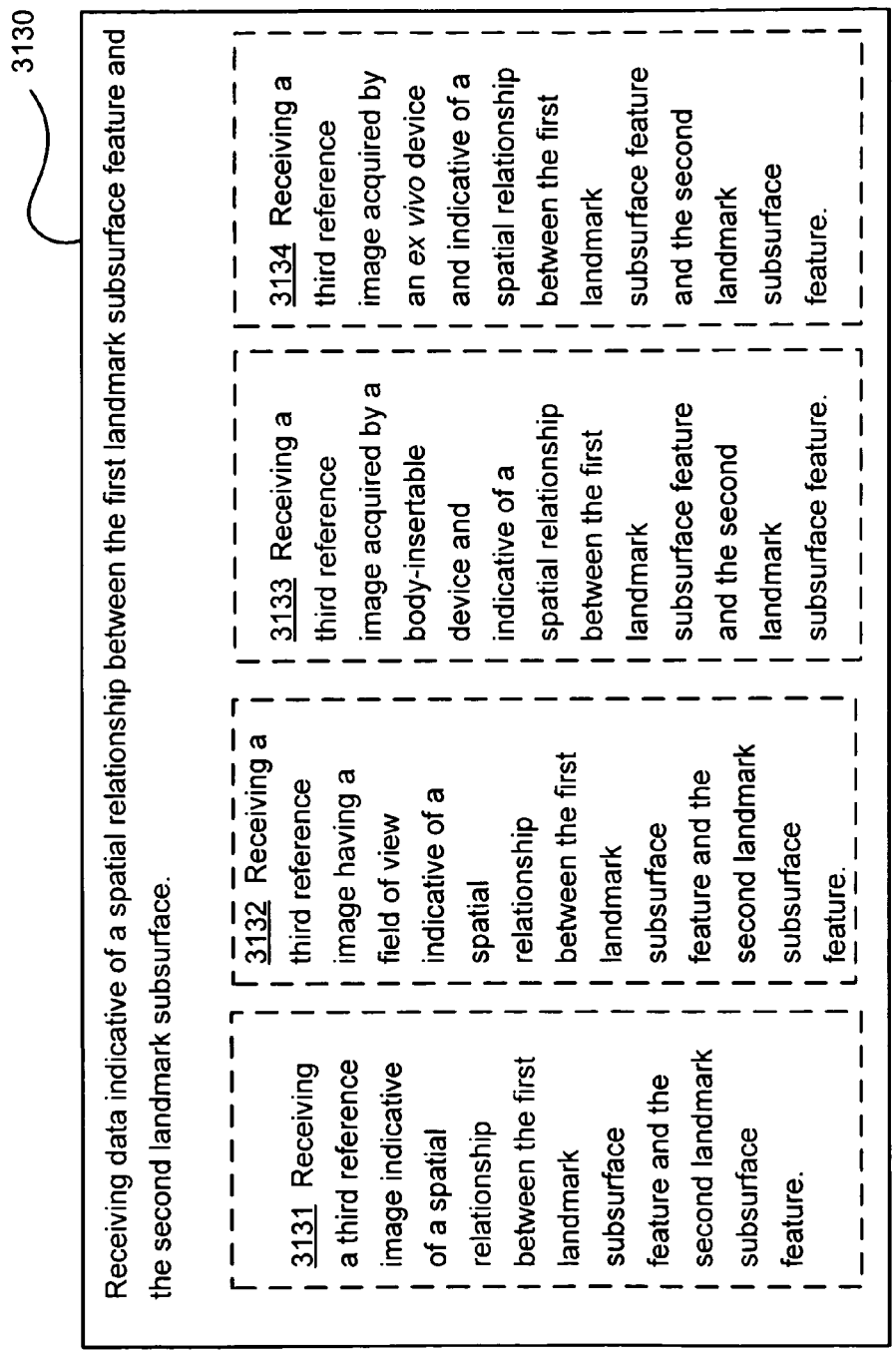
FIG. 70 illustrates an alternative embodiment of the operational flow of FIG. 68.

FIG. 70 illustrates an alternative embodiment of the third reception operation 3130 of FIG. 68. The third reception operation may include at least one additional embodiment. The at least one additional embodiment may include an operation 3131, an operation 3132, an operation 3133, or an operation 3134. The operation 3131 includes receiving a third reference image indicative of a spatial relationship between the first landmark subsurface feature and the second landmark subsurface feature. The operation 3132 includes receiving a third reference image having a field of view indicative of a spatial relationship between the first landmark subsurface feature and the second landmark subsurface feature. The operation 3133 includes receiving a third reference image that was acquired by a body-insertable device and indicative of a spatial relationship between the first landmark subsurface feature and the second landmark subsurface feature. The operation 3134 includes receiving a third reference image that was acquired by an ex vivo device and indicative of a spatial relationship between the first landmark subsurface feature and the second landmark subsurface feature.

Figure 71:
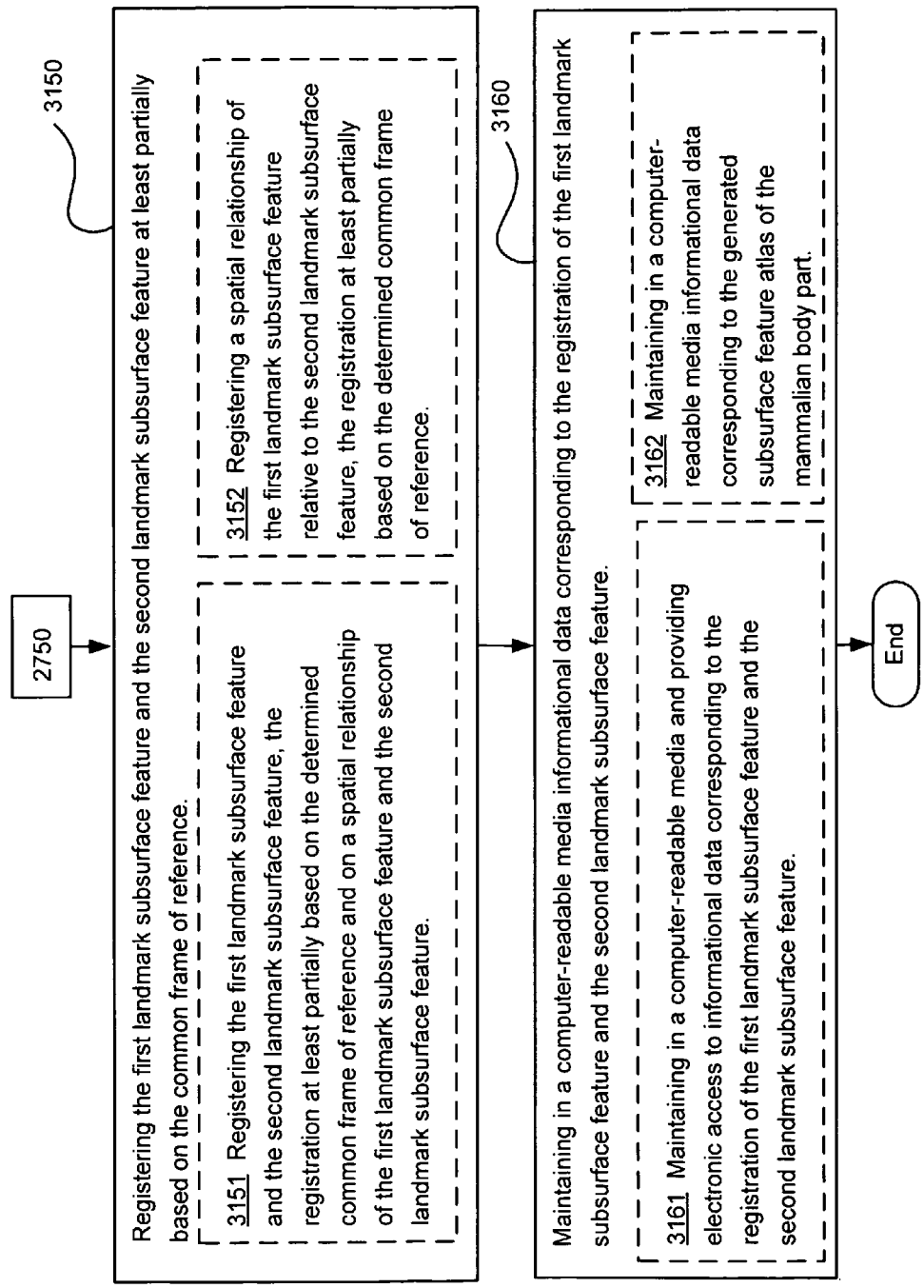
FIG. 71 illustrates an alternative embodiment of the operational flow 3100 of FIG. 68.

FIG. 71 illustrates an alternative embodiment of the operational flow 3000 of FIG. 68. In an embodiment, the registration operation 3150 may include at least one additional embodiment, such as an operation 3151 or an operation 3152. The operation 3151 includes registering the first landmark subsurface feature and the second landmark subsurface feature, the registration is at least partially based on the determined common frame of reference and on a spatial relationship of the first landmark subsurface feature and the second landmark subsurface feature. The operation 3152 includes registering a spatial relationship of the first landmark subsurface feature relative to the second landmark subsurface feature, the registration is at least partially based on the determined common frame of reference. In an embodiment, the storage operation 3160 may include at least one additional embodiment, such as an operation 3161 or an operation 3162. The operation 3161 includes maintaining in a computer-readable media and providing electronic access to informational data corresponding to the registration of the first landmark subsurface feature and the second landmark subsurface feature. The operation 3162 includes maintaining in a computer-readable media informational data corresponding to the generated subsurface feature atlas of the mammalian body part.

Figure 72:
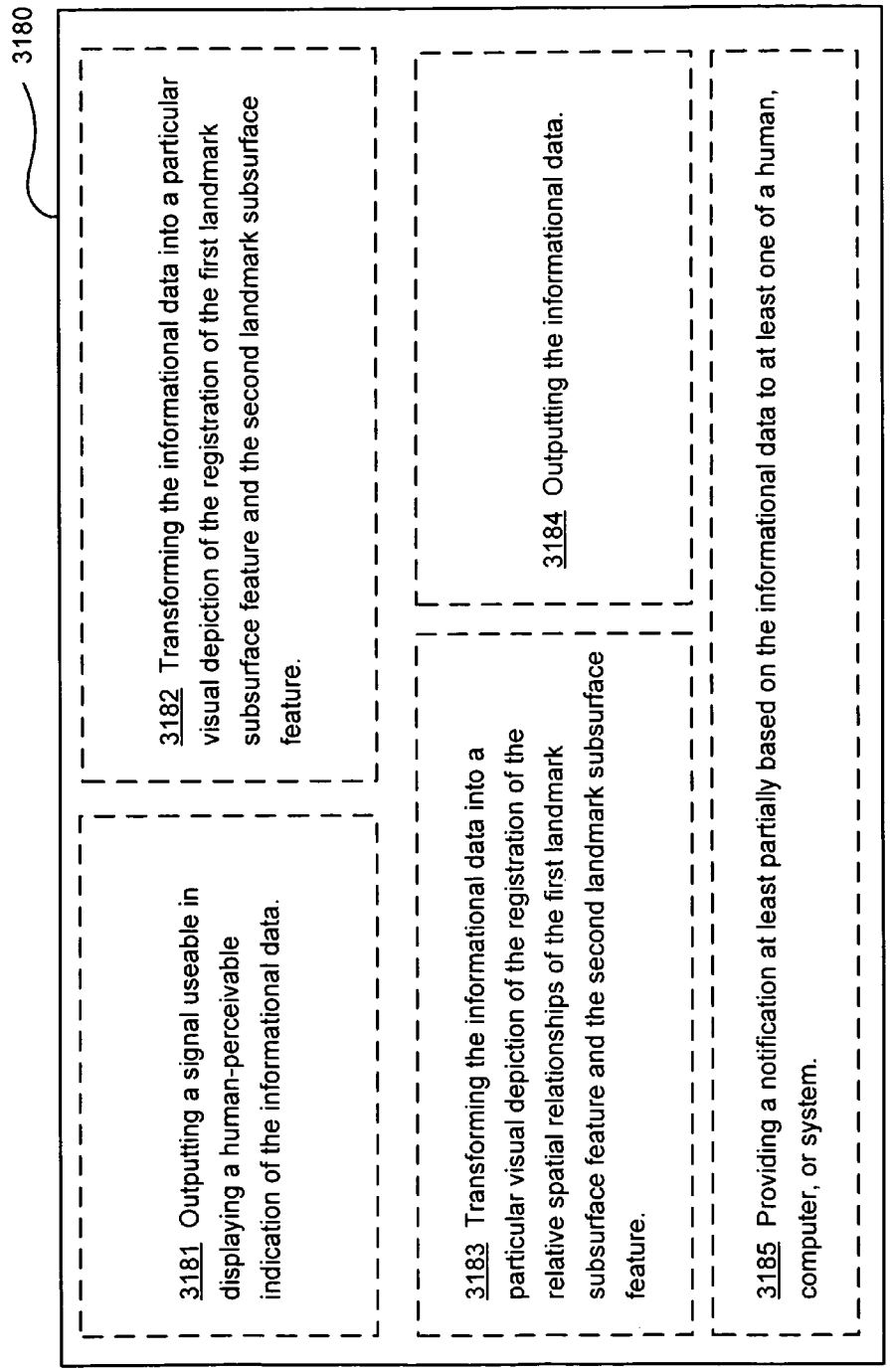
FIG. 72 illustrates an alternative embodiment of the operational flow 3100 of FIG. 68.

FIG. 72 illustrates an alternative embodiment of the operational flow 3000 of FIG. 68. The operational flow may include at least one additional embodiment 3180. The at least one additional embodiment may include an operation 3181, an operation 3182, an operation 3183, an operation 3184, or an operation 3185. The operation 3181 includes outputting a signal useable in displaying a human-perceivable indication of the registration of the first landmark subsurface feature and the second landmark subsurface. The operation 3182 includes transforming the informational data into a particular visual depiction of the registration of the first landmark subsurface feature and the second landmark subsurface feature. The operation 3183 includes transforming the informational data into a particular visual depiction of the registration of the relative spatial relationships of the first landmark subsurface feature and the second landmark subsurface feature. The operation 3184 includes outputting the informational data. The operation 3185 includes providing a notification that is at least partially based on the informational data to at least one of a human, computer, or system.

FIG. 73 illustrates an example computer program product 3200. The program product includes a computer-readable medium 3210 bearing program instructions 3220. The program instructions, when executed by a processor of a computing device, cause the computing device to perform a process. The process includes receiving a first reference image that includes a first landmark subsurface feature of a mammalian body part. The process includes receiving a second reference image that includes a second landmark subsurface feature of the mammalian body part. The process includes receiving data indicative of a spatial relationship between the first landmark subsurface feature and the second landmark subsurface feature. The process includes determining a common frame of reference that is at least partially based on the first landmark subsurface feature or the second landmark subsurface feature. The process includes registering the first landmark subsurface feature and the second landmark subsurface feature at least partially based on the common frame of reference. The process includes storing in another computer-readable medium operably coupled with the processor informational data corresponding to the registration of the first landmark subsurface feature and the second landmark subsurface feature.

In an embodiment, the computer-readable media 3210 includes a tangible computer-readable media 3212. In an embodiment, the computer-readable media includes a communications medium 3214.

In an embodiment, the registering process includes a process 3222 registering the first landmark subsurface feature and the second landmark subsurface feature. The registration is at least partially based on the determined common frame of reference and on a spatial relationship of the first landmark subsurface feature and the second landmark subsurface feature. In an embodiment, the process further includes 3224 generating a subsurface feature atlas of the mammalian body part that is at least partially based on the registration of the first landmark subsurface feature and the second landmark subsurface feature.

Figure 74:
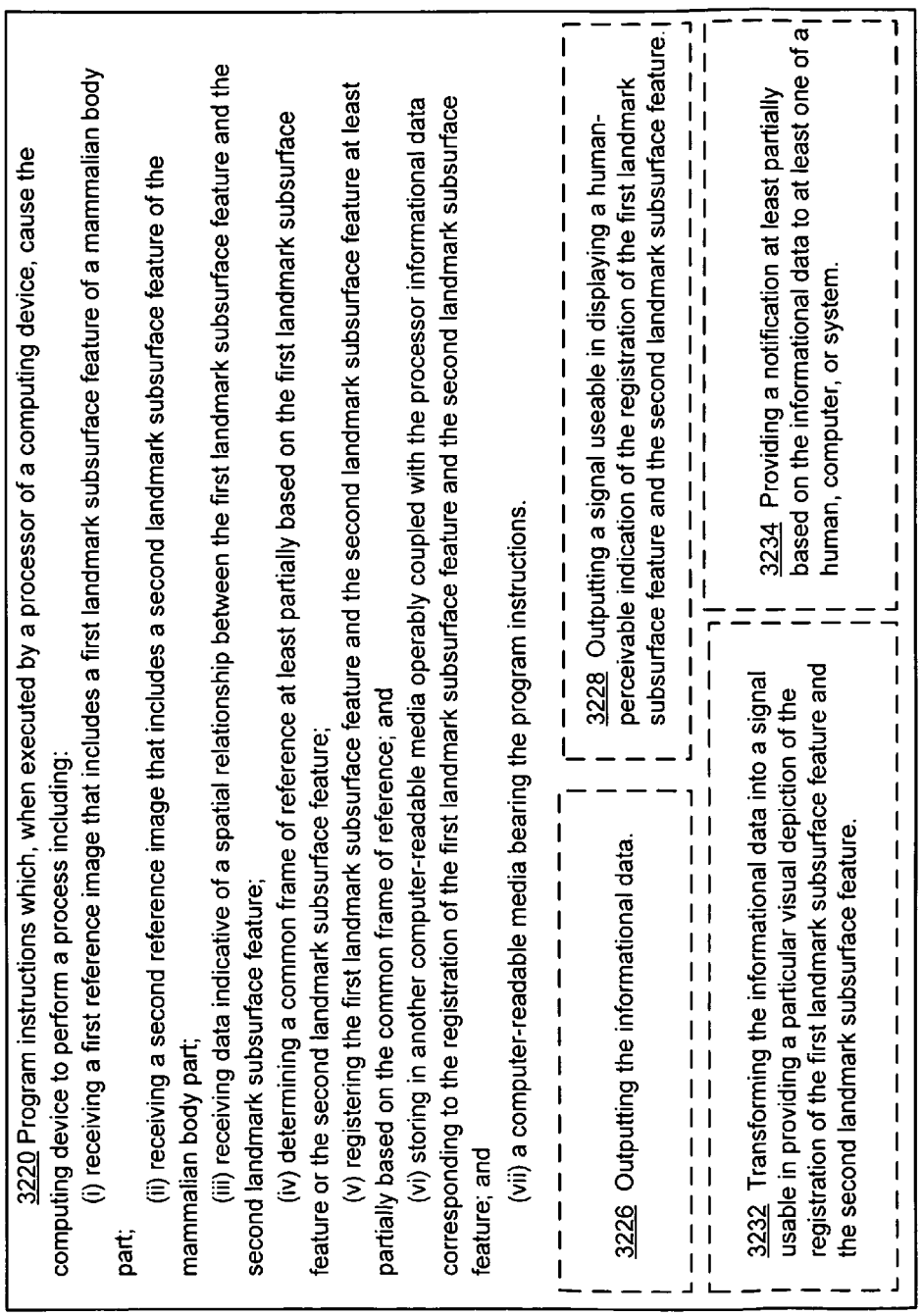
FIG. 74 illustrates an alternative embodiment of the computer program product of FIG. 73.

FIG. 74 illustrates an alternative embodiment of the process 3220 of the computer program product 3200 of FIG. 73. In an embodiment, the process further includes 3226 outputting the informational data. In an embodiment, the process further includes 3228 outputting a signal useable in displaying a human-perceivable indication of the registration of the first landmark subsurface feature and the second landmark subsurface feature. In an embodiment, the process further includes 3232 transforming the informational data into a signal usable in providing a particular visual depiction of the registration of the first landmark subsurface feature and the second landmark subsurface feature. In an embodiment, the process further includes 3234 providing a notification that is at least partially based on the informational data to at least one of a human, computer, or system.

Figure 75:
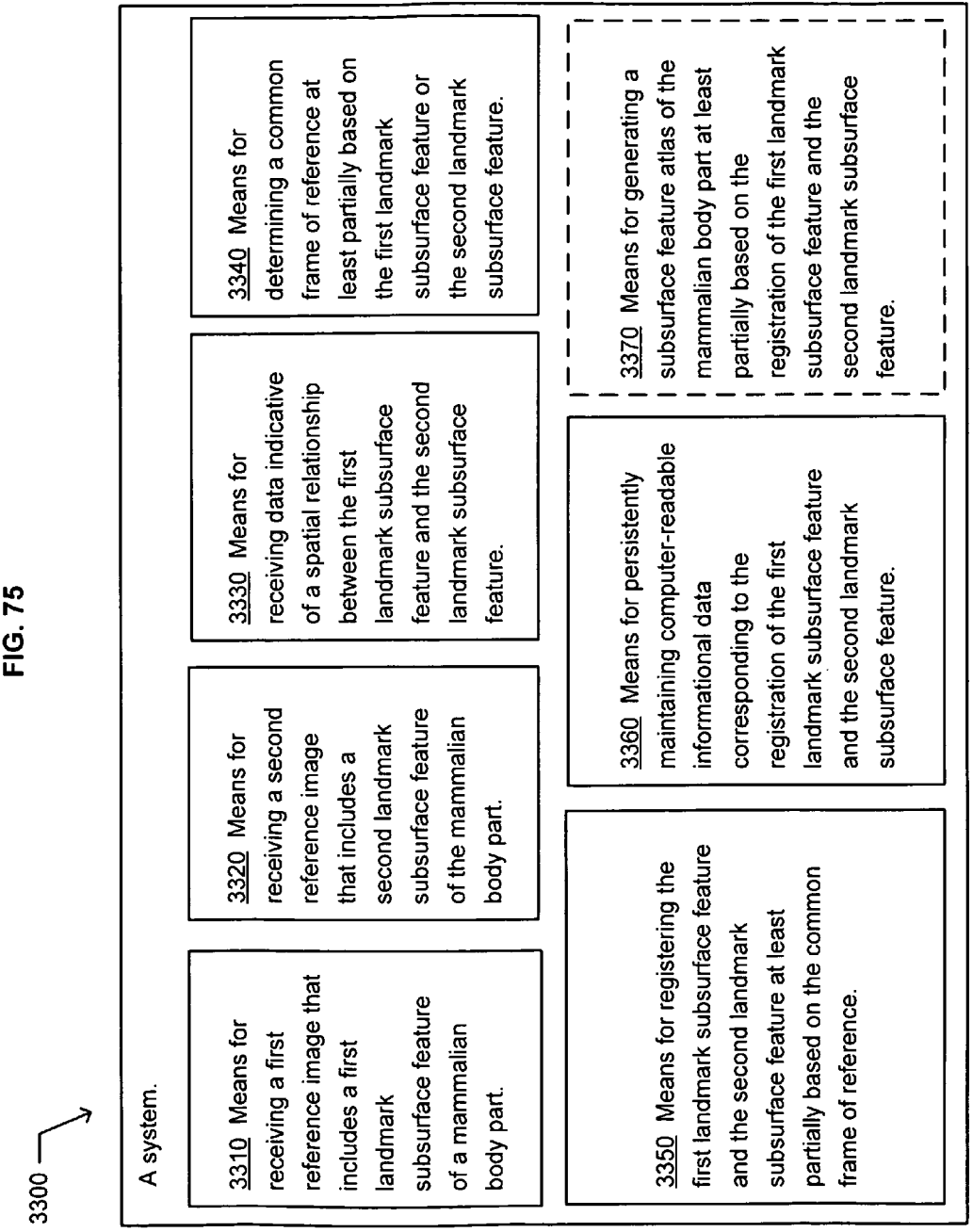
FIG. 75 illustrates an example system.

FIG. 75 illustrates an example system 3300. The system includes means 3310 for receiving a first reference image that includes a first landmark subsurface feature of a mammalian body part. The system includes means 3320 for receiving a second reference image that includes a second landmark subsurface feature of the mammalian body part. The system includes means 3330 for receiving data indicative of a spatial relationship between the first landmark subsurface feature and the second landmark subsurface feature. The system includes means 3340 for determining a common frame of reference that is at least partially based on the first landmark subsurface feature or the second landmark subsurface feature. The system includes means 3350 for registering the first landmark subsurface feature and the second landmark subsurface feature at least partially based on the common frame of reference. The system includes means 3360 means for persistently maintaining computer-readable informational data corresponding to the registration of the first landmark subsurface feature and the second landmark subsurface feature. In an alternative embodiment, the system includes means 3370 for generating a subsurface feature atlas of the mammalian body part that is at least partially based on the registration of the first landmark subsurface feature and the second landmark subsurface feature.

Returning to FIG. 67, FIG. 67 illustrates an alternative embodiment of the system 3020. The alternative embodiment includes the coordinate analysis circuit 3024, the registration circuit 3026, and the computer-readable media 235. In the alternative embodiment, the coordinate analysis circuit 3024 is configured to determine a common frame of reference at least partially based on a first landmark subsurface feature of a mammalian body part 210 or the second landmark subsurface feature of the mammalian body part. In the alternative embodiment, the registration circuit 3026 is configured to register the first landmark subsurface feature and the second landmark subsurface feature, the registration is at least partially based on the common frame of reference. In the alternative embodiment, the computer-readable media 235 is configured to maintain informational data corresponding to the registration of the first landmark subsurface feature and the second landmark subsurface feature.

In an embodiment of the alternative embodiment of the system 3020, the coordinate analysis circuit 3024 is configured to determine a common frame of reference at least partially based on a first landmark subsurface feature of a mammalian body part and the second landmark subsurface feature of the mammalian body part. In an embodiment of the alternative embodiment, the coordinate analysis circuit is configured to determine a common frame of reference at least partially based on a first landmark subsurface feature of a cavity or lumen of a mammalian body part or the second landmark subsurface feature of the cavity or lumen of the mammalian body part.

In an embodiment of the alternative embodiment of the system 3020, the registration circuit 3026 is configured to register the first landmark subsurface feature and the second landmark subsurface feature. The registration is at least partially based on the common frame of reference and on data indicative of a spatial relationship between the first landmark subsurface feature and the second landmark subsurface feature. In an embodiment of the alternative embodiment of the system, the atlas generation circuit 3028 is configured to generate a subsurface feature atlas of the mammalian body part. The subsurface feature atlas is at least partially based on the registration of the first landmark subsurface feature and the second landmark subsurface feature. In an embodiment of the alternative embodiment of the system, the computer-readable media is configured to maintain informational data corresponding to the subsurface feature atlas of the mammalian body part.

In an embodiment of the alternative embodiment of the system 3020, the communication circuit 3042 is configured to output the informational data. In an embodiment of the alternative embodiment of the system, the communication circuit is configured to provide a notification that is at least partially based on the informational data to at least one of a human, computer, or system. In an embodiment of the alternative embodiment, the system includes the computing device 292 configured to display on the screen 294 a human-perceivable depiction of the subsurface feature atlas of the mammalian body part 210.

Figure 76:
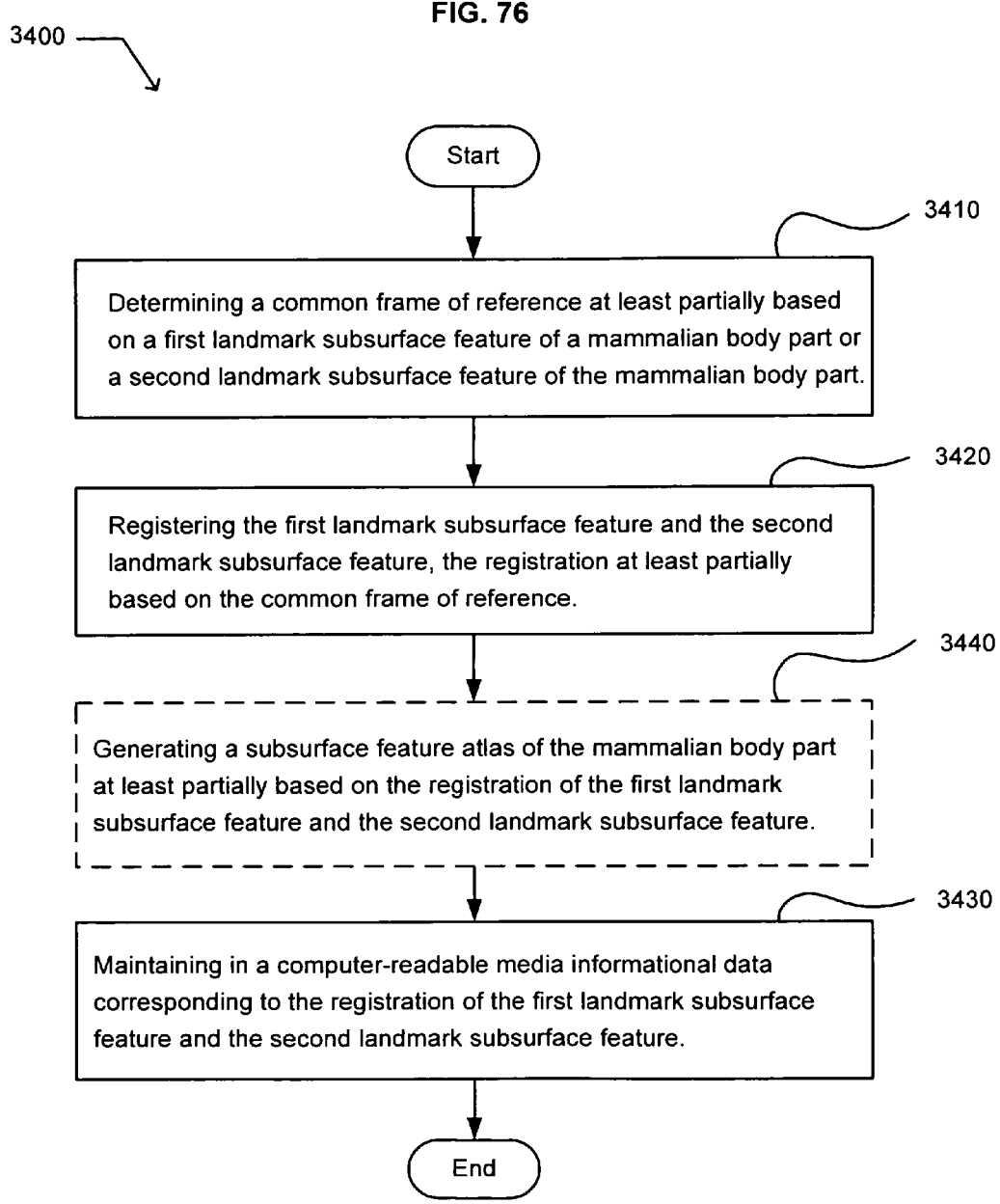
FIG. 76 illustrates an example operational flow.

FIG. 76 illustrates an example operational flow 3400. The operational flow includes a start operation. The operational flow includes a reference operation 3410. The reference operation includes determining a common frame of reference at least partially based on a first landmark subsurface feature of a mammalian body part or a second landmark subsurface feature of the mammalian body part. In an embodiment, the reference operation may be implemented using the coordinate analysis circuit 3024 described in conjunction with FIG. 67. A registration operation 3420 includes registering the first landmark subsurface feature and the second landmark subsurface feature. The registration is at least partially based on the common frame of reference. The registration operation may be implemented using the registration circuit 3026 described in conjunction with FIG. 67. A storage operation 3430 includes maintaining in a computer-readable media informational data corresponding to the registration of the first landmark subsurface feature and the second landmark subsurface feature. The storage operation may be implemented using the computer-readable media 235 described in conjunction with FIG. 3. The operational flow includes an end operation.

In an embodiment, the operational flow 3400 includes a map operation 3440. The map operation includes generating a subsurface feature atlas of the mammalian body part that is at least partially based on the registration of the first landmark subsurface feature and the second landmark subsurface feature.

FIG. 77 illustrates an alternative embodiment of the example operational flow 3400 of FIG. 76. In an embodiment, the registration operation 3420 includes at least one additional embodiment, such as an operation 3422. The operation 3422 includes registering the first landmark subsurface feature and the second landmark subsurface feature. The registration is at least partially based on the determined common frame of reference and on a spatial relationship of the first landmark subsurface feature and the second landmark subsurface feature. In an embodiment, the storage operation 3430 includes at least one additional embodiment, such as an operation 3432. The operation 3431 includes maintaining in a computer-readable media informational data corresponding to (i) to the registration of the first landmark subsurface feature and the second landmark subsurface feature and (ii) to the subsurface feature atlas of the mammalian body part.

FIG. 78 illustrates an example computer program product 3600. The computer program product includes a computer-readable media 3610 bearing program instructions 3620. The program instructions, when executed by a processor of a computing device, cause the computing device to perform a process. The process includes determining a common frame of reference that is at least partially based on a first landmark subsurface feature of a mammalian body part or the second landmark subsurface feature of the mammalian body part. The process includes registering the first landmark subsurface feature and the second landmark subsurface feature. The registration is at least partially based on the common frame of reference. The process includes storing in another computer-readable media operably coupled with the processor informational data corresponding to the registration of the first landmark subsurface feature and the second landmark subsurface feature.

In an embodiment, the computer-readable media 3610 includes a tangible computer-readable media 3612. In an embodiment, the computer-readable media includes a communications media 3614.

In an embodiment, the registering includes 3622 registering the first landmark subsurface feature and the second landmark subsurface feature, the registration is at least partially based on the determined common frame of reference and on a spatial relationship of the first landmark subsurface feature and the second landmark subsurface feature. In an embodiment, the process further includes 3624 generating a subsurface feature atlas of the mammalian body part. The subsurface atlas is at least partially based on the registration of the first landmark subsurface feature and the second landmark subsurface feature.

FIG. 79 illustrates an example system 3700. The system includes means 3710 for determining a common frame of reference that is at least partially based on a first landmark subsurface feature of a mammalian body part or the second landmark subsurface feature of the mammalian body part. The system includes means 3720 for registering the first landmark subsurface feature and the second landmark subsurface feature. The registration is at least partially based on the common frame of reference. The system includes means 3730 for persistently maintaining in a computer-readable media informational data corresponding to the registration of the first landmark subsurface feature and the second landmark subsurface feature.

FIG. 80 illustrates an example environment 3800. The environment includes the mammalian body part 210 of the mammal 205, and a system 3820. The system includes a receiver circuit 3822 configured to receive at least two reference images. Each reference image of the at least two reference images including a respective landmark subsurface feature of a mammalian body part, illustrated as the mammalian body part 210. The receiver circuit is also configured to receive data indicative of a spatial relationship among each respective landmark subsurface feature of the at least two reference images. For example, FIG. 42 illustrates an embodiment including the reference image 1992A, which includes the landmark subsurface feature 216A, and the reference image 1992B, which includes the landmark subsurface feature 216B. FIG. 42 also illustrates the spatial relationship 213C among the landmark subsurface feature 216A and the landmark subsurface feature 216B. Continuing with FIG. 80, the system includes a coordinate analysis circuit 3824 configured to determine a common frame of reference that is at least partially based on a landmark subsurface feature of the mammalian body part included in a reference image of the at least two reference images. The system includes a registration circuit 3826 configured to register the respective landmark subsurface feature of the mammalian body part included in each reference image of the at least two reference images. The registration is at least partially based on the determined common frame of reference and on the data indicative of a spatial relationship among each respective landmark subsurface feature of the at least two reference images. The system includes the computer-readable media 235 configured to maintain informational data corresponding to the registration of the respective landmark subsurface feature of the mammalian body part included in each reference image of the at least two reference images.

In an embodiment, the receiver circuit 3822 is configured to receive (i) at least two reference images, and (ii) data indicative of a spatial relationship between each respective landmark subsurface feature of the at least two reference images. Each reference image of the at least two reference images includes a respective landmark subsurface feature of a cavity or lumen of a mammalian body part. In an embodiment, the receiver circuit is configured to receive (i) at least two reference images, and (ii) data indicative of a spatial relationship between each respective landmark subsurface feature of the at least two reference images. Each reference image of the at least two reference images includes a respective machine-discernible landmark subsurface feature of a mammalian body part. In an embodiment, the receiver circuit is configured to receive (i) at least two reference images and (ii) data useable in determining or inferring a spatial relationship between each respective landmark subsurface feature of the at least two reference images. Each reference image of the at least two reference images includes a respective landmark subsurface feature of a mammalian body part. In an embodiment, the receiver circuit is configured to receive (i) at least two reference images. Each reference image of the at least two reference images includes a respective landmark subsurface feature of a mammalian body part. The receiver is also configured to receive (ii) data indicative of a spatial relationship between a first landmark subsurface feature of a first reference image of the at least two reference images and a second landmark subsurface feature of a second reference image of the at least two reference images. For example, the data indicative of a spatial relationship may include data indicative of an overlapped third landmark subsurface feature. In an embodiment, the receiver circuit is configured to receive (i) at least two reference images. Each reference image of the at least two reference images includes a respective landmark subsurface feature of a mammalian body part. The receiver circuit is also configured to receive (ii) data indicative of a spatial relationship between each respective landmark subsurface feature of the at least two reference images. The data indicative of an edge content overlap of an edge content of a field of view of a first reference image of the at least two reference images and an edge content of field of view of a second reference image of the at least two reference images. In an embodiment, the coordinate analysis circuit 3824 is configured to determine a common frame of reference that is at least partially based on the edge content overlap between the edge content of the field of view of the first reference image of the at least two reference images and the edge content of the field of view of the second reference image of the at least two reference images.

In an embodiment, the coordinate analysis circuit 3824 is configured to determine a common frame of reference that is at least partially based on (i) a first landmark subsurface feature of the mammalian body part included in the first reference image of the at least two reference images, and (ii) a second landmark subsurface feature of the mammalian body part included in the second reference image of the at least two reference images. In an embodiment, the registration circuit 3826 is configured to register a spatial relationship of the respective landmark subsurface feature of the mammalian body part included in each reference image of the at least two reference images. The registration is at least partially based on the determined common frame of reference and on the data indicative of spatial relationships between the at least two landmark subsurface features of a mammalian body part. In an embodiment, the registration circuit is configured to register a spatial relationship and an orientation of the respective landmark subsurface feature of the mammalian body part included in each reference image of the at least two reference images. The registration is at least partially based on the determined common frame of reference and on the data indicative of spatial relationships between the at least two landmark subsurface features of a mammalian body part.

In an embodiment, the system 3820 includes an atlas generation circuit 3828 configured generate a subsurface feature atlas of the mammalian body part. The subsurface feature atlas includes a spatial relationship of the respective landmark subsurface feature of the mammalian body part included in each reference image of the at least two reference images. The subsurface feature atlas is at least partially based on the registration of the respective landmark subsurface feature of the mammalian body part included in each reference image of the at least two reference images. In an embodiment, the computer-readable media 235 is configured to maintain informational data (i) corresponding to the registration of the respective landmark subsurface feature of the mammalian body part included in each reference image of the at least two reference images, and (ii) informational data corresponding to the generated subsurface feature atlas of the mammalian body part.

FIG. 81 illustrates an example operational flow 3900. The operational flow includes a start operation. The operational flow includes a reception operation 3910. The reception operation includes receiving at least two reference images, each reference image of the at least two reference images includes a respective landmark subsurface feature of a mammalian body part. The reception operation also includes receiving data indicative of a spatial relationship between each respective landmark subsurface feature of the at least two reference images. In an embodiment, the reception operation may be performed using the receiver circuit 3822 described in conjunction with FIG. 80. A reference operation 3920 includes determining a common frame of reference that is at least partially based on a landmark subsurface feature of the mammalian body part included in a reference image of the at least two reference images. In an embodiment, the reference operation may be performed using the coordinate analysis circuit 3824 described in conjunction with FIG. 80. A registration operation 3930 includes registering the respective landmark subsurface feature of the mammalian body part included in each reference image of the at least two reference images. The registration is at least partially based on the determined common frame of reference and on the data indicative of spatial relationships between the at least two landmark subsurface features of a mammalian body part. In an embodiment, the registration operation may be implemented using the registration circuit 3826. A storage operation 3940 includes maintaining in a computer-readable media informational data corresponding to the registration of the respective landmark subsurface feature of the mammalian body part included in each reference image of the at least two reference images. In an embodiment, the storage operation may be implemented using the computer-readable media 235 described in conjunction with FIG. 80. The operational flow includes an end operation.

In an embodiment, the operational flow 3900 may include at least one additional embodiment, such as a mapping operation 3950. The mapping operation includes generating a subsurface feature atlas of the mammalian body part, the subsurface feature atlas includes a spatial relationship of the respective landmark subsurface feature of the mammalian body part included in each reference image of the at least two reference images. The subsurface feature atlas is at least partially based on the registration of the respective landmark subsurface feature of the mammalian body part included in each reference image of the at least two reference images.

FIG. 82 illustrates an alternative embodiment of the operational flow 3900 of FIG. 81. In an embodiment, the reception operation 3910 may include at least one additional embodiment, such as an operation 3911. The operation 3911 includes receiving at least two reference images, each reference image of the at least two reference images includes a respective landmark subsurface feature of a cavity or lumen of a mammalian body part. The operation 3911 also includes receiving data indicative of a respective spatial relationship among each respective landmark subsurface feature of the at least two reference images. In an embodiment, the reference operation 3920 may include at least one additional embodiment, such as an operation 3921. The operation 3921 includes determining a common frame of reference is at least partially based on a first landmark subsurface feature of the mammalian body part included in a first reference image of the at least two reference images and on a second landmark subsurface feature of the mammalian body part included in a second reference image of the at least two reference images. In an embodiment, the registration operation 3930 may include at least one additional embodiment. The at least one additional embodiment may include an operation 3931, an operation 3932, or an operation 3933. The operation 3931 includes registering the respective landmark subsurface feature of the mammalian body part included in each reference image of the at least two reference images. The registration is at least partially based on the determined common frame of reference and on the data indicative of a respective spatial relationship among each respective landmark subsurface feature of the at least two reference images. The data includes data indicative of a content overlap between a content of a field of view of a first reference image of the at least two reference images and a content of a field of view of a second reference image of the at least two reference images. The operation 3932 includes registering the respective landmark subsurface feature of the mammalian body part included in each reference image of the at least two reference images. The registration is at least partially based on the determined common frame of reference and on the data indicative of spatial relationships between the at least two landmark subsurface features of a mammalian body part. The data includes data indicative of an edge content overlap between an edge content of a field of view of a first reference image of the at least two reference images and an edge content of field of view of a second reference image of the at least two reference images. The operation 3933 includes registering a spatial relationship of the respective landmark subsurface feature of the mammalian body part included in each reference image of the at least two reference images, the registration is at least partially based on the determined common frame of reference and on the data indicative of a respective spatial relationship among each respective landmark subsurface feature of the at least two reference images. In an embodiment, the storage operation 3940 may include at least one additional embodiment. The at least one additional embodiment may include an operation 3941 or an operation 3942. The operation 3941 includes maintaining in a computer-readable media informational data corresponding to the spatial relationship of the respective landmark subsurface feature of the mammalian body part included in each reference image of the at least two reference images. The operation 3942 includes maintaining in a computer-readable media (i) informational data corresponding to the registration of the respective landmark subsurface feature of the mammalian body part included in each reference image of the at least two reference images, and (ii) informational data corresponding to the subsurface feature atlas of the mammalian body part.

Figure 83:
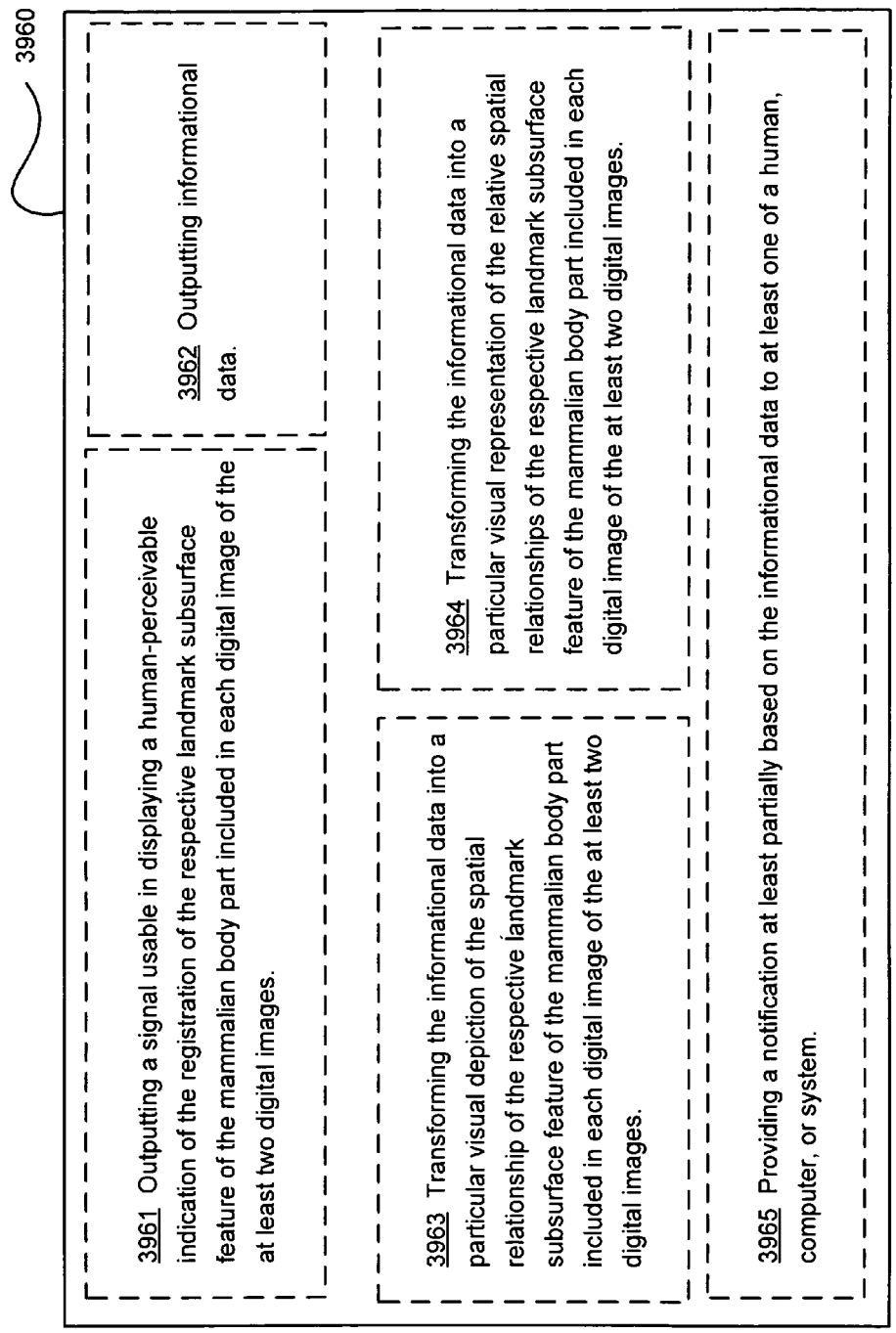
FIG. 83 illustrates an alternative embodiment of the operational flow.

FIG. 83 illustrates an alternative embodiment of the operational flow 3900. In an embodiment, the operational flow may include at least one additional embodiment 3960. The at least one additional embodiment 3960 may include an operation 3961, an operation 3962, an operation 3963, an operation 3964, or an operation 3965. The operation 3961 includes outputting a signal usable in displaying a human-perceivable indication of the registration of the respective landmark subsurface feature of the mammalian body part included in each reference image of the at least two reference images. The operation 3962 includes outputting the informational data. The operation 3963 includes transforming the informational data corresponding to the registration of the respective landmark subsurface feature of the mammalian body part included in each reference image of the at least two reference images into a particular visual depiction of the spatial relationship of the respective landmark subsurface feature of the mammalian body part included in each reference image of the at least two reference images. The operation 3964 includes transforming the informational data corresponding to the registration of the respective landmark subsurface feature of the mammalian body part included in each reference image of the at least two reference images into a particular visual representation of the relative spatial relationships of the respective landmark subsurface feature of the mammalian body part included in each reference image of the at least two reference images. The operation 3965 includes providing a notification that is at least partially based on the informational data to at least one of a human, computer, or system.

FIG. 84 illustrates an example computer program product 4000. The computer program product includes a computer-readable medium 4010 bearing program instructions 4020. The program instructions, when executed by a processor of a computing device, cause the computing device to perform a process. The process includes receiving at least two reference images. Each reference image of the at least two reference images includes a respective landmark subsurface feature of a mammalian body part. The process includes receiving data indicative of a respective spatial relationship among each respective landmark subsurface feature of the at least two reference images. The process includes determining a common frame of reference at least partially based on a landmark subsurface feature of the mammalian body part included in a reference image of the at least two reference images. The process includes registering the respective landmark subsurface feature of the mammalian body part included in each reference image of the at least two reference images. The registration is at least partially based on the determined common frame of reference and on the data indicative of a respective spatial relationship among each respective landmark subsurface feature of the at least two reference images. The process includes storing in another computer-readable medium operably coupled with the processor informational data corresponding to the registration of the respective landmark subsurface feature of the mammalian body part included in each reference image of the at least two reference images.

In an embodiment, the computer-readable media 4010 includes a tangible computer-readable media 4012. In an embodiment, the computer-readable media includes a communications media 4014.

Figure 85:
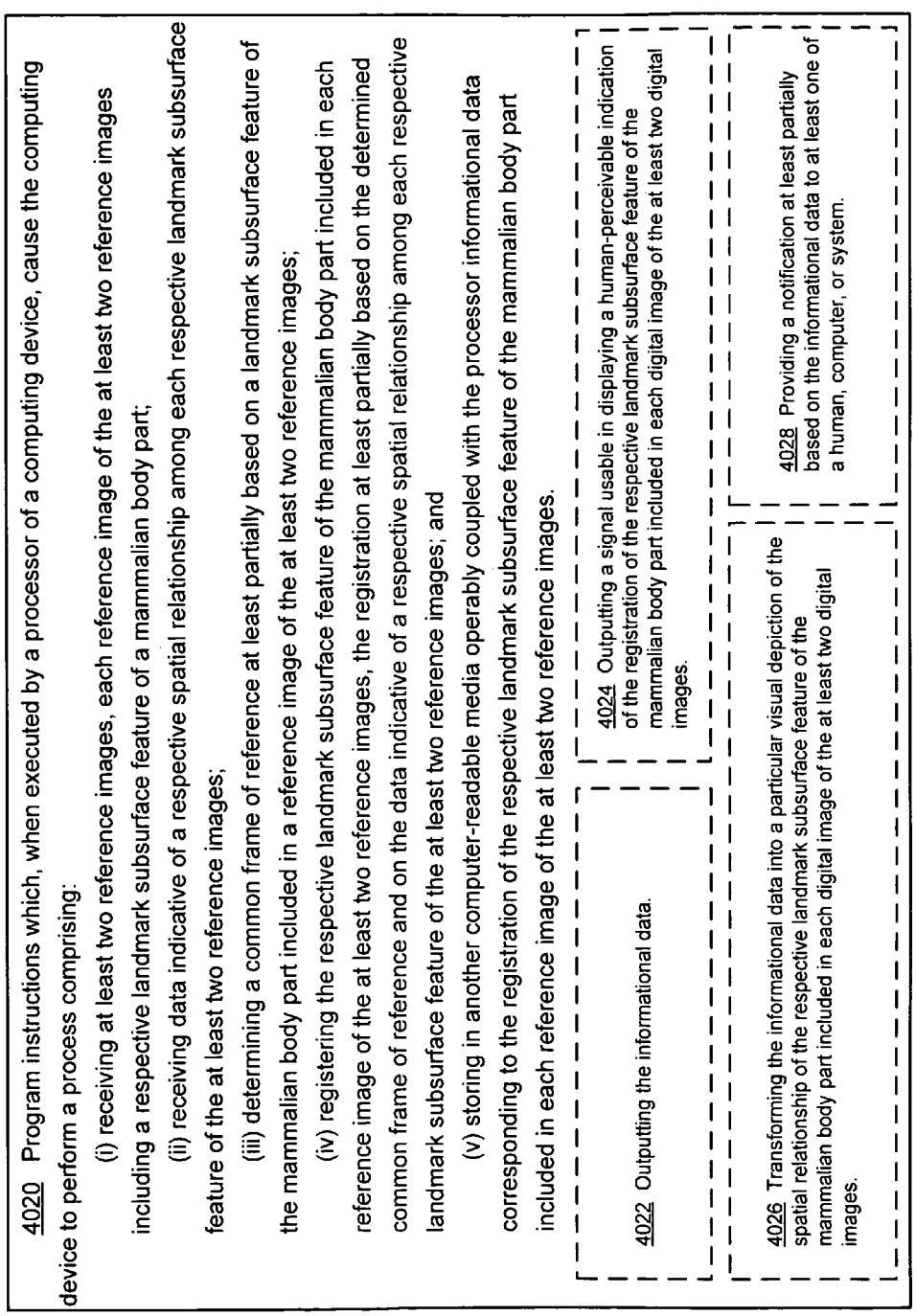
FIG. 85 illustrates an alternative embodiment of the computer program product 4000 of FIG. 84.

FIG. 85 illustrates an alternative embodiment of the computer program product 4000 of FIG. 84. In an embodiment, the program instructions 4020 which, when executed by a processor of a computing device, cause the computing device to perform at least one additional process. The at least one additional process may include a process 4022, a process 4024, a process 4026, or a process 4028. In an embodiment, the process further includes 4022 outputting the informational data. In an embodiment, the process further includes 4024 outputting a signal usable in displaying a human-perceivable indication of the registration of the respective landmark subsurface feature of the mammalian body part included in each reference image of the at least two reference images. In an embodiment, the process further includes 4026 transforming the informational data into a particular visual depiction of the spatial relationship of the respective landmark subsurface feature of the mammalian body part included in each reference image of the at least two reference images. In an embodiment, the process further includes 4028 providing a notification that is at least partially based on the informational data to at least one of a human, computer, or system.

Figure 86:
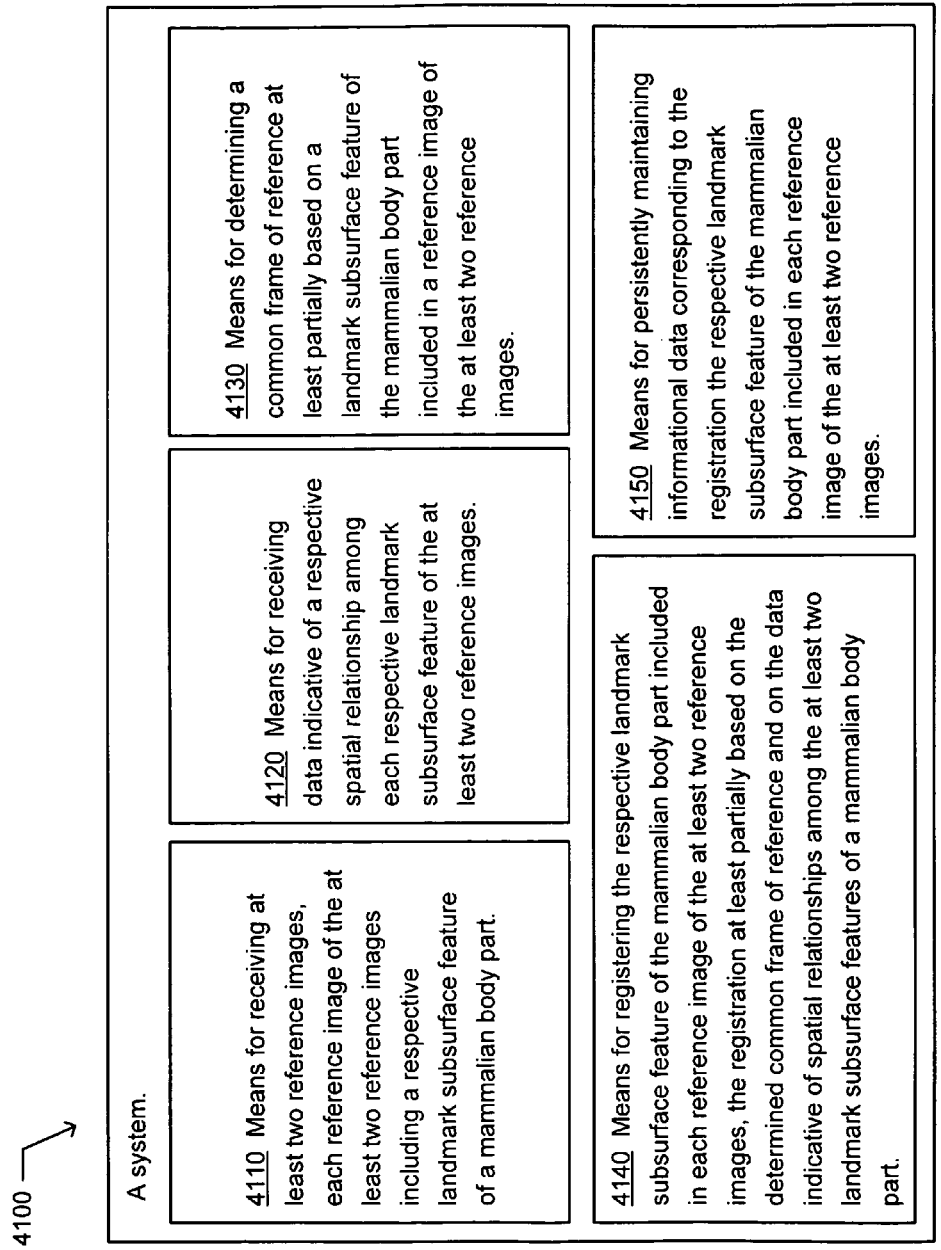
FIG. 86 illustrates an example system 4100.

FIG. 86 illustrates an example system 4100. The system includes means 4110 for receiving at least two reference images. Each reference image of the at least two reference images includes a respective landmark subsurface feature of a mammalian body part. The system includes means 4120 for receiving data indicative of a respective spatial relationship among each respective landmark subsurface feature of the at least two reference images. The system includes means 4130 for determining a common frame of reference that is at least partially based on a landmark subsurface feature of the mammalian body part included in a reference image of the at least two reference images. The system includes means 4140 for registering the respective landmark subsurface feature of the mammalian body part included in each reference image of the at least two reference images. The registration is at least partially based on the determined common frame of reference and on the data indicative of spatial relationships between the at least two landmark subsurface features of a mammalian body part. The system includes means 4150 for persistently maintaining informational data corresponding to the registration the respective landmark subsurface feature of the mammalian body part included in each reference image of the at least two reference images.

Returning to FIG. 80, FIG. 80 illustrates an alternative embodiment of the system 3820. In the alternative embodiment of the system, the system includes the coordinate analysis circuit 3824, the registration circuit 3826, and the computer-readable media 235. In the alternative embodiment of the system, the coordinate analysis circuit 3824 is configured to determine a common frame of reference that is at least partially based on a landmark subsurface feature of a mammalian body part included in a reference image of at least two reference images. Each reference image of the at least two reference images includes a respective landmark subsurface feature of a mammalian body part. In the alternative embodiment of the system, the registration circuit 3826 is configured to register the respective landmark subsurface feature of the mammalian body part included in each reference image of the at least two reference images. The registration is at least partially based on the determined common frame of reference. In the alternative embodiment of the system, the computer-readable media 235 is configured to maintain informational data corresponding to the registration of the respective landmark subsurface feature of the mammalian body part included in each reference image of the at least two reference images.

In an embodiment of the alternative embodiment of the system 3820, the coordinate analysis circuit 3824 is configured to determine a common frame of reference at least partially based on a landmark subsurface feature of a cavity or lumen of a mammalian body part included in a reference image of at least two reference images. Each reference image of the at least two reference images includes a respective landmark subsurface feature of the cavity or lumen of a mammalian body part. In an alternative embodiment, the registration circuit 3826 is configured to register the respective landmark subsurface feature of the mammalian body part included in each reference image of the at least two reference images. The registration is at least partially based on the determined common frame of reference and on data indicative of a spatial relationship among each respective landmark subsurface feature of the at least two reference images.

In an embodiment of the alternative embodiment of the system 3820, the atlas generation circuit 3828 is configured generate a subsurface feature atlas of the mammalian body part. The subsurface feature atlas includes a spatial relationship of the respective landmark subsurface feature of the mammalian body part included in each reference image of the at least two reference images. The subsurface feature atlas is at least partially based on the registration of the respective landmark subsurface feature of the mammalian body part included in each reference image of the at least two reference images. In an alternative embodiment of the alternative embodiment of the system, the computer-readable media 235 is configured to maintain (i) informational data corresponding to the registration of the respective landmark subsurface feature of the mammalian body part included in each reference image of the at least two reference images and (ii) informational data corresponding to the subsurface feature atlas of the mammalian body part.

FIG. 87 illustrates an example operational flow 4100. The operational flow includes a start operation. The operational flow includes a reference operation 4110 that includes determining a common frame of reference that is at least partially based on a landmark subsurface feature of a mammalian body part included in a reference image of at least two reference images. Each reference image of the at least two reference images includes a respective landmark subsurface feature of a mammalian body part. In an embodiment, the reference operation may be implemented using the coordinate analysis circuit 3824 described in conjunction with FIG. 80. The operational flow includes a registration operation 4120 that includes registering the respective landmark subsurface feature of the mammalian body part included in each reference image of the at least two reference images, the registration is at least partially based on the determined common frame of reference. In an embodiment, the registration operation may be implemented using the registration circuit 3826 described in conjunction with FIG. 80. The operational flow includes a storage operation 4130 that includes maintaining in a computer-readable media informational data corresponding to the registration of the respective landmark subsurface feature of the mammalian body part included in each reference image of the at least two reference images. In an embodiment, the storage operation may be implemented using the computer-readable media 235 described in conjunction with FIG. 80. The operational flow includes an end operation.

In an alternative embodiment, the operational flow 4100 includes a mapping operation 4140 that includes generating a subsurface feature atlas of the mammalian body part. The subsurface feature atlas includes a spatial relationship of the respective landmark subsurface feature of the mammalian body part included in each reference image of the at least two reference images. The subsurface feature atlas is at least partially based on the registration the respective landmark subsurface feature of the mammalian body part included in each reference image of the at least two reference images.

FIG. 88 illustrates an alternative embodiment of the operational flow 4100. In an embodiment, reference operation 4110 may include at least one additional embodiment, such as an operation 4111. The operation 4111 includes determining a common frame of reference that is at least partially based on a landmark subsurface feature of a cavity or lumen of a mammalian body part included in a reference image of at least two reference images. Each reference image of the at least two reference images includes a respective landmark subsurface feature of the cavity or lumen of a mammalian body part. In an embodiment, the registration operation 4120 may include at least one additional embodiment. The at least one additional embodiment may include an operation 4121 or an operation 4122. The operation 4121 includes registering the respective landmark subsurface feature of the mammalian body part included in each reference image of the at least two reference images. The registration is at least partially based on the determined common frame of reference and on data indicative of a spatial relationship among each respective landmark subsurface feature, of the at least two reference images. The operation 4122 includes registering a spatial relationship of the respective landmark subsurface feature of the mammalian body part included in each reference image of the at least two reference images. The registration is at least partially based on the determined common frame of reference. In an embodiment, the storage operation 4130 may include at least one additional embodiment, such as the operation 4131. The operation 4131 includes maintaining in a computer-readable media informational data corresponding to (i) the registration of the at least two landmark subsurface features included in the reference image and (ii) the generated subsurface feature atlas of the mammalian body part.

FIG. 89 illustrates a computer program product 4200. The computer program product includes a computer-readable medium 4210 bearing program instructions 4220. The program instructions, when executed by a processor of a computing device, cause the computing device to perform a process. The process includes determining a common frame of reference that is at least partially based on a landmark subsurface feature of a mammalian body part included in a reference image of at least two reference images. Each reference image of the at least two reference images includes a respective landmark subsurface feature of a mammalian body part. The process includes registering the respective landmark subsurface feature of the mammalian body part included in each reference image of the at least two reference images. The registration is at least partially based on the determined common frame of reference. The process includes storing in another computer-readable medium operably coupled with the processor informational data corresponding to the registration of the respective landmark subsurface feature of the mammalian body part included in each reference image of the at least two reference images.

In an embodiment, the registering process includes 4222 registering the respective landmark subsurface feature of the mammalian body part included in each reference image of the at least two reference images. The registration is at least partially based on the determined common frame of reference and on data indicative of a spatial relationship among each respective landmark subsurface feature of the at least two reference images. In an embodiment, the process further includes 4224 generating a subsurface feature atlas of the mammalian body part. The subsurface feature atlas includes a spatial relationship of the respective landmark subsurface feature of the mammalian body part included in each reference image of the at least two reference images. The subsurface feature atlas is at least partially based on the registration of the respective landmark subsurface feature of the mammalian body part included in each reference image of the at least two reference images.

In an embodiment, the computer-readable media 4210 includes a tangible computer-readable media 4212. In an embodiment, the computer-readable media includes a communications media 4214.

Figure 90:
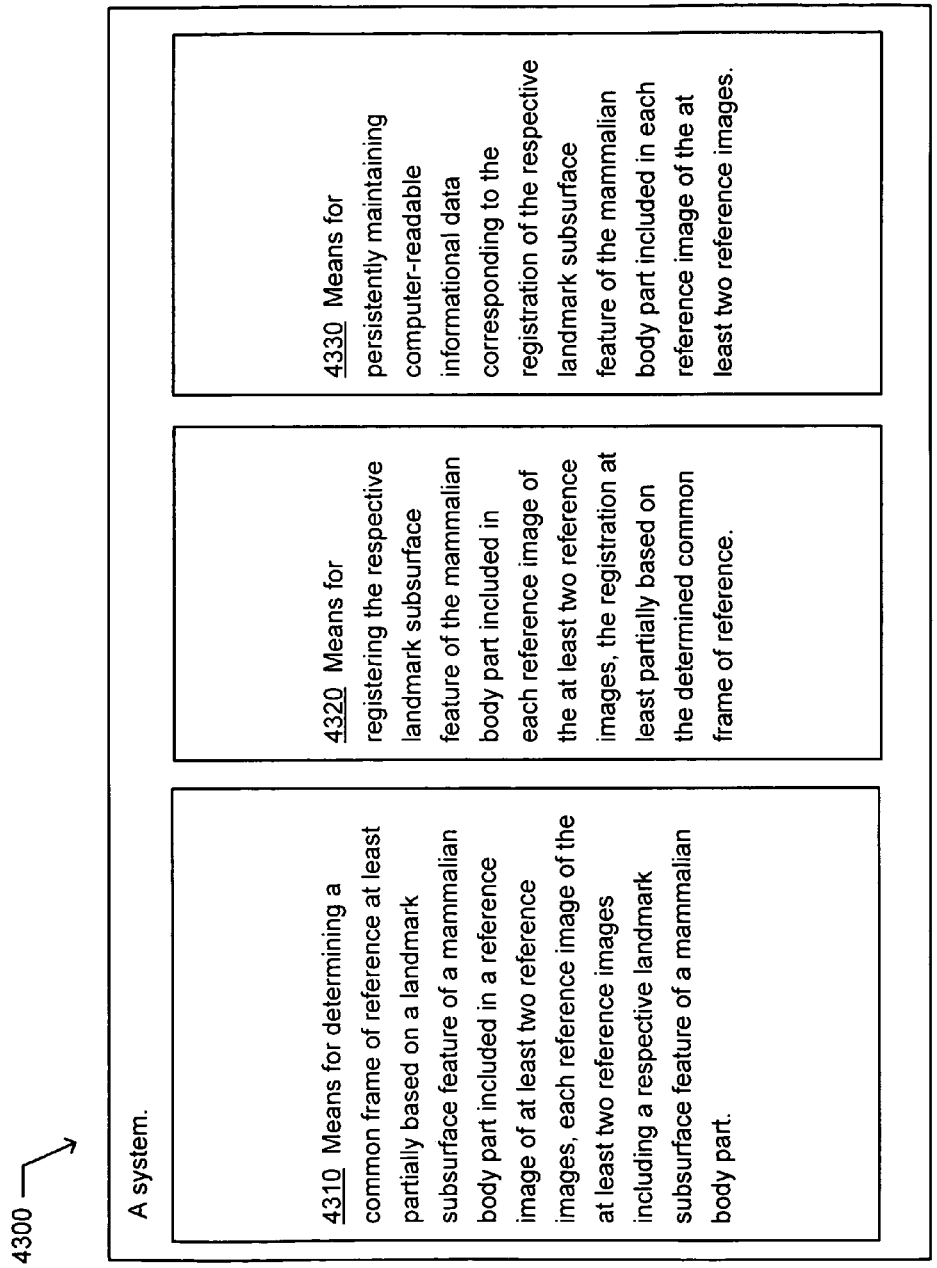
FIG. 90 illustrates an example system.

FIG. 90 illustrates an example system 4300. The system includes means 4310 for determining a common frame of reference that is at least partially based on a landmark subsurface feature of a mammalian body part included in a reference image of at least two reference images. Each reference image of the at least two reference images includes a respective landmark subsurface feature of a mammalian body part. The system includes means 4320 for registering the respective landmark subsurface feature of the mammalian body part included in each reference image of the at least two reference images. The registration is at least partially based on the determined common frame of reference. The system includes means 4330 for persistently maintaining computer-readable informational data corresponding to the registration of the respective landmark subsurface feature of the mammalian body part included in each reference image of the at least two reference images.

Figure 91:
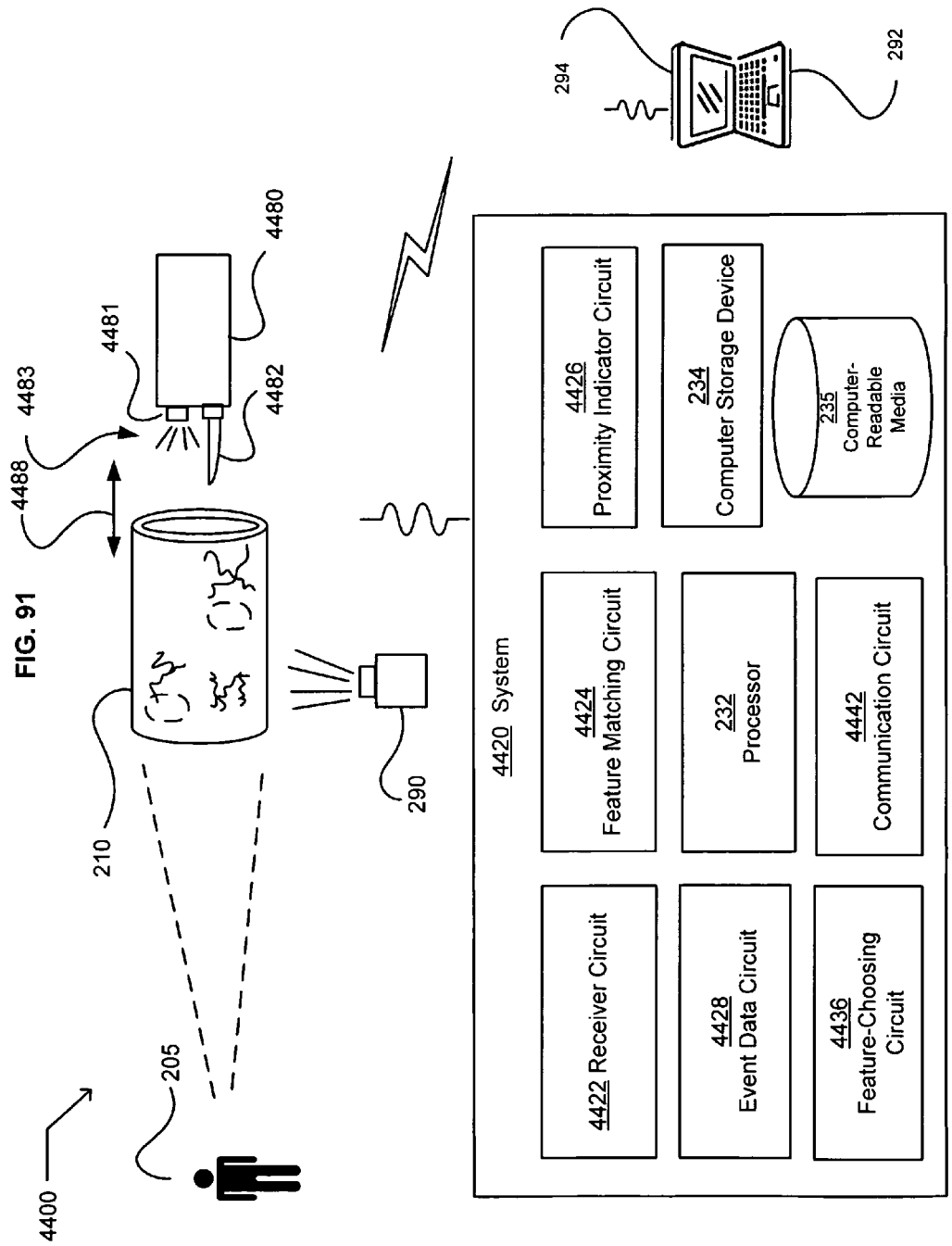
FIG. 91 illustrates an example environment.

FIG. 91 illustrates an example environment 4400. The environment includes the mammalian body part 210 of the mammal 205, and a system 4420. The environment includes a body-insertable device 4480 moveable 4488 through the cavity or lumen 211 of the mammalian body part 210. The body insertable device includes a distal end portion 4483. The distal end portion may include a digital image acquisition device 4481, such as a digital camera. The distal end portion 4482 may include an active element, such as an effector, scalpel, or an ablation element. The system includes a receiver circuit 4422. The receiver circuit is configured to receive a first reference image that includes an objective landmark subsurface feature of a mammalian body part. The objective landmark subsurface feature has a first spatial relationship to a destination region of interest of the mammalian body part. For example, the objective landmark subsurface feature or the destination region of interest may be provided by a human or a machine, a feature choosing circuit, or from an atlas. In an embodiment, for example, the objective landmark subsurface feature may be considered as a goal, a marker, or something that is being aimed-at or sought because once the objective landmark subsurface feature is located, the destination region of interest may be located by virtue of its first spatial relationship to the objective landmark subsurface feature. In an embodiment, the first reference image may have been acquired in an earlier colonoscopy, and may depict a region of interest to which the health care provider wants to return for a procedure or further examination. FIG. 92 illustrates an alternative embodiment of the environment 4400 including additional details of the mammalian body part 210 illustrated in FIG. 4. For example, the objective landmark subsurface feature may be the landmark subsurface feature 216A having a first spatial relationship 217A to the destination region of interest 214A of the mammalian body part 210 illustrated in View 92B of FIG. 92. In another example, the objective landmark subsurface feature may be the landmark subsurface feature 216B having a first spatial relationship 217B to the destination region of interest 214B of the mammalian body part 210 illustrated in View 92B of FIG. 92.

Returning to FIG. 91, the receiver circuit 4422 is also configured to receive a second reference image that includes a present-location landmark subsurface feature of the mammalian body part. The present-location landmark subsurface feature has a second spatial relationship to a distal end portion of a body-insertable device. View 92B of FIG. 92 illustrates the body-insertable device 4480 deployed in the cavity or lumen 211 of the mammalian body part 210. View 92B also illustrates an embodiment where the present-location landmark subsurface feature is landmark subsurface feature 216B having a second spatial relationship 4815 to the operative portion, illustrated as the distal end portion 4483 of the body-insertable device deployed operationally proximate to the mammalian body part. For example, the body insertable device may include an endoscope having an ablation tool 4482 at a distal end, and inserted in the mammalian body part by the health care provider to perform a procedure. For example, operationally proximate may include where the ablation tool at a distal end of an endoscope can reach and ablate at least a portion of the destination region of interest.

The system 4420 includes a feature matching circuit 4424 configured to determine a substantial correspondence between the present-location landmark subsurface feature and the objective landmark subsurface feature. For example, substantial correspondence may be determined using a pattern matching technique. For example, if the objective landmark subsurface feature is the landmark subsurface feature 216A having a spatial relationship 217A to the region of interest 214A of the mammalian body part 210 illustrated in illustrated in View 92B of FIG. 92, and if the present-location landmark subsurface feature is the landmark subsurface feature 216B having the spatial relationship 4815 to the operative portion, illustrated as the distal end portion 4483 of the body-insertable device, the feature matching circuit will determine no substantial correspondence. In such an example, a determined "no substantial correspondence" indicates the health care provider does not have the operative portion of the body-insertable device deployed operationally proximate to the region of interest. In another example, if the objective landmark subsurface feature is the landmark subsurface feature 216B having the spatial relationship 217B to the region of interest 214B of the mammalian body part 210 illustrated in FIG. 92, and if the present-location landmark subsurface feature is the landmark subsurface feature 216B having a spatial relationship 4815 to the operative portion, illustrated as the distal end portion 4483 of the body-insertable device, the feature matching circuit will determine a substantial correspondence. In such an example, a determined "substantial correspondence" indicates the health care provider has the operative portion of the body-insertable device deployed operationally proximate to the region of interest.

Continuing with FIG. 91, the system 4420 includes a proximity indicator circuit 4426 configured to generate informational data indicative of an operational proximity of the distal end portion of the body-insertable device 4480 to the destination region of interest. The informational data indicative of operational proximity is at least partially based on the determined substantial correspondence.

In an embodiment of the system 4420, the first reference image includes an objective landmark subsurface feature of a mammalian body part. The objective landmark subsurface feature has a first spatial relationship to a destination region of interest of the mammalian body part, and the objective landmark subsurface feature is distinguishable from other landmark subsurface features of the mammalian body part. For example, the objective landmark subsurface feature may be detectible by a fluoroscope, ultrasound, or x-ray and machine-distinguishable from other landmark subsurface features of the mammalian body part.

In an embodiment, first reference image includes an objective landmark subsurface feature of a mammalian body part. The objective landmark subsurface feature has an indicated, determinable, estimable, or inferable first spatial relationship to a destination region of interest of the mammalian body part. In an embodiment, the first reference image includes an objective landmark subsurface feature of a mammalian body part. The objective landmark subsurface feature has a spatial relationship to a region of interest of a cavity or lumen of the mammalian body part. In an embodiment, the first reference image includes an objective landmark subsurface feature of a mammalian body part. The objective landmark subsurface feature has a first spatial relationship to a region of interest of a surface of a cavity or lumen of the mammalian body part. In an embodiment, the first reference image includes a first reference image acquired by an ex vivo device and includes an objective landmark subsurface feature of a mammalian body part. The objective landmark subsurface feature has a first spatial relationship to a region of interest of the mammalian body part. In an embodiment, the first reference image includes a first reference image acquired by the body-insertable device and includes an objective landmark subsurface feature of a mammalian body part. The objective landmark subsurface feature has a first spatial relationship to a region of interest of the mammalian body part.

In an embodiment of the system 4420, the second reference image includes a present-location landmark subsurface feature of the mammalian body part. The present-location landmark subsurface feature having a second spatial relationship to a distal end of a body-insertable device deployed operationally proximate to the mammalian body part. In an embodiment, the second reference image includes a present-location landmark subsurface feature of the mammalian body part. The present-location landmark subsurface feature having a second spatial relationship to an operative end of a body-insertable device deployed operationally proximate to the mammalian body part. In an embodiment, the second reference image includes a present-location landmark subsurface feature of the mammalian body part. The present-location landmark subsurface feature having a second spatial relationship to an operative and movable distal end portion of a body-insertable device deployed operationally proximate to the mammalian body part. In an embodiment, the second reference image includes a present-location landmark subsurface feature of the mammalian body part. The present-location landmark subsurface feature having a second spatial relationship to a distal end portion of the body-insertable device deployed in a cavity or lumen of the mammalian body part. In an embodiment, the second reference image includes a second reference image acquired by a body-insertable device and includes a present-location landmark subsurface feature of the mammalian body part. The present-location landmark subsurface feature has a second spatial relationship to a portion of the body-insertable device deployed operationally proximate to the mammalian body part. In an embodiment, the second reference image includes a second reference image acquired by an ex vivo device and includes a present-location landmark subsurface feature of the mammalian body part. The present-location landmark subsurface feature has a second spatial relationship to a portion of a body-insertable device deployed operationally proximate to the mammalian body part.

In an embodiment, the feature matching circuit 4424 is configured to determine at least one of a structural, pattern, orientation, physical characteristic, or identification correspondence between the present-location landmark subsurface feature and the objective landmark subsurface feature. In an embodiment, the feature matching circuit is configured to determine a match between the present-location landmark subsurface feature and the objective landmark subsurface feature.

In an embodiment, the proximity indicator circuit 4426 is configured to generate informational data indicative of an operational proximity of the distal end portion of the body-insertable device to the destination region of interest. The informational data is at least partially based on a scale suitable for operational use of the body-insertable device with respect to the destination region of interest. The informational data is at least partially based on the determined substantial correspondence between the present-location landmark subsurface feature and the objective landmark subsurface feature. For example, the operational proximity may be indicated based upon a scale of inches, centimeters, or millimeters suitable for an operational use of the body-insertable device relative to the region of interest. In an embodiment, the proximity indicator circuit is configured to generate informational data indicative of a distance of less than four centimeters between the distal end portion of the body-insertable device and the destination region of interest. In an embodiment, the proximity indicator circuit is configured to generate informational data indicative of a distance of less than two centimeters between the distal end portion of the body-insertable device and the destination region of interest. In an embodiment, the proximity indicator circuit is configured to generate informational data indicative of a distance of less than one centimeter between the distal end distal end portion of the body-insertable device and the destination region of interest.

In an embodiment, the proximity indicator circuit 4426 is to generate informational data indicative of a proximity distance of the distal end portion of the body-insertable device to the destination region of interest. The informational data is at least partially based on a determined substantial correspondence between the landmark subsurface feature of the mammalian body part and the present-location subsurface feature of the mammalian body part. The indicated distance includes a distance within a user-selected range. For example, a user-selected range may be a range of less than 4 cm, or less than 2 cm. In an embodiment, the proximity indicator circuit is configured to generate informational data indicative of an absence of a proximity between the distal end portion of the body-insertable device and the destination region of interest. The informational data is at least partially based on the determined substantial correspondence between the present-location landmark subsurface feature and the objective landmark subsurface feature. In an embodiment, the proximity indicator circuit is configured to output a signal usable in displaying a human-perceivable indication of an operational proximity of the distal end portion of the body-insertable device to the destination region of interest. The signal is at least partially based on the determined substantial correspondence between the present-location landmark subsurface feature and the objective landmark subsurface feature. In an embodiment, the proximity indicator circuit is configured to generate informational data indicative of an operational proximity of the distal end portion of the body-insertable device to the destination region of interest in response to the determined substantial correspondence between the present-location landmark subsurface feature and the objective landmark subsurface feature; otherwise, to generate informational data indicative of an absence of an operational proximity of the distal end portion of the body-insertable device to the destination region of interest.

In an embodiment, the system 4420 includes an event data circuit 4428 configured to generate operational-proximity event informational data indicative of an operational proximity of the distal end portion of the body-insertable device to the destination region of interest. An occurrence of an operational-proximity event is at least partially based on the informational data indicative of an operational proximity of the distal end portion of the body-insertable device to the destination region of interest.

In an embodiment, the system includes a feature-choosing circuit 4436 configured to select the objective landmark subsurface feature of the mammalian body part. In an embodiment, the feature-choosing circuit is configured to select the objective landmark subsurface feature of the mammalian body part in response to a human user or a machine initiated input. In an embodiment, the feature-choosing circuit is configured to select the objective landmark subsurface feature of the mammalian body part from informational data indicating the spatial relationship of the region of interest relative to the objective landmark subsurface feature.

In an embodiment, the system 4420 includes the computer-readable media 235 configured to maintain the informational data corresponding to the operational proximity of the distal end portion of the body-insertable device to the destination region of interest. In an embodiment, the computer readable-media is configured to maintain (i) the informational data corresponding to the operational proximity of the distal end portion of the body-insertable device to the destination region of interest and (ii) the operational-proximity event informational data.

In an embodiment, the system includes a communication circuit 4442 configured to output the informational data operational proximity of the distal end portion of the body-insertable device to the destination region of interest. In an embodiment, the communication circuit is configured to output (i) the informational data corresponding to the operational proximity of the distal end portion of the body-insertable device to the destination region of interest and (ii) the operational-proximity event informational data. In an embodiment, the system includes the communication circuit configured to provide a notification that is at least partially based on the informational data to at least one of a human, computer, or system. In an embodiment, the system includes the communication device 292 configured to display a human-perceivable depiction of the informational data. In an embodiment, the human-perceivable depiction includes an audio or visual human-perceivable depiction of the operational proximity of the portion of the body-insertable device to the region of interest.

Figure 93:
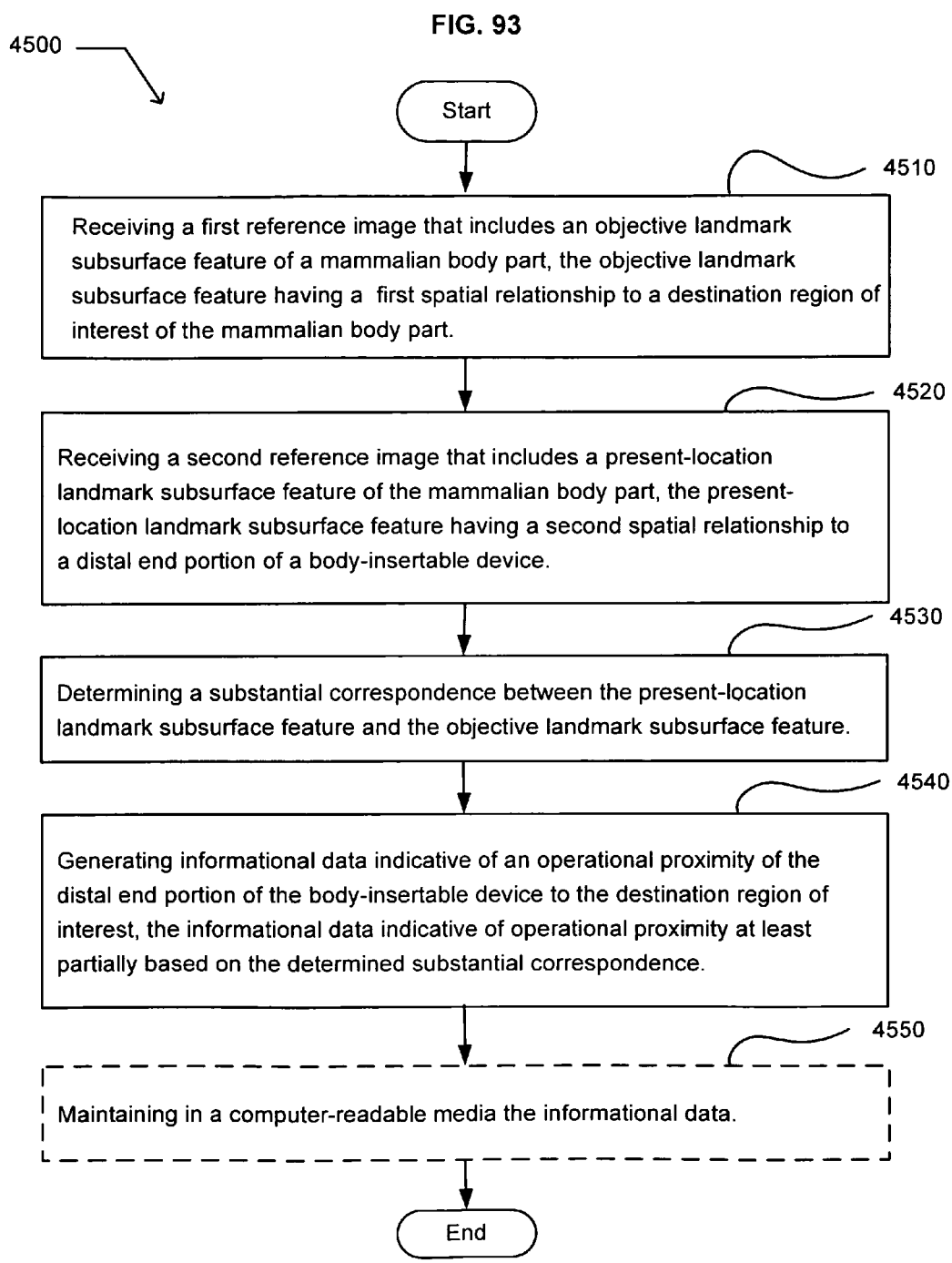
FIG. 93 illustrates an example operational flow.

FIG. 93 illustrates an example operational flow 4500. The operational flow includes a start operation. The operational flow includes a first reception operation 4510. The first reception operation includes receiving a first reference image that includes an objective landmark subsurface feature of a mammalian body part. The objective landmark subsurface feature has a first spatial relationship to a destination region of interest of the mammalian body part. A second reception operation 4520 includes receiving a second reference image that includes a present-location landmark subsurface feature of the mammalian body part. The present-location landmark subsurface feature has a second spatial relationship to a distal end portion of a body-insertable device. In an embodiment, the first reception operation or the second reception operation may be implemented using the receiver circuit 4422 described in conjunction with FIG. 91. A matching operation 4530 includes determining a substantial correspondence between the present-location landmark subsurface feature and the objective landmark subsurface feature. In an embodiment, correspondence may include a pattern matching, an orientation, or a spatial relationship correspondence. In an embodiment, the matching operation may be implemented using the feature matching circuit 4424 described in conjunction with FIG. 91. A nearness operation 4540 includes generating informational data indicative of an operational proximity of the distal end portion of the body-insertable device to the destination region of interest. The informational data indicative of operational proximity is at least partially based on the determined substantial correspondence. In an embodiment, the nearness operation may be implemented using the proximity indicator circuit 4426 described in conjunction with FIG. 91. The operational flow includes an end operation.

In an embodiment, the operational flow 4500 may include at least one additional embodiment, such as a storage operation 4550. The storage operation includes maintaining the informational data in a computer-readable media. In an embodiment, the storage operation may be implemented using the computer-readable media 235 described in conjunction with FIG. 91.

Figure 94:
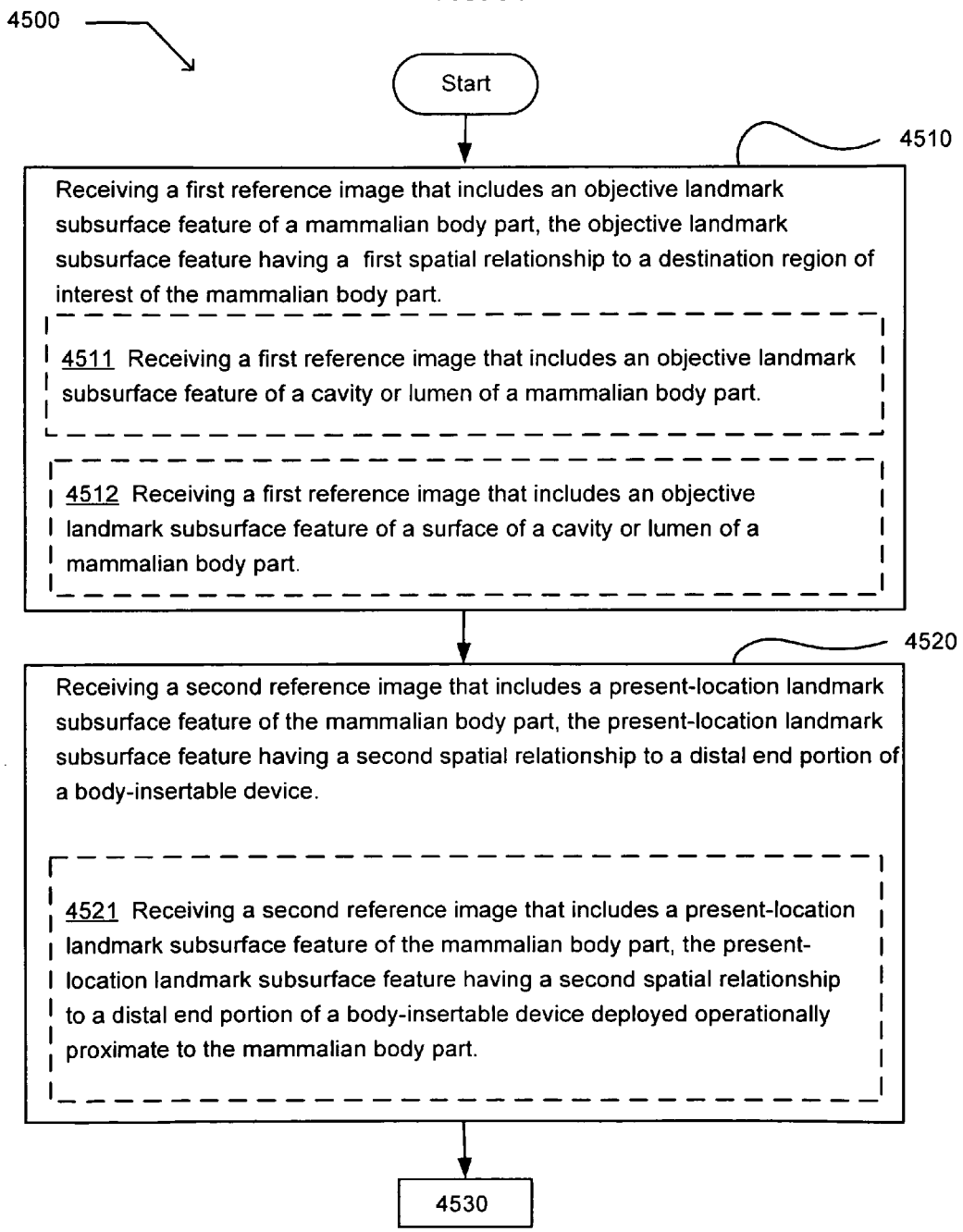
FIG. 94 illustrates an alternative embodiment of the operational flow 4500 of FIG. 93.

FIG. 94 illustrates an alternative embodiment of the operational flow 4500 of FIG. 93. In an embodiment, the first reception operation 4510 may include at least one additional embodiment. The at least one additional embodiment may include an operation 4511 or an operation 4512. The operation 4511 includes receiving a first reference image that includes an objective landmark subsurface feature of a cavity or lumen of a mammalian body part. The operation 4512 includes receiving a first reference image that includes an objective landmark subsurface feature of a surface of a cavity or lumen of a mammalian body part. In an embodiment, the second reception operation 4520 may include at least one additional embodiment. The at least one additional embodiment may include an operation 4521. The operation 4521 includes receiving a second reference image that includes a present-location landmark subsurface feature of the mammalian body part. The present-location landmark subsurface feature has a second spatial relationship to a distal end portion of a body-insertable device deployed operationally proximate to the mammalian body part.

FIG. 95 illustrates an alternative embodiment of the operational flow 4500 of FIG. 93. In an embodiment, the matching operation 4530 may include at least one additional embodiment. The at least one additional embodiment may include an operation 4531 or an operation 4532. The operation 4531 includes generating informational data indicative of an operational proximity of the distal end portion of the body-insertable device to the destination region of interest. The informational data is at least partially based on a scale suitable for medical use of the body-insertable device with respect to the destination region of interest. The informational data is further at least partially based on the determined substantial correspondence between the present-location landmark subsurface feature and the objective landmark subsurface feature The operation 4532 includes generating informational data indicative of a proximity distance of less than four centimeters between the distal end portion of the body-insertable device and the destination region of interest. The informational data is at least partially based on the determined substantial correspondence between the present-location landmark subsurface feature and the objective landmark subsurface feature.

Figure 96:
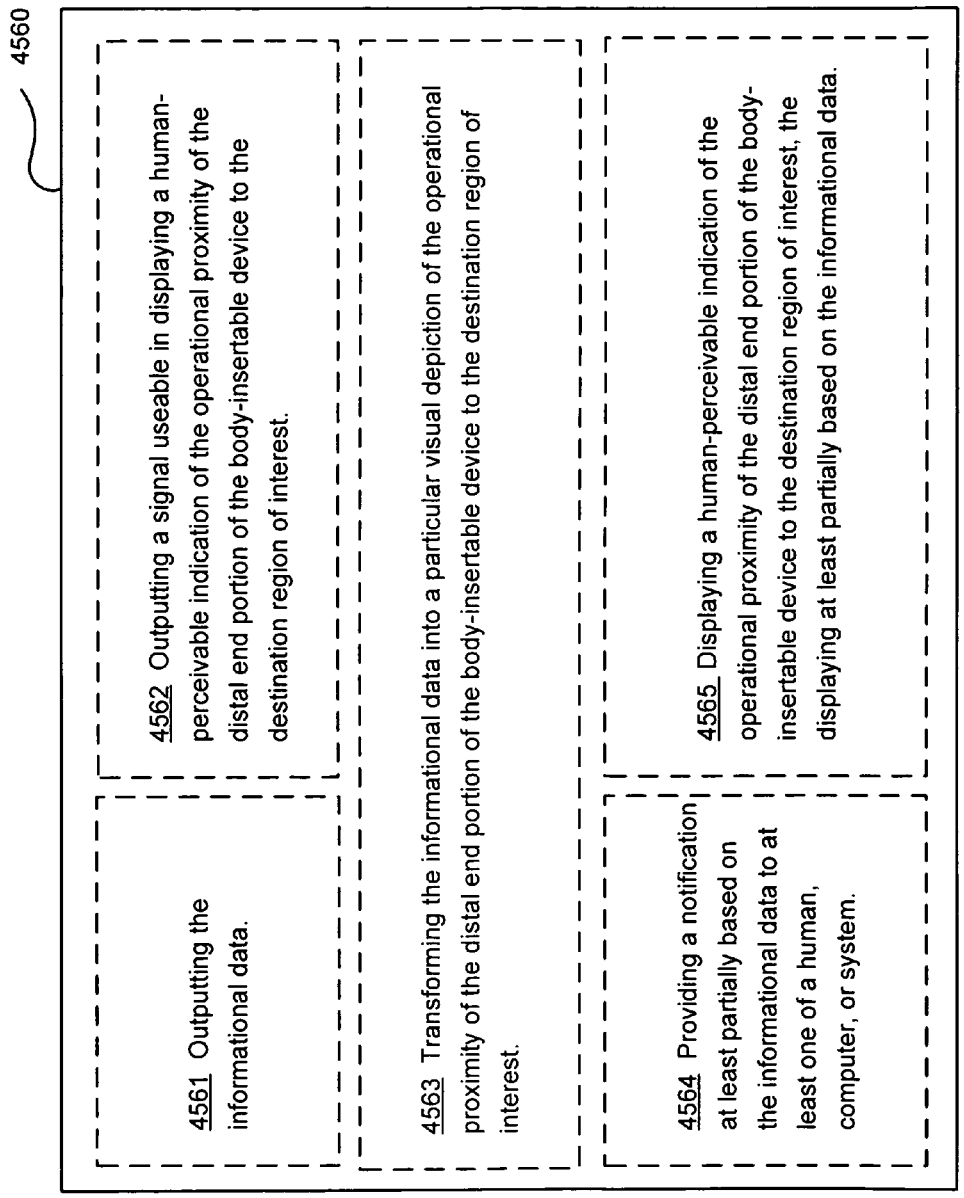
FIG. 96 illustrates an alternative embodiment of the operational flow 4500 of FIG. 93.

FIG. 96 illustrates an alternative embodiment of the operational flow 4500 of FIG. 93. In an embodiment, the operational flow may include at least one additional embodiment. The at least one additional embodiment may include an operation 4561, an operation 4562, an operation 4563, an operation 4564, or an operation 4565. The operation 4561 includes outputting the informational data. The operation 4562 includes outputting a signal useable in displaying a human-perceivable indication of the operational proximity of the distal end portion of the body-insertable device to the destination region of interest. The operation 4563 includes transforming the informational data into a particular visual depiction of the operational proximity of the distal end portion of the body-insertable device to the destination region of interest. The operation 4564 includes providing a notification that is at least partially based on the informational data to at least one of a human, computer, or system. The operation 4565 includes displaying a human-perceivable indication of the operational proximity of the distal end portion of the body-insertable device to the destination region of interest, the displaying is at least partially based on the informational data.

FIG. 97 illustrates a computer program product 4600. The computer program product includes a computer-readable computer storage medium 4610 bearing program instructions 4620. The program instructions, when executed by a processor of a computing device, cause the computing device to perform a process. The process includes receiving a first reference image that includes an objective landmark subsurface feature of a mammalian body part. The objective landmark subsurface feature has a first spatial relationship to a destination region of interest of the mammalian body part. The process includes receiving a second reference image that includes a present-location landmark subsurface feature of the mammalian body part. The present-location landmark subsurface feature has a second spatial relationship to a distal end portion of a body-insertable device. The process includes determining a substantial correspondence between the present-location landmark subsurface feature and the objective landmark subsurface feature. The process includes generating informational data indicative of an operational proximity of the distal end portion of the body-insertable device to the destination region of interest. The informational data indicative of operational proximity is at least partially based on the determined substantial correspondence between the present-location landmark subsurface feature and the objective landmark subsurface feature. The process includes outputting the informational data.

In an embodiment, the computer-readable media 4610 includes a tangible computer-readable media 4612. In an embodiment, the computer-readable media includes a communications medium 4614.

Figure 98:
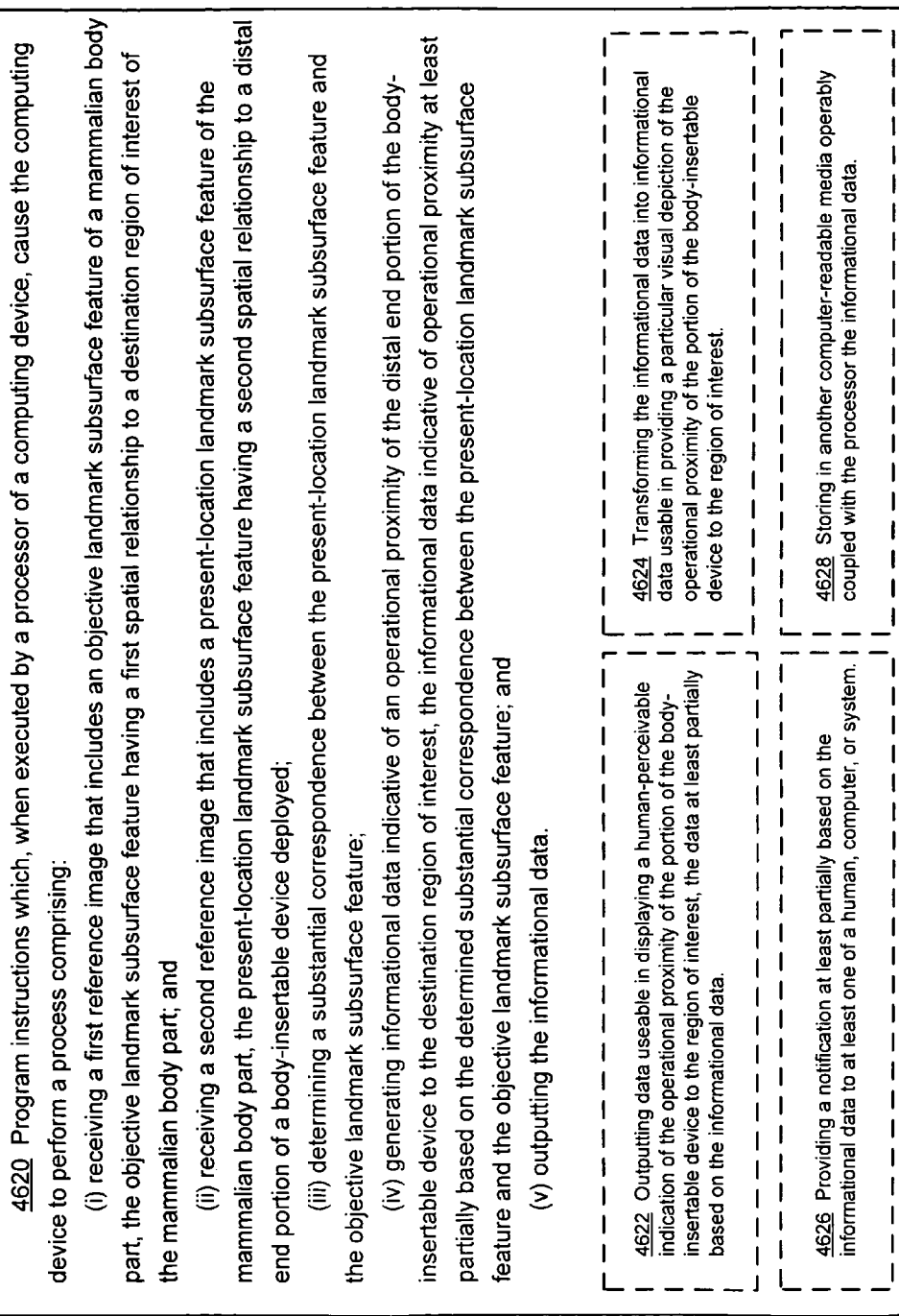
FIG. 98 illustrates an alternative embodiment of the computer program product 4600 of FIG. 97.

FIG. 98 illustrates an alternative embodiment of the computer program product 4600 of FIG. 97. In an embodiment, the outputting process includes 4622 outputting a signal useable in displaying a human-perceivable indication of the operational proximity of the portion of the body-insertable device to the region of interest. The signal is at least partially based on the informational data. In an embodiment, the process further includes 4624 transforming the informational data into a particular visual depiction of the operational proximity of the distal end portion of the body-insertable device to the destination region of interest. In an embodiment, the process further includes 4626 providing a notification that is at least partially based on the informational data to at least one of a human, computer, or system. In an embodiment, the process further includes 4628 storing in another computer-readable medium operably coupled with the processor the informational data.

Figure 99:
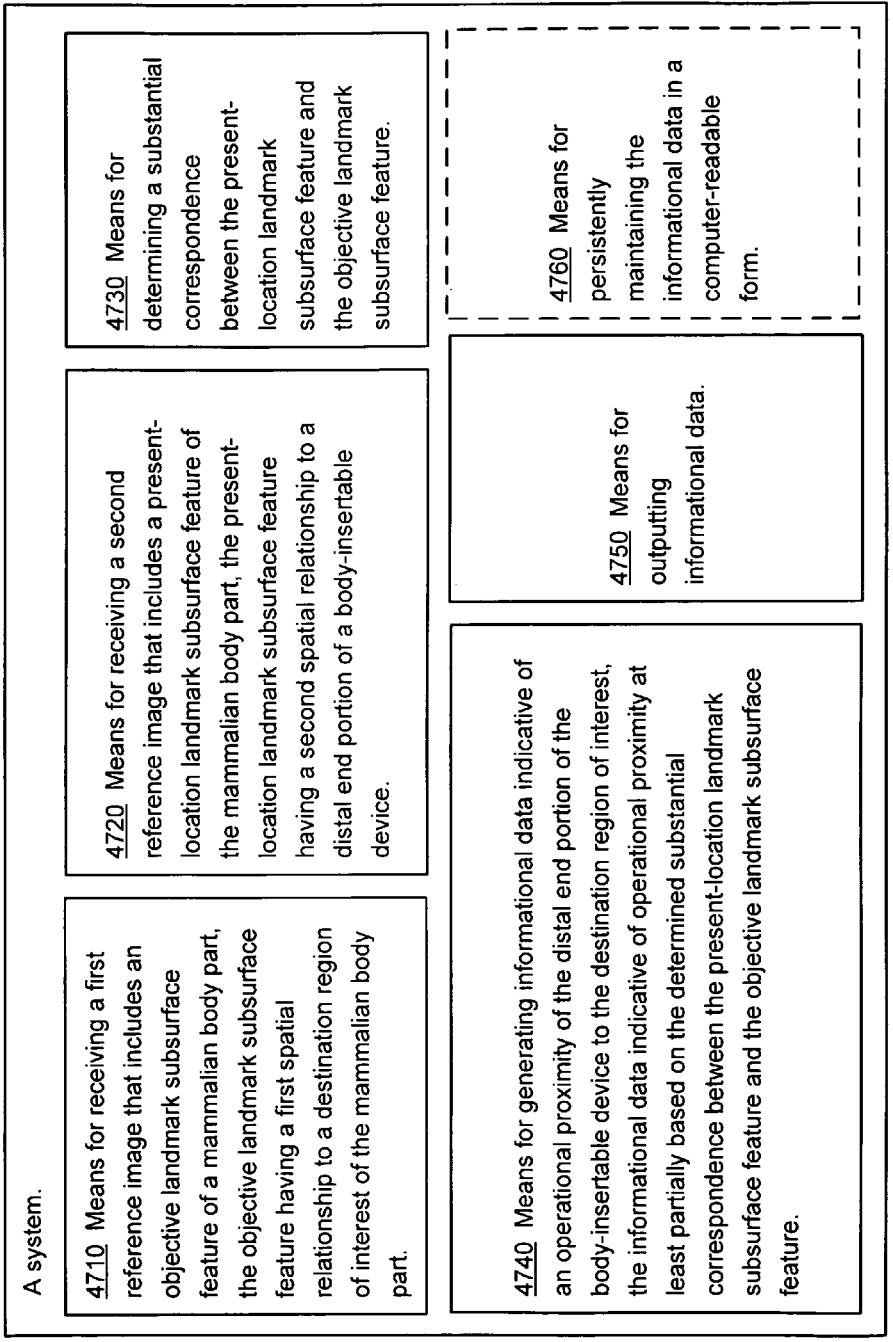
FIG. 99 illustrates an example system.

FIG. 99 illustrates an example system 4700. The system includes means 4710 for receiving a first reference image that includes an objective landmark subsurface feature of a mammalian body part. The objective landmark subsurface feature has a first spatial relationship to a destination region of interest of the mammalian body part. The system includes means 4720 for receiving a second reference image that includes a present-location landmark subsurface feature of the mammalian body part. The present-location landmark subsurface feature has a second spatial relationship to a distal end portion of a body-insertable device. The system includes means 4730 for determining a substantial correspondence between the present-location landmark subsurface feature and the objective landmark subsurface feature. The system includes means 4740 for generating informational data indicative of an operational proximity of the distal end portion of the body-insertable device to the destination region of interest. The informational data indicative of operational proximity is at least partially based on the determined substantial correspondence between the present-location landmark subsurface feature and the objective landmark subsurface feature. The system includes means 4750 for outputting informational data. In an embodiment, the system includes means 4760 for persistently maintaining the informational data in a computer-readable form.

Returning to FIG. 91, FIG. 91 illustrates an alternative embodiment of an example system 4422. In the alternative embodiment of the system, the feature matching circuit 4424 is configured to determine a substantial correspondence between a present-location landmark subsurface feature of a mammalian body part and an objective landmark subsurface feature of the mammalian body part. The objective landmark subsurface feature has a first spatial relationship to a destination region of interest of a mammalian body part, and the present-location landmark subsurface feature has a second spatial relationship to a distal end portion of a body-insertable device. In the alternative embodiment of the system, the proximity indicator circuit 4426 is configured to generate informational data indicative of an operational proximity of the distal end portion of the body-insertable device to the destination region of interest. The signal is indicative of operational proximity is at least partially based on the determined substantial correspondence between the present-location landmark subsurface feature and the objective landmark subsurface feature. In the alternative embodiment of the system, the communication circuit 4442 is configured to provide a notification that is at least partially based on the informational data to at least one of a human, computer, or system.

In an embodiment of the alternative embodiment of the system 4422, the feature matching circuit 4424 is configured to determine a substantial correspondence between a present-location landmark subsurface feature of a mammalian body part and an objective landmark subsurface feature of the mammalian body part. The objective landmark subsurface feature has a first spatial relationship to a destination region of interest of a mammalian body part, and the present-location landmark subsurface feature has a second spatial relationship to a distal end portion of a body-insertable device deployed operationally proximate to the mammalian body part.

Figure 100:
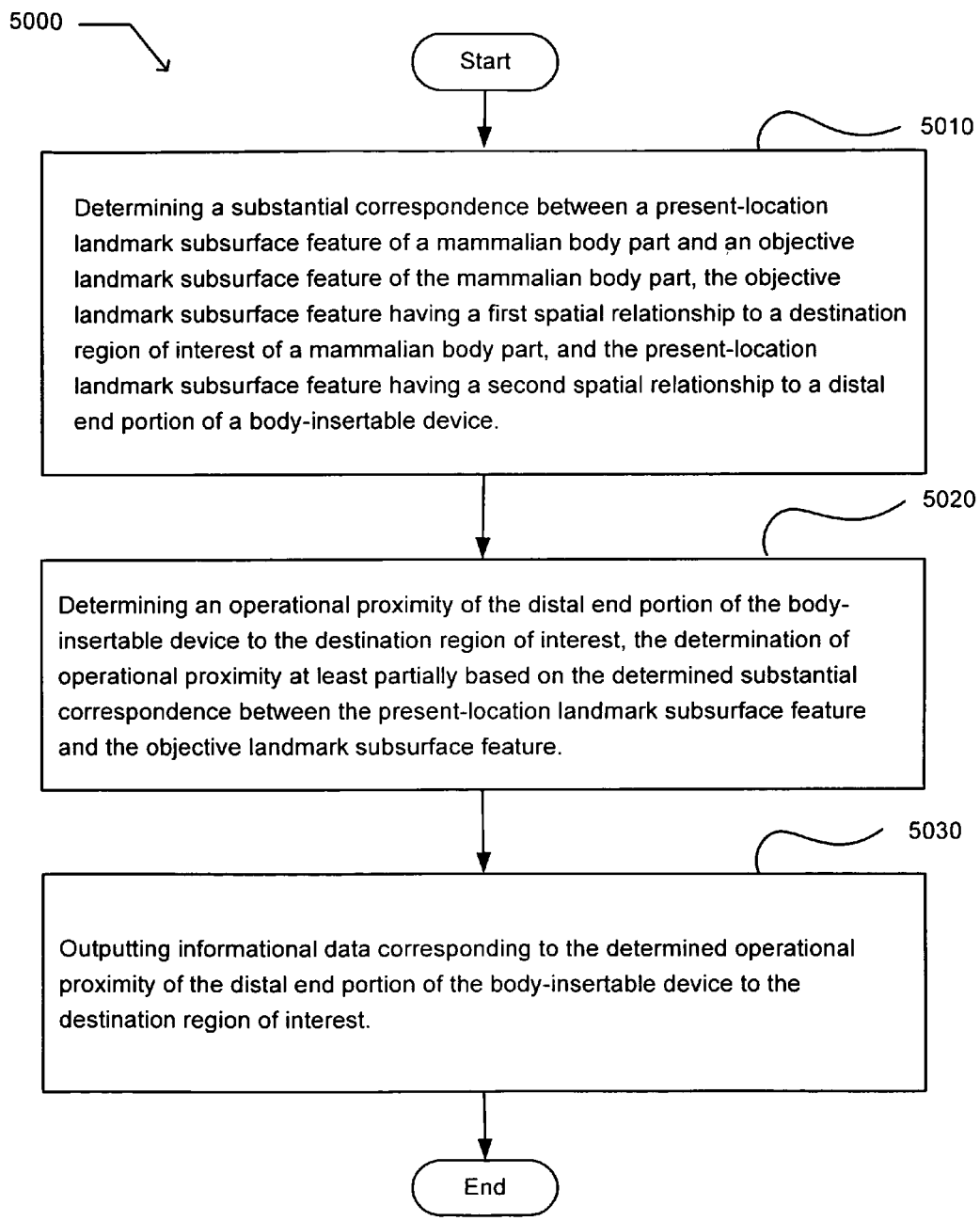
FIG. 100 illustrates an example operational flow.

FIG. 100 illustrates an example operational flow 5000 implemented in a computing device. The method includes a start operation. A matching operation 5010 includes determining a substantial correspondence between a present-location landmark subsurface feature of a mammalian body part and an objective landmark subsurface feature of the mammalian body part. The objective landmark subsurface feature has a first spatial relationship to a destination region of interest of a mammalian body part, and the present-location landmark subsurface feature has a second spatial relationship to a distal end portion of a body-insertable device. In an embodiment, the matching operation may be implemented using the feature matching circuit 4424 described in conjunction with FIG. 91. A proximity operation 5020 includes determining an operational proximity of the distal end portion of the body-insertable device to the destination region of interest. The determination of operational proximity is at least partially based on the determined substantial correspondence between the present-location landmark subsurface feature and the objective landmark subsurface feature. In an embodiment, the proximity operation may be implemented using the proximity indicator circuit 4426 described in conjunction with FIG. 91. A communication operation 5030 includes outputting informational data corresponding to the determined operational proximity of the distal end portion of the body-insertable device to the destination region of interest. In an embodiment, the communication operation may be implemented using the communications circuit 4442 described in conjunction with FIG. 91. The operational flow includes an end operation.

In an embodiment, the mammalian body part includes a cavity or lumen of a mammalian body part. In an embodiment, the mammalian body part includes a surface of a cavity or lumen of a mammalian body part.

Figure 101:
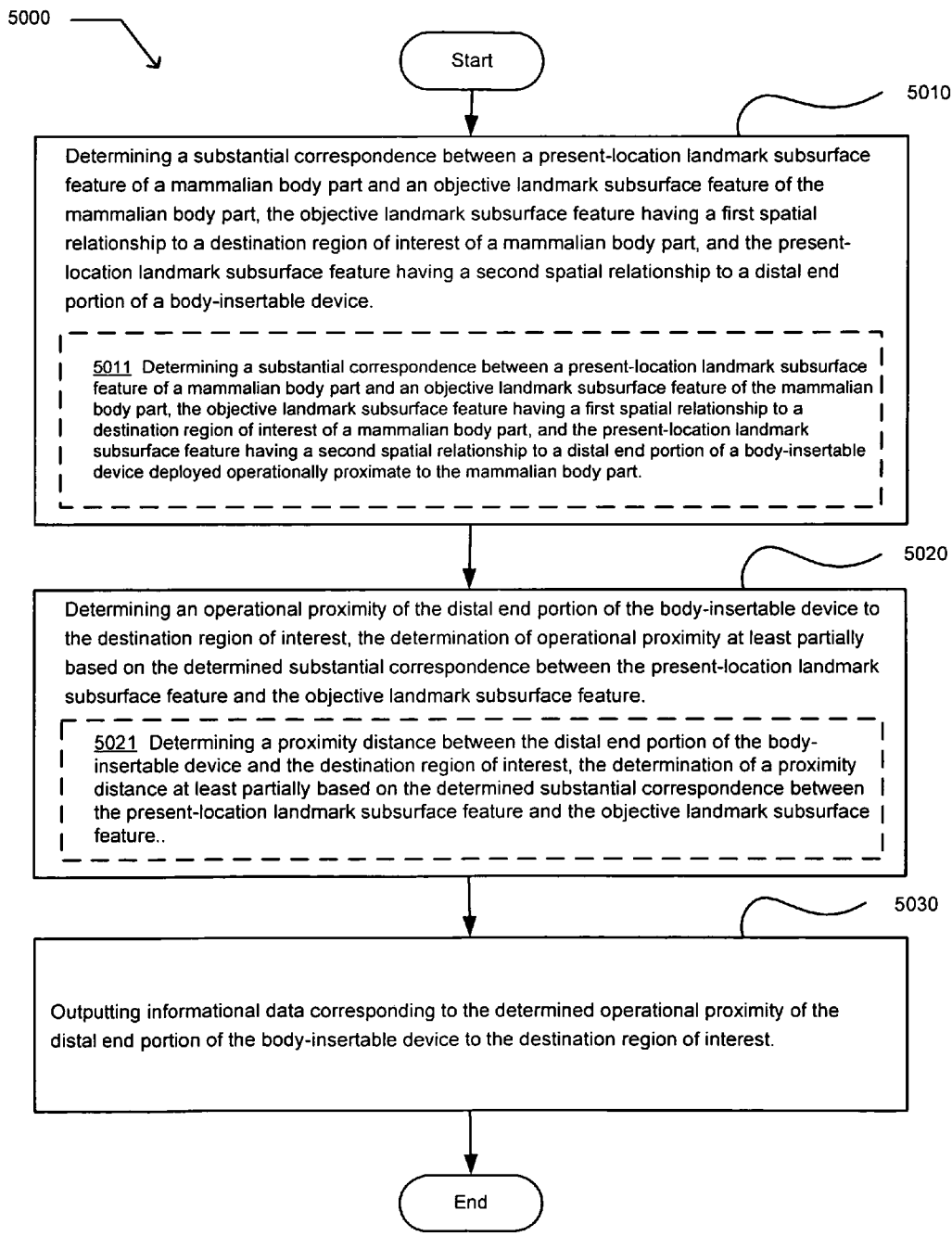
FIG. 101 illustrates an alternative embodiment of the operational flow 5000 of FIG. 100.

FIG. 101 illustrates an alternative embodiment of the operational flow 5000 of FIG. 100. In an embodiment, the matching operation 5010 may include at least one additional embodiment, such as the operation 5011. The operation 5011 includes determining a substantial correspondence between a present-location landmark subsurface feature of a mammalian body part and an objective landmark subsurface feature of the mammalian body part. The objective landmark subsurface feature has a first spatial relationship to a destination region of interest of a mammalian body part, and the present-location landmark subsurface feature has a second spatial relationship to a distal end portion of a body-insertable device deployed operationally proximate to the mammalian body part. In an embodiment, the proximity operation 5020 may include at least one additional embodiment, such as the operation 5021. The operation 5021 includes a proximity distance between the distal end portion of the body-insertable device and the destination region of interest. The determination of a proximity distance is at least partially based on the determined substantial correspondence between the present-location landmark subsurface feature and the objective landmark subsurface feature.

Figure 102:
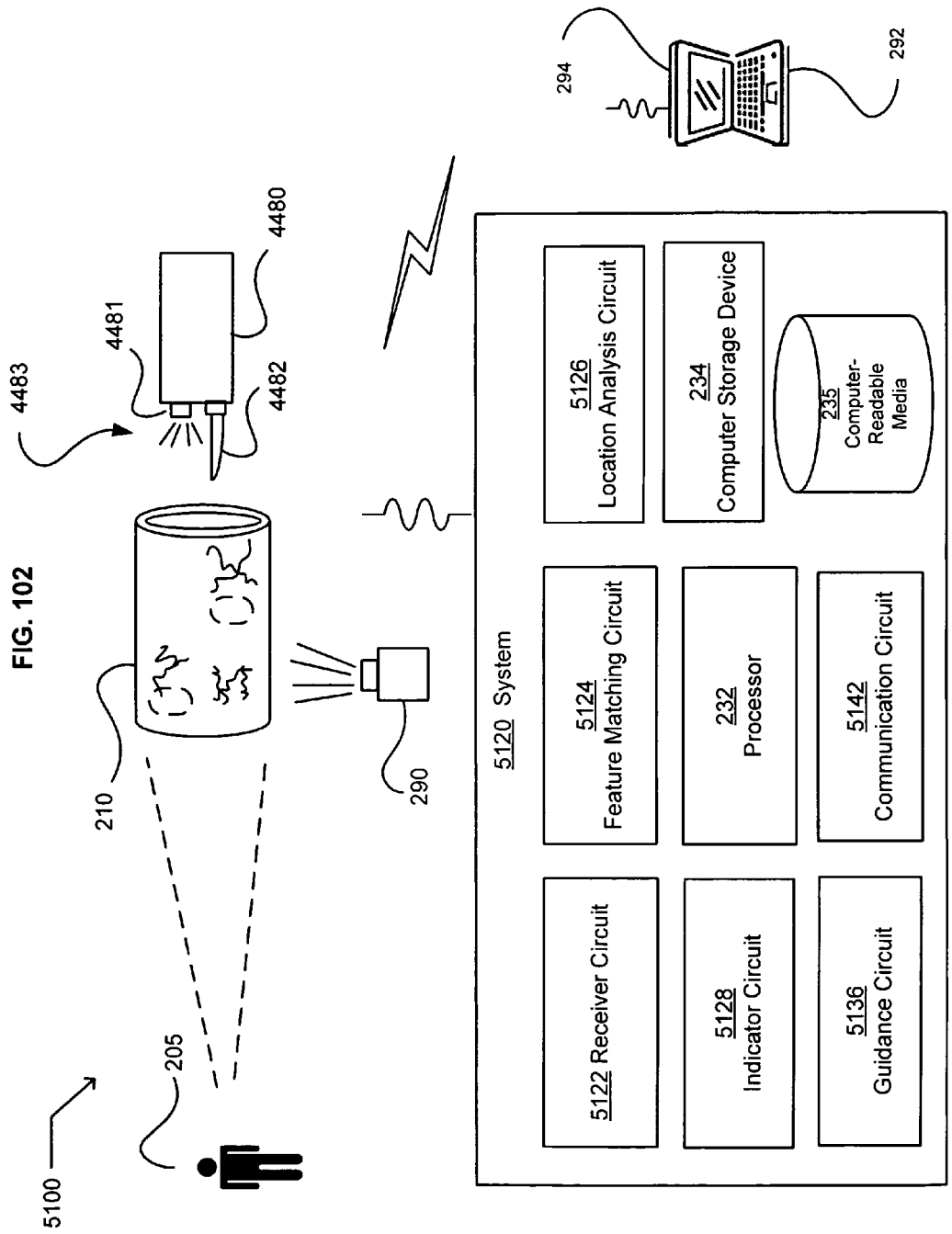
FIG. 102 illustrates an example environment.

FIG. 102 illustrates an example environment 5100. The environment includes the mammalian body part 210 of the mammal 205, the body-insertable device 4480, and a system 5120. The system 5120 includes a receiver circuit 5122 configured to receive a first reference image that includes an objective landmark subsurface feature of a mammalian body part. The objective landmark subsurface feature has a first spatial relationship to a destination region of interest of the mammalian body part. The receiver circuit is also configured to receive a second reference image that includes a present-location landmark subsurface feature of the mammalian body part. The present-location landmark subsurface feature has a second spatial relationship to a distal end portion of a body-insertable device deployed operationally proximate to the mammalian body part.

The system 5120 includes a feature matching circuit 5124 configured to determine a substantial correspondence between the objective landmark subsurface feature and a first atlas subsurface feature included in a subsurface feature atlas of the mammalian body part. In an embodiment, the subsurface feature atlas may have been prepared in a manner described in this document. In an embodiment, the subsurface feature atlas may have been prepared for an individual patient whose mammalian body part 210 is the subject of a procedure implemented in the environments 5100 and 5200. In an embodiment, the subsurface feature atlas may have been generally prepared for a mammal whose mammalian body part 210 is the subject of a procedure implemented in the environments 5100 and 5200. In an embodiment, the subsurface feature atlas may be a generally published atlas of the body part. In an embodiment, the subsurface feature atlas may be in electronic form and locally available, or may be accessed via a network. The feature matching circuit 5124 is also configured to determine a substantial correspondence between the present-location landmark subsurface feature and a second atlas subsurface feature included in the subsurface feature atlas of the mammalian body part. The subsurface feature atlas includes at least two registered subsurface features of the mammalian body part. The subsurface feature atlas includes the first atlas subsurface feature and the second atlas subsurface feature. The registration of the subsurface feature atlas includes an indication of a third spatial relationship between the first atlas subsurface feature and the second atlas subsurface feature.

The system 5120 includes a location analysis circuit 5126 configured to determine a fourth spatial relationship between the destination region of interest and the distal end portion of the body-insertable device deployed operationally proximate to the mammalian body part. The determined fourth spatial relationship is at least partially based on the third spatial relationship. For example, in an embodiment, if the first atlas subsurface feature and the second atlas subsurface feature are substantially the same, then the fourth spatial relationship distance is expected to be minimal and the body-insertable device is operationally proximate. For example, in an embodiment, if the first atlas subsurface feature and the second atlas subsurface feature are not substantially the same, then the fourth spatial relationship distance is likely more than minimal and the body-insertable device is not operationally proximate to the region of interest. The system includes an indicator circuit 5128 configured to generate informational data indicative of the determined fourth spatial relationship between the destination region of interest and the distal end portion of the body-insertable device. The informational data is at least partially based on the fourth spatial relationship between the destination region of interest and the distal end portion of the body-insertable device. The system 5120 includes the computer-readable media 235 configured to maintain the informational data.

Figure 103:
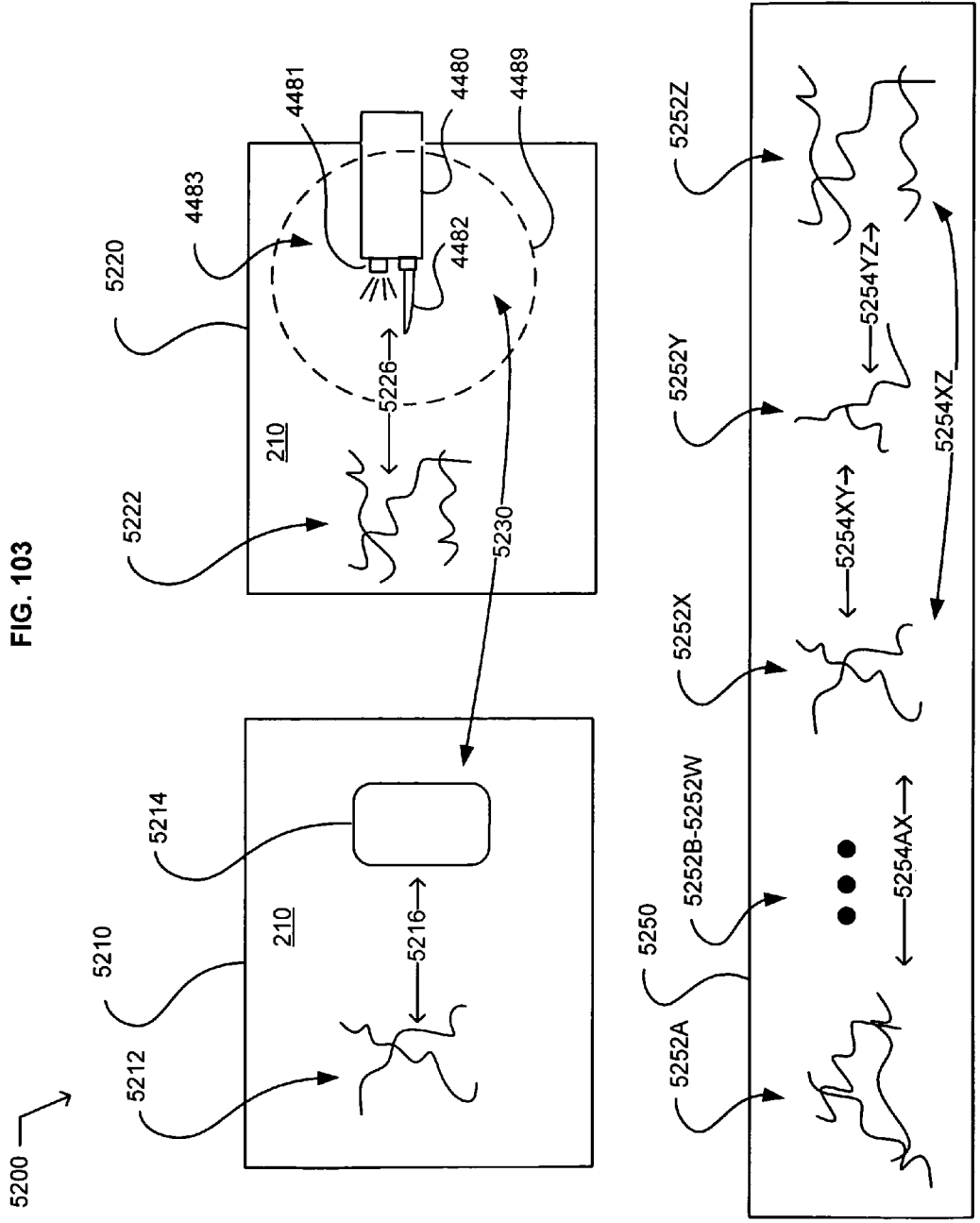
FIG. 103 illustrates an environment in which the system of FIG. 102 may be used to guide the body-insertable device into an operational proximity to a region of interest.

An example of an operation of the system 5120 may be illustrated using FIG. 103. FIG. 103 illustrates an environment 5200 in which the system 5120 may be used to guide the body-insertable device 4480 into an operational proximity to a region of interest 5214. FIG. 103 illustrates an embodiment of a subsurface feature atlas 5250 including registered atlas subsurface features A through Z, illustrated as atlas subsurface feature 5252A, and atlas subsurface features 5252X through 5252Z. The subsurface feature atlas also indicates the registration of the atlas subsurface features. The registration is indicated by the respective spatial relationships illustrated between the at least two atlas subsurface features. For example, the subsurface feature atlas illustrates a spatial relationship between an atlas subsurface feature 5252X and the atlas subsurface feature 5252Z as spatial relationship 5254XZ. In this example, the atlas subsurface feature 5252X may be described as a first atlas subsurface feature and the atlas subsurface feature 5252Z may be described as a second atlas subsurface feature, and the spatial relationship 5254XZ between them may be described as a third spatial relationship.

For example, in operation, the receiver circuit 5122 receives a first reference image 5210 that includes an objective landmark subsurface feature 5212 of a mammalian body part 210. The objective landmark subsurface feature has a first spatial relationship 5216 to a destination region of interest 5214 of the mammalian body part. The receiver circuit receives a second reference image 5220 that includes a present-location landmark subsurface feature 5222 of the mammalian body part. The present-location landmark subsurface feature has a second spatial relationship 5226 to the distal end portion 4483 of a body-insertable device 4480 deployed operationally proximate 4489 to the mammalian body part.

Continuing with the example, the feature matching circuit 5124 determines a substantial correspondence between the objective landmark subsurface feature 5212 and the first atlas subsurface feature 5252X included in the subsurface feature atlas 5250 of the mammalian body part 210. The feature matching circuit also determines a substantial correspondence between the present-location landmark subsurface feature 5222 and the second atlas subsurface feature 5252Z included in the subsurface feature atlas of the mammalian body part. The location analysis circuit 5126 determines a fourth spatial relationship 5230 between the destination region of interest 5214 and the distal end portion 4483 of the body-insertable device 4480 deployed operationally proximate 4489 to the mammalian body part 210. The determined fourth spatial relationship is at least partially based on the third spatial relationship 5254XZ between the first atlas subsurface feature 5252X and the second atlas subsurface feature 5252Z as indicated by the subsurface feature atlas. The indicator circuit 5128 generates informational data indicative of the determined fourth spatial relationship between the destination region of interest and the distal end portion of the body-insertable device. The informational data is at least partially based on the fourth spatial relationship between the destination region of interest and the distal end portion of the body-insertable device. The computer-readable media 235 maintains the informational data.

In an embodiment of the system 5120, first digital image includes a reference landmark subsurface feature of a mammalian body part. The reference landmark subsurface feature has a first spatial relationship to a region of interest of the mammalian body part. The reference landmark subsurface feature is distinguishable from other landmark subsurface features of the mammalian body part.

In an embodiment, the first digital image includes a reference landmark subsurface feature of a mammalian body part. The reference landmark subsurface feature has an indicated, determinable, estimable, or inferable first spatial relationship to a region of interest of the mammalian body part.

In an embodiment, the first reference image includes an objective landmark subsurface feature of a mammalian body part. The objective landmark subsurface feature has a first spatial relationship to a destination region of interest of the mammalian body part and is distinguishable over other landmark subsurface features of the mammalian body part. In an embodiment, the objective landmark subsurface feature has an indicated, determinable, estimable, or inferable first spatial relationship to a destination region of interest of the mammalian body part.

In an embodiment, the first reference image includes an objective landmark subsurface feature of a mammalian body part. The objective landmark subsurface feature has a first spatial relationship to a destination region of interest of a cavity or lumen of the mammalian body part. In an embodiment, the objective landmark subsurface feature has a first spatial relationship to a destination region of interest of a surface of a cavity or lumen of the mammalian body part.

In an embodiment, the first reference image was acquired by an ex vivo device, such as the ex vivo device 290, and includes an objective landmark subsurface feature of a mammalian body part. The objective landmark subsurface feature has a first spatial relationship to a destination region of interest of the mammalian body part. In an embodiment, first reference image was acquired by the body-insertable device 4480 and includes an objective landmark subsurface feature of a mammalian body part.

In an embodiment, the first reference that includes an objective landmark subsurface feature of a mammalian body part. The objective landmark subsurface feature has a first spatial relationship to a human-user selected destination region of interest of the mammalian body part. In an embodiment, the objective landmark subsurface feature has a first spatial relationship to a machine-selected destination region of interest of the mammalian body part.

In an embodiment, the second reference image includes a present-location landmark subsurface feature of the mammalian body part. The present-location landmark subsurface feature has a second spatial relationship to an effector carried by a distal end portion of a body-insertable device and deployed operationally proximate to the mammalian body part. In an embodiment, the present-location landmark subsurface feature has a second spatial relationship to an operative and movable distal end portion of a body-insertable device deployed operationally proximate to the mammalian body part. In an embodiment, the present-location landmark subsurface feature has a second spatial relationship to a distal end portion of a body-insertable device deployed in a cavity or lumen of the mammalian body part.

In an embodiment, the second reference image was acquired by a body-insertable device and includes a present-location landmark subsurface feature of the mammalian body part. The present-location landmark subsurface feature has a second spatial relationship to a distal end portion of the body-insertable device deployed operationally proximate to the mammalian body part. In an embodiment, the second reference image was acquired by an ex vivo device and includes a present-location landmark subsurface feature of the mammalian body part.

In an embodiment, the feature matching circuit 5124 is configured to determine at least one of a substantial structural, orientation, pattern, or physical characteristic correspondence between the objective landmark subsurface feature and a first atlas subsurface feature included in a subsurface feature atlas of the mammalian body part. The feature matching circuit is also configured to determine at least one of a substantial structural, orientation, pattern, or physical characteristic correspondence between the present-location landmark subsurface feature and a second atlas subsurface feature included in the subsurface feature atlas of the mammalian body part. In an embodiment, the feature matching circuit is configured to determine substantial match between the objective landmark subsurface feature and a first atlas subsurface feature included in a subsurface feature atlas of the mammalian body part. The feature matching circuit is also configured to determine a substantial match between the present-location landmark subsurface feature and a second atlas subsurface feature included in the subsurface feature atlas of the mammalian body part.

In an embodiment, the location analysis circuit 5216 is configured to determine a fourth spatial relationship between the destination region of interest and the distal end portion of the body-insertable device deployed operationally proximate to the mammalian body part. The fourth spatial relationship is determined at least partially in response to: (i) a fifth spatial relationship between the objective landmark subsurface feature and the present-location landmark subsurface feature (this determination is at least partially based on a spatial relationship between the first atlas subsurface feature and the second atlas subsurface feature as indicated by the subsurface feature atlas); (ii) the first spatial relationship between the destination region of interest and the objective landmark subsurface feature; and (iii) the second spatial relationship between the distal end portion of the body-insertable device and the present-location landmark subsurface feature. In an embodiment, the location analysis circuit is configured to determine a distance from the distal end portion of the body-insertable device to the destination region of interest. The distance determination is at least partially based on the third spatial relationship.

In an embodiment, the indicator circuit 5128 is configured to generate informational data indicative of an operational proximity of the distal end portion of the body-insertable device to the destination region of interest. The informational data is at least partially based on the determined fourth spatial relationship. In an embodiment, the indicator is configured to generate informational data indicative of a distance of less than four centimeters between the distal end portion of the body-insertable device and the destination region of interest. In an embodiment, the indicator is configured to generate informational data indicative of a distance of less than two centimeters between the distal end portion of the body-insertable device and the destination region of interest. In an embodiment, the indicator is configured to generate informational data indicative of a distance of less than one hundred millimeters between the distal end portion of the body-insertable device and the destination region of interest. In an embodiment, the indicator is configured to generate informational data indicative of a distance from the distal end portion of the body-insertable device to the destination region of interest. The informational data is at least partially based on the determined fourth spatial relationship, and the indicated distance is within a user-selected range. For example, the user-selected range may be within 2 cm.

In an embodiment, the system 5120 may include a guidance circuit 5136 configured to determine a movement of the distal end portion of the body-insertable device to produce a particular change in the spatial relationship between the distal end portion of the body-insertable device and the destination region of interest. The movement is at least partially based on the informational data indicative of the determined fourth spatial relationship between the destination region of interest and the distal end portion of the body-insertable device.

In an embodiment, the guidance circuit 5136 is configured to determine a movement of the distal end portion of the body-insertable device to produce a user-selected change of the spatial relationship between the distal end portion of the body-insertable device and the destination region of interest. The movement is at least partially based on the informational data indicative of the determined fourth spatial relationship between the destination region of interest and the distal end portion of the body-insertable device. For example, a selected change may include a decrease of the spatial relationship between the portion of the body-insertable device and the region of interest. For example, a selected change may include an increase of the spatial relationship between the portion of the body-insertable device and the region of interest. For example, a selected change may include an axial rotation of the distal end portion of the body-insertable device into an alignment with the region of interest. In an embodiment, the guidance circuit is configured to select a movement of the distal end portion of the body-insertable device likely to produce a machine-selected change of the spatial relationship between the distal end portion of the body-insertable device and the destination region of interest. In an embodiment, the guidance circuit is configured to determine a rotational, radial, or axial movement of the distal end portion of the body-insertable device to produce a particular change in the spatial relationship between the distal end portion of the body-insertable device and the destination region of interest. In an embodiment, the guidance circuit is configured to determine a movement of the distal end portion of the body-insertable device to decrease a separation between the spatial relationship between the distal end portion of the body-insertable device and the destination region of interest. In an embodiment, the guidance circuit is configured to determine a movement of the distal end portion of the body-insertable device to increase a separation between the spatial relationship between the distal end portion of the body-insertable device and the destination region of interest. In an embodiment, the indicator circuit 5128 is configured to generate informational data indicative of the determined movement of the distal end portion of the body-insertable device to produce a particular change in the spatial relationship between the distal end portion of the body-insertable device and the destination region of interest. In an embodiment, the indicator circuit 5128 is configured to generate informational data indicative of the determined movement of the distal end portion of the body-insertable device to produce a particular change in the spatial relationship between the distal end portion of the body-insertable device and the destination region of interest. The informational data is useable in facilitating an action performed by the body-insertable device relative to the destination region of interest.

In an embodiment, the system 5120 includes a communication circuit 5142 configured to output the informational data. In an embodiment, the communication circuit is configured to provide a notification that is at least partially based on the informational data to at least one of a human, computer, or system. In an embodiment, the system includes a communication device, illustrated as the computing device 292, configured to display on the screen 294 a human-perceivable depiction of the informational data.

Figure 104:
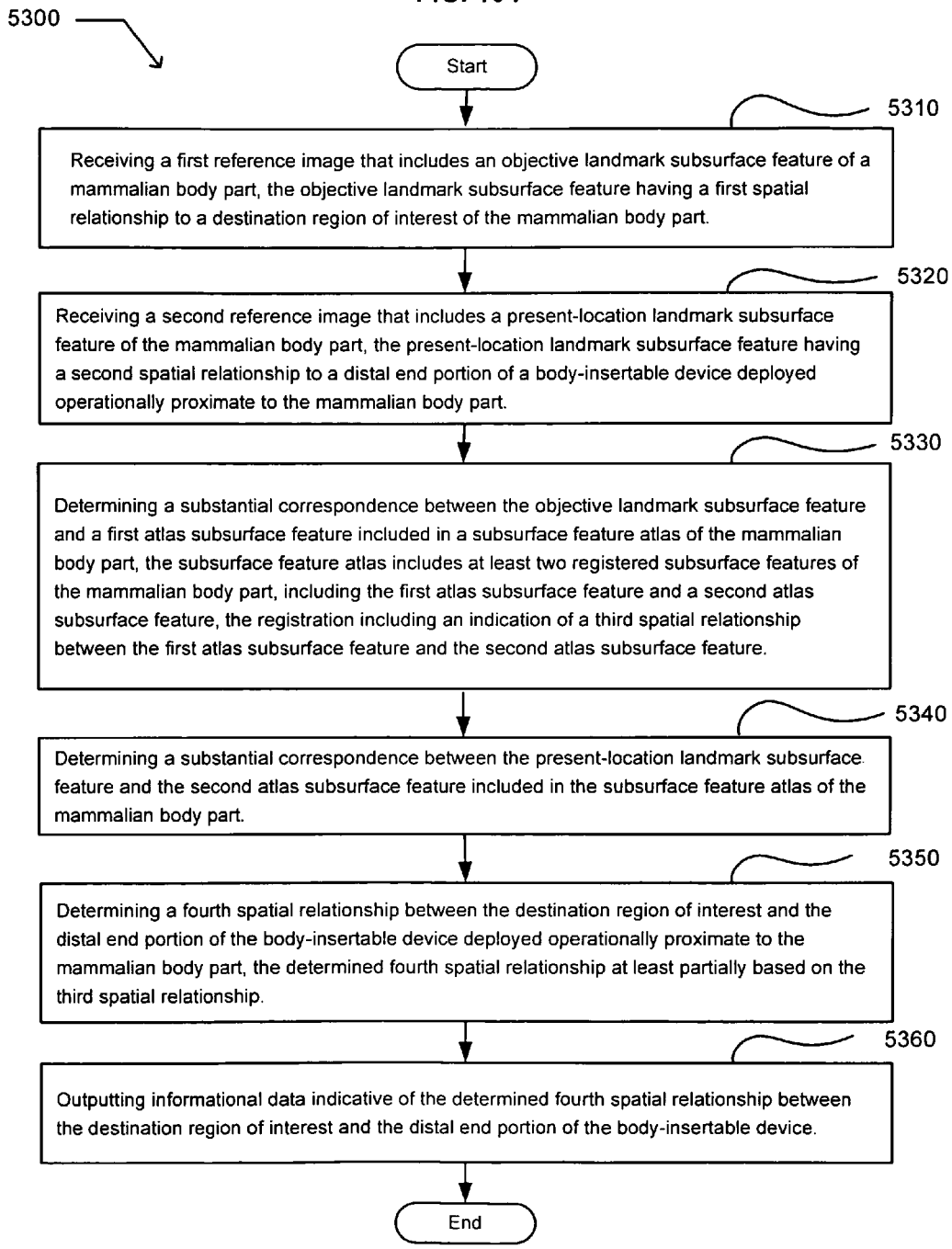
FIG. 104 illustrates an example operational flow.

FIG. 104 illustrates an example operational flow 5300 implemented using a computing device. The operational flow includes a start operation. The operational flow includes a first reception operation 5310. The first reception operation includes a first reference image that includes an objective landmark subsurface feature of a mammalian body part. The objective landmark subsurface feature has a first spatial relationship to a destination region of interest of the mammalian body part. A second reception operation 5320 includes receiving a second reference image that includes a present-location landmark subsurface feature of the mammalian body part. The present-location landmark subsurface feature has a second spatial relationship to a distal end portion of a body-insertable device deployed operationally proximate to the mammalian body part. In an embodiment, the first reception operation or the second reception operation may be implemented using the receiver circuit 5122 described in conjunction with FIG. 102. A first matching operation 5330 includes determining a substantial correspondence between the objective landmark subsurface feature and a first atlas subsurface feature included in a subsurface feature atlas of the mammalian body part. The subsurface feature atlas includes at least two registered subsurface features of the mammalian body part. The at least two registered subsurface features includes the first atlas subsurface feature and a second atlas subsurface feature. The registration includes an indication of a third spatial relationship between the first atlas subsurface feature and the second atlas subsurface feature. A second matching operation 5340 includes determining a substantial correspondence between the present-location landmark subsurface feature and the second atlas subsurface feature included in the subsurface feature atlas of the mammalian body part. In an embodiment, the first matching operation or the second matching operation may be implemented using the feature matching circuit 5124 described in conjunction with FIG. 102. A proximity operation 5350 includes determining a fourth spatial relationship between the destination region of interest and the distal end portion of the body-insertable device deployed operationally proximate to the mammalian body part. The determined fourth spatial relationship is at least partially based on the third spatial relationship. In an embodiment, the proximity operation may be implemented using the location analysis circuit 5126 described in conjunction with FIG. 102. A communication operation 5360 includes outputting informational data indicative of the determined fourth spatial relationship between the destination region of interest and the distal end portion of the body-insertable device. In an embodiment, the communication operation may be implemented using the communication circuit 5142 described in conjunction with FIG. 102. The operational flow includes an end operation.

Figure 105:
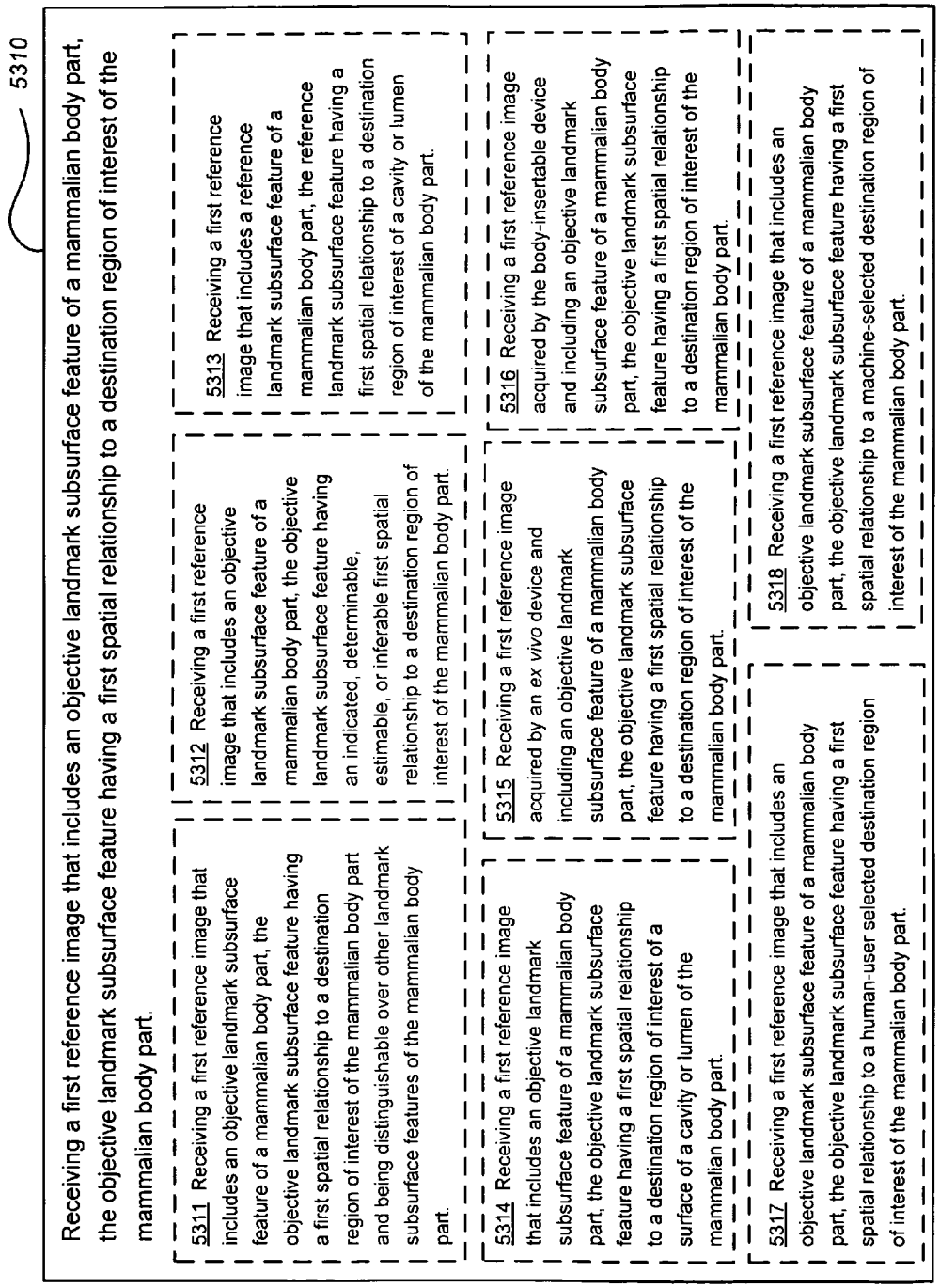
FIG. 105 illustrates an alternative embodiment of the first reception operation 5310 of FIG. 104.

FIG. 105 illustrates an alternative embodiment of the first reception operation 5310 of the operational flow 5300 of FIG. 104. The first reception operation may include at least one alternative embodiment. The at least one alternative embodiments may include an operation 5311, an operation 5312, an operation 5313, an operation 5314, an operation 5315, an operation 5316, an operation 5317, or an operation 5318. The operation 5311 includes receiving a first reference image that includes an objective landmark subsurface feature of a mammalian body part. The objective landmark subsurface feature has a first spatial relationship to a destination region of interest of the mammalian body part and is distinguishable over other landmark subsurface features of the mammalian body part. The operation 5312 includes a first reference image that includes an objective landmark subsurface feature of a mammalian body part. The objective landmark subsurface feature has an indicated, determinable, estimable, or inferable first spatial relationship to a destination region of interest of the mammalian body part. The operation 5313 includes receiving a first reference image that includes a reference landmark subsurface feature of a mammalian body part. The reference landmark subsurface feature has a first spatial relationship to a destination region of interest of a cavity or lumen of the mammalian body part. The operation 5314 includes receiving a first reference image that includes an objective landmark subsurface feature of a mammalian body part. The objective landmark subsurface feature has a first spatial relationship to a destination region of interest of a surface of a cavity or lumen of the mammalian body part. The operation 5315 includes receiving a first reference image acquired by an ex vivo device and including an objective landmark subsurface feature of a mammalian body part. The objective landmark subsurface feature has a first spatial relationship to a destination region of interest of the mammalian body part. The operation 5316 includes receiving a first reference image acquired by the body-insertable device and includes an objective landmark subsurface feature of a mammalian body part. The objective landmark subsurface feature has a first spatial relationship to a destination region of interest of the mammalian body part. The operation 5317 includes receiving a first reference image that includes an objective landmark subsurface feature of a mammalian body part. The objective landmark subsurface feature has a first spatial relationship to a human-user selected destination region of interest of the mammalian body part. The operation 5318 includes receiving a first reference image that includes an objective landmark subsurface feature of a mammalian body part. The objective landmark subsurface feature has a first spatial relationship to a machine-selected destination region of interest of the mammalian body part.

Figure 106:
FIG. 106 illustrates an alternative embodiment of the operational flow of FIG. 104.

FIG. 106 illustrates an alternative embodiment of the second reception operation 5320 of the operational flow 5300 of FIG. 104. The second reception operation may include at least one alternative embodiment. The at least one alternative embodiments may include an operation 5321, an operation 5322, an operation 5323, an operation 5324, or an operation 5325. The operation 5321 includes receiving a second reference image that includes a present-location landmark subsurface feature of the mammalian body part. The present-location landmark subsurface feature has a second spatial relationship to an effector carried by a distal end portion of a body-insertable device and deployed operationally proximate to the mammalian body part. The operation 5322 includes receiving a second reference image that includes a present-location landmark subsurface feature of the mammalian body part. The present-location landmark subsurface feature has a second spatial relationship to an operative and movable distal end portion of a body-insertable device deployed operationally proximate to the mammalian body part. The operation 5323 includes receiving a second reference image that includes a present-location landmark subsurface feature of the mammalian body part. The present-location landmark subsurface feature has a second spatial relationship to a distal end portion of a body-insertable device deployed in a cavity or lumen of the mammalian body part. The operation 5324 includes receiving a second reference image acquired by a body-insertable device and includes a present-location landmark subsurface feature of the mammalian body part. The present-location landmark subsurface feature has a second spatial relationship to a distal end portion of the body-insertable device deployed operationally proximate to the mammalian body part. The operation 5325 includes receiving a second reference image acquired by an ex vivo device and includes a present-location landmark subsurface feature of the mammalian body part. The present-location landmark subsurface feature has a second spatial relationship to a distal end portion of the body-insertable device deployed operationally proximate to the mammalian body part.

Figure 107:
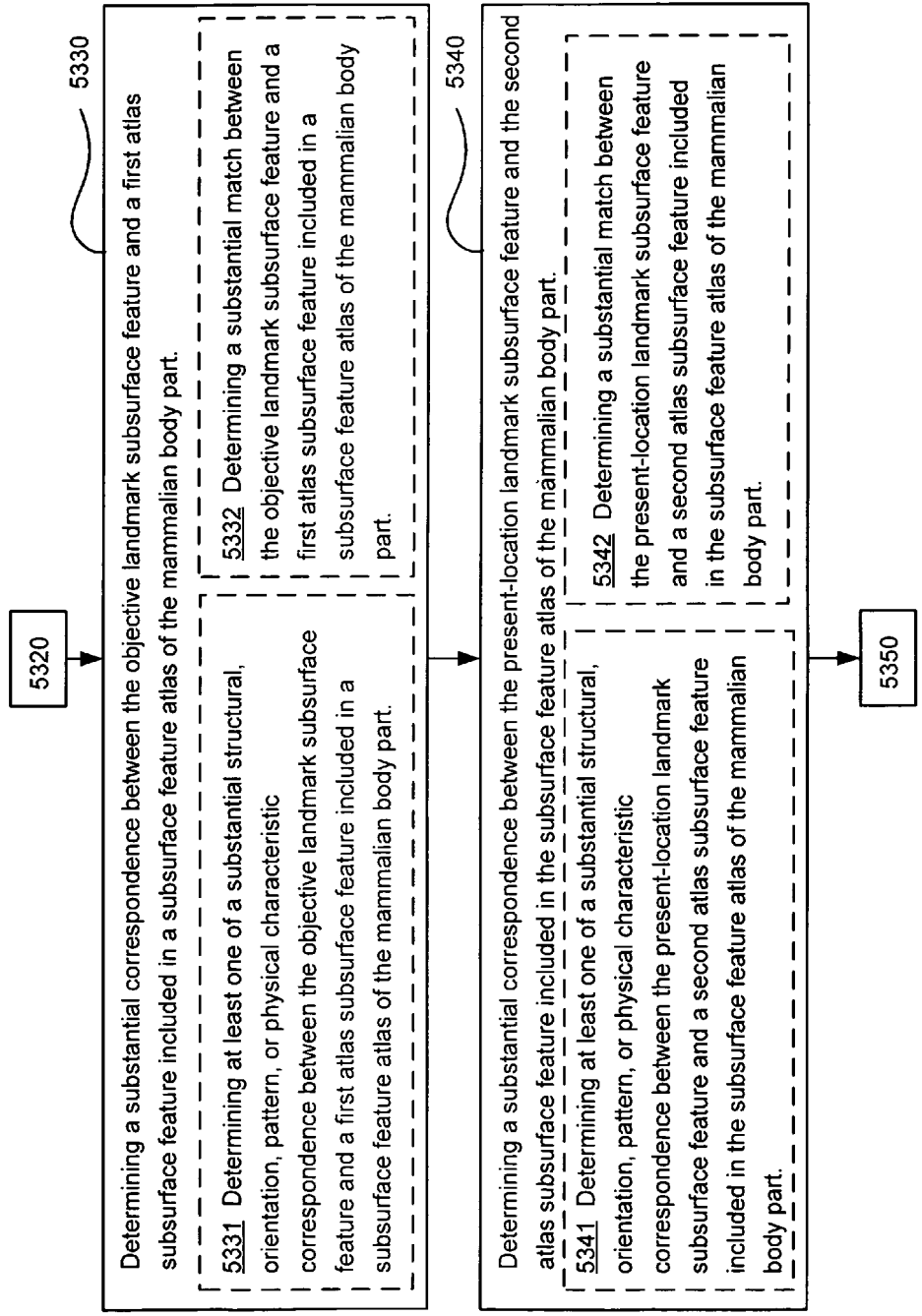
FIG. 107 illustrates an alternative embodiment of the operational flow 5300 of FIG. 104.

FIG. 107 illustrates an alternative embodiment of the operational flow 5300 of FIG. 104. In an embodiment, the first matching operation 5330 may include at least one alternative embodiment. The at least one alternative embodiments may include an operation 5331 or an operation 5332. The operation 5331 includes determining at least one of a substantial structural, orientation, pattern, or physical characteristic correspondence between the objective landmark subsurface feature and a first atlas subsurface feature included in a subsurface feature atlas of the mammalian body part. The operation 5332 includes determining a substantial match between the objective landmark subsurface feature and a first atlas subsurface feature included in a subsurface feature atlas of the mammalian body part. In an embodiment, the second matching operation 5340 may include at least one alternative embodiment. The at least one alternative embodiments may include an operation 5341 or 5342. The operation 5341 includes determining at least one of a substantial structural, orientation, pattern, or physical characteristic correspondence between the present-location landmark subsurface feature and a second atlas subsurface feature included in the subsurface feature atlas of the mammalian body part. The operation 5342 includes determining a substantial match between the present-location landmark subsurface feature and a second atlas subsurface feature included in the subsurface feature atlas of the mammalian body part.

Figure 108:
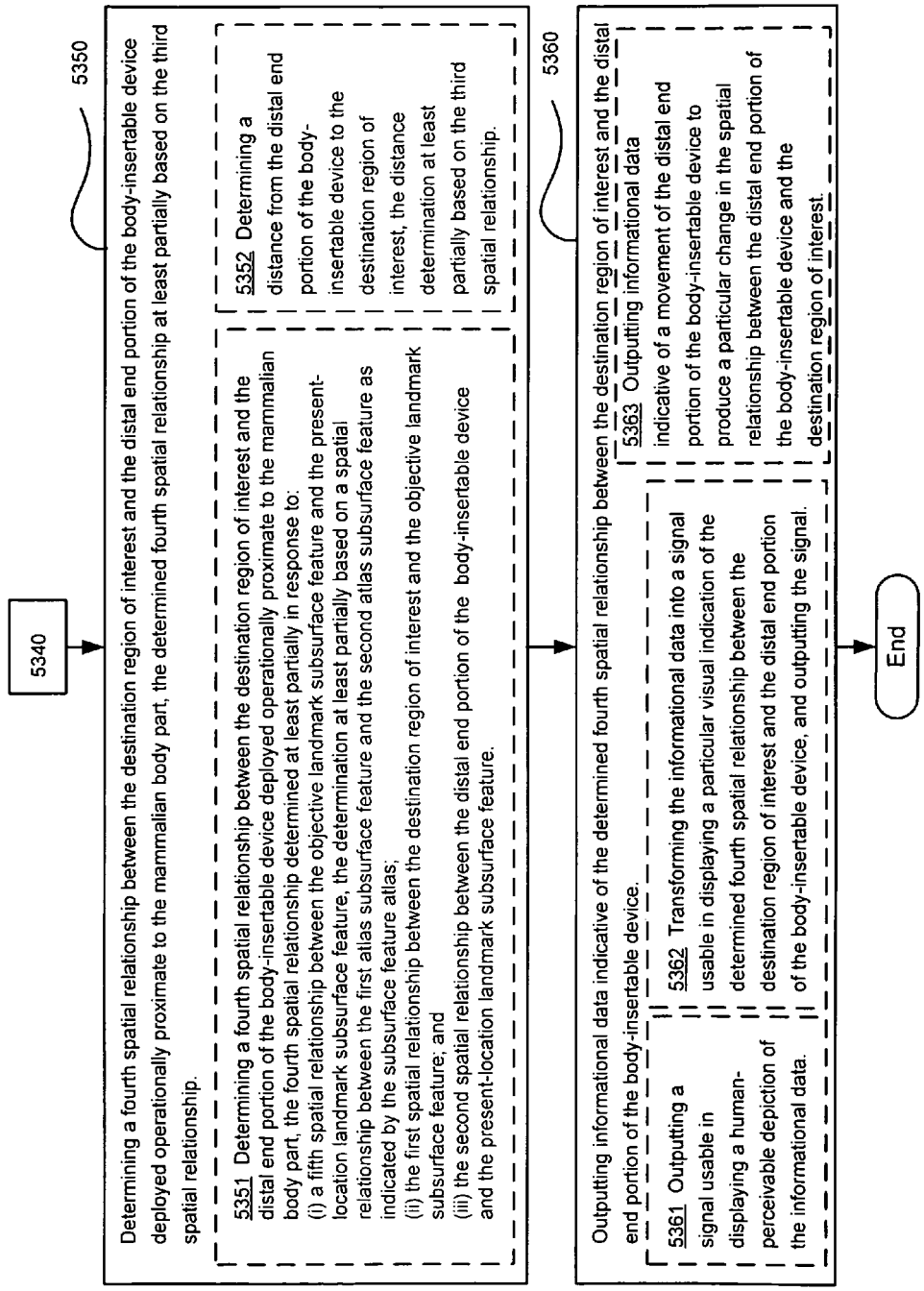
FIG. 108 illustrates an alternative embodiment of the operational flow 5300 of FIG. 104.

FIG. 108 illustrates an alternative embodiment of the operational flow 5300 of FIG. 104. In an embodiment, the proximity operation 5350 may include at least one additional embodiment. The at least one additional operation may include an operation 5351 or an operation 5352. The operation 5351 includes determining a fourth spatial relationship between the destination region of interest and the distal end portion of the body-insertable device deployed operationally proximate to the mammalian body part. The fourth spatial relationship is determined at least partially in response to: (i) a fifth spatial relationship between the objective landmark subsurface feature and the present-location landmark subsurface feature, the determination is at least partially based on a spatial relationship between the first atlas subsurface feature and the second atlas subsurface feature as indicated by the subsurface feature atlas; (ii) the first spatial relationship between the destination region of interest and the objective landmark subsurface feature; and (iii) the second spatial relationship between the distal end portion of the body-insertable device and the present-location landmark subsurface feature. In an embodiment, the determining a fourth spatial relationship includes determining a distance, a rotation, or a direction between the destination region of interest and the distal end portion of the body-insertable device deployed operationally proximate to the mammalian body part. The operation 5352 includes determining a distance from the distal end portion of the body-insertable device to the destination region of interest. The distance determination is at least partially based on the third spatial relationship.

In an embodiment, the communication operation 5360 may include at least one additional embodiment. The at least one additional embodiment may include an operation 5361, an operation 5362, or an operation 5363. The operation 5361 includes outputting a signal usable in displaying a human-perceivable depiction of the informational data. The operation 5362 includes transforming the informational data into a signal usable in displaying a particular visual indication of the determined fourth spatial relationship between the destination region of interest and the distal end portion of the body-insertable device, and outputting the signal. The operation 5363 includes outputting informational data indicative of a movement of the distal end portion of the body-insertable device to produce a particular change in the spatial relationship between the distal end portion of the body-insertable device and the destination region of interest.

Figure 109:
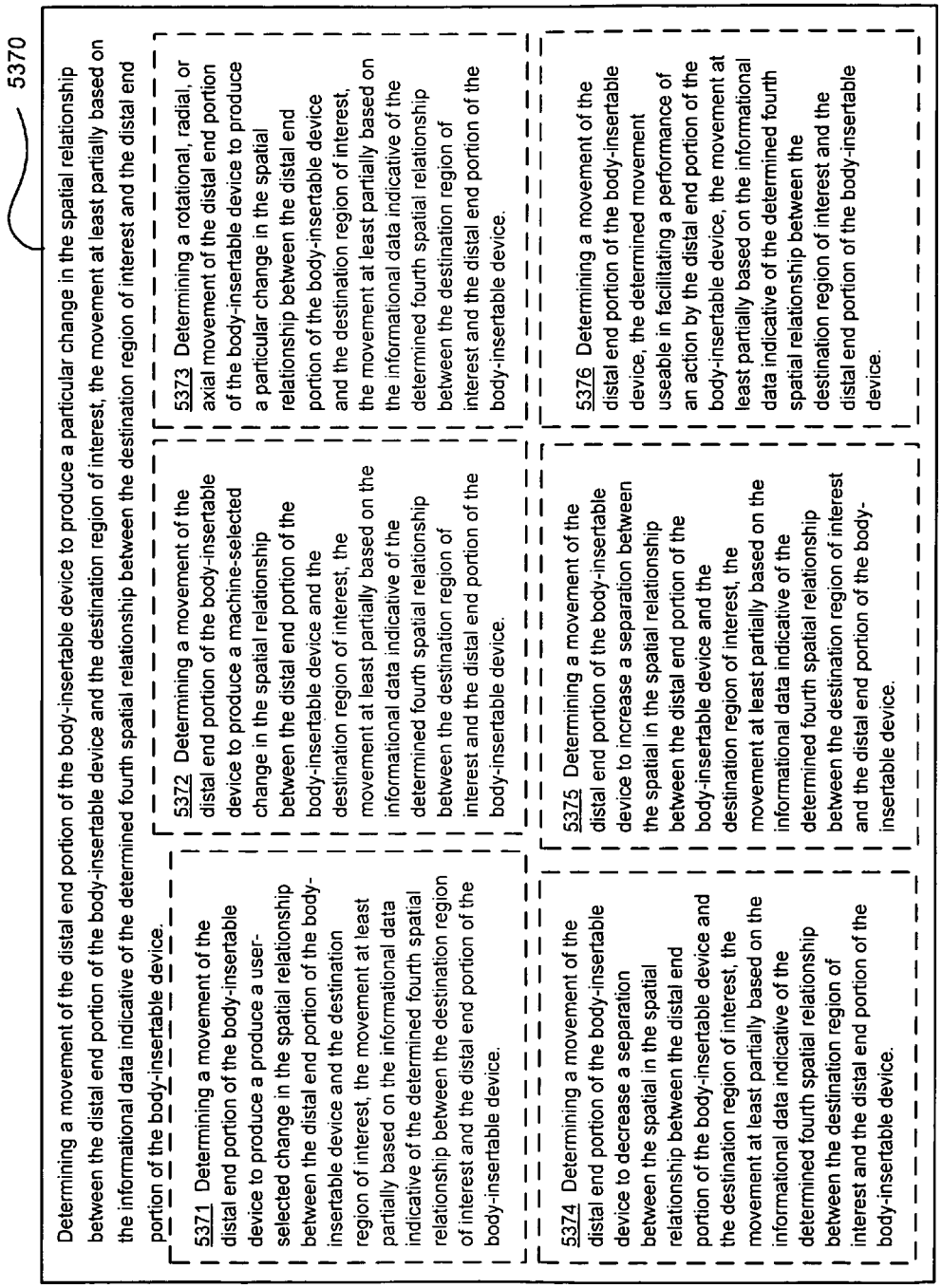
FIG. 109 illustrates an alternative embodiment of the operational flow 5300 of FIG. 104.

FIG. 109 illustrates an alternative embodiment of the operational flow 5300 of FIG. 104. In an embodiment, the operational flow may include a guidance operation 5370. The guidance operation includes determining a movement of the distal end portion of the body-insertable device to produce a particular change in the spatial relationship between the distal end portion of the body-insertable device and the destination region of interest. The movement is at least partially based on the informational data indicative of the determined fourth spatial relationship between the destination region of interest and the distal end portion of the body-insertable device. In an embodiment, the guidance operation may be implemented using the guidance circuit 5136 described in conjunction with FIG. 102.

In an embodiment, the guidance operation may include at least one additional embodiment. The at least one additional embodiment may include an operation 5371, an operation 5372, an operation 5373, an operation 5374, an operation 5375, or an operation 5376. The operation 5371 includes determining a movement of the distal end portion of the body-insertable device to produce a produce a user-selected change in the spatial relationship between the distal end portion of the body-insertable device and the destination region of interest. The determined movement is at least partially based on the informational data indicative of the determined fourth spatial relationship between the destination region of interest and the distal end portion of the body-insertable device. The operation 5372 includes determining a movement of the distal end portion of the body-insertable device to produce a machine-selected change in the spatial relationship between the distal end portion of the body-insertable device and the destination region of interest. The movement is determined at least partially based on the informational data indicative of the determined fourth spatial relationship between the destination region of interest and the distal end portion of the body-insertable device. In an embodiment, the operation 5373 includes determining a rotational, radial, or axial movement of the distal end portion of the body-insertable device to produce a particular change in the spatial relationship between the distal end portion of the body-insertable device and the destination region of interest. The movement is determined at least partially based on the informational data indicative of the determined fourth spatial relationship between the destination region of interest and the distal end portion of the body-insertable device. In an embodiment, the operation 5374 includes determining a movement of the portion of the body-insertable device operable to decrease a separation between the portion of the body-insertable device and the region of interest. The movement is determined at least partially based on the determined fourth spatial relationship between the reference landmark subsurface feature and present-location landmark subsurface feature. In an embodiment, the operation 5375 includes a movement of the distal end portion of the body-insertable device to increase a separation between the spatial in the spatial relationship between the distal end portion of the body-insertable device and the destination region of interest. The movement is determined at least partially based on the informational data indicative of the determined fourth spatial relationship between the destination region of interest and the distal end portion of the body-insertable device. In an embodiment, the operation 5376 includes determining a movement of the distal end portion of the body-insertable device, the determined movement useable in facilitating a performance of an action by the distal end portion of the body-insertable device. The movement is determined at least partially based on the informational data indicative of the determined fourth spatial relationship between the destination region of interest and the distal end portion of the body-insertable device.

Figure 110:
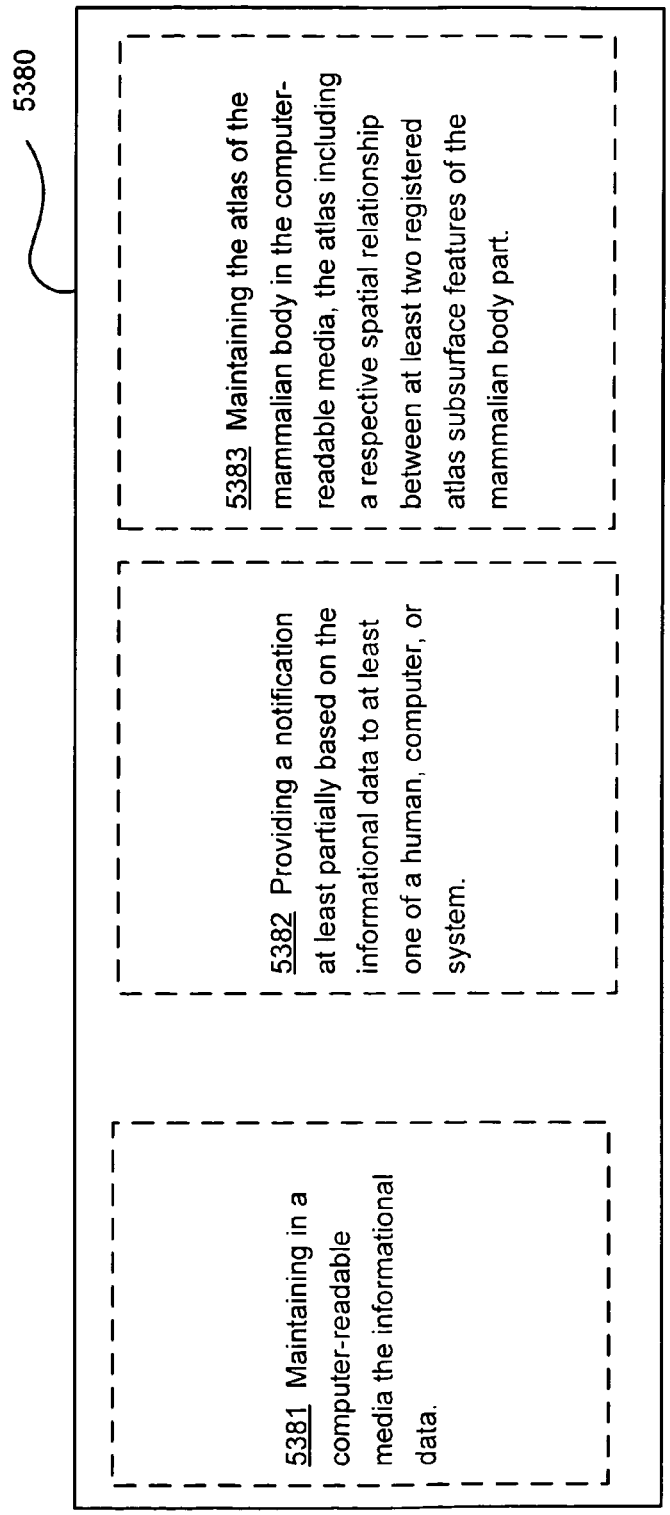
FIG. 110 illustrates an alternative embodiment of the operational flow 5300 of FIG. 104.

FIG. 110 illustrates an alternative embodiment of the operational flow 5300 of FIG. 104. In an embodiment, the operational flow may include at least one additional embodiment 5380. In an embodiment, the at least one additional embodiment may include an operation 5381, an operation 5382, or an operation 5383. The operation 5381 includes maintaining the informational data in a computer-readable media. The operation 5382 includes providing a notification that is at least partially based on the informational data to at least one of a human, computer, or system. The operation 5383 includes maintaining the atlas of the mammalian body in the computer-readable media. The atlas includes a respective spatial relationship between at least two registered atlas subsurface features of the mammalian body part. In an embodiment, the atlas may have been prepared prior to the capture of the first reference image or the second reference image. In an embodiment, the atlas may be a general atlas of the mammalian body part.

FIG. 111 illustrates an example computer program product 5400. The computer program product includes a computer-readable media 5410 bearing program instructions 5420. The program instructions, when executed by a processor of a computing device, cause the computing device to perform a process. The process includes receiving a first reference image that includes an objective landmark subsurface feature of a mammalian body part. The objective landmark subsurface feature has a first spatial relationship to a destination region of interest of the mammalian body part. The process includes receiving a second reference image that includes a present-location landmark subsurface feature of the mammalian body part. The present-location landmark subsurface feature has a second spatial relationship to a distal end portion of a body-insertable device deployed operationally proximate to the mammalian body part. The process includes determining a substantial correspondence between the objective landmark subsurface feature and a first atlas subsurface feature included in a subsurface feature atlas of the mammalian body part. The subsurface feature atlas includes at least two registered subsurface features of the mammalian body part, including the first atlas subsurface feature and a second atlas subsurface feature. The registration includes an indication of a third spatial relationship between the first atlas subsurface feature and the second atlas subsurface feature. The process includes determining a substantial correspondence between the present-location landmark subsurface feature and the second atlas subsurface feature included in the subsurface feature atlas of the mammalian body part. The process includes determining a fourth spatial relationship between the destination region of interest and the distal end portion of the body-insertable device deployed operationally proximate to the mammalian body part. The determined fourth spatial relationship is at least partially based on the third spatial relationship. The process includes outputting informational data indicative of the determined fourth spatial relationship between the destination region of interest and the distal end portion of the body-insertable device.

In an embodiment, the computer-readable media 5410 includes a tangible computer-readable media 5412. In an embodiment, the computer-readable media includes a communications medium 5414.

FIG. 112 illustrates an alternative embodiment of the computer program product 5400 of FIG. 111. In an embodiment, the process includes 5422 transforming the informational data into a signal usable in displaying a particular visual indication of the determined fourth spatial relationship between the destination region of interest and the distal end portion of the body-insertable device, and outputting the data. In an embodiment, the process further includes 5424 providing a notification that is at least partially based on the informational data to at least one of a human, computer, or system. In an embodiment, the process further includes 5426 storing the informational data in another computer-readable media operably coupled with the processor.

FIG. 113 illustrates an example system 5500. The system includes means 5510 for receiving a first reference image that includes an objective landmark subsurface feature of a mammalian body part. The objective landmark subsurface feature has a first spatial relationship to a destination region of interest of the mammalian body part. The system includes means 5520 for receiving a second reference image that includes a present-location landmark subsurface feature of the mammalian body part. The present-location landmark subsurface feature has a second spatial relationship to a distal end portion of a body-insertable device deployed operationally proximate to the mammalian body part. The system includes means 5530 for determining a substantial correspondence between the objective landmark subsurface feature and a first atlas subsurface feature included in a subsurface feature atlas of the mammalian body part. The subsurface feature atlas includes at least two registered subsurface features of the mammalian body part, including the first atlas subsurface feature and a second atlas subsurface feature. The registration includes an indication of a third spatial relationship between the first atlas subsurface feature and the second atlas subsurface feature. The system includes means 5540 for determining a substantial correspondence between the present-location landmark subsurface feature and the second atlas subsurface feature included in the subsurface feature atlas of the mammalian body part. The system includes means 5550 for determining a fourth spatial relationship between the destination region of interest and the distal end portion of the body-insertable device deployed operationally proximate to the mammalian body part. The fourth spatial relationship is determined at least partially based on the third spatial relationship. The system includes means 5560 for outputting informational data indicative of the determined fourth spatial relationship between the destination region of interest and the distal end portion of the body-insertable device.

Returning to FIG. 102, FIG. 102 illustrates alternative embodiment of the system 5120. In the alternative embodiment, the feature matching circuit 5124 is configured to determine a substantial correspondence between an objective landmark subsurface feature of a mammalian body part and a first atlas subsurface feature included in a subsurface feature atlas. The objective landmark subsurface feature has a first spatial relationship to a destination region of interest of the mammalian body part. The subsurface feature atlas includes at least two registered subsurface features of the mammalian body part including the first atlas subsurface feature and a second atlas subsurface feature. The feature matching circuit is also configured to determine a substantial correspondence between a present-location landmark subsurface feature of the mammalian body part and the second atlas subsurface feature included in the subsurface feature atlas. The present-location landmark subsurface feature has a second spatial relationship to a distal end portion of a body-insertable device deployed operationally proximate to the mammalian body part.

In the alternative embodiment, the location analysis circuit 5126 is configured to determine a fourth spatial relationship between the destination region of interest and the distal end portion of the body-insertable device deployed operationally proximate to the mammalian body part. The fourth spatial relationship is determined at least partially based on the third spatial relationship. In the alternative embodiment, the indicator circuit 5128 is configured to generate informational data indicative of the determined fourth spatial relationship between the destination region of interest and the distal end portion of the body-insertable device. The informational data is at least partially based on the fourth spatial relationship between the destination region of interest and the distal end portion of the body-insertable device. In the alternative embodiment, the computer-readable media 235 is configured to maintain informational data.

FIG. 114 illustrates an example operational flow 5600. The operational flow includes a start operation. The operational flow includes a first matching operation 5610. The first matching operation includes determining a substantial correspondence between an objective landmark subsurface feature of a mammalian body part and a first atlas subsurface feature included in a subsurface feature atlas. The objective landmark subsurface feature has a first spatial relationship to a destination region of interest of the mammalian body part. The subsurface feature atlas includes at least two registered subsurface features of the mammalian body part including the first atlas subsurface feature and a second atlas subsurface feature. A second matching operation 5620 includes determining a substantial correspondence between a present-location landmark subsurface feature the mammalian body part and the second atlas subsurface feature included in the subsurface feature atlas. The present-location landmark subsurface feature has a second spatial relationship to a distal end portion of a body-insertable device deployed operationally proximate to the mammalian body part. A proximity operation 5630 includes determining a fourth spatial relationship between the destination region of interest and the distal end portion of the body-insertable device deployed operationally proximate to the mammalian body part. The fourth spatial relationship is determined at least partially based on the third spatial relationship. A communication operation 5650 includes outputting the informational data.

FIG. 115 illustrates an example environment 5700. The environment includes the mammalian body part 210 of an individual patient illustrated as the mammal 205, and a system 5720. The system includes a receiver circuit 5722 configured to receive first medical image that includes a selected target region of interest of a body part of an individual patient (hereafter "individual patient body part"). The first medical image also includes a landmark subsurface feature of the individual patient body part having a first spatial relationship with the selected target region of interest (hereafter "associated landmark subsurface feature"). For example, the first digital image may be provided by a human or a machine. For example, the region of interest may be indicated by a human, machine, a feature choosing circuit, or by an atlas of the patient body part. The receiver circuit is also configured to receive a second medical image that includes a candidate region of interest of the individual patient body part. The second medical image also includes a landmark feature of the individual patient body part having a second spatial relationship with the candidate region of interest (hereafter "candidate landmark subsurface feature"). The system includes a feature matching circuit 5724 configured to determine a substantial correspondence between the candidate landmark subsurface feature and the associated landmark subsurface feature. A reporting circuit 5736 is to generate informational data indicating the second medical image includes at least a portion of the selected target region of interest. The informational data is at least partially based on the determined substantial correspondence between the candidate landmark subsurface feature and the associated landmark subsurface feature. The system includes a communication circuit 5742 configured to output the informational data.

For example, in an embodiment of the system 5720 in use, the system may be used in conjunction with a follow-up colonoscopy. The first medical image may include an image that was acquired during a previous colonoscopy, and may include a suspicious polyp that the physician selects as a target region of interest to follow in a future exam. The second medical image may include an image that was acquired during a follow-up exam one year later. The feature matching circuit 5724 determines whether a substantial correspondence exists between the candidate landmark subsurface feature of the second or subsequent medical image and the associated landmark subsurface feature of the first medical image. If a substantial correspondence exists between the landmark subsurface features, the reporting circuit 5736 generates informational data indicating the second medical image includes at least a portion of the selected target region of interest. The communication circuit 5742 outputs the informational data. The informational data indicates to the physician that the second digital image includes at least a portion of the selected target region of interest.

For example, in another embodiment of the system 5720 in use, the first medical image depicts a selected target region of interest of the individual patient body part 210, and depicts a landmark subsurface feature of the individual patient body part has a first spatial relationship with the selected target region of interest (the "associated landmark subsurface feature"). The second medical image depicts a candidate region of interest of the individual patient body part, and includes a landmark feature of the individual patient body part having a second spatial relationship with the candidate region of interest (the "candidate landmark subsurface feature.") If the feature matching circuit determines a substantial correspondence between the candidate landmark subsurface feature and the associated landmark subsurface feature, and if feature matching circuit determines a substantial correspondence between the first spatial relationship and the second spatial relationship, the reporting circuit 5736 generates informational data indicating the second medical image includes at least a portion of the selected target region of interest. The communication circuit 5742 outputs the informational data. The informational data indicates to the physician that the second digital image includes at least a portion of the selected target region of interest.

In an embodiment, the first medical image includes a selected target region of interest of a cavity or lumen 211 of an individual patient body part 210, and includes an associated landmark subsurface feature. In an embodiment, the second medical image includes a candidate region of interest of the cavity or lumen of the individual patient body part, and includes a candidate landmark subsurface feature. In an embodiment, the first medical image includes a target region of interest that includes a selected target region of interest of a surface of a cavity or lumen of an individual patient body part, and includes an associated landmark subsurface feature. In an embodiment, the second medical image includes a candidate region of interest of the surface of the cavity or lumen of the individual patient body part, and includes a candidate landmark subsurface feature. In an embodiment, the first medical image includes a selected surface region of interest of an individual patient body part, and includes an associated landmark subsurface feature. In an embodiment, the second medical image includes a candidate surface region of interest of the individual patient body part, and includes a candidate landmark feature of the individual patient body part. In an embodiment, the first medical image includes a selected subsurface region of interest of an individual patient body part, and includes an associated landmark subsurface feature. In an embodiment, the second medical image includes a candidate subsurface region of interest of the individual patient body part, and includes a candidate landmark feature of the individual patient body part. In an embodiment, the first medical image includes a selected target region of interest of an individual patient body part, and includes an associated landmark subsurface feature machine-distinguishable from other landmark features of the individual patient body part. In an embodiment, the second medical image includes a candidate region of interest of the individual patient body part, and includes a candidate landmark feature of the individual patient body part machine-distinguishable from other landmark features of the individual patient body part. In an embodiment, the first medical image includes a machine-selected target region of interest of an individual patient body part, and that includes an associated landmark subsurface feature. In an embodiment, the first medical image includes a human-selected target region of interest of an individual patient body part, and that includes an associated landmark subsurface feature.

In an embodiment, the feature matching circuit 5724 is configured to determine a substantial correspondence between the candidate landmark subsurface feature and the associated landmark subsurface feature, and to determine a substantial correspondence between the first spatial relationship and the second spatial relationship. In an embodiment, the reporting circuit 5736 is configured to generate informational data indicating the second medical image includes at least a portion of the selected target region of interest, the informational data is at least partially based on (i) the determined substantial correspondence between the candidate landmark subsurface feature and the associated landmark subsurface feature, and (ii) the determined substantial correspondence between the first spatial relationship and the second spatial relationship. In an embodiment, the reporting circuit configured to generate informational data indicating the second medical image includes at least a portion of the selected target region of interest, the informational data is at least partially based on (i) the determined substantial correspondence between the candidate landmark subsurface feature and the associated landmark subsurface feature, (ii) the first spatial relationship between the selected target region of interest and the associated landmark subsurface feature, and (iii) the second spatial relationship between the candidate region of interest and the candidate landmark subsurface feature. In an embodiment, the feature matching circuit is configured to determine at least one of a structural, pattern, orientation, physical characteristic, or identification-based substantial correspondence between the candidate landmark subsurface feature and the associated landmark subsurface feature. In an embodiment, the reporting circuit is configured to generate informational data indicating the candidate region of interest of the second medical image includes at least a portion of the selected target region of interest, the informational data is at least partially based on the determined substantial correspondence between the candidate landmark subsurface feature and the associated landmark subsurface feature. In an embodiment, the reporting circuit is configured to generate informational data indicating the second medical image includes at least a portion of the selected target region of interest, the informational data is at least partially based on the determined substantial correspondence between the candidate landmark subsurface feature and the associated landmark subsurface feature; otherwise the reporting circuit is configured to generate informational data indicating the second medical image does not include the target region of interest. The another informational data is at least partially based on an absence of a determined substantial correspondence between the candidate landmark subsurface feature and the associated landmark subsurface feature.

In an embodiment, the communication circuit 5742 is configured to provide a notification that is at least partially based on the informational data to at least one of a human, computer, or system. In an embodiment, the system 5720 may include an indicator circuit 5728 configured to display a human-perceivable indication that the second medical image includes at least a portion of the target region of interest. In an embodiment, the system may include a computer-readable media configured to maintain the informational data, such as the computer-readable media 235.

FIG. 116 illustrates an example operational flow 5800. The operational flow includes a start operation. The operational flow includes a first reception operation 5810. The first reception operation includes receiving a first medical image that includes a selected target region of interest of a body part of an individual patient (hereafter "individual patient body part"). The first medical image also includes a landmark subsurface feature of the individual patient body part having a first spatial relationship with the selected target region of interest (hereafter "associated landmark subsurface feature"). A second reception operation 5820 includes receiving a second medical image that includes a candidate region of interest of the individual patient body part, and that includes a landmark feature of the individual patient body part having a second spatial relationship with the candidate region of interest (hereafter "candidate landmark subsurface feature"). In an embodiment, the first reception operation or the second reception operation may be performed using the receiver circuit 5722 described in conjunction with FIG. 115. A matching operation 5830 includes determining a substantial correspondence between the candidate landmark subsurface feature and the associated landmark subsurface feature. In an embodiment, the matching operation may be implemented using the feature matching circuit 5724 described in conjunction with FIG. 115. A reporting operation 5840 includes generating informational data indicating the second medical image includes at least a portion of the selected target region of interest. The informational data is at least partially based on the determined substantial correspondence between the candidate landmark subsurface feature and the associated landmark subsurface feature. In an embodiment, the reporting operation may be implement using the reporting circuit 5736 described in conjunction with FIG. 115. A communication operation 5850 includes outputting the informational data. In an embodiment, the communication operation may be implemented using the communications circuit 5742 described in conjunction with FIG. 115. The operational flow includes an end operation.

FIG. 117 illustrates an alternative embodiment of the operational flow 5800 of FIG. 116. In an embodiment, the first receiving operation 5810 may include at least one alternative embodiment. The at least one alternative embodiment may include an operation 5811, an operation 5812, an operation 5813, an operation 5814, or an operation 5815. In an embodiment, the operation 5811 includes receiving a first medical image that includes a selected target region of interest of a cavity or lumen of an individual patient body part, and that includes an associated landmark subsurface feature. In an operation, the operation 5812 includes receiving a first medical image that includes a target region of interest that includes a selected target region of interest of a surface of a cavity or lumen of an individual patient body part, and that includes an associated landmark subsurface feature. In an embodiment, the operation 5813 includes receiving a first medical image that includes a selected surface region of interest of an individual patient body part, and that includes an associated landmark subsurface feature. In an embodiment, the operation 5814 includes receiving a first medical image that includes a selected subsurface region of interest of an individual patient body part, and that includes an associated landmark subsurface feature. In an embodiment, the operation 5815 includes receiving a first medical image that includes a selected target region of interest of an individual patient body part, and that includes an associated landmark subsurface feature machine-distinguishable from other landmark features of the individual patient body part.

In an embodiment, the second receiving operation 5820 may include at least one alternative embodiment. The at least one alternative embodiment may include an operation 5821, an operation 5822, an operation 5823, an operation 5824, or an operation 5825. In an embodiment, the operation 5821 includes receiving a second medical image that includes a candidate region of interest of the cavity or lumen of the individual patient body part, and that includes a candidate landmark subsurface feature. In an embodiment, the operation 5822 includes receiving a second medical image that includes a candidate region of interest of the surface of the cavity or lumen of the individual patient body part, and that includes a candidate landmark subsurface feature. In an embodiment, the operation 5823 includes receiving a second medical image that includes a candidate surface region of interest of the individual patient body part, and that includes a candidate landmark feature of the individual patient body part. In an embodiment, the operation 5824 includes receiving a first medical image that includes a selected subsurface region of interest of an individual patient body part, and that includes an associated landmark subsurface feature.

Figure 118:
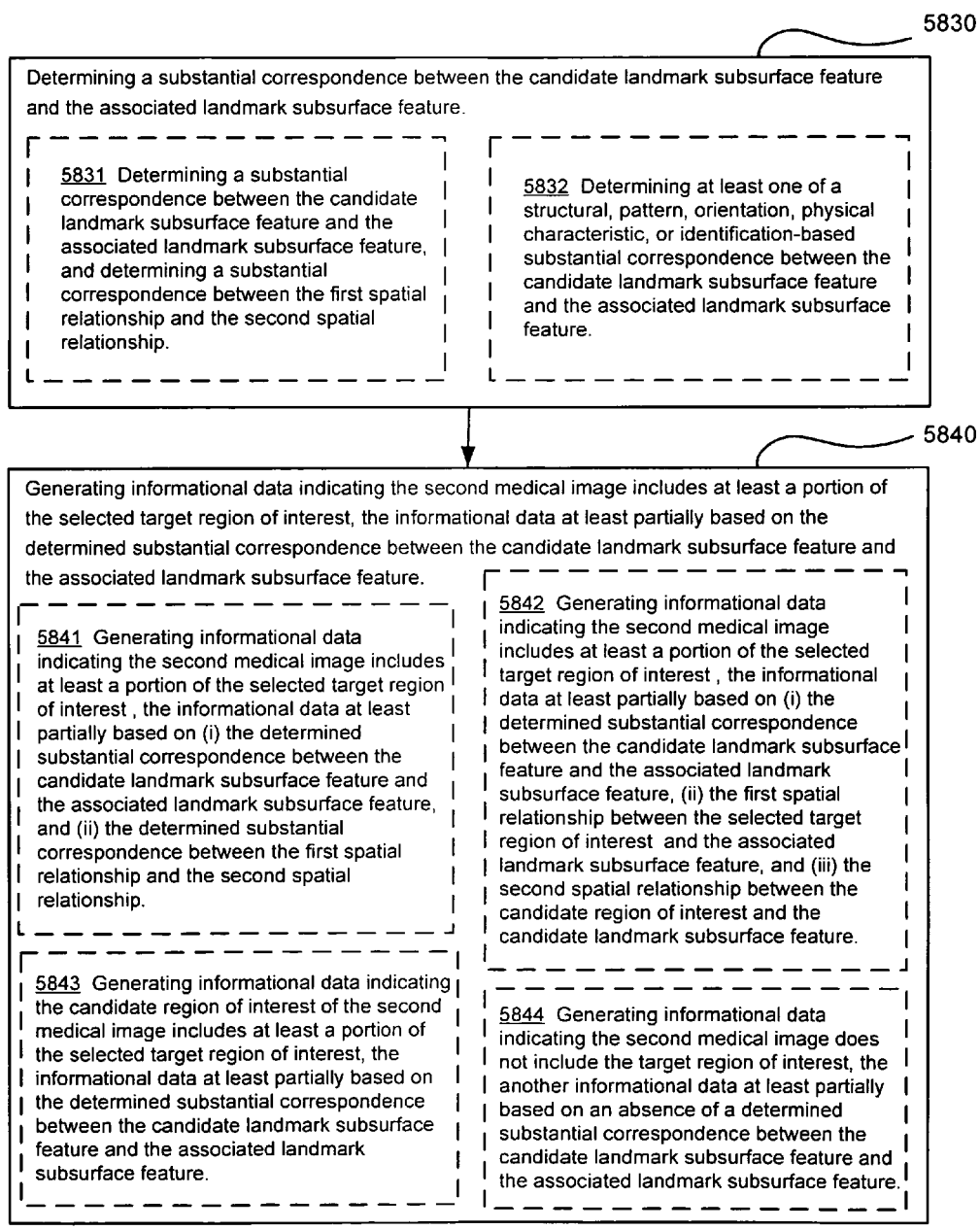
FIG. 118 illustrates an alternative embodiment of the operational flow of FIG. 116.

FIG. 118 illustrates an alternative embodiment of the operational flow 5800 of FIG. 116. In an embodiment, the matching operation 5830 includes at least one alternative embodiment. The at least alternative embodiment may include an operation 5831 or an operation 5832. The operation 5831 includes determining a substantial correspondence between the candidate landmark subsurface feature and the associated landmark subsurface feature, and determining a substantial correspondence between the first spatial relationship and the second spatial relationship. The operation 5832 includes determining at least one of a structural, pattern, orientation, physical characteristic, or identification-based substantial correspondence between the candidate landmark subsurface feature and the associated landmark subsurface feature.

In an embodiment, the reporting operation 5840 may include at least one alternative embodiment. The at least one alternative embodiment may include an operation 5841, an operation 5842, an operation 5843, or an operation 5844. The operation 5841 includes generating informational data indicating the second medical image includes at least a portion of the selected target region of interest. The informational data is at least partially based on (i) the determined substantial correspondence between the candidate landmark subsurface feature and the associated landmark subsurface feature, and (ii) the determined substantial correspondence between the first spatial relationship and the second spatial relationship. The operation 5842 includes generating informational data indicating the second medical image includes at least a portion of the selected target region of interest. The informational data is at least partially based on (i) the determined substantial correspondence between the candidate landmark subsurface feature and the associated landmark subsurface feature, (ii) the first spatial relationship between the selected target region of interest and the associated landmark subsurface feature, and (iii) the second spatial relationship between the candidate region of interest and the candidate landmark subsurface feature. The operation 5843 includes generating informational data indicating the candidate region of interest of the second medical image includes at least a portion of the selected target region of interest. The informational data is at least partially based on the determined substantial correspondence between the candidate landmark subsurface feature and the associated landmark subsurface feature. The operation 5844 includes generating informational data indicating the second medical image includes at least a portion of the selected target region of interest; the informational data is at least partially based on the determined substantial correspondence between the candidate landmark subsurface feature and the associated landmark subsurface feature—otherwise generating informational data indicating the second medical image does not include the target region of interest; the another informational data is at least partially based on an absence of a determined substantial correspondence between the candidate landmark subsurface feature and the associated landmark subsurface feature.

Figure 119:
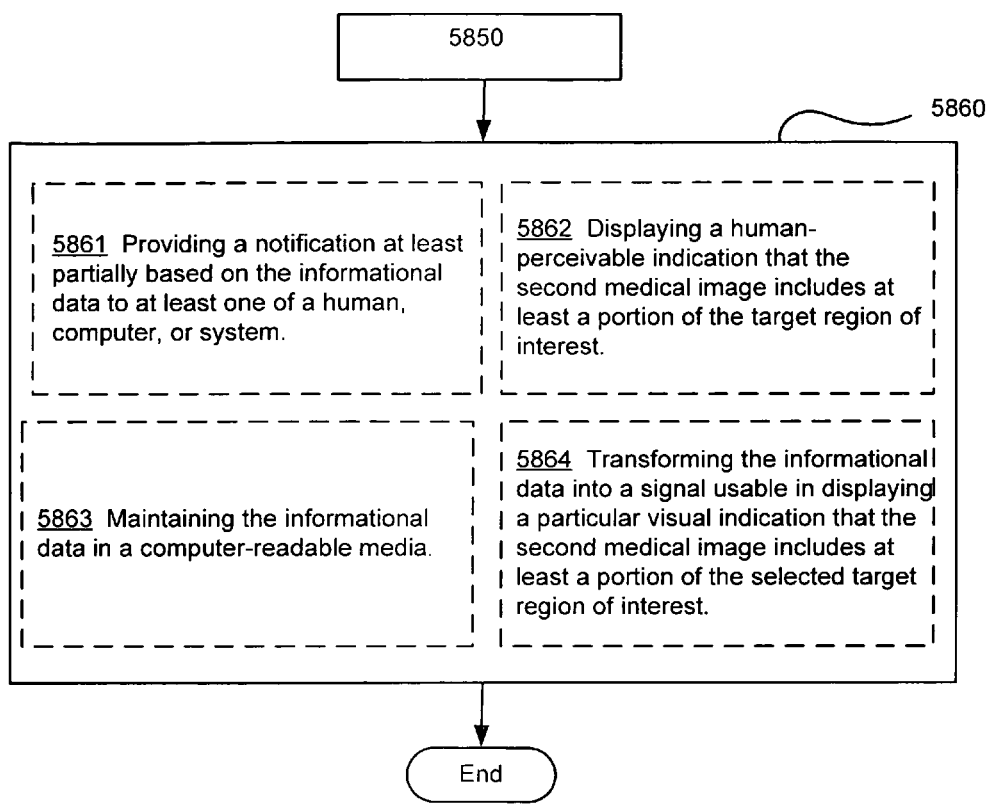
FIG. 119 illustrates an alternative embodiment of the operational flow of FIG. 116.

FIG. 119 illustrates an alternative embodiment of the operational flow 5800 of FIG. 116. In an embodiment, the operational flow may include at least one alternative embodiment 5860. The at least one alternative embodiment may include an operation 5861, an operation 5862, an operation 5863, or an operation 5864. The operation 5861 includes providing a notification that is at least partially based on the informational data to at least one of a human, computer, or system. The operation 5862 includes displaying a human-perceivable indication that the second medical image includes at least a portion of the target region of interest. The operation 5863 includes maintaining the informational data in a computer-readable media. The operation 5864 includes transforming the informational data into a signal usable in displaying a particular visual indication that the second medical image includes at least a portion of the selected target region of interest.

FIG. 120 illustrates a computer program product. The computer program product includes a computer-readable computer storage medium 5910 bearing program instructions 5920. The program instructions which, when executed by a processor of a computing device, cause the computing device to perform a process. The process includes receiving a first medical image that includes a selected target region of interest of a body part of an individual patient (hereafter "individual patient body part"). The first medical image also includes a landmark subsurface feature of the individual patient body part having a first spatial relationship with the selected target region of interest (hereafter "associated landmark subsurface feature"). The process includes receiving a second medical image that includes a candidate region of interest of the individual patient body part. The second medical image also includes a landmark feature of the individual patient body part having a second spatial relationship with the candidate region of interest (hereafter "candidate landmark subsurface feature"). The process includes determining a substantial correspondence between the candidate landmark subsurface feature and the associated landmark subsurface feature. The process includes generating informational data indicating the second medical image includes at least a portion of the selected target region of interest. The informational data is at least partially based on the determined substantial correspondence between the candidate landmark subsurface feature and the associated landmark subsurface feature. The process includes outputting the informational data.

In an embodiment, the process further includes 5922 storing the informational data in another computer-readable media operably coupled with the processor. In an embodiment, the process further includes 5924 transforming the informational data into a signal usable in providing a particular visual indication that the second medical image includes at least a portion of the selected target region of interest. In an embodiment, the process further includes 5926 providing a notification that is at least partially based on the informational data to at least one of a human, computer, or system.

In an embodiment, the computer-readable media 5910 includes a tangible computer-readable media 5912. In an embodiment, the computer-readable media includes a communications medium 5914.

FIG. 121 illustrates an example system 6000. The system includes means 6010 for receiving a first medical image that includes a selected target region of interest of a body part of an individual patient (hereafter "individual patient body part"). The first medical image also includes a landmark subsurface feature of the individual patient body part having a first spatial relationship with the selected target region of interest (hereafter "associated landmark subsurface feature"). The system includes means 6020 for receiving a second medical image that includes a candidate region of interest of the individual patient body part, and that includes a landmark feature of the individual patient body part having a second spatial relationship with the candidate region of interest (hereafter "candidate landmark subsurface feature"). The system includes means 6030 for determining a substantial correspondence between the candidate landmark subsurface feature and the associated landmark subsurface feature. The system include means 6040 for generating informational data indicating the second medical image includes at least a portion of the selected target region of interest, the informational data is at least partially based on the determined substantial correspondence between the candidate landmark subsurface feature and the associated landmark subsurface feature. The system includes means 6050 for outputting the informational data.

In an alternative embodiment, the system 6000 may includes means 6060 for persistently maintaining the informational data. In an embodiment, the system includes means 6070 for transforming the informational data into a signal usable in providing a particular visual indication that the second medical image includes at least a portion of the selected target region of interest.

FIG. 122 illustrates an example environment 6100. The environment includes the mammalian body part 210 of an individual patient illustrated as the mammal 205, the body-insertable device 4480, and a system 6120. The system includes a feature matching circuit 6124, which is configured to determine a substantial correspondence between a present-location landmark subsurface feature of a body part 210 of the individual patient 205 (hereafter "individual patient body part") and a candidate reference landmark subsurface feature of the individual patient body part. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part.

The system includes an event data circuit 6128 configured to generate data indicative of a proximity event. The proximity event includes the distal end portion of the body-insertable device being present at a location proximate to the particular target region of interest of the individual patient body part. The proximity event is at least partially based on the determined substantial correspondence. The system includes a list management circuit 6134 configured to add the proximity event to a proximity event list for the individual patient body part. The system includes a computer-readable media 235 configured to maintain informational data corresponding to the proximity event list for the individual patient body part. The system includes a communications circuit configured to output the informational data.

In an embodiment of the system 6120, the feature matching circuit 6124 includes a feature matching circuit configured to determine a substantial correspondence between a present-location landmark subsurface feature of a cavity or lumen of an individual patient body part and a candidate reference landmark subsurface feature of the cavity or lumen of the individual patient body part. The present-location landmark subsurface feature has a first spatial relationship to a distal end portion of a body-insertable device deployed in the cavity or lumen of the individual patient. The candidate reference landmark subsurface feature has a second spatial relationship to a particular target region of interest of the cavity or lumen of the individual patient body part. In an embodiment, the feature matching circuit includes a feature matching circuit configured to determine a substantial correspondence between a present-location landmark subsurface feature of a cavity or lumen of an individual patient body part and a candidate reference landmark subsurface feature of the cavity or lumen of the individual patient body part. The present-location landmark subsurface feature has a first spatial relationship to a distal end portion of a body-insertable device deployed in the cavity or lumen of the individual patient. The candidate reference landmark subsurface feature has a second spatial relationship to a particular target region of interest of a surface of the cavity or lumen of the individual patient body part In an embodiment of the system 6120, the distal end portion 4483, of the body-insertable device 4480 deployed in the individual patient 205 includes an operative distal end portion of a body-insertable device deployed in the individual patient. In an embodiment of the system, the distal end portion of a body-insertable device deployed in the individual patient includes a moveable distal end portion of a body-insertable device deployed in the individual patient. In an embodiment, the distal end portion of a body-insertable device deployed in the individual patient includes an effector carried on a distal end portion of a body-insertable device deployed in the individual patient.

FIG. 103 illustrates a first spatial relationship between the present-location landmark subsurface feature, illustrated as the landmark subsurface feature 5222, and the distal end portion 4483 of the body-insertable device 4480 deployed in the body part 210 of the individual patient, illustrated as the mammal 205. In an embodiment of the system 6120, the first spatial relationship includes a distance of less than about six centimeters. In an embodiment of the system, the first spatial relationship includes a distance of less than about three centimeters. In an embodiment of the system, the first spatial relationship includes a distance of less than about one centimeter. In an embodiment of the system, the first spatial relationship includes a distance of less than about fifty millimeters. In an embodiment, the first spatial relationship may include a bearing and distance.

Returning to FIG. 122, in an embodiment of the system 6120, the candidate reference landmark subsurface feature of the individual patient body part is selected from a patient examination table that includes the at least two reference landmark subsurface features of the individual patient body part. Each candidate reference landmark subsurface feature of the at least two candidate reference landmark subsurface features has a respective spatial relationship to a respective particular selected target region of interest. The following Table 1 illustrates an example patient examination table.

TABLE 1

PATIENT EXAMINATION TABLE

| Target Regions of Interest | Associated Reference Landmark Subsurface Features |
|---|---|
| 1 | A |
| 2 | ... |
| 3 | ... |
| 4 | X |

TABLE 1-continued

PATIENT EXAMINATION TABLE

| Target Regions of Interest | Associated Reference Landmark Subsurface Features |
|---|---|
| 5 | Y |
| 6 | Z |

For example, the patient examination table may be prepared based upon a virtual colonoscopy performed on an individual patient. Certain regions of the individual patient's colon may be selected from the virtual colonoscopy as appropriate for further investigation. These regions are described as "target regions of interest" in conjunction with the description of the system 6120. For example, the region of interest 5214 described in conjunction with FIG. 103 may be selected as a target region of interest. In addition, certain landmark subsurface features of the patient's colon have respective spatial relationships to the target regions of interest may also be selected from the virtual colonoscopy. These landmark subsurface features are described as "associated reference landmark subsurface features" in conjunction with the description of the system 6120. For example, the landmark subsurface feature 5212 described in conjunction with FIG. 103 may be selected as the associated reference landmark subsurface feature for the region of interest 5214. In another embodiment, the certain landmark subsurface features of the individual patient's colon have respective spatial relationships to the target regions of interest may also be selected from a generalized atlas of the mammalian body part 210, or a specific atlas of the individual patient's colon. For example, the atlas 5250 described in conjunction with FIG. 103 may illustrate the generalized atlas or the specific atlas of the individual patient's colon.

Continuing with FIG. 122, in an embodiment of the system 6120, the patient examination table is at least partially based on a colonoscopy of the individual patient. In an embodiment, the patient examination table is at least partially based on a virtual colonoscopy of the individual patient. In an embodiment, the patient examination table may be at least partially based on another other suitable imaging technique, such as CAT scan, MRI, or ultrasound. In an embodiment, the patient examination table is at least partially based on a subsurface feature atlas configured for the individual patient. In an embodiment, the patient examination table is configured to facilitate an interested party to test, diagnose, or treat a possible medical condition of the individual patient.

In an embodiment, the system 6120 includes a proximity indicator circuit 6132 configured to generate a proximity indication if the first spatial relationship is not greater than an operational reach of the distal end portion of the body-insertable device. For example, FIG. 103 illustrates the distal end portion 4483 of a body-insertable device 4480 deployed in the individual patient body part, indicated as mammalian body part 210. FIG. 103 illustrates an example where the first spatial relationship, illustrated by the spatial relationship 5226, is greater than the operational reach, indicated by the dashed circle of operationally proximate 4489, of the distal end portion of the body-insertable device. In FIG. 103, the operational reach of the distal end portion, such as an effector or camera, illustrated the digital image acquisition device 4481 and the active element 4482, indicated by the dashed circle of operationally proximate, is less than the first spatial relationship, illustrated by the spatial relationship 5226. In this event, the proximity indicator would not generate a proximity indication. In another example, which is not illustrated by FIG. 103, where the first spatial relationship, such as illustrated by the spatial relationship 5226, is not greater than the operational reach, indicated by the dashed circle of operationally proximate 4489, of the distal end portion 4483 of the body-insertable device, the proximity indicator will generate a proximity indication. For example, the operational reach may include a distance where an effector of the distal end portion is operable to resect or ablate tissue lying within the particular target region of interest.

Continuing with reference to FIG. 122, in an embodiment, the event data circuit 6128 is configured to generate data indicative of a proximity event. The proximity event includes the distal end portion of the body-insertable device being present at a location that is operationally proximate to the particular target region of interest of the individual patient body part. The proximity event is at least partially based on the determined substantial correspondence and on the proximity indication. For example, the proximity event may involve the body-insertable device, or the proximity event may involve another device.

In an embodiment, the system 6120 includes a receiver circuit 6122 configured to receive data indicative of an activity or action performed proximate to the present-location landmark subsurface feature. In an embodiment, the system 6120 includes the event data circuit 6128 configured to (i) generate data indicative of a proximity event, and (ii) associate with the data indicative of a proximity event the data indicative of an activity or action performed proximate to the present-location landmark subsurface feature. The proximity event is at least partially based on the determined substantial correspondence and on the proximity indication. The proximity event includes the distal end portion of the body-insertable device present at a location operationally proximate to the particular target region of interest of the individual patient body part.

In an embodiment, the system 6120 includes a receiver circuit 6122 that is configured to receive a first reference image that includes the present-location landmark subsurface of the individual patient body part. In an embodiment, the receiver circuit is configured to receive a first reference image acquired by the body-insertable device deployed in the individual patient and including the present-location landmark subsurface of the individual patient body part. In an embodiment, the receiver circuit is configured to receive a first reference image acquired by an ex vivo device and including the present-location landmark subsurface of the individual patient body part. In an embodiment, the receiver circuit is configured to receive a first reference image acquired by an ex vivo device and including the present-location landmark subsurface of the individual patient body part. In an embodiment, the receiver circuit is configured to receive a second reference image that includes the candidate reference landmark subsurface feature of the individual patient body part. In an embodiment, the receiver circuit is configured to receive from a local computer-readable media a second reference image that includes the candidate reference landmark subsurface feature of the individual patient body part. In an embodiment, the receiver circuit is configured to receive from a remote computer-readable media via a network a second reference image that includes the candidate reference landmark subsurface feature of the individual patient body part. In an embodiment, the receiver circuit is configured to receive (i) a first reference image that includes the present-location landmark subsurface of the individual patient body part, and (ii) a second reference image that includes the candidate reference landmark subsurface feature of the individual patient body part.

In an embodiment, the system 6120 includes the communication circuit 6142 that is configured to provide a notification that is at least partially based on the informational data to at least one of a human, computer, or system. In an embodiment, the system 6120 includes a communication device configured to display a human-perceivable depiction of the proximity event list for the individual patient body part. The communication device is illustrated by the computing device 292.

FIG. 103 illustrates an example of a use of an embodiment of the system 6120. For example, the present location-landmark subsurface feature of the patient body part 210 may be illustrated by the landmark subsurface feature 5222 having the spatial relationship 5226 to the distal end portion 4483 of the body-insertable device 4480 deployed in the individual patient 205. The candidate reference landmark subsurface feature may be illustrated as the landmark subsurface feature 5212 having the spatial relationship 5216 to the region of interest 5214 of the individual patient body part. In such an example of an embodiment, the feature matching circuit 6124 would determine no substantial correspondence between the present location-landmark subsurface feature (illustrated as the landmark subsurface feature 5222) and the candidate reference landmark subsurface feature (illustrated as the landmark subsurface feature 5212), so data indicative of a proximity event would not be generated by the event data circuit 6128. However, in an example of an embodiment where the candidate reference landmark subsurface feature is illustrated by the landmark subsurface feature 5212, the feature matching circuit 6124 would determine a substantial correspondence between the present-location landmark subsurface feature and the candidate reference landmark subsurface feature. Data indicative of a proximity event would be generated by the event data circuit. The list management circuit 6134 would add this proximity event to a proximity event list for the individual patient body part. Informational data corresponding to the proximity event list for the individual patient body part is maintained in the computer-readable media 235, and would be outputted by the communication circuit 6142.

FIG. 123 illustrates an example operational flow 6200. The operational flow includes a start operation. The operational flow includes a matching operation 6210. The matching operation includes determining a substantial correspondence between (x) a present-location landmark subsurface feature of a body part of an individual patient (hereafter "individual patient body part") and (y) a candidate reference landmark subsurface feature of the individual patient body part. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part. In an embodiment, the matching operation may be implemented using the feature matching circuit 6124 described in conjunction with FIG. 122. A nearness operation 6220 includes generating a proximity indication if the first spatial relationship is not greater than an operational reach of the distal end portion of the body-insertable device. In an embodiment, the nearness operation may be implemented using the proximity indicator circuit 6132 described in conjunction with FIG. 122. A reporting operation 6230 includes generating data indicative of a proximity event. The proximity event includes an instance where the distal end portion of the body-insertable device is present at a location operationally proximate to the particular target region of interest of the individual patient body part. The proximity event is at least partially based on the determined substantial correspondence and on the proximity indication. In an embodiment, the reporting operation may be implemented using event data circuit 6128 described in conjunction with FIG. 122. A list management operation 6240 includes adding the proximity event to a proximity event list for the individual patient body part. In an embodiment, the list management operation may be implemented using the list management circuit 6134 described in conjunction with FIG. 122. A communication operation 6250. The communication operation includes outputting informational data corresponding to the proximity event list for the individual patient body part. In an embodiment, the communication operation may be implemented using the communication circuit 6142. The operational flow includes an end operation. In an alternative embodiment, the operational flow includes a storage operation 6260 that maintaining the informational data in a computer-readable media. FIG. 124 illustrates an alternative embodiment of the operational flow 6200 of FIG. 123. In the alternative embodiment, the matching operation 6210 may include at least one additional embodiment. The at least one additional embodiment may include an operation 6211, an operation 6212, or an operation 6213. The operation 6211 includes determining a substantial correspondence between (x) a present-location landmark subsurface feature of a cavity or lumen of an individual patient body part and (y) a candidate reference landmark subsurface feature of the cavity or lumen of the individual patient body part. The present-location landmark subsurface feature has a first spatial relationship to a distal end portion of a body-insertable device deployed in the cavity or lumen of the individual patient. The candidate reference landmark subsurface feature has a second spatial relationship to a particular target region of interest of the cavity or lumen of the individual patient body part. The operation 6212 includes determining a substantial correspondence between (x) a present-location landmark subsurface feature of a cavity or lumen of an individual patient body part and (y) a candidate reference landmark subsurface feature of the cavity or lumen of the individual patient body part. The present-location landmark subsurface feature has a first spatial relationship to a distal end portion of a body-insertable device deployed in the cavity or lumen of the individual patient. The candidate reference landmark subsurface feature has a second spatial relationship to a particular target region of interest of a surface of the cavity or lumen of the individual patient body part. The operation 6213 includes determining a substantial correspondence between (x) a present-location landmark subsurface feature of a body part of an individual patient and (y) a candidate reference landmark subsurface feature of the individual patient body part. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part. The candidate reference landmark subsurface feature is selected from a patient examination table that includes the at least two reference landmark subsurface features of the individual patient body part. Each candidate reference landmark subsurface feature of the at least two candidate reference landmark subsurface features has a respective spatial relationship to a respective particular selected target region of interest.

Figure 125:
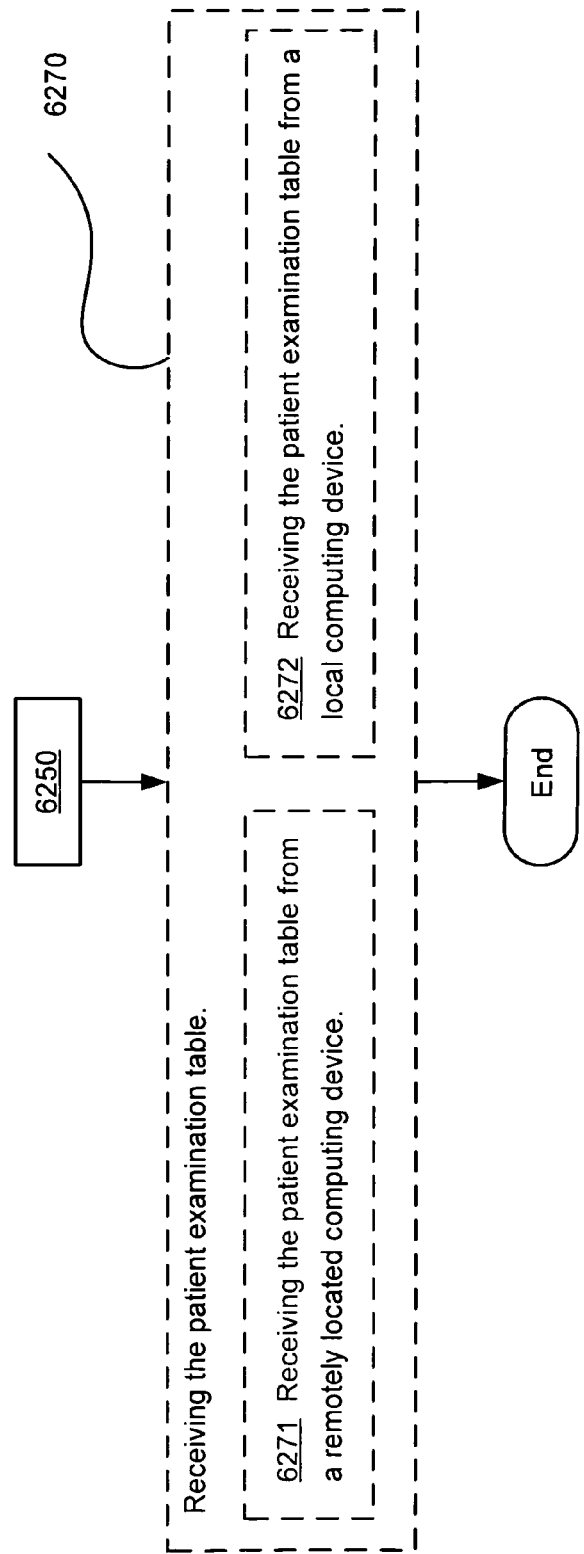
FIG. 125 illustrates an alternative embodiment of the operational flow of FIG. 123.

FIG. 125 illustrates an alternative embodiment of the operational flow 6200. The operational flow may include at least one additional operation, such as an operation 6270. The operation 6270 includes receiving the patient examination table. The operation 6270 may include at least one additional embodiment. The at least one additional embodiment may include an operation 6271 or an operation 6272. The operation 6271 includes receiving the patient examination table from a remotely located computing device. The operation 6272 includes receiving the patient examination table from a local computing device.

Figure 126:
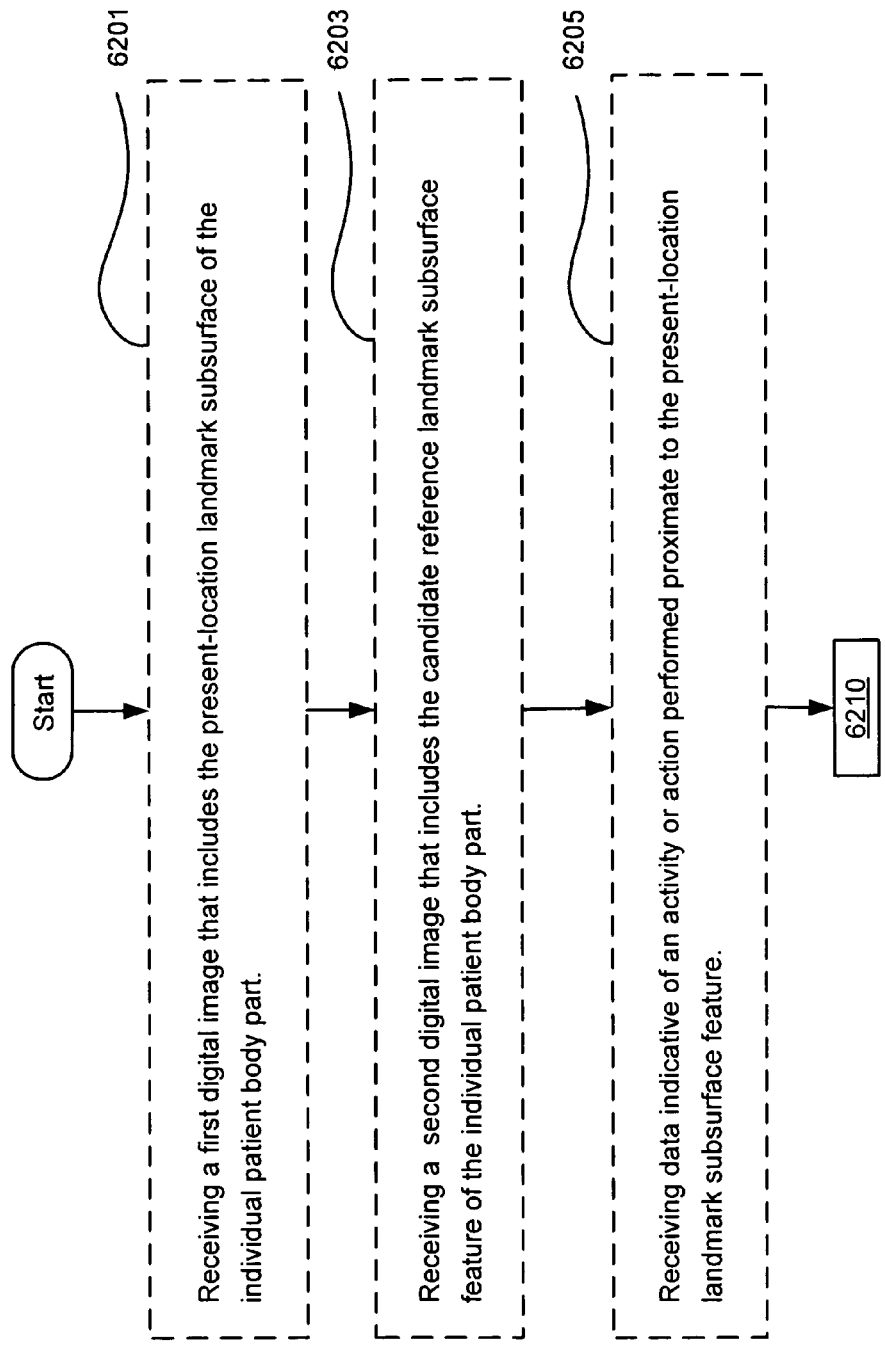
FIG. 126 illustrates an alternative embodiment of the operational flow of FIG. 123.

FIG. 126 illustrates an alternative embodiment of the operational flow 6200. The operational flow may include at least one additional embodiment. The at least one additional embodiment may include an operation 6201, an operation 6203, or an operation 6205. The operation 6201 includes receiving a first digital image that includes the present-location landmark subsurface of the individual patient body part. The operation 6203 includes a second digital image that includes the candidate reference landmark subsurface feature of the individual patient body part. The operation 6205 includes receiving data indicative of an activity or action performed proximate to the present-location landmark subsurface feature.

Figure 127:
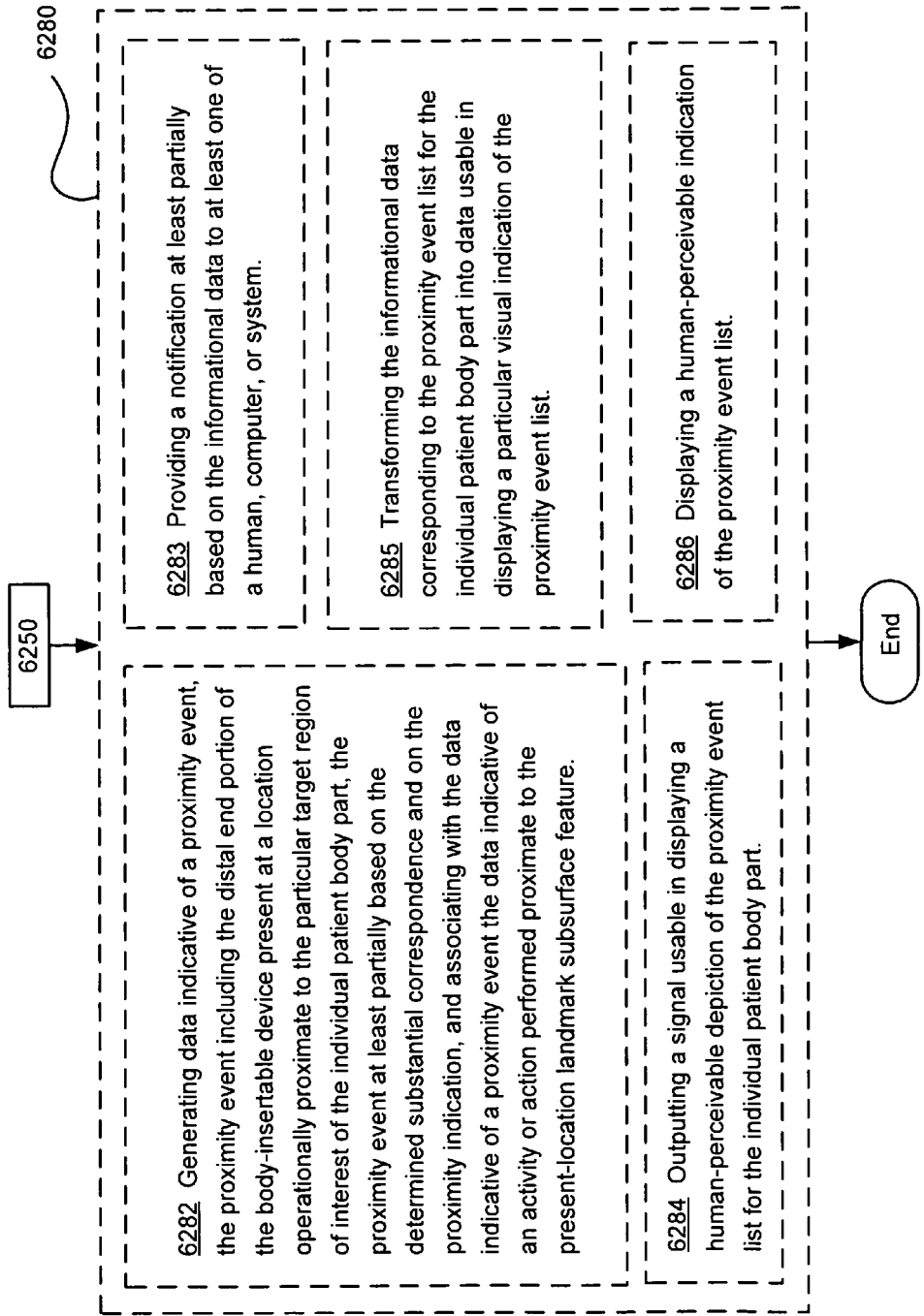
FIG. 127 illustrates an alternative embodiment of the operational flow of FIG. 123.

FIG. 127 illustrates an alternative embodiment of the operational flow 6200. The operational flow may include at least one additional embodiment 6280. The at least one additional embodiment 6280 may include an operation 6282, an operation 6283, an operation 6284, an operation 6285, or an operation 6286. The operation 6282 includes generating data indicative of a proximity event. The proximity event includes the distal end portion of the body-insertable device present at a location operationally proximate to the particular target region of interest of the individual patient body part. The proximity event is at least partially based on the determined substantial correspondence and on the proximity indication. The operation 6282 also includes associating with the data indicative of a proximity event the data indicative of an activity or action performed proximate to the present-location landmark subsurface feature. The operation 6283 includes providing a notification at least partially based on the informational data to at least one of a human, computer, or system. The operation 6284 includes outputting a signal usable in displaying a human-perceivable depiction of the proximity event list for the individual patient body part. For example, the depiction may include an audio depiction, or a visual depiction of the proximity event list. For example, the depiction of the proximity event list may include a depiction of a distance, or a depiction of an orientation. The operation 6285 includes transforming the informational data corresponding to the proximity event list for the individual patient body part into data usable in displaying a particular visual indication of the proximity event list. The operation 6286 includes displaying a human-perceivable indication of the proximity event list.

FIG. 128 illustrates an example computer program product 6300. The computer program product includes a computer-readable computer storage medium 6310 bearing program instructions 6320. The program instructions, when executed by a processor of a computing device, cause the computing device to perform a process. The process includes determining a substantial correspondence between (x) a present-location landmark subsurface feature of a body part of an individual patient and (y) a candidate reference landmark subsurface feature of the individual patient body part. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part. The process includes generating a proximity indication if the first spatial relationship is not greater than an operational reach of the distal end portion of the body-insertable device. The process includes generating data indicative of a proximity event. The proximity event includes the distal end portion of the body-insertable device present at a location operationally proximate to the particular target region of interest of the individual patient body part. The proximity event is at least partially based on the determined substantial correspondence and on the proximity indication. The process includes adding the proximity event to a proximity event list for the individual patient body part. The process includes storing in another computer-readable media operably coupled with the processor informational data corresponding to the proximity event list for the individual patient body part.

In an alternative embodiment of the program instructions 6320, the determining process includes 6322 determining a substantial correspondence between (x) a present-location landmark subsurface feature of a body part of an individual patient and (y) a candidate reference landmark subsurface feature of the individual patient body part. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part. The candidate reference landmark subsurface feature is selected from a patient examination table that includes the at least two reference landmark subsurface features of the individual patient body part. Each candidate reference landmark subsurface feature of the at least two candidate reference landmark subsurface features has a respective spatial relationship to a respective particular selected target region of interest.

In an embodiment, the computer-readable media 6310 includes a tangible computer-readable media 6312. In an embodiment, the computer-readable media includes a communications medium 6314.

FIG. 129 illustrates an alternative embodiment of the program instructions 6320. In an embodiment, the process further includes 6324 receiving the patient examination table. In an embodiment, the process further includes 6326 outputting the informational data. The process further includes 6328 transforming the informational data into signal usable in providing a particular visual depiction of the proximity event list for the individual patient body part. The process further includes 6332 providing a notification that is at least partially based on the informational data to at least one of a human, computer, or system.

Figure 130:
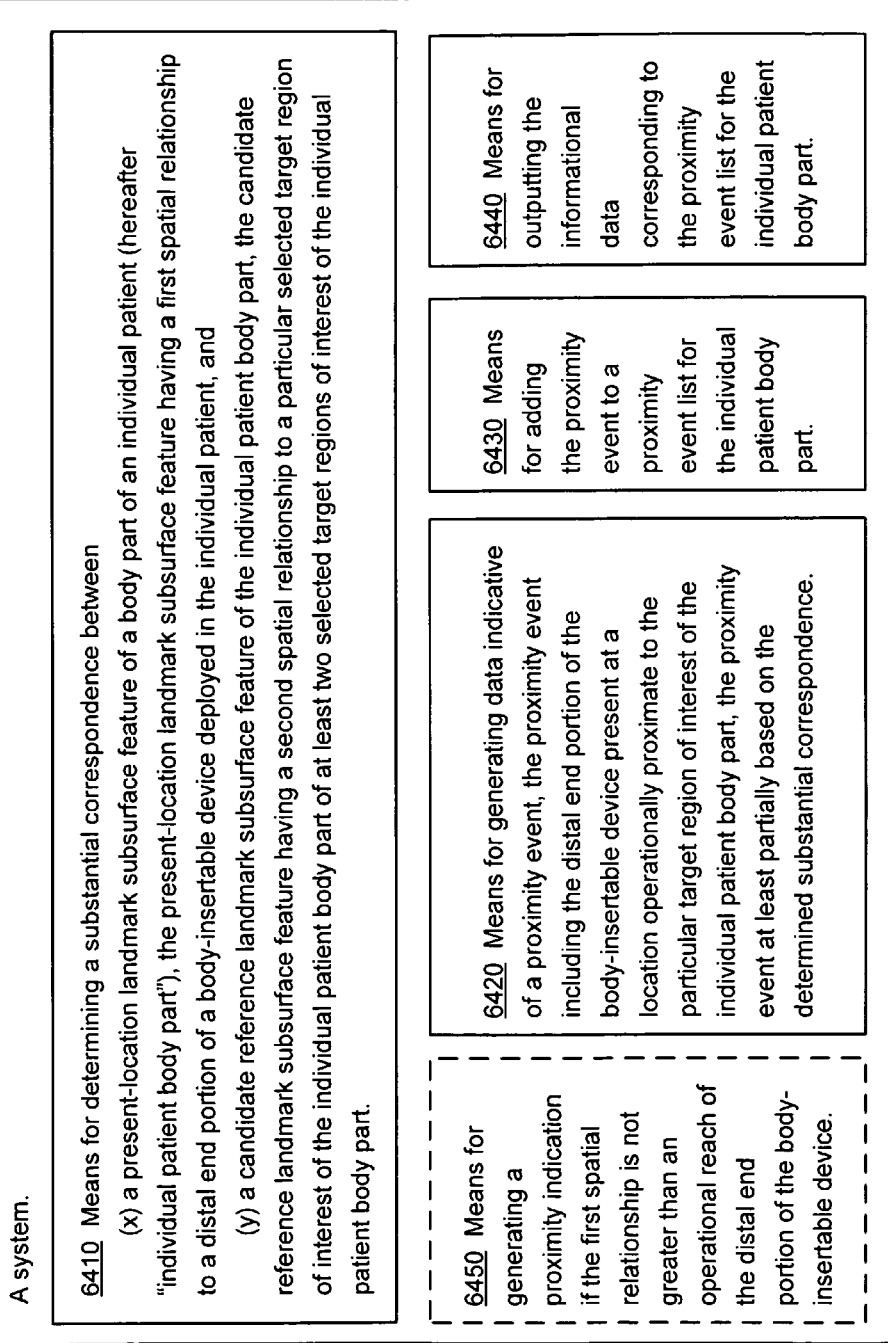
FIG. 130 illustrates an example system.

FIG. 130 illustrates an example system 6400. The system includes means 6410 for determining a substantial correspondence between (x) a present-location landmark subsurface feature of a body part of an individual patient and (y) a candidate reference landmark subsurface feature of the individual patient body part. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part. The system includes means 6420 for generating data indicative of a proximity event. The proximity event includes the distal end portion of the body-insertable device present at a location operationally proximate to the particular target region of interest of the individual patient body part. The proximity event is at least partially based on the determined substantial correspondence. The system includes means 6430 for the proximity event to a proximity event list for the individual patient body part. The system includes means 6440 for outputting the informational data corresponding to the proximity event list for the individual patient body part.

Returning to FIG. 122, FIG. 122 illustrates an alternative embodiment of the system 6120. The alternative embodiment of the system includes the receiver circuit 6122 configured to receive (i) a first reference image that includes a present-location landmark subsurface feature of a body part of an individual patient (hereafter "individual patient body part"). The present-location landmark subsurface feature has a first spatial relationship to a distal end portion of a body-insertable device deployed in the individual patient. The receiver circuit is also configured to receive a second reference image that includes a candidate reference landmark subsurface feature of the individual patient body part. The candidate reference landmark subsurface feature has a second spatial relationship to a particular selected target region of interest of the individual patient body part of at least two selected target regions of interest of the individual patient body part. The alternative embodiment of the system includes the feature matching circuit 6124 configured to determine a substantial correspondence between (x) the present-location landmark subsurface feature and (y) the candidate reference landmark subsurface feature. The alternative embodiment of the system includes the event data circuit 6128 configured to generate data indicative of an occurrence of a proximity event. The occurrence of the proximity event includes the distal end portion of the body-insertable device being present at a location operationally proximate to the particular target region of interest of the individual patient body part. The occurrence of the proximity event is at least partially based on the determined substantial correspondence. The alternative embodiment of the system includes the list management circuit 6134 configured to add the proximity event to a proximity event list for the individual patient body part. The alternative embodiment of the system includes the communication circuit 6142 configured to output informational data corresponding to the proximity event list.

In an embodiment of the alternative embodiment of the system 6120, the candidate reference landmark subsurface feature of the individual patient body part is selected from a patient examination table that includes the at least two reference landmark subsurface features of the individual patient body part. Each candidate reference landmark subsurface feature of the at least two candidate reference landmark subsurface features has a respective spatial relationship to a respective particular selected target region of interest. In an embodiment of the alternative embodiment of the system, the patient examination table is at least partially based on a virtual colonoscopy of the individual patient. In an embodiment of the alternative embodiment of the system, the patient examination table is at least partially based on a subsurface feature atlas configured for the individual patient. In an embodiment of the alternative embodiment of the system, the patient examination table is configured to facilitate an interested party to test, diagnose, or treat a possible medical condition of the individual patient.

In an embodiment of the alternative embodiment of the system 6120, the receiver circuit is configured to receive (i) a first reference image that includes a present-location landmark subsurface feature of a body part of an individual patient; (ii) a second reference image that includes a candidate reference landmark subsurface feature of the individual patient body part; and (iii) activity data indicative of a medical activity or action performed by the body-insertable device proximate to the present-location landmark subsurface feature. The present-location landmark subsurface feature has a first spatial relationship to a distal end portion of a body-insertable device deployed in the individual patient. The candidate reference landmark subsurface feature has a second spatial relationship to a particular selected target region of interest of the individual patient body part of at least two selected target regions of interest of the individual patient body part. The activity data may be acquired by the body-insertable device 4480, by another device, such as the ex vivo device 290, an activity data generator circuit [not illustrated], or by a user illustrated as the person 296, such as a health care provider, entering the activity data using the computing device 292 for direct reception by the receiver circuit 6122 or for reception by the activity data generator for processing and provision to the receiver circuit. For example, the activity data may include activity data indicative of an activity or action performed by the distal end portion of the body-insertable device while located operationally proximate to the present-location landmark subsurface feature. For example, the activity data may include activity data indicative of an activity or action performed by a device other than the body-insertable device while located operationally proximate to the present-location landmark subsurface feature. For example, the activity data may include activity data indicative of a therapeutic activity or action performed proximate to the present-location landmark subsurface feature. For example, the activity data may include activity data indicative of a treatment activity or action performed proximate to the present-location landmark subsurface feature. For example, the activity data may include activity data indicative of a maneuvering by the distal end portion of the body-insertable device while located operationally proximate to the present-location landmark subsurface feature. For example, the activity data may include activity data indicative of an activity or action performed proximate to the present-location landmark subsurface feature, the data includes a time stamp. For example, a time stamp may include a sequence of characters denoting the date and/or time at which the activity or action was performed. For example, the activity data may include activity data indicative of an absence of an activity or action by the distal end portion of the body-insertable device while located operationally proximate to the present-location landmark subsurface feature.

In an embodiment of the alternative embodiment of the system 6120, the event data circuit 6128 includes an event data circuit configured to generate data indicative of an occurrence of a proximity event. The occurrence of the proximity event includes the distal end portion of the body-insertable device being present at a location operationally proximate to the particular target region of interest of the individual patient body part. The occurrence of the proximity event is at least partially based on (i) the determined substantial correspondence, (ii) the proximity indication, and (iii) the activity data.

In an embodiment of the alternative embodiment of the system 6120, the receiver circuit 6122 is further configured to receive a patient examination table that includes at least two reference landmark subsurface features of the individual patient body part. Each reference landmark subsurface feature of the at least two reference landmark subsurface features has a respective spatial relationship to a respective particular target region of interest.

In an embodiment of the alternative embodiment of the system 6120, the system includes the proximity indicator circuit 6132 configured to generate a proximity indication if the first spatial relationship is not greater than an operational reach of the distal end portion of the body-insertable device. In an embodiment of the alternative embodiment of the system, the event data circuit 6128 is configured to generate data indicative of an occurrence of a proximity event. The occurrence of the proximity event includes the distal end portion of the body-insertable device being present at a location operationally proximate to the particular target region of interest of the individual patient body part. The occurrence of the proximity event is at least partially based on the determined substantial correspondence and on the proximity indication.

Figure 131:
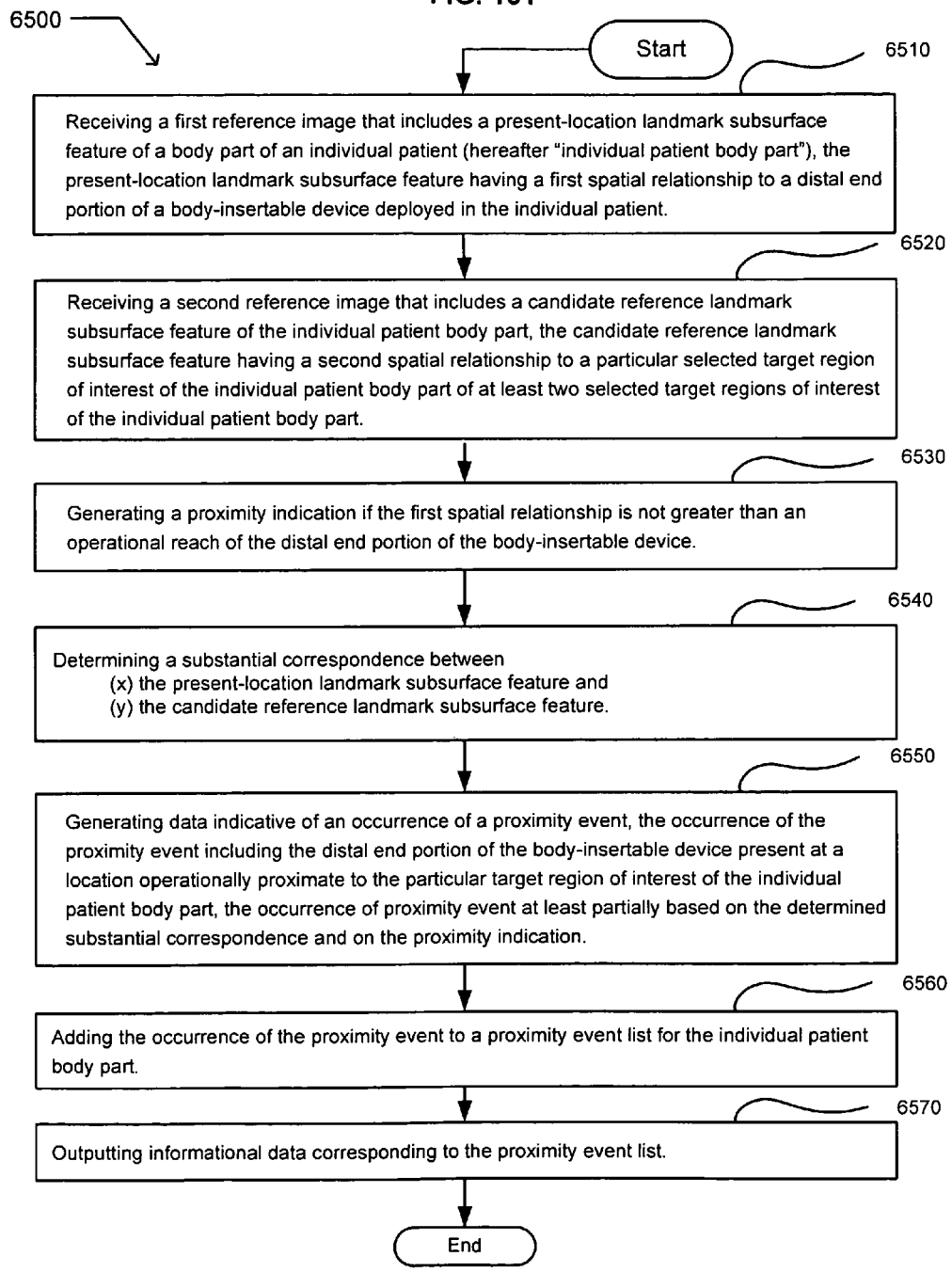
FIG. 131 illustrates an example operational flow.

FIG. 131 illustrates an example operational flow 6500. The operational flow includes a start operation. The operational flow includes a first reception operation 6510. The first reception operation includes receiving a first reference image that includes a present-location landmark subsurface feature of a body part of an individual patient (hereafter "individual patient body part"). The present-location landmark subsurface feature has a first spatial relationship to a distal end portion of a body-insertable device deployed in the individual patient. A second reception operation 6520 includes receiving a second reference image that includes a candidate reference landmark subsurface feature of the individual patient body part. The candidate reference landmark subsurface feature has a second spatial relationship to a particular selected target region of interest of the individual patient body part of at least two selected target regions of interest of the individual patient body part. In an embodiment, the first reception operation or the second reception operation may be implemented using the receiver circuit 6122 described in conjunction with FIG. 121. A nearness operation 6530 includes generating a proximity indication if the first spatial relationship is not greater than an operational reach of the distal end portion of the body-insertable device. In an embodiment, the nearness operation may be implemented using the proximity indicator circuit 6132 described in conjunction with FIG. 122. A matching operation 6540 includes determining a substantial correspondence between (x) the present-location landmark subsurface feature and (y) the candidate reference landmark subsurface feature. In an embodiment, the matching operation may be implemented using the feature matching circuit 6124 described in conjunction with FIG. 122. A reporting operation 6550 includes generating data indicative of an occurrence of a proximity event. The occurrence of the proximity event includes the distal end portion of the body-insertable device being present at a location operationally proximate to the particular target region of interest of the individual patient body part. The occurrence of the proximity event is at least partially based on the determined substantial correspondence and on the proximity indication. In an embodiment, the reporting operation may be implemented using the event data circuit 6128 described in conjunction with FIG. 122. A list management operation 6560 includes adding the occurrence of the proximity event to a proximity event list for the individual patient body part. In an embodiment, the list management operation may be implemented using the list management circuit 6134 described in conjunction with FIG. 122. A communication operation 6570 includes outputting informational data corresponding to the proximity event list. In an embodiment, the communication operation may be implemented using the communication circuit 6142 described in conjunction with FIG. 122. The operational flow includes an end operation.

Figure 132:
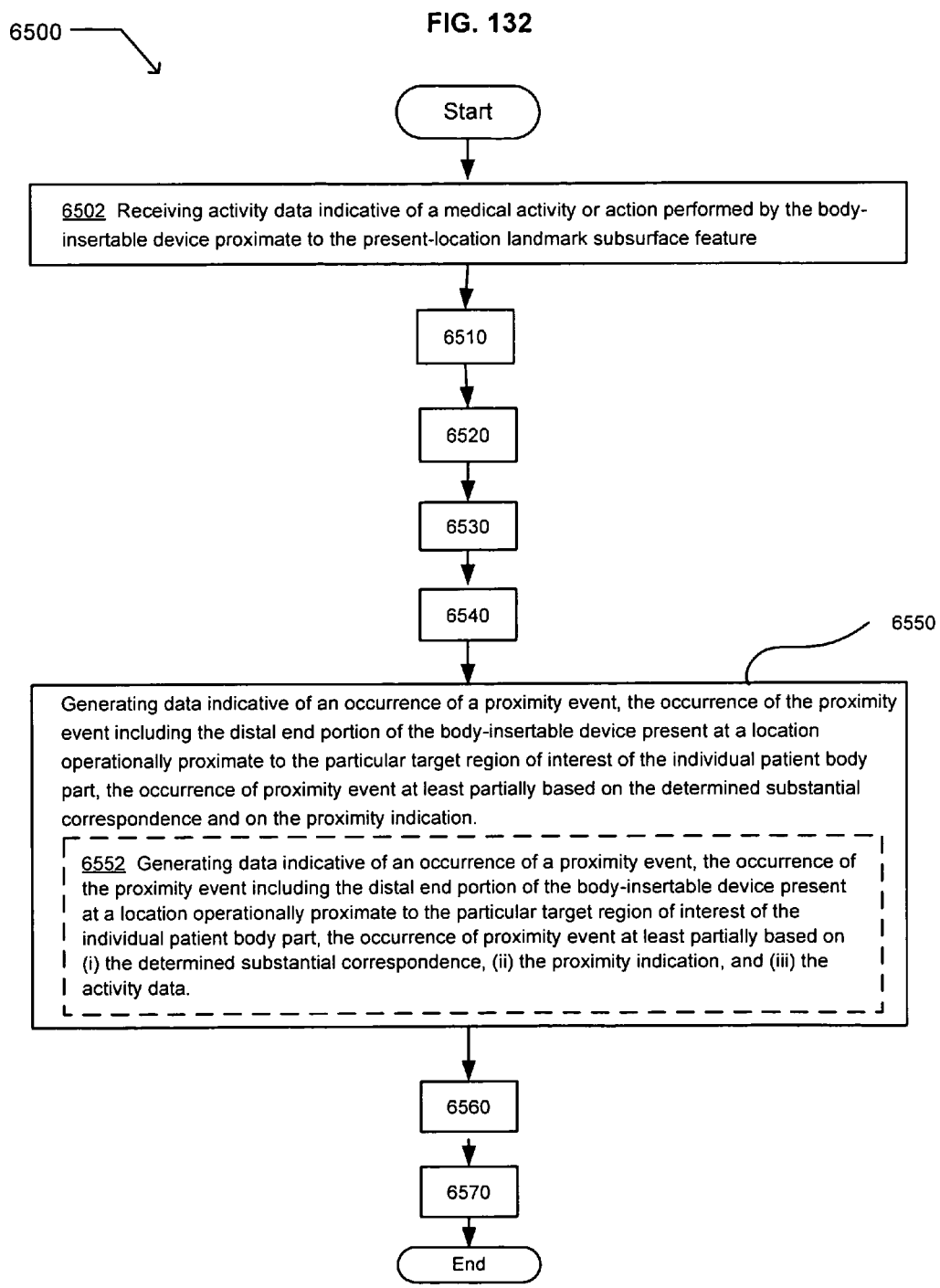
FIG. 132 illustrates an alternative embodiment of the operational flow of FIG. 131.

FIG. 132 illustrates an alternative embodiment of the operational flow 6500 of FIG. 131. The operational flow may include at least one additional operation, such as an operation 6502. The operation 6502 includes receiving activity data indicative of a medical activity or action performed by the body-insertable device proximate to the present-location landmark subsurface feature. In an embodiment, the reporting operation 6550 may include at least one additional operation, such as an operation 6552. The operation 6552 includes generating data indicative of an occurrence of a proximity event. The occurrence of the proximity event includes the distal end portion of the body-insertable device being present at a location operationally proximate to the particular target region of interest of the individual patient body part. The occurrence of the proximity event is at least partially based on (i) the determined substantial correspondence, (ii) the proximity indication, and (iii) the activity data.

In an embodiment, the candidate reference landmark subsurface feature of the individual patient body part is selected from a patient examination table that includes the at least two reference landmark subsurface features of the individual patient body part, each candidate reference landmark subsurface feature of the at least two candidate reference landmark subsurface features having a respective spatial relationship to a respective particular selected target region of interest. In an embodiment, the patient examination table is at least partially based on a virtual colonoscopy of the individual patient. In an embodiment, the patient examination table is at least partially based on a subsurface feature atlas configured for the individual patient. In an embodiment, the patient examination table is configured to facilitate an interested party to test, diagnose, or treat a possible medical condition of the individual patient.

FIG. 133 illustrates an example computer program product 6600. The computer program product includes a computer-readable computer storage medium 6610 bearing program instructions 6620. The program instructions, when executed by a processor of a computing device, cause the computing device to perform a process. The process includes receiving a first reference image that includes a present-location landmark subsurface feature of a body part of an individual patient. The present-location landmark subsurface feature has a first spatial relationship to a distal end portion of a body-insertable device deployed in the individual patient. The process includes receiving a second reference image that includes a candidate reference landmark subsurface feature of the individual patient body part. The candidate reference landmark subsurface feature has a second spatial relationship to a particular selected target region of interest of the individual patient body part of at least two selected target regions of interest of the individual patient body part. The process includes generating a proximity indication if the first spatial relationship is not greater than an operational reach of the distal end portion of the body-insertable device. The process includes determining a substantial correspondence between (x) present-location landmark subsurface feature and (y) the candidate reference landmark subsurface feature. The process includes generating data indicative of an occurrence of a proximity event. The occurrence of the proximity event includes the distal end portion of the body-insertable device being present at a location operationally proximate to the particular target region of interest of the individual patient body part. The occurrence of the proximity event is at least partially based on the determined substantial correspondence and on the proximity indication. The process includes adding the proximity event to a proximity event list for the individual patient body part. The process includes outputting informational data corresponding to the proximity event list.

FIG. 134 illustrates an example environment 6700. The environment includes the mammalian body part 210 of a known patient, illustrated as a mammal 6705, a person presenting 6707, and a system 6720. For example and without limitation, the system uses a distinctive landmark subsurface feature of a body part of a known patient to verify that a person presenting themselves for treatment or health care is the known patient. The system includes a receiver circuit 6722 configured to receive a first reference image that includes a representation of a distinctive landmark subsurface feature of a body part of a known patient. The first reference image was acquired by the body-insertable device 280 deployed in a body part 210 of the known patient. For example, a known patient includes one who has previously received or requested medical treatment. For example, the distinctive landmark subsurface feature may include a physical structure, nerve, void, border, component, tissue, structural feature, or density variation of the body part. For example, the physical structure may include a duct, a bend or curve in a tubular structure, or an organ such as a colon. For example, a distinctive landmark subsurface feature may include a landmark subsurface unique to the known patient, much like a finger print is considered unique to a person. For example, a distinctive landmark subsurface feature may include a landmark subsurface that occurs infrequently or rarely, such a degree of distinctiveness as may be necessary to impart a reasonable degree of confidence as a useful tool in distinguishing between persons likely to present themselves.

The receiver circuit 6722 is also configured to receive a second reference image that includes a representation of a contemporaneously acquired landmark subsurface feature of a body part of a person presenting. The second reference image was acquired by another body-insertable device deployed in a body part of the person presenting. The body part of the known patient and the body part of the person presenting are the same kind of body part. For example, the kind of body part of the known patient and the person presenting may be the colon. For example, the kind of body part of the known patient and the person presenting may be the stomach. For example, a contemporaneously acquired landmark subsurface feature may include a landmark subsurface feature acquired when a patient presents themselves to a heath care provider or facility at an appointed time for treatment or diagnosis.

The system 6720 includes a feature matching circuit 6724 configured to determine a substantial correspondence between (x) the distinctive landmark subsurface feature of a body part of a known patient and (y) the contemporaneously-acquired landmark subsurface feature of a body part of a person presenting. The system includes a data circuit 6728 is configured to generate informational data indicative of a verification of the person presenting with respect to the known patient. The verification is at least partially based on the determined substantial correspondence between the distinctive landmark subsurface feature and the contemporaneously-acquired landmark subsurface feature. For example, the system treats a determination of a substantial correspondence as an indication that the distinctive landmark subsurface feature and the contemporaneously-acquired landmark subsurface feature are the same landmark subsurface feature, and infers that the person presenting is the known patient. If a substantial correspondence is determined, the system generates informational data indicative of a verification of the person presenting with respect to the known patient. The system includes a communications circuit 6742 configured to output the informational data corresponding to the verification of the person presenting with respect to the known patient. The informational data may be presented to the health care provider or their staff for use in deciding whether to treat the person presenting.

In an embodiment, the reference landmark subsurface feature includes a reference landmark subsurface feature of the cavity or lumen 211 of the body part 210 of the known patient 6705. In an embodiment, the reference landmark subsurface feature includes a reference landmark subsurface feature of a body part of a known patient designated for an evaluation, test, diagnosis, or treatment of a possible medical condition. In an embodiment, the known patient includes a patient scheduled or expected for an evaluation, test, diagnosis, or treatment of a possible medical condition. For example, a known patient may include a patient scheduled for removal of a polyp from their colon. In an embodiment, the contemporaneously acquired landmark subsurface feature of a body part of a person presenting 6707 themselves for the evaluation, test, diagnosis, or treatment of a possible medical condition. In an embodiment, the reference landmark subsurface feature includes a reference landmark subsurface feature of a body part of a known patient, and acquired from an electronically maintained record of the known patient. In an embodiment, the reference landmark subsurface feature includes a reference landmark subsurface feature of a body part of a known patient, and acquired from an electronically maintained landmark subsurface feature library of the known patient. In an embodiment, the reference landmark subsurface feature includes a reference landmark subsurface feature of a body part of a known patient, and acquired from an electronically maintained landmark subsurface feature atlas of the known patient. In an embodiment, the reference landmark subsurface feature includes a reference landmark subsurface feature included in a digital image of a body part of a known patient. In an embodiment, the reference landmark subsurface feature includes a reference landmark subsurface feature of a body part of a known patient included in a digital image acquired by a body-insertable device has a portion deployed in the cavity or lumen of the body part of the known patient.

In an embodiment, the contemporaneously acquired landmark subsurface feature includes a contemporaneously acquired landmark subsurface feature of the body part 210 of a person currently presenting 6707. In an embodiment, the contemporaneously acquired landmark subsurface feature includes a contemporaneously acquired landmark subsurface feature of a body part of a person currently presenting themselves for an evaluation, test, diagnosis, or treatment of a possible medical condition. In an embodiment, the contemporaneously acquired landmark subsurface feature includes a contemporaneously acquired landmark subsurface feature of a body part of a person presenting themselves as the known patient. In an embodiment, the contemporaneously acquired landmark subsurface feature includes a contemporaneously acquired landmark subsurface feature of a body part of a person presenting and included in digital image. In an embodiment, the contemporaneously acquired landmark subsurface feature includes a contemporaneously acquired landmark subsurface feature of a body part of a person presenting and included in digital image acquired by a body-insertable device has a portion deployed in a cavity or lumen of the body part of the person presenting. In an embodiment, the contemporaneously acquired landmark subsurface feature includes a contemporaneously acquired landmark subsurface feature of a body part of a person presenting and included in digital image acquired by an ex vivo device.

In an embodiment, the first reference image was acquired by a body-insertable device deployed in a cavity or lumen of a body part of the known patient 6705. In an embodiment, the second reference image is acquired by another body-insertable device deployed in a cavity or lumen of a body part of the person presenting 6707. In an embodiment, the distinctive landmark subsurface feature includes a distinctive landmark subsurface feature of a cavity or lumen of a body part of a known patient. In an embodiment, the contemporaneously acquired landmark subsurface feature includes a contemporaneously acquired landmark subsurface feature of a cavity or lumen of a body part of a person presenting. In an embodiment, the distinctive landmark subsurface feature includes a distinctive landmark subsurface feature of a body part of a known patient designated for an evaluation, test, diagnosis, or treatment of a possible medical condition. For example, the known patient may be scheduled or expected for a medical procedure. In an embodiment, the contemporaneously-acquired landmark subsurface feature includes a contemporaneously-acquired landmark subsurface feature of a body part of a person presenting themselves for the evaluation, test, diagnosis, or treatment of a possible medical condition. In an embodiment, the distinctive landmark subsurface feature includes a distinctive landmark subsurface feature of a body part of a known patient. The distinctive landmark subsurface feature acquired by the system from an electronically maintained record of the known patient. In an embodiment, the distinctive landmark subsurface feature includes a distinctive landmark subsurface feature of a body part of a known patient, and acquired by the system from an electronically maintained landmark subsurface feature atlas. In an embodiment, the contemporaneously-acquired landmark subsurface feature includes a contemporaneously-acquired landmark subsurface feature of a body part of a person currently presenting for an evaluation, test, diagnosis, or treatment of a possible medical condition. In an embodiment, the contemporaneously-acquired landmark subsurface feature includes a contemporaneously-acquired landmark subsurface feature of a body part of a person presenting themselves as the known patient.

In an embodiment, the data circuit 6728 is configured to generate informational data indicative of a patient verification. The patient verification includes a verification of the person presenting 6707 with respect to the known patient 6705. The patient verification is at least partially based on the determined substantial correspondence between the reference landmark subsurface feature and the contemporaneously acquired landmark subsurface feature. Otherwise, the data circuit is configured to generate informational data indicative of an absence of a verification of the person presenting with respect to the known patient. The absence of a verification is at least partially based on an absence of a determined substantial correspondence between the reference landmark subsurface feature and the contemporaneously acquired landmark subsurface feature. In an embodiment, the communications circuit 6742 is configured to output the informational data indicative of a verification of the person presenting with respect to the known patient, or to output the informational data indicative of an absence of a verification of the person presenting with respect to the known patient. The notification corresponding to the verification of the person presenting 6707 with respect to the known patient 6705.

In an embodiment, the communication circuit 6742 includes a communication circuit configured to provide a notification that is at least partially based on the informational data to at least one of a human, computer, or system. In an embodiment, the system 6720 includes a computer-readable media 235 configured to maintain the informational data. In an embodiment, the system 6720 includes communication device 292 configured to display a human-perceivable depiction of the informational data.

In an embodiment, the body-insertable device 280 and the another body-insertable device are substantially the same type of body-insertable device. In an embodiment, the body-insertable device and the another body-insertable device are a substantially different type of body-insertable device.

FIG. 135 illustrates an example operational flow 6800. The operational flow includes a start operation. The operational flow includes a first reception operation 6810. The first reception operation includes receiving a first reference image that includes a representation of a distinctive landmark subsurface feature of a body part of a known patient. The first reference image is acquired by a body-insertable device deployed in a body part of the known patient. A second reception operation 6820 includes receiving a second reference image that includes a representation of a contemporaneously acquired landmark subsurface feature of a body part of a person presenting. The second reference image is acquired by another body-insertable device deployed in a body part of the person presenting. The body part of the known patient and the body part of the person presenting being the same kind of body part. In an embodiment, the first reception operation or the second reception operation may be implemented using the receiver circuit 6722 described in conjunction with FIG. 134. A matching operation 6830 includes determining a substantial correspondence between (x) the distinctive landmark subsurface feature of a body part of a known patient and (y) the contemporaneously-acquired landmark subsurface feature of a body part of a person presenting. In an embodiment, the matching operation may be implemented using the feature matching circuit described in conjunction with FIG. 134. A patient verification operation 6840 includes generating informational data indicative of a verification of the person presenting with respect to the known patient. The patient verification is at least partially based on the determined substantial correspondence between the distinctive landmark subsurface feature and the contemporaneously-acquired landmark subsurface feature. In an embodiment, the verification operation may be implemented using the data circuit 6728 described in conjunction with FIG. 134. A communication operation 6850 includes outputting the informational data. The communication operation may be implemented using the communication circuit 6742 described in conjunction with FIG. 134. The operational flow includes an end operation.

Figure 136:
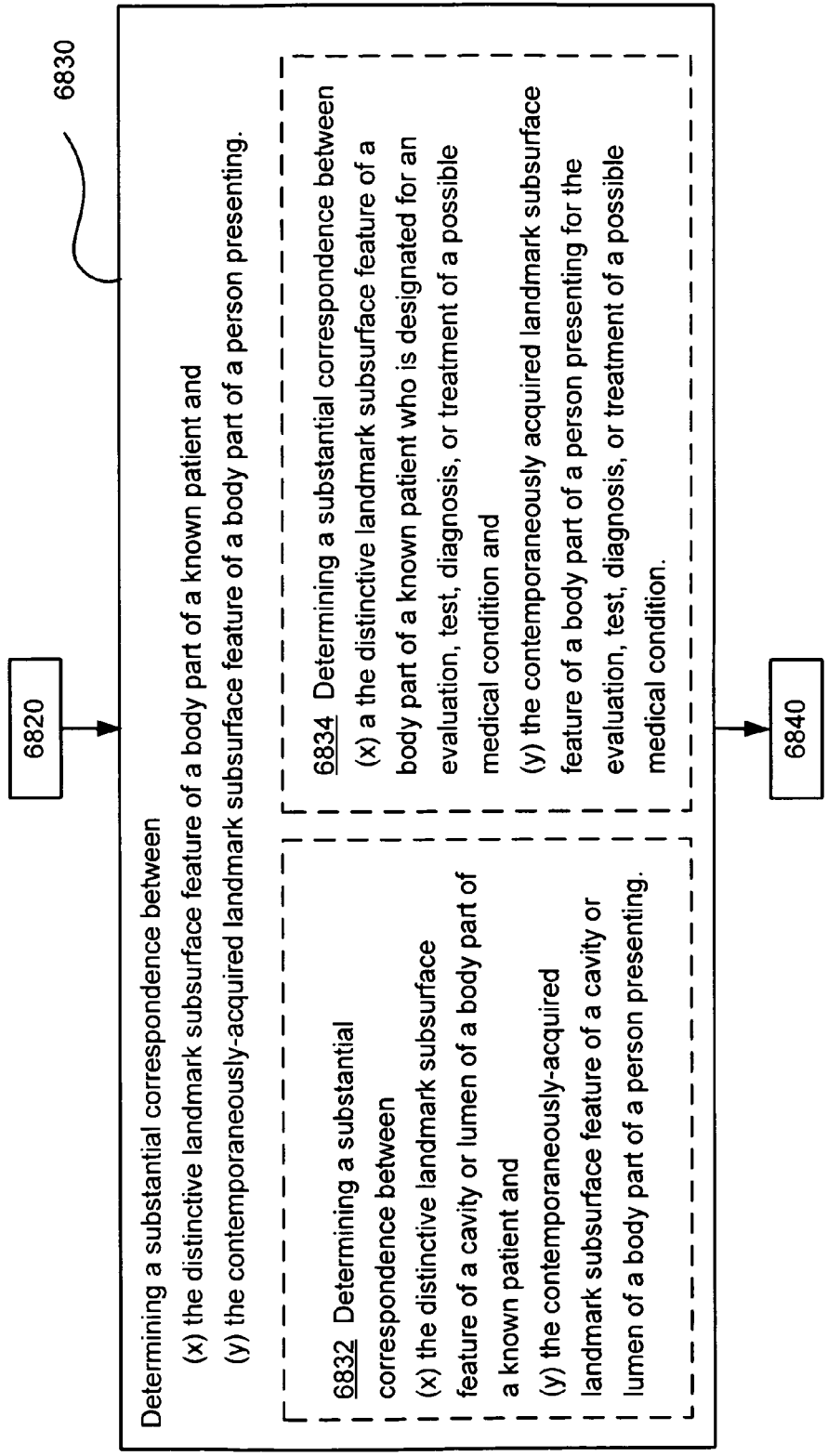
FIG. 136 illustrates an alternative embodiment of the operational flow 6700 of FIG. 134.

FIG. 136 illustrates an alternative embodiment of the operational flow 6800 of FIG. 135. In an embodiment, the patient verification operation 6830 may include at least one additional embodiment. The at least one additional embodiment may include an operation 6832 or an operation 6834. The operation 6832 includes determining a substantial correspondence between (x) the distinctive landmark subsurface feature of a cavity or lumen of a body part of a known patient and (y) the contemporaneously-acquired landmark subsurface feature of a cavity or lumen of a body part of a person presenting. The operation 6834 includes determining a substantial correspondence between (x) the distinctive landmark subsurface feature of a body part of a known patient who is designated for an evaluation, test, diagnosis, or treatment of a possible medical condition and (y) the contemporaneously acquired landmark subsurface feature of a body part of a person presenting for the evaluation, test, diagnosis, or treatment of a possible medical condition.

Figure 137:
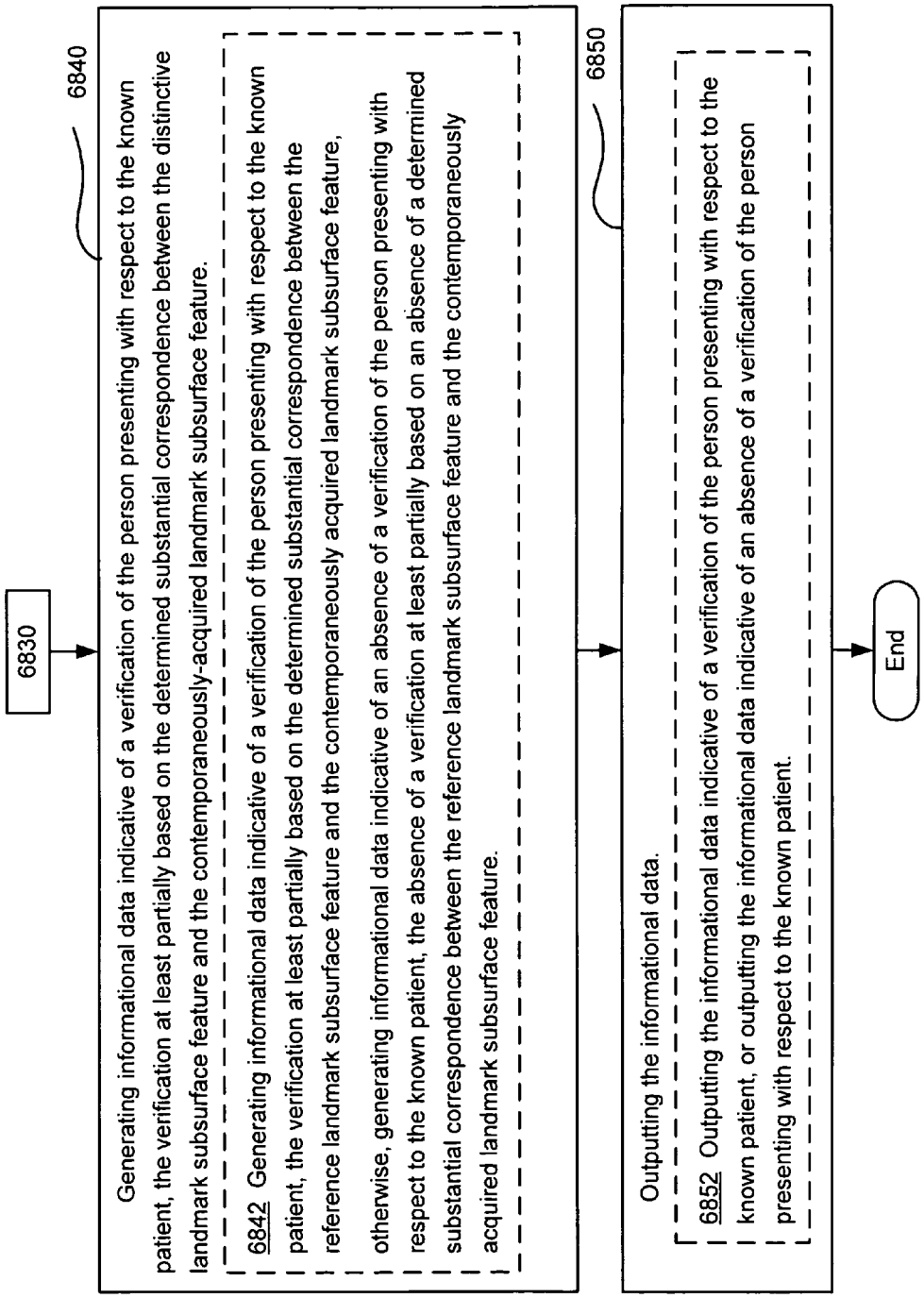
FIG. 137 illustrates an alternative embodiment of the operational flow 6600 of FIG. 133.

FIG. 137 illustrates an alternative embodiment of the operational flow 6800 of FIG. 135. In an embodiment, the patient verification operation 6840 may include at least one additional operation, such as include an operation 6842. The operation 6842 includes generating informational data indicative of a verification of the person presenting with respect to the known patient; the verification is at least partially based on the determined substantial correspondence between the reference landmark subsurface feature and the contemporaneously acquired landmark subsurface feature—otherwise, generating informational data indicative of an absence of a verification of the person presenting with respect to the known patient; the absence of a verification is at least partially based on an absence of a determined substantial correspondence between the reference landmark subsurface feature and the contemporaneously acquired landmark subsurface feature. In this alternative embodiment, the communication operation 6850 may include at least one additional operation, such as an operation 6852. The operation 6852 includes outputting the informational data indicative of a verification of the person presenting with respect to the known patient, or outputting the informational data indicative of an absence of a verification of the person presenting with respect to the known patient.

Figure 138:
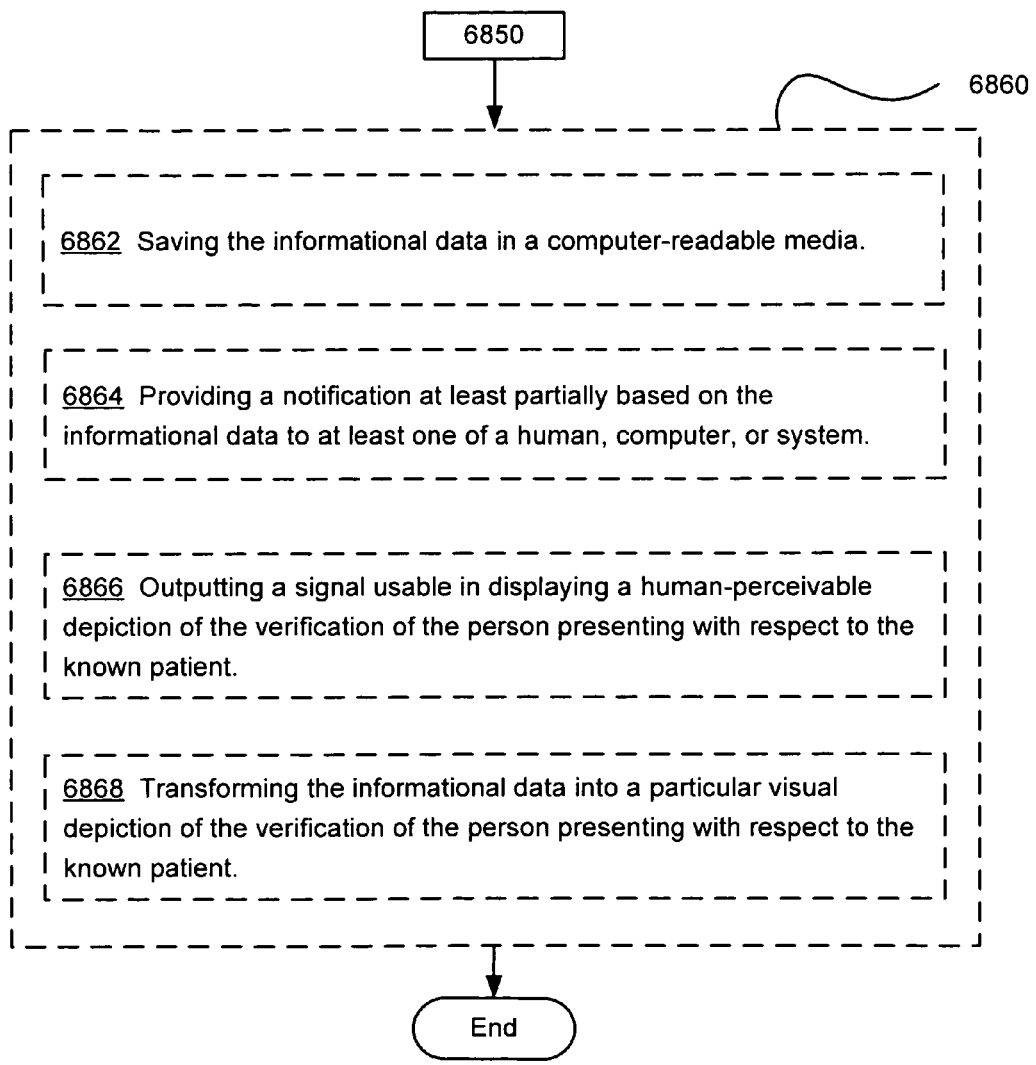
FIG. 138 illustrates an alternative embodiment of the operational flow 6600 of FIG. 133.

FIG. 138 illustrates an alternative embodiment of the operational flow 6800 of FIG. 135. In an embodiment, the operational flow 6800 may include at least one additional operation. The at least one additional operation is illustrated as operation 6860. The operation 6860 may include an operation 6862, an operation 6864, an operation 6866, or an operation 6868. The operation 6862 includes saving the informational data in a computer-readable media. The 6864 includes providing a notification that is at least partially based on the informational data to at least one of a human, computer, or system. The operation 6866 includes outputting a signal usable in displaying a human-perceivable depiction of the verification of the person presenting with respect to the known patient. The operation 6868 includes transforming the informational data into a particular visual depiction of the verification of the person presenting with respect to the known patient.

FIG. 139 illustrates a computer program product 6900. The computer program product includes a computer-readable media 6910 bearing the program instructions 6920. The program instructions, when executed by a processor of a computing device, cause the computing device to perform a process. The process includes receiving a first reference image that includes a representation of a distinctive landmark subsurface feature of a body part of a known patient. The first reference image was acquired by a body-insertable device deployed in a body part of the known patient. The process includes receiving a second reference image that includes a representation of a contemporaneously acquired landmark subsurface feature of a body part of a person presenting. The second reference image was acquired by another body-insertable device deployed in a body part of the person presenting, the body part of the known patient and the body part of the person presenting being the same kind of body part. The process includes determining a substantial correspondence between (x) the distinctive landmark subsurface feature of a body part of a known patient and (y) the contemporaneously-acquired landmark subsurface feature of a body part of a person presenting. The process includes generating informational data indicative of a verification of the person presenting with respect to the known patient. The verification is at least partially based on the determined substantial correspondence between the distinctive landmark subsurface feature and the contemporaneously-acquired landmark subsurface feature. The process includes outputting the informational data.

In an embodiment, the process of generating informational data includes 6922 generating informational data indicative of a verification of the person presenting with respect to the known patient; the verification is at least partially based on the determined substantial correspondence between the reference landmark subsurface feature and the contemporaneously acquired landmark subsurface feature—otherwise, generating informational data indicative of an absence of a verification of the person presenting with respect to the known patient, the absence of a verification is at least partially based on an absence of a determined substantial correspondence between the reference landmark subsurface feature and the contemporaneously acquired landmark subsurface feature. In this embodiment, the process of outputting the informational data may include 6924 outputting the informational data indicative of a verification of the person presenting with respect to the known patient, or outputting the informational data indicative of an absence of a verification of the person presenting with respect to the known patient.

In an embodiment, the program instructions 6920 may cause the computing device to perform an additional process. The additional process may include a process 6932, a process 6934, a process 6936, or a process 6938. The process 6932 includes providing a notification that is at least partially based on the informational data to at least one of a human, computer, or system. The process 6934 includes outputting a signal usable in displaying a human-perceivable depiction of the verification of the person presenting with respect to the known patient. The process 6936 includes transforming the informational data into a signal usable in displaying a particular visual depiction of the verification of the person presenting with respect to the known patient. The process 6938 includes storing in another computer-readable media operably coupled with the processor informational data corresponding to the verification of the person presenting with respect to the known patient.

In an embodiment, the computer-readable media 6910 includes a tangible computer-readable media 6912. In an embodiment, the computer-readable media includes a communications media 6914.

FIG. 140 illustrates an example system 7000. The system includes means 7010 for receiving a first reference image that includes a representation of a distinctive landmark subsurface feature of a body part of a known patient. The first reference image was acquired by a body-insertable device deployed in a body part of the known patient. The system includes means 7020 for receiving a second reference image that includes a representation of a contemporaneously acquired landmark subsurface feature of a body part of a person presenting. The second reference image was acquired by another body-insertable device deployed in a body part of the person presenting. The body part of the known patient and the body part of the person presenting being the same kind of body part. The system includes means 7030 for determining a substantial correspondence between (x) the distinctive landmark subsurface feature of a body part of a known patient and (y) the contemporaneously acquired landmark subsurface feature of a body part of a person presenting. The system includes means 7040 for generating informational data indicative of a verification of the person presenting with respect to the known patient. The verification is at least partially based on the determined substantial correspondence between the distinctive landmark subsurface feature and the contemporaneously-acquired landmark subsurface feature. The system includes means 7050 for outputting the informational data.

Figure 141:
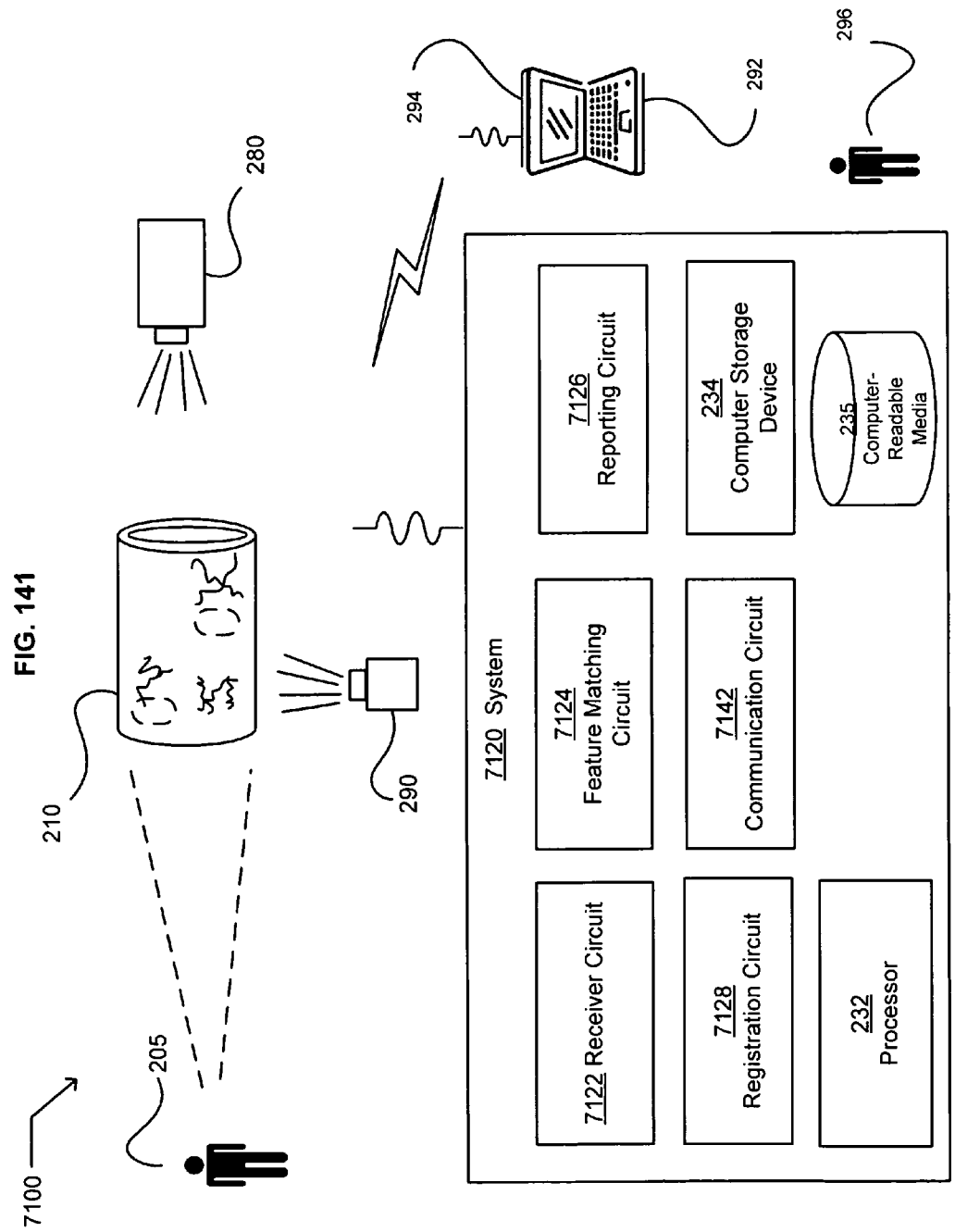
FIG. 141 illustrates an example environment.

FIG. 141 illustrates an example environment 7100. The environment includes the mammalian body part 210 of the mammal 205, and a system 7120. The system includes a receiver circuit 7122 configured to receive at least two reference images of a patient body part. Each reference image of the at least two reference images includes a respective landmark subsurface feature of the patient body part (hereafter "imaged landmark subsurface feature"). Each imaged landmark subsurface feature has a respective spatial relationship to a respective region of a surface of the patient body part imaged during a medical examination (hereafter "imaged region"). The system includes a feature matching circuit 7124 configured to determine a correspondence between (x) each atlas landmark subsurface feature of the patient body part of at least two atlas landmark subsurface features of the patient body part included in a landmark subsurface feature atlas and (y) each respective imaged landmark subsurface feature of the patient body part included in the at least two reference images. For example, the subsurface feature atlas may be substantially similar to a generated subsurface feature atlas, such as the subsurface feature atlas generated by the atlas generation circuit 3028 described in conjunction with FIG. 67, or generated by the process 3224 described in conjunction with FIG. 73 or by the mapping operation 3950 described in conjunction with FIG. 81. For example, the subsurface feature atlas may be a generally published atlas of the body part.

The system 7120 includes a reporting circuit 7126 configured to generate informational data reporting a depiction of an area of the surface of the patient body part by at least two adjacent imaged regions of the surface of the patient body part, the informational data is at least partially based on the determined correspondence. The system includes a communication circuit 7142 configured to output the informational data. For example, the determined correspondence may include a determined positive correspondence, a negative correspondence, or an absence of a determined positive correspondence.

Figure 142:
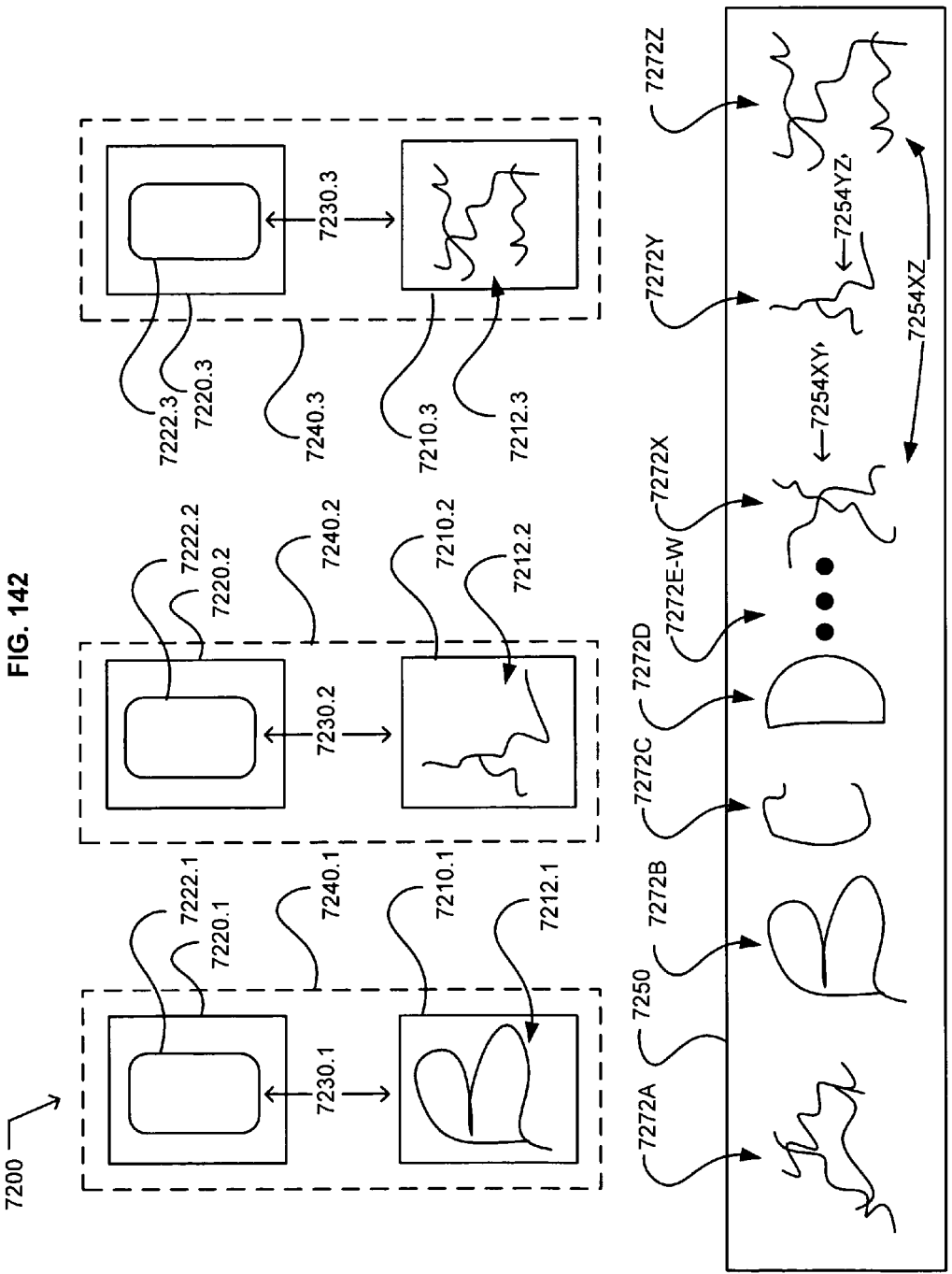
FIG. 142 illustrates an example environment.

FIG. 142 illustrates an example environment 7200 in which an embodiment of the system 7120 of FIG. 141 may be used. The example environment includes at least two reference images 7210 of a patient body part. The at least two reference images 7210 are illustrated as reference images 7210.1, 7210.2, and 7210.3. The reference images may be acquired during a course of an examination of the patient body part of a patient. Each reference image of the at least two reference images includes a respective landmark subsurface feature 7212 of the patient body part (hereafter "imaged landmark subsurface feature") has a spatial relationship to a respective imaged region of a surface of the patient body part. The respective imaged landmark subsurface features of the patient body part are illustrated as imaged landmark subsurface features of the patient body parts 7212.1, 7212.2, and 7212.3 of the reference images 7210.1, 7210.2, and 7210.3. The imaged landmark subsurface features of the patient body parts 7212.1, 7212.2, and 7212.3 have respective spatial relationships 7230.1, 7230.2, and 7230.3 with imaged regions 7222.1, 7222.2, and 7222.3 of the surface of the patient body part 210 (not shown). In an embodiment, the imaged regions 7222.1, 7222.2, and 7222.3 may be respectively included in reference images 7220.1, 7220.2, and 7220.3. In an embodiment, the imaged landmark subsurface features of the patient body part 7212.1, 7212.2, and 7212.3 having the spatial relationships 7230.1, 7230.2, and 7230.3 with imaged regions 7222.1, 7222.2, and 7222.3 of the surface of the patient body part may be respectively included in comprehensive reference images 7240.1, 7240.2, and 7240.3.

The example environment 7200 illustrates an embodiment of an example subsurface feature atlas 7250 of the patient body part 210 (not illustrated). The example subsurface feature atlas 7250 includes registered atlas subsurface features A through Z, illustrated as atlas subsurface features 7272A through 7272D, and atlas subsurface features 7272X through 7272Z. In an embodiment, the subsurface feature atlas indicates the registration of the atlas subsurface features. The registration is indicated by the respective spatial relationships illustrated between the at least two atlas subsurface features. For example, the subsurface feature atlas illustrates a spatial relationship between the atlas subsurface feature 7272X and the atlas subsurface feature 7272Z as a spatial relationship 7254XZ.

An example of an operation of an embodiment of the system 7120 may be illustrated using FIG. 142. For example, a health care provider illustrated as the person 296 may be conducting a colon examination and taking medical images that include regions of the surface of the colon (imaged regions) that are medically interesting. The health care provider may want informational data indicating which portions of the colon are included in the imaged regions, or whether they have taken medical images across a portion of the surface of the colon, or the entire surface of the colon. Alternatively, the health care provider may be taking reference images of surgical procedure sites of a surface of a colon, such as removing polyps. In this case, the health care provider may want informational data indicating which regions of the colon will be or have been the subject of surgical procedures, or if they have missed any regions.

In this example of a use of an embodiment of the system 7120, the receiver circuit 7122 receives the at least two reference images 7210 of the patient body part, which are illustrated as the reference images 7210.1, 7210.2, and 7210.3. As described above, the reference images 7210.1, 7210.2, and 7210.3 include the imaged landmark subsurface features of the patient body part 7212.1, 7212.2, and 7212.3 having the spatial relationships 7230.1, 7230.2, and 7230.3 with imaged regions 7222.1, 7222.2, and 7222.3 of the surface of the patient body part. The feature matching circuit 7124 determines a correspondence between an atlas landmark subsurface feature and an imaged landmark subsurface feature of the patient body part. For example, the feature matching circuit will determine a correspondence between the atlas landmark subsurface feature 7272A and the imaged landmark subsurface feature 7212.1. As can be seen from FIG. 142, the feature matching circuit will find a negative or no correspondence between the atlas landmark subsurface feature 7272A and the imaged landmark subsurface feature 7212.1, which may be indicated by outputting a "0". The feature matching circuit will determine a correspondence between the atlas landmark subsurface feature 7272B and the imaged landmark subsurface feature 7212.1. As can be seen from FIG. 142, the feature matching circuit will indicate a positive correspondence between the atlas landmark subsurface feature 7272B and the imaged landmark subsurface feature 7212.1, which may be indicated by a "1". The correspondence determination continues for the remaining the atlas landmark subsurface features, which as can be seen from FIG. 142, the feature matching circuit will find a negative correspondence, which may be indicated by outputting a "0" for each of the remaining atlas landmark subsurface features. The feature matching circuit may proceed iteratively through a selected portion of the subsurface feature atlas, or through the entire subsurface feature atlas determining correspondences. In an embodiment, the feature matching circuit may perform its operations in any manner that determines a correspondence between a selected range of the atlas landmark subsurface features and a selected range of the landmark subsurface features. For example, the feature matching circuit proceeds iteratively through the landmark subsurface features determining correspondences with the atlas landmark subsurface features, or may proceed iteratively through the atlas landmark subsurface features determining correspondences with the landmark subsurface features.

In this example of a use of an embodiment of the system 7120, the report circuit 7126 generates informational data that is at least partially based on the determined correspondence for at least one atlas landmark subsurface feature of the at least two atlas landmark subsurface features included in the subsurface feature atlas 7250. For example, the report circuit may generate informational data indicating one positive correspondence between the atlas landmark subsurface feature 7272B and the imaged landmark subsurface feature 7212.1. Such informational data when communicated to the health care provider may inform them they have imaged the region of the surface of the patient body part spatially related 7230.1 to atlas landmark subsurface feature 7272B. In another example, the report circuit may generate informational data indicating all negative correspondences for atlas landmark subsurface feature 7272C. Such informational data when communicated to the health care provider may inform them they have not imaged the region of the surface of the patient body part spatially related to atlas landmark subsurface feature 7272C.

In this example of a use of an embodiment of the system 7120, the communication circuit 7142 outputs the informational data. In an embodiment, the informational data may be displayed on the screen 294 of the computing device 292 to the person 296, as described in conjunction with FIG. 3. In an embodiment, the informational data may be displayed on a screen associated with the system 7120 (not shown).

Returning to FIG. 141, in an embodiment of the system 7120, the at least two reference images include at least two reference images of a patient body part having a cavity or lumen, each reference image of the at least two reference images includes a respective landmark subsurface feature of the patient body part. Each imaged landmark subsurface feature has a respective spatial relationship to a respective region of a surface of the cavity or lumen of the patient body part imaged during a medical examination. In an embodiment, the at least two reference images includes at least two reference images of a patient body part acquired by an ex vivo device. Each reference image of the at least two reference images includes a respective landmark subsurface feature of the patient body part. Each imaged landmark subsurface feature has a respective spatial relationship to a respective region of a surface of the patient body part imaged during a medical examination.

In an embodiment, each imaged landmark subsurface feature has a respective spatial relationship of less than about six centimeters to a respective region of a surface of the patient body part imaged during a medical examination. In an embodiment, each imaged landmark subsurface feature has a respective spatial relationship of less than about three centimeters to a respective region of a surface of the patient body part imaged during a medical examination. In an embodiment, each imaged landmark subsurface feature has a respective spatial relationship of less than about one centimeter to a respective region of a surface of the patient body part imaged during a medical examination. In an embodiment, each imaged landmark subsurface feature has a respective spatial relationship of less than about fifty millimeters to a respective region of a surface of the patient body part imaged during a medical examination. In an embodiment, each imaged landmark subsurface feature has a respective spatial relationship of less than about twenty-five millimeters to a respective region of a surface of the patient body part imaged during a medical examination.

In an embodiment, the reporting circuit 7126 is configured to generate informational data reporting a surface area of the patient body part collectively depicted by at least two imaged regions. The informational data is at least partially based on the determined correspondence. In an embodiment, the reporting circuit is configured to generate informational data reporting a surface area of the patient body part not collectively depicted by any imaged region. The informational data is at least partially based on the determined correspondence. In an embodiment, the reporting circuit is configured to generate informational data reporting a determined positive correspondence for at least one atlas landmark subsurface feature of the at least two atlas landmark subsurface features. The informational data is at least partially based on the determined correspondence. For example, the reporting circuit may generate informational data of a "1"—indicating a determined positive correspondence for at least one atlas landmark subsurface feature of the at least two atlas landmark subsurface features. In an embodiment, the reporting circuit is configured to generate informational data reporting a determined negative or absence of a correspondence for at least one atlas landmark subsurface feature of the at least two atlas landmark subsurface features. The informational data is at least partially based on the determined correspondence. For example, the reporting circuit may generate informational data of a "0"—indicating a determined negative or absence of a correspondence for at least one atlas landmark subsurface feature of the at least two atlas landmark subsurface features.

In an embodiment, the reporting circuit 7126 is configured to generate informational data reporting a determined positive correspondence between (x) a particular atlas landmark subsurface feature of the at least two atlas landmark subsurface features and (y) an imaged landmark subsurface feature of the patient body part. The reporting circuit is also configured to generate informational data reporting a determined negative correspondence between (x) another atlas landmark subsurface feature immediately spatially adjacent to the particular atlas landmark subsurface feature and (y) each other respective imaged landmark subsurface feature of the patient body part. An example in use of this embodiment of the reporting circuit may be illustrated in reference to FIG. 142. If the atlas landmark subsurface feature 7272Y was the particular atlas landmark subsurface feature, the informational data would indicate (i) a determined positive correspondence between the atlas landmark subsurface feature 7272Y and the imaged landmark subsurface feature 7212.2; and (ii) a determined negative correspondence between the atlas landmark subsurface 7272X feature immediately spatially adjacent to the particular atlas landmark subsurface feature 7272Y and each other respective imaged landmark subsurface feature of the patient body part. Such informational data when communicated to the health care provider may inform them that the imaged the region 7222.2 of the surface of the patient body part is spatially adjacent to an un-imaged region or regions of the surface of the patient body part.

In an embodiment, the reporting circuit 7126 is configured to generate informational data reporting a determined positive correspondence between (x) a first atlas landmark subsurface feature of the at least two atlas landmark subsurface features and (y) an imaged landmark subsurface feature. The reporting circuit is also configured to generate informational data reporting a first determined negative correspondence between (x) a second atlas landmark subsurface feature immediately spatially adjacent to the first atlas landmark subsurface feature and (y) each other respective imaged landmark subsurface feature of the patient body part. The reporting circuit is also configured to generate informational data reporting a second determined negative correspondence between (x) a third atlas landmark subsurface feature also immediately spatially adjacent to the first atlas landmark subsurface feature and (y) each other respective imaged landmark subsurface feature of the patient body part. An example in use of this embodiment the report circuit may be illustrated in reference to FIG. 142. If the atlas landmark subsurface feature 7272B was the particular atlas landmark subsurface feature, the informational data would indicate (i) a determined positive correspondence between the atlas landmark subsurface feature 7272B and the imaged landmark subsurface feature 7212.1; (ii) a determined negative correspondence between the atlas landmark subsurface 7272A feature immediately spatially adjacent to the particular atlas landmark subsurface feature 7272B and each other respective imaged landmark subsurface feature of the patient body part; and (iii) a determined negative correspondence between the atlas landmark subsurface 7272C feature also immediately spatially adjacent to the particular atlas landmark subsurface feature 7272B and each other respective imaged landmark subsurface feature of the patient body part. Such informational data when communicated to the health care provider may inform them that the imaged the region 7222.1 of the surface of the patient body part is spatially adjacent on two sides to un-imaged regions of the surface of the patient body part.

In an embodiment, the reporting circuit 7126 is configured to generate informational data reporting at least two spatially adjacent atlas landmark subsurface features respectively having a determined negative correspondence with each imaged landmark subsurface feature of the patient body part. An example in use of this embodiment of the reporting circuit may be illustrated in reference to FIG. 142. If the at least two spatially adjacent atlas landmark subsurface features include spatially adjacent atlas landmark subsurface features 7272C and 7272D, the informational data would indicate adjacent atlas landmark subsurface features 7272C and 7272D respectively have a determined negative correspondence with each imaged landmark subsurface feature of the patient body part. Such informational data when communicated to the health care provider may inform them of a zone of adjacent or contiguous un-imaged regions of the surface of the patient body part.

In an embodiment, the reporting circuit 7126 is configured to generate informational data reporting at least two spatially adjacent atlas landmark subsurface features respectively having a determined negative correspondence with each respective imaged landmark subsurface feature of the patient body part. The reporting circuit is also configured to generate informational data reporting a first determined positive correspondence between (x) a first atlas landmark subsurface feature of the at least two atlas landmark subsurface features and (y) an imaged landmark subsurface feature. The first atlas landmark subsurface feature is spatially adjacent to a terminal atlas landmark subsurface feature of the at least two spatially adjacent atlas landmark subsurface features having the determined negative correspondence. The reporting circuit is also configured to generate informational data reporting a second determined positive correspondence between (x) a second atlas landmark subsurface feature of the at least two atlas landmark subsurface features and (y) an imaged landmark subsurface feature. The second atlas landmark subsurface feature is spatially adjacent to a second terminal atlas landmark subsurface feature of the at least two spatially adjacent atlas landmark subsurface features having the determined negative correspondence. An example in use of this embodiment the report circuit may be illustrated in reference to FIG. 142. If the at least two spatially adjacent atlas landmark subsurface features include spatially adjacent atlas landmark subsurface features 7272C and 7272X, the report circuit would generate informational data indicating atlas landmark subsurface features 7272B and 7272Y are at the opposing regions of a zone of adjacent or contiguous atlas landmark subsurface features having determined negative correspondences or absence of correspondence. For example, the informational data may report [1001].

In an embodiment, the report circuit 7126 is configured to generate informational data indicative of a determined positive correspondence between an imaged landmark subsurface feature of the patient body part and at least one atlas landmark subsurface feature of the at least two atlas landmark subsurface features. In an embodiment, the report circuit is configured to generate informational data indicative of a determined negative or absence of a correspondence between an imaged landmark subsurface feature of the patient body part and each atlas landmark subsurface feature of the at least two atlas landmark subsurface features. In an embodiment, the report circuit is configured to output informational data indicative of a predicted likelihood that a surface region of the patient body part is substantially absent from the respective imaged regions of the surface of the patient body part of the at least two reference images.

In an embodiment, the subsurface feature atlas includes a subsurface feature atlas including a spatial relationship between the at least two atlas landmark subsurface features of the patient body part. For example, FIG. 142 illustrates the subsurface feature atlas 7250 indicating a spatial relationship 7254XY between atlas landmark subsurface feature 7272X and 7272Y. In an embodiment, the subsurface feature atlas includes a registration of the at least two atlas landmark subsurface features of the patient body part. In an embodiment, the subsurface feature atlas includes at least two atlas landmark subsurface features of the patient body part. The subsurface feature atlas previously prepared in connection with a testing, diagnosis, or treatment of a possible reference condition of the patient. In an embodiment, the subsurface feature atlas includes a published subsurface feature atlas including at least two atlas landmark subsurface features of the patient body part. The subsurface feature atlas is arranged in a manner facilitating a testing, diagnosis, or treatment of a possible medical condition of patients.

In an embodiment, the system 7120 includes a registration circuit 7128 configured to register a spatial relationship of the respective imaged landmark subsurface feature of each reference image of the at least two reference images. In an embodiment, the system includes the computer-readable media 235 configured to maintain the informational data. In an embodiment, the computer-readable media includes a computer-readable media configured to maintain and to provide electronic access to the informational data.

FIG. 143 illustrates an example operational flow 7300. After a start operation, the operational flow includes a reception operation 7310. The reception operation includes receiving at least two reference images of a patient body part. Each reference image of the at least two reference images includes a respective landmark subsurface feature of the patient body part (hereafter "imaged landmark subsurface feature"). Each imaged landmark subsurface feature has a respective spatial relationship to a respective region of a surface of the patient body part imaged during a medical examination (hereafter "imaged region"). In an embodiment, the reception operation may be implemented using the receiver circuit 7122 described in conjunction with FIG. 141. A matching operation 7320 includes determining a correspondence between (x) each atlas landmark subsurface feature of the patient body part of at least two atlas landmark subsurface features of the patient body part included in a landmark subsurface feature atlas of the patient body part and (y) each respective imaged landmark subsurface feature of the patient body part included in the at least two reference images. In an embodiment, the matching operation may be implemented using the feature matching circuit 7124 described in conjunction with FIG. 141. In an embodiment, the subsurface atlas may be substantially similar to the subsurface atlas 7250 described in conjunction with FIG. 142. In an embodiment, the subsurface atlas may be substantially similar to the subsurface atlas 5250 described in conjunction with FIG. 103. A surface coverage reporting operation 7330 includes generating informational data reporting a depiction of an area of the surface of the patient body part by at least two adjacent imaged regions. The informational data is at least partially based on the determined correspondence. In an embodiment, the reporting operation may be implemented using the reporting circuit 7126 described in conjunction with FIG. 141. A communication operation 7350 includes outputting the informational data. In an embodiment, the communication operation may be implemented using the communications circuit 7142 described in conjunction with FIG. 141. The operational flow includes an end operation.

In an alternative embodiment, the operational flow may include an information storage operation 7360. The information storage operation includes saving the informational data in a computer-readable medium.

FIG. 144 illustrates an alternative embodiment of the operational flow 7300 of FIG. 143. In an embodiment, the reception operation 7310 may include at least one additional embodiment. The at least one additional embodiment may include an operation 7311, an operation 7312, or an operation 7313. The operation 7311 includes receiving at least two reference images of a patient body part having a cavity or lumen. Each reference image of the at least two reference images includes a respective landmark subsurface feature of the patient body part has a respective spatial relationship to a respective imaged region of a surface of the cavity or lumen of the patient body part. The operation 7312 includes receiving at least two reference images of a patient body part, each reference image of the at least two reference images acquired by a body-insertable device and including a respective landmark subsurface feature of the patient body part. Each imaged landmark subsurface feature has a respective spatial relationship to a respective region of a surface of the patient body part imaged during a medical examination. The operation 7313 includes receiving at least two reference images of a patient body part, each reference image of the at least two reference images acquired by an ex vivo device and including a respective landmark subsurface feature of the patient body part. Each imaged landmark subsurface feature has a respective spatial relationship to a respective region of a surface of the patient body part imaged during a medical examination.

Figure 145:
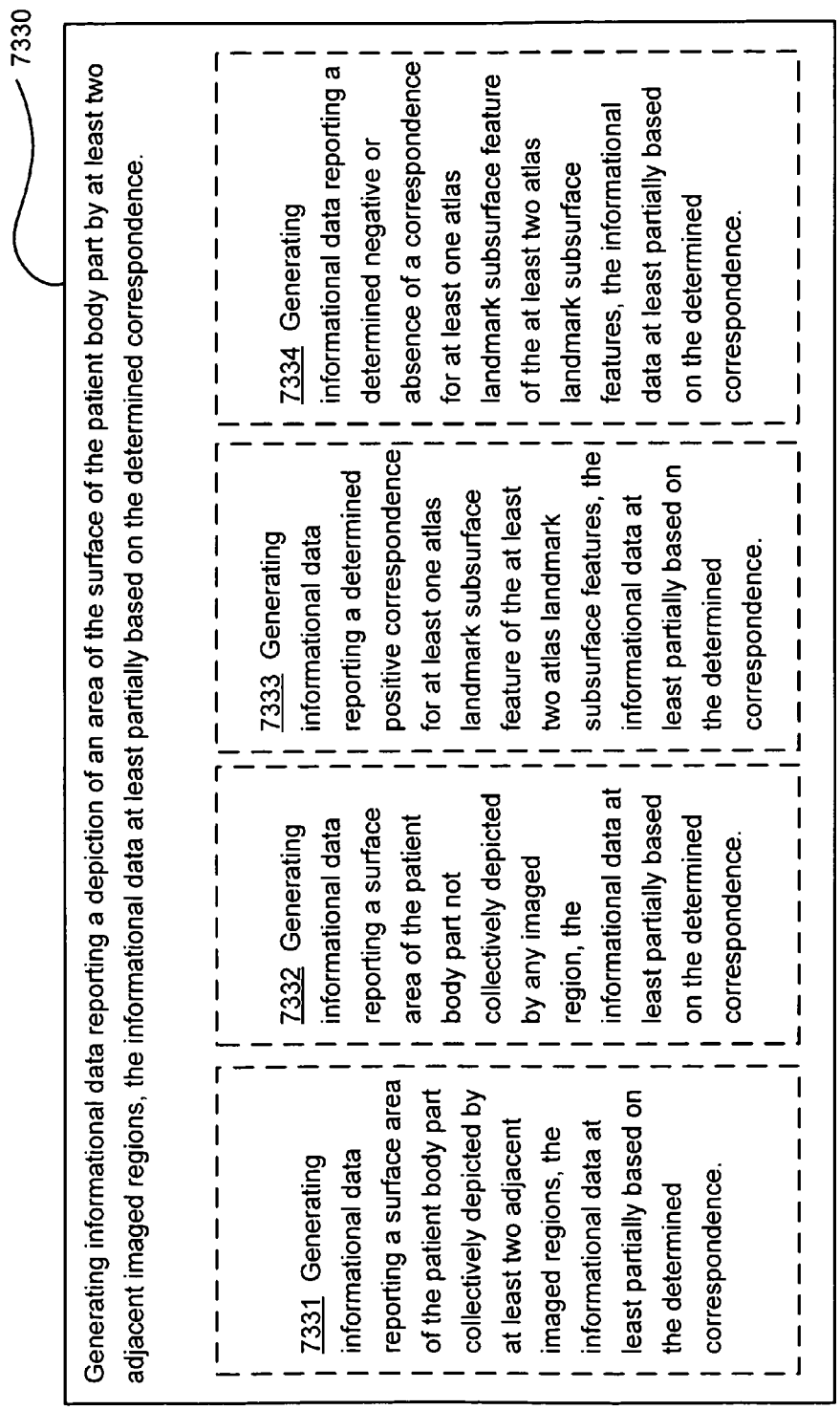
FIG. 145 illustrates an alternative embodiment of the operational flow 7200 of FIG. 142.

FIG. 145 illustrates an alternative embodiment of the operational flow 7300 of FIG. 143. In an embodiment, the surface coverage operation 7330 may include at least one additional embodiment. The at least one additional embodiment may include an operation 7331, an operation 7332, an operation 7333, or an operation 7334. The operation 7331 includes generating informational data reporting a surface area of the patient body part collectively depicted by at least two adjacent imaged regions. The informational data is at least partially based on the determined correspondence. The operation 7332 includes generating informational data reporting a surface area of the patient body part not collectively depicted by any imaged region. The informational data is at least partially based on the determined correspondence. The operation 7333 includes generating informational data reporting a determined positive correspondence for at least one atlas landmark subsurface feature of the at least two atlas landmark subsurface features. The informational data is at least partially based on the determined correspondence. The operation 7334 includes generating informational data reporting a determined negative or absence of a correspondence for at least one atlas landmark subsurface feature of the at least two atlas landmark subsurface features. The informational data is at least partially based on the determined correspondence.

FIG. 146 illustrates an alternative embodiment of the operational flow 7300 of FIG. 143. In an embodiment, the surface coverage operation 7330 may include at least one additional embodiment. The at least one additional embodiment may include an operation 7335, an operation 7336, or an operation 7337. The operation 7335 includes generating informational data reporting (i) a determined positive correspondence between (x) a particular atlas landmark subsurface feature of the at least two atlas landmark subsurface features and (y) an imaged landmark subsurface feature of the patient body part. The operation 7335 also includes generating informational data reporting (ii) a determined negative correspondence between (x) another atlas landmark subsurface feature immediately spatially adjacent to the particular atlas landmark subsurface feature and (y) each other respective imaged landmark subsurface feature of the patient body part. The operation 7336 also includes generating informational data reporting (i) a determined positive correspondence between (x) a first atlas landmark subsurface feature of the at least two atlas landmark subsurface features and (y) an imaged landmark subsurface feature. The operation 7336 also includes generating informational data reporting (ii) a first determined negative correspondence between (x) a second atlas landmark subsurface feature immediately spatially adjacent to the first atlas landmark subsurface feature and (y) each other respective imaged landmark subsurface feature of the patient body part. The operation 7336 also includes generating informational data reporting (iii) a second determined negative correspondence between (x) a third atlas landmark subsurface feature also immediately spatially adjacent to the first atlas landmark subsurface feature and (y) each other respective imaged landmark subsurface feature of the patient body part. The operation 7337 includes generating informational data reporting at least two spatially adjacent atlas landmark subsurface features respectively having a determined negative correspondence with each imaged landmark subsurface feature of the patient body part.

Figure 147:
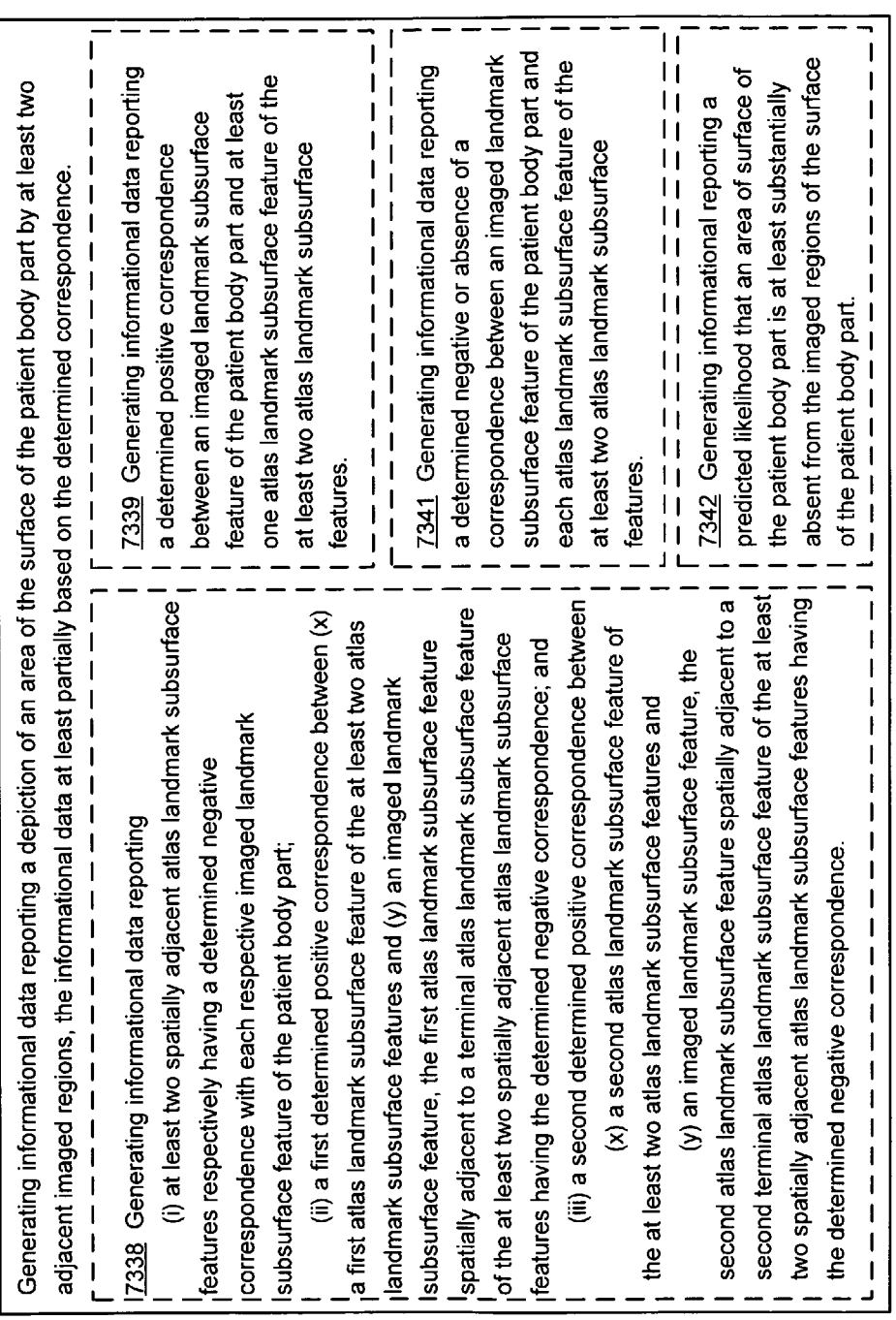
FIG. 147 illustrates an alternative embodiment of the operational flow 7200 of FIG. 142.

FIG. 147 illustrates an alternative embodiment of the operational flow 7300 of FIG. 143. In an embodiment, the surface coverage operation 7330 may include at least one additional embodiment. The at least one additional embodiment may include an operation 7338, an operation 7339, an operation 7341, or an operation 7342. The operation 7338 includes generating informational data reporting (i) at least two spatially adjacent atlas landmark subsurface features respectively having a determined negative correspondence with each respective imaged landmark subsurface feature of the patient body part. The operation 7338 also includes generating informational data reporting (ii) a first determined positive correspondence between (x) a first atlas landmark subsurface feature of the at least two atlas landmark subsurface features and (y) an imaged landmark subsurface feature. The first atlas landmark subsurface feature is spatially adjacent to a terminal atlas landmark subsurface feature of the at least two spatially adjacent atlas landmark subsurface features having the determined negative correspondence. The operation 7338 also includes generating informational data reporting (iii) a second determined positive correspondence between (x) a second atlas landmark subsurface feature of the at least two atlas landmark subsurface features and (y) an imaged landmark subsurface feature, the second atlas landmark subsurface feature spatially adjacent to a second terminal atlas landmark subsurface feature of the at least two spatially adjacent atlas landmark subsurface features having the determined negative correspondence. The operation 7339 includes generating informational data reporting a determined positive correspondence between an imaged landmark subsurface feature of the patient body part and at least one atlas landmark subsurface feature of the at least two atlas landmark subsurface features. The operation 7341 includes generating informational data reporting a determined negative or absence of a correspondence between an imaged landmark subsurface feature of the patient body part and each atlas landmark subsurface feature of the at least two atlas landmark subsurface features. The operation 7342 includes generating informational reporting a predicted likelihood that an area of surface of the patient body part is at least substantially absent from the imaged regions of the surface of the patient body part.

FIG. 148 illustrates an alternative embodiment of the operational flow 7300 of FIG. 143. In an embodiment, the communication operation 7350 may include at least one additional embodiment. The at least one additional embodiment may include an operation 7351, an operation 7352, an operation 7353, or an operation 7354. The operation 7351 includes outputting informational data usable in displaying a human-perceivable indication of the determined correspondence for at least one atlas landmark subsurface feature of the at least two atlas landmark subsurface features included in the subsurface feature atlas. The operation 7352 includes transforming the informational data into a particular visual depiction of a location of an un-imaged region of the surface of the patient body part relative to a larger portion of the surface of the patient body part, and outputting the transformed informational data. The operation 7353 includes transforming the informational data into a particular visual depiction of a location of at least two un-imaged regions of the surface of the patient body part relative to a larger portion of the surface of the patient body part, and outputting the transformed informational data. The operation 7354 includes transforming the informational data into a particular visual depiction of relative spatial positions of the respective image regions of the surface of the patient body part and outputting the transformed informational data.

FIG. 149 illustrates an example computer program product 7400. The computer program product includes a computer-readable media 7410 bearing program instructions 7420. The program instructions, when executed by a processor of a computing device, cause the computing device to perform a process. The process includes receiving at least two reference images of a patient body part. Each reference image of the at least two reference images includes a respective landmark subsurface feature of the patient body part (hereafter "imaged landmark subsurface feature"). Each imaged landmark subsurface feature has a respective spatial relationship to a respective region of a surface of the patient body part imaged during a medical examination (hereafter "imaged region"). The process includes determining a correspondence between (x) each atlas landmark subsurface feature of the patient body part of at least two atlas landmark subsurface features of the patient body part included in a landmark subsurface feature atlas of the patient body part and (y) each respective imaged landmark subsurface feature of the patient body part included in the at least two reference images. The process includes generating informational data reporting a depiction of an area of the surface of the patient body part by at least two adjacent imaged regions, the informational data is at least partially based on the determined correspondence. The process includes outputting the informational data. In an embodiment, the process further includes 7422 storing the informational data in another computer-readable media operably coupled with the processor.

In an embodiment, the computer-readable media 7410 includes a tangible computer-readable media 7412. In an embodiment, the computer-readable media includes a communications media 7414.

FIG. 150 illustrates an example system 7500. The system includes means 7510 for receiving at least two reference images of a patient body part. Each reference image of the at least two reference images includes a respective landmark subsurface feature of the patient body part (hereafter "imaged landmark subsurface feature"). Each imaged landmark subsurface feature has a respective spatial relationship to a respective region of a surface of the patient body part imaged during a medical examination (hereafter "imaged region"). The system includes means 7520 for determining a correspondence between (x) each atlas landmark subsurface feature of the patient body part of at least two atlas landmark subsurface features of the patient body part included in a landmark subsurface feature atlas of the patient body part and (y) each respective imaged landmark subsurface feature of the patient body part included in the at least two reference images. The system includes means 7530 for generating informational data reporting a depiction of an area of the surface of the patient body part by at least two adjacent imaged regions, the informational data is at least partially based on the determined correspondence. The system includes means 7540 for outputting the informational data.

An embodiment includes a system (not shown) that indicates a possible or a determined unimaged region of a surface of a mammalian body. In an embodiment, a system includes an image receiver circuit configured to receive a plurality of medical images. Each medical image of the plurality of medical images has at least one peripheral edge portion, and each medical image of the plurality of medical images including a respective imaged region of a mammalian body part. For example, the imaged region may include an imaged region of a surface of a mammalian body part. For example, the imaged region may include an imaged region of a surface of a cavity or lumen of a mammalian body part. For example, a medical image may have been acquired by a body-insertable device while present within the mammalian body. The system also includes an analysis circuit configured to determine an edge overlap status of a peripheral edge of the at least one peripheral edge of a selected medical image of the plurality of medical images. The peripheral edge overlap status is responsive to or at least partially based on a correspondence between (x) a content of the peripheral edge of the at least one peripheral edge of a selected medical image and (y) a content of each medical image of the plurality of medical images other than the selected medical image. In other words, the content of the peripheral edge of a selected medical image is attempted to be matched to the content of all the peripheral edges of another medical image. In an embodiment, (y) may include a content of each peripheral edge of each medical image of the plurality of medical images other than the selected medical image. The system further includes list management circuit configured to add the determined peripheral edge overlap status to an edge overlap list for the mammalian body part. For example, a determination of an edge overlap may be indicated by a "1" on the edge overlap list for the peripheral edge of the at least one peripheral edge of the selected medical image, and a determination of no edge overlap may be indicated by a "0" on the edge overlap list for the peripheral edge of the at least one peripheral edge of a selected medical image. The system also includes a data analysis circuit configured to determine that a particular region of the mammalian body part is not included in the plurality of medical images (hereafter "non-imaged region"). The determination is at least partially based on at least one instance of a non-overlapped edge status for a peripheral edge of a medical image of the plurality of medical images indicated on the edge overlap list. The system includes a communications circuit configured to output the informational data. In an embodiment, the system may include an edge overlap analysis circuit configured to predict a likelihood that a surface region of the patient body part is substantially absent from the respective imaged regions of the surface of the patient body part included in the at least two medical images. The predicting is at least partially based on the edge overlap list. An example of imagery coverage estimates and analyses is provided by C. Gebhardt, *RCC Imagery Analysis Procedures Explored in STS-127 TPS Documentation*, http://www.nasaspaceflight.com/2009/07/rcc-procedures-explored-sts-127-tps/ (accessed Aug. 18, 2011).

An embodiment includes a system that indicates a possible or a determined unimaged surface of an mammalian body part (not illustrated). In an embodiment, a system includes an image receiver circuit configured to receive a plurality of medical images. Each medical image of the plurality of medical images has at least one peripheral edge portion, and each medical image of the plurality of medical images including a respective imaged region of a mammalian body part. For example, the imaged region may include an imaged region of a surface of a mammalian body part. For example, the imaged region may include an imaged region of a surface of a cavity or lumen of a mammalian body part. For example, a medical image may have been acquired by a body-insertable device while present within the mammalian body. The system also includes a detection circuit configured to detect a feature of a peripheral edge of the at least one peripheral edge of a medical image of the plurality of medical images (hereafter "detected peripheral edge feature"). The system includes an edge-overlap analysis circuit configured to determine an edge overlap status of a peripheral edge of the at least one peripheral edge of a selected medical image of the plurality of medical images. The peripheral edge overlap status is responsive to or at least partially based on a correspondence between (x) a detected peripheral edge feature of a peripheral edge of the at least one peripheral edge of a selected medical image and (y) each detected peripheral edge feature of each peripheral edge of each medical image of the plurality of medical images other than the selected medical image. In other words, the detected peripheral edge feature of the peripheral edge of a selected medical image is attempted to be matched to the detected peripheral edge features of all of the medical images. For example, if a negative or no correspondence is found, i.e., there is no common detected peripheral edge feature with at least one of the remaining medical images, the system presumes or interprets the negative correspondence as an indication that there is an unimaged adjacent region adjacent to the selected medical image. For example, if a positive correspondence is found, i.e., there is a common detected peripheral edge feature with at least one of the remaining medical images, the system presumes or interprets the positive correspondence as an indication that the region adjacent to the selected medical image is likely imaged. The system further includes list management circuit configured to add the determined peripheral edge overlap status to an edge overlap list for the mammalian body part. For example, a determination of an edge overlap may be indicated by a "1" on the edge overlap list for the peripheral edge of the at least one peripheral edge of the selected medical image, and a determination of no edge overlap may be indicated by a "0" on the edge overlap list for the peripheral edge of the at least one peripheral edge of a selected medical image. The system also includes a first data analysis circuit configured to determine that a particular region of the mammalian body part is not included in the plurality of medical images (hereafter "non-imaged region"). The indication of a non-imaged region is at least partially based on at least one instance of a non-overlapped edge status for a peripheral edge of a medical image of the plurality of medical images indicated on the edge overlap list. The system includes a data analysis circuit configured to determine that a particular region of the mammalian body part is not included in the respective imaged regions of the mammalian body part of the plurality of medical images (hereafter "particular non-imaged region"). The data analysis circuit is also configured to determine a spatial relationship between the particular non-imaged region and a detected peripheral edge feature of the selected medical image of the plurality of medical images. The determinations are at least partially based on the indication of a non-imaged region and the edge overlap list. The system includes a computer-readable media configured to maintain informational data corresponding to the particular non-imaged region. The system includes a communications device configured to output informational data.

In an embodiment, the system may include an edge overlap analysis circuit configured to predict a likelihood that a surface region of the patient body part is substantially dabsent from the respective imaged regions of the surface of the patient body part included in the at least two medical images.

In an embodiment, the detection circuit includes a feature detection circuit configured to detect a surface feature proximate to at least one peripheral edge of a respective imaged region of the surface of the cavity or lumen of the body part included in each medical image of the plurality of medical images. In an embodiment, the detection circuit includes a feature detection circuit configured to detect a subsurface feature proximate to at least one peripheral edge of a respective imaged region of the surface of the cavity or lumen of the patient body part included in each medical image of the plurality of medical images. In an embodiment, the detection circuit includes a feature detection circuit configured to detect and extract a feature proximate to at least one peripheral edge of a respective imaged region of the surface of the cavity or lumen of the patient body part included in each medical image of the plurality of medical images. In an embodiment, the detection circuit includes a feature detection circuit configured to detect at least one of an anatomical feature of the cavity or lumen, a pattern, or a feature of the image proximate to at least one peripheral edge of a respective imaged region of the surface of the cavity or lumen of the patient body part included in each medical image of the plurality of medical images. In an embodiment, the detection circuit includes a feature detection circuit configured to detect a feature proximate to each peripheral edge of a respective imaged region of the surface of the cavity or lumen of the patient body part included in each medical image of the plurality of medical images.

In an embodiment, the edge overlap analysis circuit includes an edge overlap analysis circuit configured to determine an absence of a peripheral edge overlap in response to a negative correspondence between (x) a detected peripheral edge feature of an imaged region of the surface of the cavity or lumen of the patient body part included in a first medical image of the plurality of medical images and (y) each detected peripheral edge feature of each imaged region of the surface of the cavity or lumen of the patient body part included the remaining medical images of the plurality of medical images. In an embodiment, the edge overlap analysis circuit includes an edge overlap analysis circuit configured to determine a correspondence between (x) a detected peripheral edge feature of an imaged region of the surface of the cavity or lumen of the patient body part included in a first medical image of the plurality of medical images and (y) each detected peripheral edge feature of each imaged region of the surface of the cavity or lumen of the patient body part included the remaining medical images of the plurality of medical images, and to iteratively determine a correspondence between each detected peripheral edge feature of each imaged region included in each medical image of the plurality of medical images and each detected peripheral edge feature of each imaged region of each other medical image of the plurality of medical images. In an embodiment, the edge overlap analysis circuit includes an edge overlap analysis circuit configured to determine an absence of a peripheral edge overlap by mapping (x) each detected peripheral edge feature of an imaged region of the surface of the cavity or lumen of the patient body part included in each medical image of the plurality of medical images to (y) each detected peripheral edge feature of each imaged region of each other medical image of the plurality of medical images.

In an embodiment, the data analysis circuit includes a data analysis circuit configured to gather data indicative of a determined absence of a detected peripheral edge feature overlap for at least one peripheral edge feature of an imaged region of the surface of the cavity or lumen of the patient body part included in a medical image of the plurality of medical images. In an embodiment, the data analysis circuit includes a data analysis circuit configured to gather data indicative of a determined presence of a detected peripheral edge feature overlap for at least one peripheral edge feature of an imaged region of the surface of the cavity or lumen of the patient body part included in a medical image of the plurality of medical images.

In an embodiment, the communication device includes a communication device configured to display the informational data, including a human-perceivable indication of a possible non-imaged region, the indication of the possible non-imaged region at least partially based on a determined negative correspondence by the edge overlap analysis circuit. In an embodiment, the communication device includes a communication device configured to display the informational data, including a human-perceivable indication of a non-imaged region, the indication of the non-imaged region at least partially based on a determined absence of a detected peripheral edge feature overlap for the first medical image by the edge overlap analysis circuit. In an embodiment, the communication device includes a communication device configured to display the informational data, including displaying a human-perceivable indication of a non-imaged region, and a location [with reference to subsurface feature] of the non-imaged region, the indication and the location of the non-imaged region at least partially based on a determination by the edge overlap analysis circuit of an absence of an edge overlap.

In an embodiment, the system includes an edge detection circuit configured to detect a peripheral edge of a selected medical image. In an embodiment, the system includes a location analysis circuit configured to indicate a location of the non-imaged region. The location indication is at least partially based on the portion of the edge overlap list indicative of a determined negative correspondence. In an embodiment, the location analysis circuit includes a location analysis circuit configured to indicate a location of the possible non-imaged region, the location indication is at least partially based on the edge overlap list indicative of a determined negative correspondence by the edge overlap analysis circuit. In an embodiment, the location analysis circuit includes a location analysis circuit configured to indicate a location of the non-imaged region. The location is indicated relative to the imaged region of the surface of the cavity or lumen of the patient body part included in the first medical image of the plurality of medical images, and the location indication at least partially based on the gathered data indicative of the determined correspondence by the edge overlap analysis circuit. In an embodiment, the location analysis circuit includes a location analysis circuit configured to indicate a location of the non-imaged region, The location is indicated relative to a site within the imaged region of the surface of the cavity or lumen of the patient body part included in the first medical image of the plurality of medical images, and the location indication at least partially based on the gathered data indicative of a determined negative correspondence by the edge overlap analysis circuit. In an embodiment, the location analysis circuit includes a location analysis circuit configured to indicate a location of the non-imaged region. The location is indicated (i) relative to a site within the imaged region and (ii) relative to the determined non-overlapped detected peripheral edge feature of the surface of the cavity or lumen of the patient body part included in the first medical image of the plurality of medical images, and the location indication at least partially based on the gathered data indicative of the determined correspondence by the edge overlap analysis circuit. In an embodiment, the location analysis circuit includes a location analysis circuit configured to indicate a location of a non-imaged region. The location is indicated by a line substantially perpendicular to the peripheral edge of the first medical image having a detected peripheral edge feature with a determined negative correspondence (i.e. non-overlapped), and the location indication at least partially based on the gathered data indicative of the determined correspondence by the edge overlap analysis circuit. In an embodiment, the location analysis circuit includes a location analysis circuit configured to indicate a location of a non-imaged region. The location indication is at least partially based on a closed curve substantially formed by linking (i) the peripheral edge having a detected peripheral edge feature with a determined negative correspondence (non-overlapped, all "0" correspondences) of the first medical image and (ii) a respective peripheral edge having a detected peripheral edge feature with a determined negative correspondence of at least one other proximate medical image of the plurality of medical images. In an embodiment, the location analysis circuit includes a location analysis circuit configured to indicate a location of a non-imaged site of the surface of the cavity or lumen of the patient body part. The indication of the site is at least partially based on a closed curve substantially formed by linking (i) the peripheral edge having a detected peripheral edge feature with a determined negative correspondence (i.e. non-overlapped, all "0" correspondences) of the first medical image and (ii) a respective peripheral edge having a detected peripheral edge feature with a determined negative correspondence of at least one other proximate medical image of the plurality of medical images. In an embodiment, the location analysis circuit includes a location analysis circuit configured to indicate a possible non-imaged region of the surface of the cavity or lumen of the patient body part. The indication of a non-imaged region is at least partially based on a negative determined correspondence for at least two proximate detected peripheral edge features of one peripheral edge of a respective imaged region of the surface of the cavity or lumen of the patient body part included in the first medical image. For example, if a negative correspondence {all="0"} for two proximate detected peripheral edge features is found with any other detected peripheral edge feature of the remaining medical images there is no edge overlap and a possible non-imaged region exists.

In an embodiment, the system includes a filter circuit configured to receive a medical image determined by the edge overlap analysis circuit to have a negative correspondence (an absence of an edge overlap). The filter circuit is also configured to determine that the imaged region of the surface of the cavity or lumen of the patient body part included in the received medical image includes an end-region of the cavity or lumen proximate to a terminus of the surface of the cavity or lumen of the patient body part. The filter circuit is also configured to remove the medical image from the at least two medical images (hereafter "filtered at least two medical images").

All references cited herein are hereby incorporated by reference in their entirety or to the extent their subject matter is not otherwise inconsistent herewith.

In some embodiments, "configured" includes at least one of designed, set up, shaped, implemented, constructed, or adapted for at least one of a particular purpose, application, or function.

It will be understood that, in general, terms used herein, and especially in the appended claims, are generally intended as "open" terms. For example, the term "including" should be interpreted as "including but not limited to." For example, the term "having" should be interpreted as "having at least." For example, the term "has" should be interpreted as "having at least." For example, the term "includes" should be interpreted as "includes but is not limited to," etc. It will be further understood that if a specific number of an introduced claim recitation is intended, such an intent will be explicitly recited in the claim, and in the absence of such recitation no such intent is present. For example, as an aid to understanding, the following appended claims may contain usage of introductory phrases such as "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a receiver" should typically be interpreted to mean "at least one receiver"); the same holds true for the use of definite articles used to introduce claim recitations. In addition, even if a specific number of an introduced claim recitation is explicitly recited, it will be recognized that such recitation should typically be interpreted to mean at least the recited number (e.g., the bare recitation of "at least two chambers," or "a plurality of chambers," without other modifiers, typically means at least two chambers).

In those instances where a phrase such as "at least one of A, B, and C," "at least one of A, B, or C," or "an [item] selected from the group consisting of A, B, and C," is used, in general such a construction is intended to be disjunctive (e.g., any of these phrases would include but not be limited to systems that have A alone, B alone, C alone, A and B together, A and C together, B and C together, or A, B, and C together, and may further include more than one of A, B, or C, such as $A_1$, $A_2$, and C together, A, $B_1$, $B_2$, $C_1$, and $C_2$ together, or $B_1$ and $B_2$ together). It will be further understood that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable or physically interacting components or wirelessly interactable or wirelessly interacting components.

With respect to the appended claims the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Use of "Start," "End," "Stop," or the like blocks in the block diagrams is not intended to indicate a limitation on the beginning or end of any operations or functions in the diagram. Such flowcharts or diagrams may be incorporated into other flowcharts or diagrams where additional functions are performed before or after the functions shown in the diagrams of this application. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
  (a) a receiver circuit configured to receive
    (i) a first reference image that includes an objective landmark subsurface feature of a mammalian body part, the objective landmark subsurface feature having a first spatial relationship to a destination region of interest of the mammalian body part;
   (ii) a second reference image that includes a present-location landmark subsurface feature of the mammalian body part, the present-location landmark subsurface feature having a second spatial relationship to a distal end portion of a body-insertable device deployed operationally proximate to the mammalian body part;
(b) a computer-readable media configured to store a subsurface feature atlas of the mammalian body part;
(c) a feature matching circuit configured to determine
   (i) a substantial correspondence between the objective landmark subsurface feature and a first atlas subsurface feature included in the subsurface feature atlas of the mammalian body part, and
   (ii) a substantial correspondence between the present-location landmark subsurface feature and a second atlas subsurface feature included in the subsurface feature atlas of the mammalian body part,
the subsurface feature atlas includes at least two registered subsurface features of the mammalian body part, including the first atlas subsurface feature and the second atlas subsurface feature having at least one intervening atlas subsurface feature therebetween, the registration including an indication of a third spatial relationship and orientation between the first atlas subsurface feature and the second atlas subsurface feature;
(d) a location analysis circuit configured to determine a fourth spatial relationship and orientation between the destination region of interest and the distal end portion of the body-insertable device deployed operationally proximate to the mammalian body part, the determined fourth spatial relationship and orientation at least partially based on the third spatial relationship;
(e) an indicator circuit configured to generate informational data indicative of the determined fourth spatial relationship and orientation between the destination region of interest and the distal end portion of the body-insertable device, the informational data at least partially based on the fourth spatial relationship and orientation between the destination region of interest and the distal end portion of the body-insertable device; and
(f) the computer-readable media further configured to maintain the informational data.

2. The system of claim 1, wherein the first reference image includes:
   a first reference image that includes an objective landmark subsurface feature of a mammalian body part, the objective landmark subsurface feature having an indicated, determinable, estimable, or inferable first spatial relationship to a destination region of interest of the mammalian body part.

3. The system of claim 1, wherein the first reference image includes:
   a first reference image that includes an objective landmark subsurface feature of a mammalian body part, the objective landmark subsurface feature having a first spatial relationship to a destination region of interest of a cavity or lumen of the mammalian body part.

4. The system of claim 1, wherein the first reference image includes:
   a first reference image that includes an objective landmark subsurface feature of a mammalian body part, the objective landmark subsurface feature having a first spatial relationship to a human-user selected destination region of interest of the mammalian body part.

5. The system of claim 1, wherein the first reference image includes:
   a first reference image that includes an objective landmark subsurface feature of a mammalian body part, the objective landmark subsurface feature having a first spatial relationship to a machine-selected destination region of interest of the mammalian body part.

6. The system of claim 1, wherein the second reference image includes:
   a second reference image that includes a present-location landmark subsurface feature of the mammalian body part, the present-location landmark subsurface feature having a second spatial relationship to an effector carried by a distal end portion of a body-insertable device and deployed operationally proximate to the mammalian body part.

7. The system of claim 1, wherein the second reference image includes:
   a second reference image that includes a present-location landmark subsurface feature of the mammalian body part, the present-location landmark subsurface feature having a second spatial relationship to an operative and movable distal end portion of a body-insertable device deployed operationally proximate to the mammalian body part.

8. The system of claim 1, wherein the feature matching circuit includes:
   a feature matching circuit configured to determine
      (i) at least one of a substantial structural, orientation, pattern, or physical characteristic correspondence between the objective landmark subsurface feature and a first atlas subsurface feature included in a subsurface feature atlas of the mammalian body part, and
      (ii) at least one of a substantial structural, orientation, pattern, or physical characteristic correspondence between the present-location landmark subsurface feature and a second atlas subsurface feature included in the subsurface feature atlas of the mammalian body part.

9. The system of claim 1, wherein the feature matching circuit includes:
   a feature matching circuit configured to determine
      (i) a substantial match between the objective landmark subsurface feature and a first atlas subsurface feature included in a subsurface feature atlas of the mammalian body part, and
      (ii) a substantial match between the present-location landmark subsurface feature and a second atlas subsurface feature included in the subsurface feature atlas of the mammalian body part.

10. The system of claim 1, wherein the location analysis circuit includes:
   a location analysis circuit configured determine a fourth spatial relationship between the destination region of interest and the distal end portion of the body-insertable device deployed operationally proximate to the mammalian body part, the fourth spatial relationship determined at least partially in response to:
      (i) a fifth spatial relationship between the objective landmark subsurface feature and the present-location landmark subsurface feature, the determination at least partially based on a spatial relationship between the first atlas subsurface feature and the second atlas subsurface feature as indicated by the subsurface feature atlas;

(ii) the first spatial relationship between the destination region of interest and the objective landmark subsurface feature; and (iii) the second spatial relationship between the distal end portion of the body-insertable device and the present-location landmark subsurface feature.

11. The system of claim 1, wherein the indicator circuit includes:
an indicator circuit configured to generate informational data indicative of an operational proximity of the distal end portion of the body-insertable device to the destination region of interest, the informational data at least partially based on the determined fourth spatial relationship.

12. The system of claim 1, wherein the indicator circuit includes:
an indicator circuit configured to generate informational data indicative of a distance of less than four centimeters between the distal end portion of the body-insertable device and the destination region of interest, the informational data at least partially based on the determined fourth spatial relationship.

13. The system of claim 1, wherein the indicator circuit includes:
an indicator circuit configured to generate informational data indicative of a distance of less than one hundred millimeters between the distal end portion of the body-insertable device and the destination region of interest, the informational data at least partially based on the determined fourth spatial relationship.

14. The system of claim 1, wherein the indicator circuit includes:
an indicator circuit configured to generate informational data indicative of a distance from the distal end portion of the body-insertable device to the destination region of interest, the informational data at least partially based on the determined fourth spatial relationship, and wherein the indicated distance is within a user-selected range.

15. The system of claim 1, further comprising:
a guidance circuit configured to determine a movement of the distal end portion of the body-insertable device to produce a particular change in the spatial relationship between the distal end portion of the body-insertable device and the destination region of interest, the movement at least partially based on the informational data indicative of the determined fourth spatial relationship between the destination region of interest and the distal end portion of the body-insertable device.

16. The system of claim 15, wherein the guidance circuit includes:
a guidance circuit configured to determine a movement of the distal end portion of the body-insertable device to produce a user-selected change of the spatial relationship between the distal end portion of the body-insertable device and the destination region of interest, the movement at least partially based on the informational data indicative of the determined fourth spatial relationship between the destination region of interest and the distal end portion of the body-insertable device.

17. The system of claim 15, wherein the guidance circuit includes:
a guidance circuit configured to determine a rotational, radial, or axial movement of the distal end portion of the body-insertable device to produce a particular change in the spatial relationship between the distal end portion of the body-insertable device and the destination region of interest, the movement at least partially based on the informational data indicative of the determined fourth spatial relationship between the destination region of interest and the distal end portion of the body-insertable device.

18. The system of claim 15, wherein the guidance circuit includes:
a guidance circuit configured to determine a movement of the distal end portion of the body-insertable device to decrease a separation between the spatial relationship between the distal end portion of the body-insertable device and the destination region of interest, the movement at least partially based on the informational data indicative of the determined fourth spatial relationship between the destination region of interest and the distal end portion of the body-insertable device.

19. The system of claim 15, wherein the indicator circuit includes:
an indicator circuit configured to generate informational data indicative of the determined movement of the distal end portion of the body-insertable device to produce a particular change in the spatial relationship between the distal end portion of the body-insertable device and the destination region of interest.

20. The system of claim 1, further comprising:
a communication circuit configured to output the informational data.

21. A method implemented using a computing device, the method comprising:
(a) receiving a first reference image that includes an objective landmark subsurface feature of a mammalian body part, the objective landmark subsurface feature having a first spatial relationship to a destination region of interest of the mammalian body part;

(b) receiving a second reference image that includes a present-location landmark subsurface feature of the mammalian body part, the present-location landmark subsurface feature having a second spatial relationship to a distal end portion of a body-insertable device deployed operationally proximate to the mammalian body part;

(c) determining a substantial correspondence between the objective landmark subsurface feature and a first atlas subsurface feature included in a subsurface feature atlas of the mammalian body part, the subsurface feature atlas includes at least two registered subsurface features of the mammalian body part, including the first atlas subsurface feature and a second atlas subsurface feature having at least one intervening atlas subsurface feature therebetween, the registration including an indication of a third spatial relationship and orientation between the first atlas subsurface feature and the second atlas subsurface feature;

(d) determining a substantial correspondence between the present-location landmark subsurface feature and the second atlas subsurface feature included in the subsurface feature atlas of the mammalian body part;

(e) determining a fourth spatial relationship and orientation between the destination region of interest and the distal end portion of the body-insertable device deployed operationally proximate to the mammalian body part, the determined fourth spatial relationship and orientation at least partially based on the third spatial relationship; and (f) outputting informational data indicative of the determined fourth spatial relationship and orientation between the destination region of interest and the distal end portion of the body-insertable device.

22. The method of claim 21, further comprising:
determining a movement of the distal end portion of the body-insertable device to produce a particular change in the spatial relationship between the distal end portion of the body-insertable device and the destination region of interest, the movement at least partially based on the informational data indicative of the determined fourth spatial relationship between the destination region of interest and the distal end portion of the body-insertable device.

23. The method of claim 22, wherein the outputting informational data includes:
outputting informational data indicative of the determined movement of the distal end portion of the body-insertable device to produce a particular change in the spatial relationship between the distal end portion of the body-insertable device and the destination region of interest.

24. The method of claim 21, further comprising:
maintaining the informational data in a computer-readable media.

25. The method of claim 21, further comprising:
providing a notification at least partially based on the informational data to at least one of a human, computer, or system.

26. The method of claim 21, further comprising:
maintaining the atlas of the mammalian body in the computer-readable media, the atlas including a respective spatial relationship between at least two registered atlas subsurface features of the mammalian body part.

27. A computer program product comprising:
(a) a non-transitory computer-readable medium including program instructions stored thereon which, when executed by a processor of a computing device, cause the computing device to perform a process including:
  (i) receiving a first reference image that includes an objective landmark subsurface feature of a mammalian body part, the objective landmark subsurface feature having a first spatial relationship to a destination region of interest of the mammalian body part;
  (ii) receiving a second reference image that includes a present-location landmark subsurface feature of the mammalian body part, the present-location landmark subsurface feature having a second spatial relationship to a distal end portion of a body-insertable device deployed operationally proximate to the mammalian body part;
  (iii) determining a substantial correspondence between the objective landmark subsurface feature and a first atlas subsurface feature included in a subsurface feature atlas of the mammalian body part stored on the non-transitory computer-readable medium including, the subsurface feature atlas includes at least two registered subsurface features of the mammalian body part, including the first atlas subsurface feature and a second atlas subsurface feature having at least one intervening atlas subsurface feature therebetween, the registration including an indication of a third spatial relationship and orientation between the first atlas subsurface feature and the second atlas subsurface feature;
  (iv) determining a substantial correspondence between the present-location landmark subsurface feature and the second atlas subsurface feature included in the subsurface feature atlas of the mammalian body part;
  (v) determining a fourth spatial relationship and orientation between the destination region of interest and the distal end portion of the body-insertable device deployed operationally proximate to the mammalian body part, the determined fourth spatial relationship and orientation at least partially based on the third spatial relationship; and
  (vi) outputting informational data indicative of the determined fourth spatial relationship and orientation between the destination region of interest and the distal end portion of the body-insertable device.

28. The computer program product of claim 27, wherein the non-transitory computer-readable medium includes a tangible computer-readable media.

29. The computer program product of claim 27, wherein the non-transitory computer-readable medium includes a communications media.

30. A system comprising:
(a) means for receiving a first reference image that includes an objective landmark subsurface feature of a mammalian body part, the objective landmark subsurface feature having a first spatial relationship to a destination region of interest of the mammalian body part;
(b) means for receiving a second reference image that includes a present-location landmark subsurface feature of the mammalian body part, the present-location landmark subsurface feature having a second spatial relationship to a distal end portion of a body-insertable device deployed operationally proximate to the mammalian body part;
(c) means for determining a substantial correspondence between the objective landmark subsurface feature and a first atlas subsurface feature included in a subsurface feature atlas of the mammalian body part, the subsurface feature atlas includes at least two registered subsurface features of the mammalian body part, including the first atlas subsurface feature and a second atlas subsurface feature having at least one intervening atlas subsurface feature therebetween, the registration including an indication of a third spatial relationship and orientation between the first atlas subsurface feature and the second atlas subsurface feature;
(d) means for determining a substantial correspondence between the present-location landmark subsurface feature and the second atlas subsurface feature included in the subsurface feature atlas of the mammalian body part;
(e) means for determining a fourth spatial relationship and orientation between the destination region of interest and the distal end portion of the body-insertable device deployed operationally proximate to the mammalian body part, the determined fourth spatial relationship and orientation at least partially based on the third spatial relationship; and
(f) means for outputting informational data indicative of the determined fourth spatial relationship and orientation between the destination region of interest and the distal end portion of the body-insertable device.

\* \* \* \* \*

UNITED STATES PATENT AND TRADEMARK OFFICE
CERTIFICATE OF CORRECTION

| | | |
|---|---|---|
| PATENT NO. | : 8,908,941 B2 | Page 1 of 1 |
| APPLICATION NO. | : 13/200112 | |
| DATED | : December 9, 2014 | |
| INVENTOR(S) | : Roderick A. Hyde et al. | |

It is certified that error appears in the above-identified patent and that said Letters Patent is hereby corrected as shown below:

In the Claims

Column 134
Claim 10, Line 56, change "a location analysis circuit configured determine a fourth" to --a location analysis circuit configured to determine a fourth--

Signed and Sealed this
Twenty-first Day of April, 2015

Michelle K. Lee
*Director of the United States Patent and Trademark Office*